US012799228B2

(12) United States Patent
Seeberger et al.

(10) Patent No.: US 12,799,228 B2
(45) Date of Patent: Nov. 17, 2026

(54) SINGLE DOMAIN ANTIBODIES SPECIFICALLY BINDING GLOBO-SERIES GLYCANS

(71) Applicant: Max-Planck-Gesellschaft zur Förderung der Wissenschaften e.V., Munich (DE)

(72) Inventors: Peter H. Seeberger, Kleinmachnow (DE); Oren Moscovitz, Berlin (DE)

(73) Assignee: Max-Planck-Gesellschaft zur Förderung der Wissenschaften e.V, Munich (DE)

( * ) Notice: Subject to any disclaimer, the term of this patent is extended or adjusted under 35 U.S.C. 154(b) by 1172 days.

(21) Appl. No.: 17/766,052

(22) PCT Filed: Oct. 2, 2020

(86) PCT No.: PCT/EP2020/077754

§ 371 (c)(1),
(2) Date: Apr. 1, 2022

(87) PCT Pub. No.: WO2021/064227

PCT Pub. Date: Apr. 8, 2021

(65) Prior Publication Data

US 2022/0380485 A1 Dec. 1, 2022

(30) Foreign Application Priority Data

Oct. 4, 2019 (EP) .................................... 19201562

(51) Int. Cl.

| | |
|---|---|
| ***C07K 16/44*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |

(52) U.S. Cl.

CPC .............. *C07K 16/44* (2013.01); *A61K 40/11* (2025.01); *A61K 40/31* (2025.01); *A61K 40/4261* (2025.01); *A61P 35/00* (2018.01); *C07K 2317/24* (2013.01); *C07K 2317/35* (2013.01); *C07K 2317/567* (2013.01); *C07K 2317/569* (2013.01)

(58) Field of Classification Search

CPC ........................... C07K 16/44; C07K 2317/24; C07K 2317/35; C07K 2317/567; C07K 2317/569; C07K 2317/22; C07K 16/30; A61K 40/11; A61K 40/31; A61K 40/4261; A61K 2039/505; A61P 35/00; G01N 33/57407; G01N 33/574

See application file for complete search history.

(56) References Cited

FOREIGN PATENT DOCUMENTS

| | | | |
|---|---|---|---|
| JP | 2014-527065 A | 10/2014 | |
| JP | 2018-504410 A | 2/2018 | |
| WO | WO 2013/030604 | 3/2013 | |
| WO | WO 2015/143123 | 9/2015 | |
| WO | WO 2015/143126 | 9/2015 | |
| WO | WO 2016/118733 | 7/2016 | |
| WO | WO 2018/054353 | 3/2018 | |
| WO | WO-2018054353 A1 * | 3/2018 | ............. C07K 16/44 |

OTHER PUBLICATIONS

African Journal of Biotechnology, 10(79):18294-18302, 2011 (Year: 2011).*
Annu. Rev. Biophys. Biophys. Chem., 16: 139-159, 1987 (Year: 1987).*
J. Immunol. Methods, 251(1-2): 137-149, 2001 (Year: 2001).*
Henry, et al: "Role of the non-hypervariable FR3 D-E loop in single-domain antibody recognition of haptens and carbohydrates", Journal of Molecular Recognition. (Aug. 18, 2019) 32(11):e2805-e2805.
International Search Report and Written Opinion mailed Feb. 2, 2021 in PCT Application PCT/EP2020/077754, filed Oct. 2, 2020.
Office Action dated Japanese Patent Application No. 2022-520820 dated Feb. 25, 2025, filed Oct. 2, 2020.

* cited by examiner

*Primary Examiner* — Nelson B Moseley, II
*Assistant Examiner* — Josephine K Darpolor
(74) *Attorney, Agent, or Firm* — Knobbe, Martens, Olson & Bear, LLP

(57) ABSTRACT

The present invention relates to the field of single-domain antibodies (sdAb) directed towards the glycans of the globo series, and in particular Globo H. More in detail, the present invention relates to sdAbs specifically binding one or more glycans selected from Globo H, Gb3, Gb4, and Gb5. The invention also provides polypeptides comprising multimeric single domain antibodies, as well as T cell chimeric antigen receptors comprising said anti-glycan sdAbs. Thus, the present invention provides polypeptides that can be used for targeting and/or treating several types of cancers associated with cells over-expressing said Globo H and/or Gb3, Gb4, Gb5. The present invention also relates to recombinant nucleic acid sequences encoding said polypeptides, and expression vectors and host cells comprising the same.

16 Claims, 24 Drawing Sheets

Specification includes a Sequence Listing.

sdAb 46

Kinetics (1:1 binding)

| KD [M] | $R_{max}$[RU] | $\chi^2$ | p [%] |
|---|---|---|---|
| **$1.9x10^{-6}$** | 22.1 | 0.446 | 95-99 |
| **$2.8x10^{-7}$** | 1.7 | 0.066 | >99 |

Affinity (steady-state)

| KD [M] | $R_{max}$[RU] | $\chi^2$ | p[%] |
|---|---|---|---|
| **$3,8x10^{-6}$** | 28,93 | 0,106 | ~95 |
| **$1.3x10^{-8}$** | 60 | 0.267 | 90-95 |

| KD [M] | $R_{max}$[RU] | $\chi^2$ | p[%] |
|---|---|---|---|
| $5.4x10^{-8} \pm 3.1x10^{-8}$ (3 repeats) | 28.2 | 1.55 | 75-90 |
| | 107.2 | 32.3 | <1 |
| | 47.9 | 3.17 | 25-50 |

| KD [M] | $R_{max}$[RU] | $\chi^2$ | p[%] |
|---|---|---|---|
| $5.6x10^{-7} \pm 3.1x10^{-7}$ | 52.1 | 0,882 | 50-75 |
| | 738.5 | 5.66 | 5-10 |
| | 134.5 | 0.448 | 75-90 |

| KD [M] | $R_{max}$[RU] | $\chi^2$ | p[%] |
|---|---|---|---|
| **$1.9x10^{-7}$** | 23.01 | 1.39 | 75-90 |

| KD [M] | $R_{max}$[RU] | $\chi^2$ | p[%] |
|---|---|---|---|
| **$2.1x10^{-6}$** | 40.18 | 2.25 | 10-25 |

Figure 14 (*continue*)
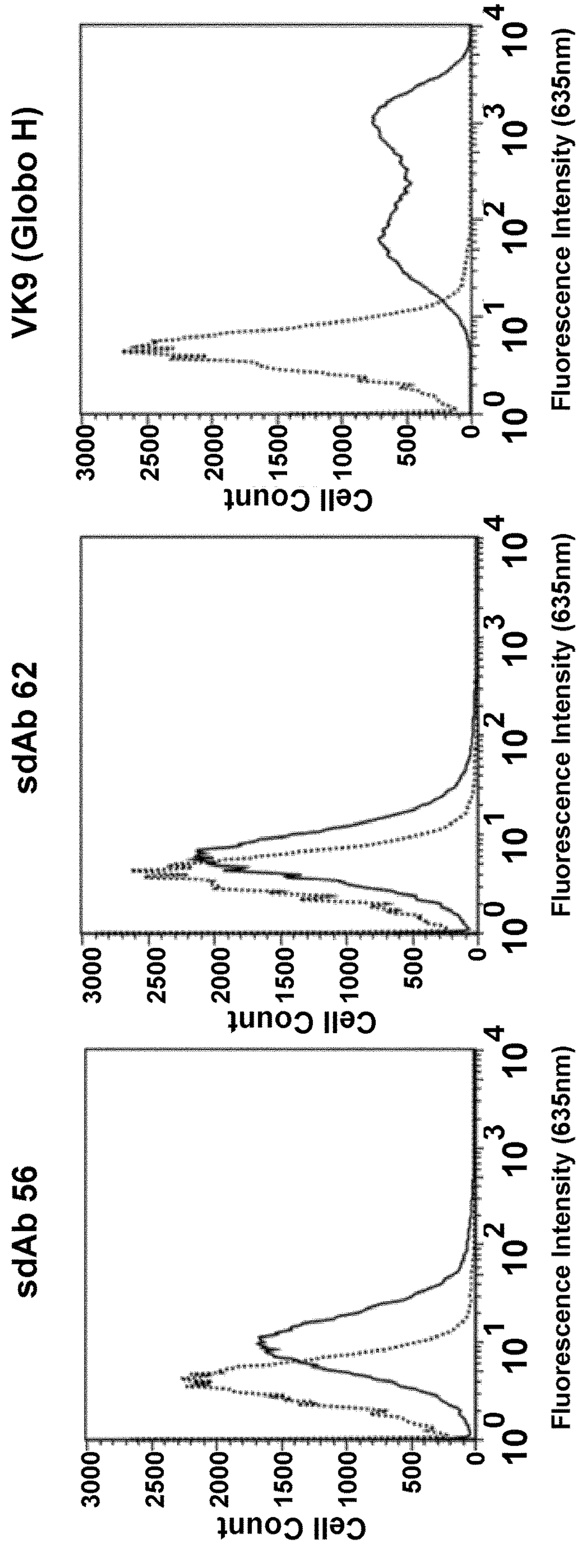

a)

b)

a)

Figure 18 (*continue*)
b)
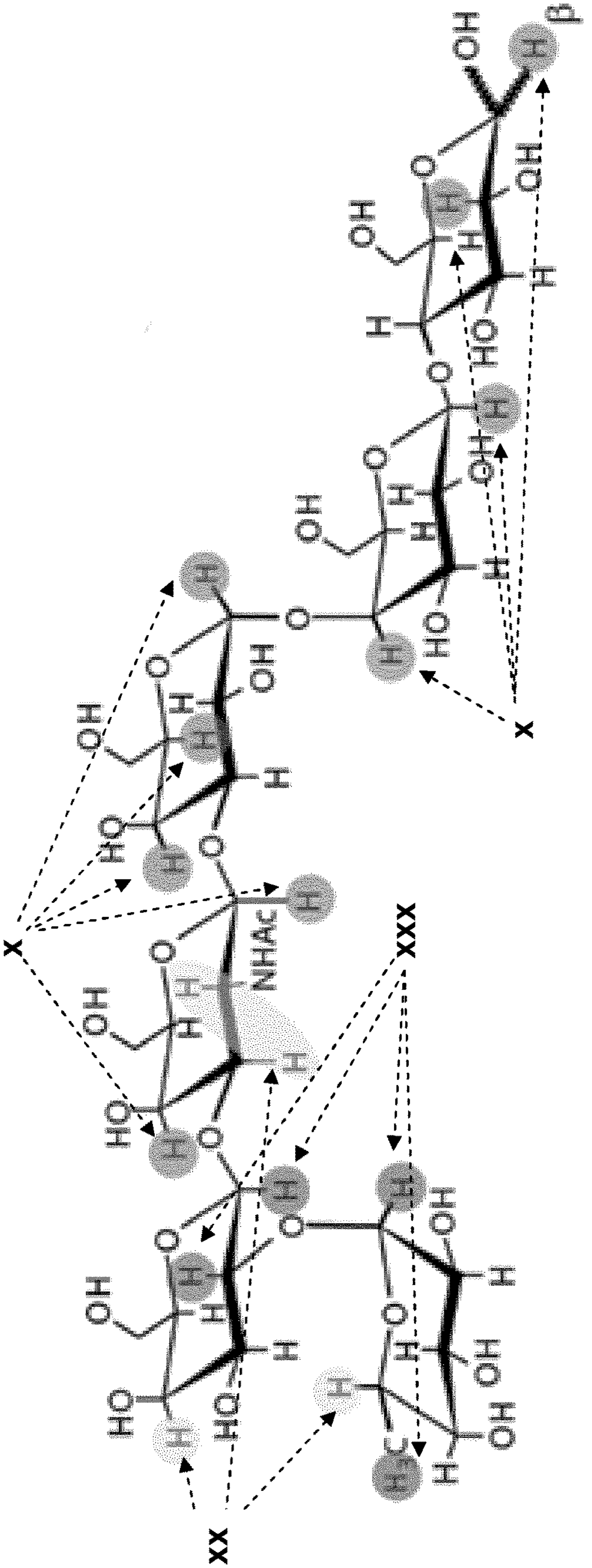

Figure 18 (*continue*)
c)
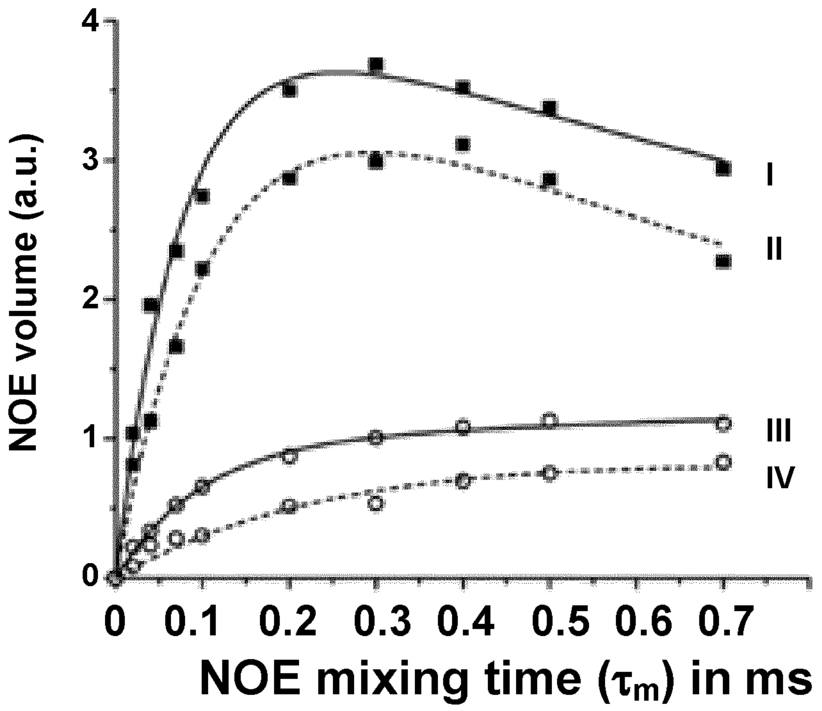

a)

b)

Figure 19 (*continue*)
c)
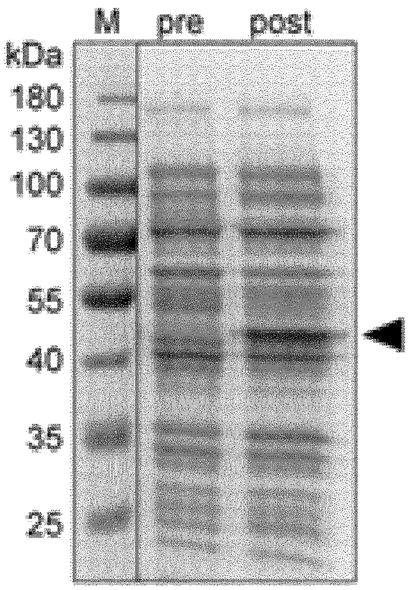
d)
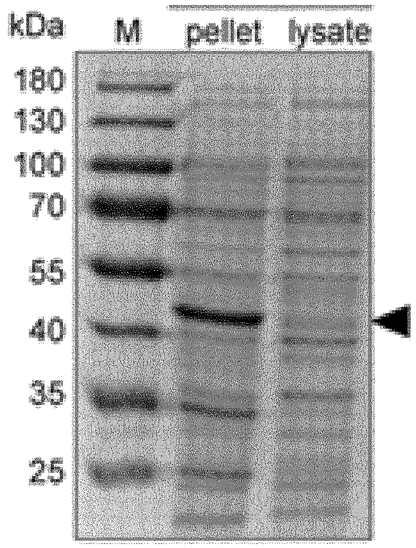
e)
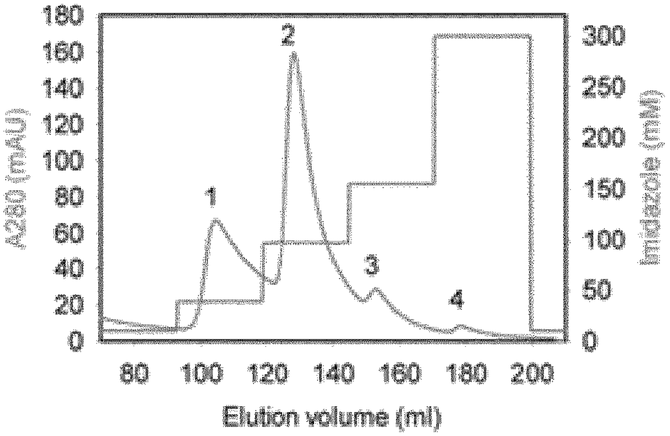
f)
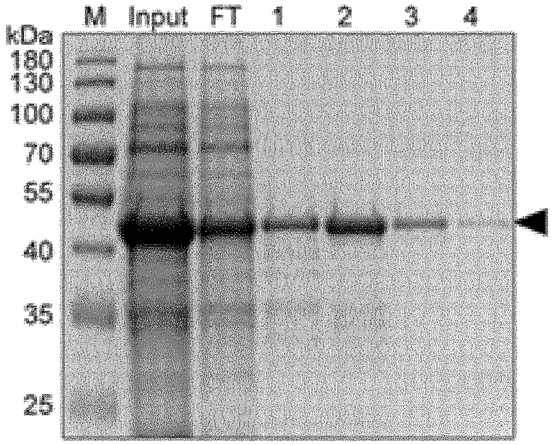

a)

Figure 20 (*continue*)
b)
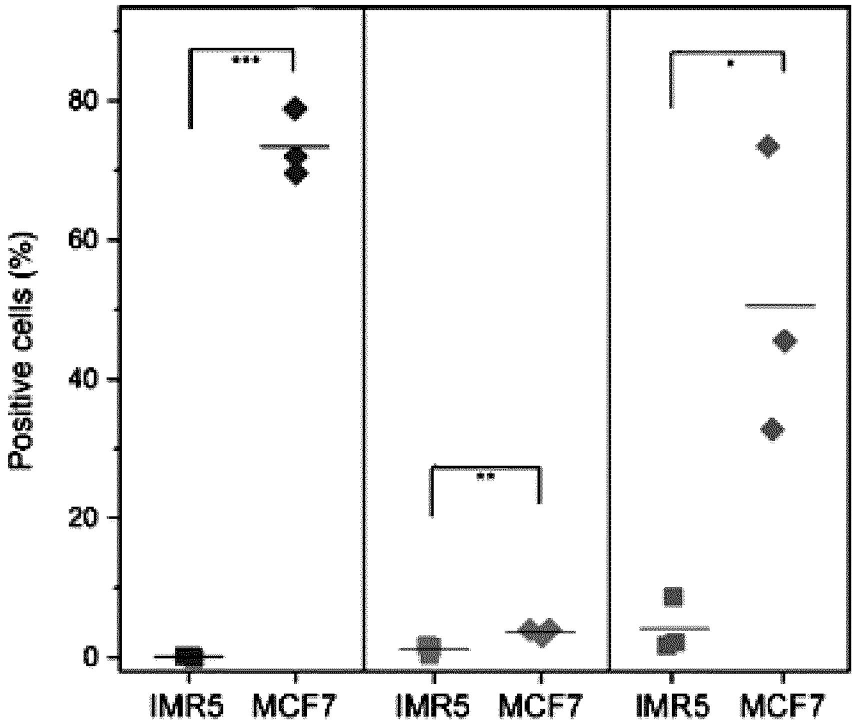

Figure 20 *(continue)*
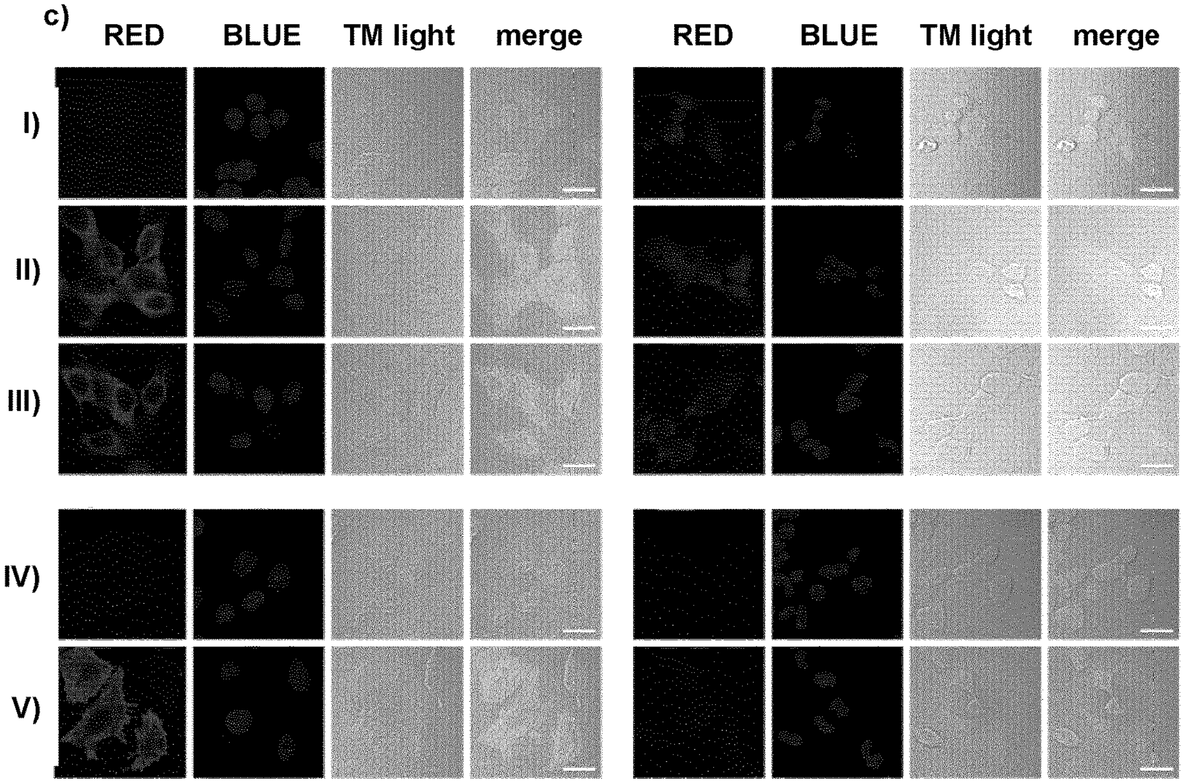

SEQUENCE LISTING

```
<160> NUMBER OF SEQ ID NOS: 228

<210> SEQ ID NO 1
<211> LENGTH: 126
<212> TYPE: PRT
<213> ORGANISM: Vicugna pacos
```

-continued

<400> SEQUENCE: 1

Met Gly Ala His Val Gln Leu Val Glu Ser Gly Gly Gly Leu Val Gln
1               5                   10                  15

Pro Gly Gly Ser Leu Arg Leu Ser Cys Glu Gly Ser Gly Met Thr Phe
            20                  25                  30

Ser Ile Tyr Asp Phe Gly Trp Tyr Arg Gln Val Pro Gly Asn Gln Arg
        35                  40                  45

Glu Leu Val Ala Ser Ile Gly Phe Gly Gly Asn Ile Asp Tyr Ala Asn
    50                  55                  60

Ser Val Lys Gly Arg Phe Thr Ile Ser Arg Asp Gly Asp Lys Asn Met
65                  70                  75                  80

Val Ser Leu Gln Met Asn Thr Leu Arg Pro Glu Asp Thr Ala Ile Tyr
                85                  90                  95

Tyr Cys Val Ala Arg Trp Thr Phe Gly Ile Gln Arg Gly Asp Tyr Tyr
            100                 105                 110

Ile Trp Ser Trp Lys Gln Gly Thr Gln Val Thr Val Ser Ser
        115                 120                 125

<210> SEQ ID NO 2
<211> LENGTH: 379
<212> TYPE: DNA
<213> ORGANISM: Vicugna pacos
<220> FEATURE:
<223> OTHER INFORMATION: nucleic acid

<400> SEQUENCE: 2
atgggagcac acgtccagct tgtagagtca gggggcggct tagtccagcc aggtggaagt 60
ttacgtctta gttgtgaagg gtcggggatg accttctcta tatacgactt cggttggtat 120
cgtcaggtgc cagggaatca gcgcgagtta gttgcaagca ttggctttgg gggcaacatt 180
gattacgcaa actctgttaa aggacgcttc acgatctccc gtgatggtga caaaaacatg 240
gttagtctgc aaatgaatac gctgcgccca gaggatacag caatttatta ttgcgtggct 300
cgttggacgt tcggaataca gagaggagat tactacatat ggtcgtggaa gcaaggtaca 360
caagtaacag taagttccg 379

<210> SEQ ID NO 3
<211> LENGTH: 125
<212> TYPE: PRT
<213> ORGANISM: Vicugna pacos

<400> SEQUENCE: 3

Met Gly Asp Val Gln Leu Gln Glu Ser Gly Gly Gly Leu Ala Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Ala Arg Gln Ala Pro Gly Lys Gly Leu Glu
        35                  40                  45

Trp Val Ser Gly Ile Tyr Arg Asp Gly Ile Asp Thr Tyr Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Thr Ala Leu Tyr
                85                  90                  95

Tyr Cys Ala Lys Asp Leu Leu Ala Gly Trp Gly Pro Leu Ile Ser Trp
            100                 105                 110

His Tyr Trp Gly Lys Gly Thr Gln Val Thr Val Ser Ser
        115                 120                 125

<210> SEQ ID NO 4
<211> LENGTH: 375
<212> TYPE: DNA
<213> ORGANISM: Vicugna pacos

<400> SEQUENCE: 4
atgggagacg ttcaactgca ggaatcgggg ggcggactgg cacagccggg aggctcttta 60
agactgagct gcgccgcctc tggcttcact ttctcctcct atgcgatgag ctgggcacgc 120
caggctccag gaaagggcct ggagtgggta tcgggtatat accgggatgg gatagacact 180
tactacgcgg atagcgtcaa ggggcggttt acgatctctc gtgataatgc caaaaatacc 240
ctgtacctgc aaatgaacag cctgaagcca gaagatacag cgttatatta ttgtgcgaaa 300
gatttactgg cagggtgggg gccattaatc agttggcact actggggtaa ggggacacaa 360
gtaacagtaa gttcc 375

<210> SEQ ID NO 5
<211> LENGTH: 126
<212> TYPE: PRT
<213> ORGANISM: Vicugna pacos

<400> SEQUENCE: 5

Met Gly Asp Val Gln Leu Gln Glu Ser Gly Gly Gly Leu Val His Pro
1               5                   10                  15

Gly Gly Ser Leu Arg Leu Ser Cys Val Ala Ser Gly Phe Thr Phe Asp
            20                  25                  30

Asp Tyr Ala Leu Thr Trp Val Arg Gln Ala Pro Gly Lys Gly Leu Glu
        35                  40                  45

Trp Val Ser Gly Ile Asn Trp Asn Gly Asp Asp Thr Tyr Tyr Thr Gln
    50                  55                  60

Ser Met Lys Gly Arg Phe Thr Ile Ser Arg Asp Asn Ala Lys Asn Thr
65                  70                  75                  80

Leu Tyr Leu Gln Met Asn Ser Leu Lys Ser Glu Asp Thr Ala Val Tyr
                85                  90                  95

Phe Cys Thr Lys Asn Val Gly Gly Asn Trp Val Ser Gly Asp Tyr Gly
            100                 105                 110

Leu Asp Tyr Trp Gly Gln Gly Thr Gln Val Thr Val Ser Ser
        115                 120                 125

<210> SEQ ID NO 6
<211> LENGTH: 378
<212> TYPE: DNA
<213> ORGANISM: Vicugna pacos

<400> SEQUENCE: 6
atgggagatg ttcaactgca agaatctggc ggcggtctgg ttcatccggg cggtagtctg 60
cgtctgtctt gcgttgcgag cggctttacc tttgatgatt atgcgctgac ctgggttcgt 120
caagcaccgg gtaaaggtct ggagtgggta tctggtatca actggaacgg cgacgatacc 180
tactacaccc aaagcatgaa aggccgcttt accatcagtc gcgataacgc gaaaaacacc 240
ctgtacctgc agatgaacag cctgaaaagc gaagacaccg cggtttactt ctgcaccaaa 300
aacgtcggcg gtaattgggt ttctggggat tacggtctgg attattgggg tcagggtacc 360
caagttaccg ttagttct 378

<210> SEQ ID NO 7
<211> LENGTH: 123
<212> TYPE: PRT
<213> ORGANISM: Vicugna pacos

<400> SEQUENCE: 7

```
Met Gly Asp Val Gln Leu Val Glu Ser Gly Gly Gly Leu Val Gln Pro
1               5                   10                  15

Gly Gly Ser Leu Arg Leu Ser Cys Thr Ala Ser Gly Phe Thr Phe Gly
            20                  25                  30

Asn His Trp Met Tyr Trp Val Arg Gln Thr Pro Gly Lys Gly Leu Glu
        35                  40                  45

Trp Val Ala Thr Ala Asn Thr Gly Gly Arg Asp Thr Tyr Tyr Ala Asp
    50                  55                  60

Ser Val Trp Gly Arg Phe Thr Ile Ser Gly Asp Asn Ala Lys Asn Thr
65                  70                  75                  80

Leu Tyr Leu Gln Met Asn Asn Leu Lys Ser Glu Asp Thr Ala Ile Tyr
                85                  90                  95

Tyr Cys Ala Arg Glu Val Asn Asp Tyr Leu Glu Tyr Ala Leu Gly Tyr
            100                 105                 110

Trp Gly Gln Gly Thr Gln Val Thr Val Ser Ser
        115                 120
```

<210> SEQ ID NO 8
<211> LENGTH: 371
<212> TYPE: DNA
<213> ORGANISM: Vicugna pacos

<400> SEQUENCE: 8

```
atgggagatg ttcaactggt tgaatctggc ggcggtctgg ttcaaccggg cggtagtctg      60

cgtctgtctt gtaccgcaag cggttttacc tttggcaacc actggatgta ctgggttcgt     120

caaaccccgg gtaaaggtct ggagtgggtt gcaaccgcaa ataccggcgg tcgcgatacc     180

tattatgcag atagcgtctg ggtcgtttt accatttctg gcgataacgc gaaaaacacc      240

ctgtacctgc agatgaacaa cctgaaaagc gaggacaccg cgatctatta ttgcgcacgc     300

gaagttaacg actacctgga atacgcgctg ggttattggg gtcaaggtac ccaagttacc     360

gttagctctg g                                                          371
```

<210> SEQ ID NO 9
<211> LENGTH: 125
<212> TYPE: PRT
<213> ORGANISM: Vicugna pacos

<400> SEQUENCE: 9

```
Met Gly Asp Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Trp Met His Trp Val Arg Gln Ala Pro Gly Lys Gly Leu Glu
        35                  40                  45

Cys Val Ser Val Ile Asn Thr Gly Asn Gly Ser Pro Tyr Tyr Ala Asp
    50                  55                  60

Ser Val Lys Gly Arg Phe Thr Ile Ser Thr Asp Asn Ala Lys Asn Thr
65                  70                  75                  80

Leu Tyr Leu Gln Met Asn Ser Leu Lys Ser Glu Asp Thr Ala Val Tyr
```

-continued

```
                85                  90                  95

Tyr Cys Ala Arg Asp Ile Pro Asp Pro Ala Gly Arg Ala Gly Gly Met
            100                 105                 110

Asp Tyr Trp Gly Lys Gly Thr Gln Val Thr Val Ser Ser
        115                 120                 125
```

<210> SEQ ID NO 10
<211> LENGTH: 375
<212> TYPE: DNA
<213> ORGANISM: Vicugna pacos

<400> SEQUENCE: 10

```
atgggtgacg ttcaactggt tgaatctggc ggcggtctgg ttcaaccggg cggtagtctg      60

cgtctgagtt gcgcagcatc tggttttacc ttctcctcct actggatgca ttgggttcgt     120

caagcaccgg gtaaaggtct ggagtgcgtc agcgttatta ataccggcaa cggtagtccg     180

tactacgcgg atagcgttaa aggccgtttc accatcagca ccgataacgc gaaaaacacc     240

ctgtacctgc agatgaacag cctgaaaagc gaagataccg cggtttatta ttgcgcacgc     300

gatattccgg atccggcagg tcgcgctggc ggtatggatt attggggtaa aggcacccag     360

gttaccgtta gcagc                                                      375
```

<210> SEQ ID NO 11
<211> LENGTH: 121
<212> TYPE: PRT
<213> ORGANISM: Vicugna pacos

<400> SEQUENCE: 11

```
Met Gly Ala Gln Val Gln Leu Val Glu Ser Gly Gly Gly Leu Val Gln
1               5                   10                  15

Pro Gly Gly Ser Leu Thr Val Ser Cys Ala Ala Ser Gly Phe Thr Phe
            20                  25                  30

Ser Arg Tyr Gly Val Thr Trp His Arg Gln Ala Pro Gly Lys Glu Arg
        35                  40                  45

Glu Leu Val Ala Asp Ile Ile Phe Thr Gly Leu Asn Pro Thr Tyr Ser
    50                  55                  60

Asp Ser Val Lys Gly Arg Phe Thr Ile Ser Arg Asp Asn Asp Lys Asn
65                  70                  75                  80

Val Ala Tyr Leu Gln Met Asn Ser Leu Lys Pro Glu Asp Thr Ala Lys
                85                  90                  95

Tyr Tyr Cys Asn Val Asn Asp Ile Val Val Arg Gly Asn Tyr Trp Gly
            100                 105                 110

Gln Glu Thr Gln Val Thr Val Ser Ser
        115                 120
```

<210> SEQ ID NO 12
<211> LENGTH: 365
<212> TYPE: DNA
<213> ORGANISM: Vicugna pacos

<400> SEQUENCE: 12

```
atgggtgcgc aagttcagct ggttgaatct ggcggtggtc tggttcaacc gggcggtagt      60

ctgaccgtta gttgcgcagc atctggtttt acctttagcc gttacggcgt tacctggcat     120

cgtcaagcac cgggtaaaga acgcgaactg gttgcggata tcatctttac cggcctgaac     180

ccgacctata gcgatagcgt taaaggtcgt ttcaccatca gccgcgataa cgacaaaaac     240

gtcgcctacc tgcagatgaa cagcctgaaa ccggaagata ccgcgaaata ctactgcaac     300
```

gtcaacgata tcgtcgttcg cggcaactat tggggtcaag aaacccaggt taccgtttct 360
agtgg 365

<210> SEQ ID NO 13
<211> LENGTH: 122
<212> TYPE: PRT
<213> ORGANISM: Vicugna pacos

<400> SEQUENCE: 13

Met Gly Ala Asp Val Lys Leu Val Glu Ser Gly Gly Gly Leu Val Gln
1 5 10 15

Pro Gly Gly Ser Leu Arg Leu Ser Cys Ala Val Ser Gly Thr Ile Leu
20 25 30

Gly Leu Asn Met Met Gly Trp Tyr Arg Gln Ala Pro Gly Lys Gln Arg
35 40 45

Glu Leu Val Ala Ser Ile Gly Phe Gly Gly Asn Ile Asp Tyr Ala Asn
50 55 60

Ser Val Lys Gly Arg Phe Thr Ile Ser Arg Asp Gly Asp Lys Asn Met
65 70 75 80

Val Ser Leu Gln Met Asn Thr Leu Arg Pro Glu Asp Thr Ala Ile Tyr
85 90 95

Tyr Cys Val Ala Arg Trp Thr Phe Gly Ile Gln Arg Gly Asp Tyr Trp
100 105 110

Gly Gln Gly Thr Gln Val Thr Val Ser Ser
115 120

<210> SEQ ID NO 14
<211> LENGTH: 368
<212> TYPE: DNA
<213> ORGANISM: Vicugna pacos

<400> SEQUENCE: 14
atgggcgcgg acgttaaact ggttgaatct ggcggtggtc tggttcaacc gggcggtagt 60
ctgcgtctga gttgcgcagt ttctggtacc attctgggcc tgaacatgat gggttggtat 120
cgtcaagcac cgggtaaaca acgcgaactg gttgcgagca ttggctttgg cggtaacatt 180
gattacgcga acagcgtcaa aggccgtttt accattagtc gcgacggcga caaaaacatg 240
gtctctctgc agatgaatac cctgcgtccg gaagataccg cgatttatta ctgcgtcgcg 300
cgttggacct ttggtattca acgcggcgat tattggggtc aaggtaccca ggttaccgtt 360
agcagtgg 368

<210> SEQ ID NO 15
<211> LENGTH: 131
<212> TYPE: PRT
<213> ORGANISM: Vicugna pacos

<400> SEQUENCE: 15

Met Gly Ala Asp Val Gln Leu Val Glu Ser Gly Gly Gly Met Val Gln
1 5 10 15

Pro Gly Gly Ser Leu Arg Leu Ser Cys Ala Ala Ser Gly Phe Ile Phe
20 25 30

Ser Arg His Asp Met His Trp Val Arg Gln Gly Pro Gly Lys Gly Pro
35 40 45

Glu Trp Val Ser Leu Ile Thr Thr Gly Gly Glu Gly Thr Trp Tyr Val
50 55 60

-continued

```
Asp Ser Val Lys Gly Arg Phe Ser Ile Ser Arg Asp Asn Ala Lys Asn
65                  70                  75                  80

Thr Val Tyr Leu Gln Met Asn Ala Leu Lys Pro Glu Asp Thr Ala Val
                85                  90                  95

Tyr Tyr Cys Ala Ala His Arg Ala Glu Ile Pro Arg Glu Ile Cys Tyr
            100                 105                 110

Gly Asp Ser Leu Ser Tyr Asn Tyr Trp Gly Gln Gly Thr Gln Val Thr
        115                 120                 125

Val Ser Ser
    130


<210> SEQ ID NO 16
<211> LENGTH: 393
<212> TYPE: DNA
<213> ORGANISM: Vicugna pacos

<400> SEQUENCE: 16

atgggcgcag acgttcaact ggttgaatct ggcggtggta tggttcaacc gggcggtagt      60

ctgcgtctga gttgcgcagc atctggtttt atcttctccc gccacgatat gcattgggta     120

cgtcaaggtc cgggtaaagg tccggaatgg gttagtctga ttaccaccgg cggcgaaggt     180

acctggtacg ttgatagcgt caaaggtcgt ttcagcatca gccgcgataa cgcgaaaaac     240

accgtctacc tgcagatgaa cgcactgaaa ccggaagata ccgcagttta ctattgcgca     300

gcacatcgcg cagaaattcc gcgcgaaatt tgctacggcg atagcctgag ctacaactat     360

tggggtcagg gtacccaagt taccgtttct agt                                 393


<210> SEQ ID NO 17
<211> LENGTH: 128
<212> TYPE: PRT
<213> ORGANISM: Vicugna pacos

<400> SEQUENCE: 17

Met Gly Ala Gln Val Gln Leu Val Glu Ser Gly Gly Gly Leu Val Gln
1               5                   10                  15

Leu Gly Gly Ser Leu Arg Leu Ser Cys Thr Ala Ser Glu Ile Asp Leu
            20                  25                  30

Gln Tyr Tyr Pro Ile Ala Trp Phe Arg Gln Ala Pro Gly Lys Glu Arg
        35                  40                  45

Glu Gly Val Ser Cys Ile Arg Ala Thr Asp Ser Gly Thr Tyr Tyr Ala
    50                  55                  60

Asp Ser Val Lys Gly Arg Phe Thr Ile Ala Arg Asp Asn Ala Lys Asn
65                  70                  75                  80

Thr Val Tyr Leu Gln Met Asn Asn Leu Ala Pro Glu Asp Thr Ala Val
                85                  90                  95

Tyr Tyr Cys Gly Thr Asp Asp Ser Glu Asp Cys Thr Asp Tyr Ala Pro
            100                 105                 110

Ala His Tyr Gly Tyr Trp Gly Arg Gly Thr Gln Val Thr Val Ser Ser
        115                 120                 125


<210> SEQ ID NO 18
<211> LENGTH: 386
<212> TYPE: DNA
<213> ORGANISM: Vicugna pacos

<400> SEQUENCE: 18

atgggtgcgc aagttcagct ggttgaatct ggcggtggtc tggttcaact gggcggtagt      60
```

-continued

```
ctgcgtctga gttgtaccgc aagcgaaatt gacctgcagt actacccgat tgcttggttt    120

cgtcaagctc cgggtaaaga acgcgaaggc gttagttgta ttcgcgcaac cgatagcggt    180

acctattacg cggatagcgt caaaggtcgt ttcaccattg cgcgcgataa cgcgaaaaac    240

accgtctacc tgcagatgaa caatctggca ccggaagata ccgctgttta ctattgcggt    300

accgacgata gcgaagattg caccgattac gcaccggcac attacggtta ttggggtcgc    360

ggtacccaag ttaccgttag tagtgg                                         386
```

<210> SEQ ID NO 19
<211> LENGTH: 167
<212> TYPE: PRT
<213> ORGANISM: Artificial Sequence
<220> FEATURE:
<223> OTHER INFORMATION: sdAb26 linked to the lytic peptide BMAP28A by a GS_linker
<220> FEATURE:
<221> NAME/KEY: SITE
<222> LOCATION: 128,129
<223> OTHER INFORMATION: Xaa can be any amino acid

<400> SEQUENCE: 19

```
Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
            20                  25                  30

Ile Tyr Asp Phe Gly Trp Tyr Arg Gln Val Pro Gly Asn Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Tyr Ile
            100                 105                 110

Trp Ser Trp Lys Gln Gly Thr Gln Val Thr Val Ser Ser Ala Ala Xaa
        115                 120                 125

Xaa Gly Gly Gly Gly Ser Gly Gly Gly Gly Ser Gly Gly Leu Arg Ser
    130                 135                 140

Leu Gly Arg Lys Ile Leu Arg Ala Trp Lys Lys Tyr Gly Pro Ile Ile
145                 150                 155                 160

Val Pro Ile Ile Arg Ile Gly
                165
```

<210> SEQ ID NO 20
<211> LENGTH: 172
<212> TYPE: PRT
<213> ORGANISM: Artificial Sequence
<220> FEATURE:
<223> OTHER INFORMATION: sdAb26 linked to the lytic peptide BMAP28A by a GSAA_linker
<220> FEATURE:
<221> NAME/KEY: SITE
<222> LOCATION: 128,129
<223> OTHER INFORMATION: Xaa can be any amino acid

<400> SEQUENCE: 20

```
Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
```

20 25 30

Ile Tyr Asp Phe Gly Trp Tyr Arg Gln Val Pro Gly Asn Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val
65 70 75 80

Ser Leu Gln Met Asn Thr Leu Arg Pro Glu Asp Thr Ala Ile Tyr Tyr
85 90 95

Cys Val Ala Arg Trp Thr Phe Gly Ile Gln Arg Gly Asp Tyr Tyr Ile
100 105 110

Trp Ser Trp Lys Gln Gly Thr Gln Val Thr Val Ser Ser Ala Ala Xaa
115 120 125

Xaa Gly Gly Gly Gly Ser Glu Ala Ala Ala Lys Gly Gly Gly Gly Ser
130 135 140

Gly Gly Leu Arg Ser Leu Gly Arg Lys Ile Leu Arg Ala Trp Lys Lys
145 150 155 160

Tyr Gly Pro Ile Ile Val Pro Ile Ile Arg Ile Gly
165 170

<210> SEQ ID NO 21
<211> LENGTH: 150
<212> TYPE: PRT
<213> ORGANISM: Artificial Sequence
<220> FEATURE:
<223> OTHER INFORMATION: sdAb26 linked to the lytic peptide modified cysteine deleted Tachyplesin-I by a GS_linker
<220> FEATURE:
<221> NAME/KEY: SITE
<222> LOCATION: 128,129
<223> OTHER INFORMATION: Xaa can be any amino acid

<400> SEQUENCE: 21

Gly Ala His Val Gln Leu Val Glu Ser Gly Gly Gly Leu Val Gln Pro
1 5 10 15

Gly Gly Ser Leu Arg Leu Ser Cys Glu Gly Ser Gly Met Thr Phe Ser
20 25 30

Ile Tyr Asp Phe Gly Trp Tyr Arg Gln Val Pro Gly Asn Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val
65 70 75 80

Ser Leu Gln Met Asn Thr Leu Arg Pro Glu Asp Thr Ala Ile Tyr Tyr
85 90 95

Cys Val Ala Arg Trp Thr Phe Gly Ile Gln Arg Gly Asp Tyr Tyr Ile
100 105 110

Trp Ser Trp Lys Gln Gly Thr Gln Val Thr Val Ser Ser Ala Ala Xaa
115 120 125

Xaa Gly Gly Gly Gly Ser Gly Gly Gly Gly Ser Lys Trp Phe Arg Val
130 135 140

Tyr Arg Gly Ile Tyr Arg
145 150

<210> SEQ ID NO 22
<211> LENGTH: 155
<212> TYPE: PRT
<213> ORGANISM: Artificial Sequence

```
<220> FEATURE:
<223> OTHER INFORMATION: sdAb26 linked to the lytic peptide modified
      cysteine deleted Tachyplesin-I by a GSAA_linker
<220> FEATURE:
<221> NAME/KEY: SITE
<222> LOCATION: 128,129
<223> OTHER INFORMATION: Xaa can be any amino acid

<400> SEQUENCE: 22

Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
            20                  25                  30

Ile Tyr Asp Phe Gly Trp Tyr Arg Gln Val Pro Gly Asn Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Tyr Ile
            100                 105                 110

Trp Ser Trp Lys Gln Gly Thr Gln Val Thr Val Ser Ser Ala Ala Xaa
        115                 120                 125

Xaa Gly Gly Gly Gly Ser Glu Ala Ala Ala Lys Gly Gly Gly Gly Ser
    130                 135                 140

Lys Trp Phe Arg Val Tyr Arg Gly Ile Tyr Arg
145                 150                 155


<210> SEQ ID NO 23
<211> LENGTH: 158
<212> TYPE: PRT
<213> ORGANISM: Artificial Sequence
<220> FEATURE:
<223> OTHER INFORMATION: sdAb26 linked to the lytic peptide Polybia-MP1
<220> FEATURE:
<221> NAME/KEY: SITE
<222> LOCATION: 128,129
<223> OTHER INFORMATION: Xaa can be any amino acid

<400> SEQUENCE: 23

Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
            20                  25                  30

Ile Tyr Asp Phe Gly Trp Tyr Arg Gln Val Pro Gly Asn Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Tyr Ile
            100                 105                 110

Trp Ser Trp Lys Gln Gly Thr Gln Val Thr Val Ser Ser Ala Ala Xaa
        115                 120                 125

Xaa Gly Gly Gly Gly Ser Glu Ala Ala Ala Lys Gly Gly Gly Gly Ser
```

```
    130                 135                 140

Ile Asp Trp Lys Lys Leu Leu Asp Ala Ala Lys Gln Ile Leu
145                 150                 155
```

<210> SEQ ID NO 24
<211> LENGTH: 166
<212> TYPE: PRT
<213> ORGANISM: Artificial Sequence
<220> FEATURE:
<223> OTHER INFORMATION: sdAb37 linked to the lytic peptide BMAP28A by a GS_linker
<220> FEATURE:
<221> NAME/KEY: SITE
<222> LOCATION: 127,128
<223> OTHER INFORMATION: Xaa can be any amino acid

<400> SEQUENCE: 24

```
Gly Asp Val Gln Leu Gln Glu Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Gly Lys Gly Leu Glu Trp
        35                  40                  45

Val Ser Gly Ile Tyr Arg Asp Gly Ile Asp Thr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Asp Leu Leu Ala Gly Trp Gly Pro Leu Ile Ser Trp His
            100                 105                 110

Tyr Trp Gly Lys Gly Thr Gln Val Thr Val Ser Ser Ala Ala Xaa Xaa
        115                 120                 125

Gly Gly Gly Gly Ser Gly Gly Gly Gly Ser Gly Gly Leu Arg Ser Leu
    130                 135                 140

Gly Arg Lys Ile Leu Arg Ala Trp Lys Lys Tyr Gly Pro Ile Ile Val
145                 150                 155                 160

Pro Ile Ile Arg Ile Gly
                165
```

<210> SEQ ID NO 25
<211> LENGTH: 171
<212> TYPE: PRT
<213> ORGANISM: Artificial Sequence
<220> FEATURE:
<223> OTHER INFORMATION: sdAb37 linked to the lytic peptide BMAP28A by a GSAA_linker
<220> FEATURE:
<221> NAME/KEY: SITE
<222> LOCATION: 127,128
<223> OTHER INFORMATION: Xaa can be any amino acid

<400> SEQUENCE: 25

```
Gly Asp Val Gln Leu Gln Glu Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Gly Lys Gly Leu Glu Trp
        35                  40                  45

Val Ser Gly Ile Tyr Arg Asp Gly Ile Asp Thr Tyr Tyr Ala Asp Ser
    50                  55                  60
```

Val Lys Gly Arg Phe Thr Ile Ser Arg Asp Asn Ala Lys Asn Thr Leu
65 70 75 80

Tyr Leu Gln Met Asn Ser Leu Lys Pro Glu Asp Thr Ala Leu Tyr Tyr
85 90 95

Cys Ala Lys Asp Leu Leu Ala Gly Trp Gly Pro Leu Ile Ser Trp His
100 105 110

Tyr Trp Gly Lys Gly Thr Gln Val Thr Val Ser Ser Ala Ala Xaa Xaa
115 120 125

Gly Gly Gly Gly Ser Glu Ala Ala Ala Lys Gly Gly Gly Gly Ser Gly
130 135 140

Gly Leu Arg Ser Leu Gly Arg Lys Ile Leu Arg Ala Trp Lys Lys Tyr
145 150 155 160

Gly Pro Ile Ile Val Pro Ile Ile Arg Ile Gly
165 170

<210> SEQ ID NO 26
<211> LENGTH: 149
<212> TYPE: PRT
<213> ORGANISM: Artificial Sequence
<220> FEATURE:
<223> OTHER INFORMATION: sdAb37 linked to the lytic peptide modified cysteine deleted Tachyplesin-I by a GS_linker
<220> FEATURE:
<221> NAME/KEY: SITE
<222> LOCATION: 127,128
<223> OTHER INFORMATION: Xaa can be any amino acid

<400> SEQUENCE: 26

Gly Asp Val Gln Leu Gln Glu Ser Gly Gly Gly Leu Ala Gln Pro Gly
1 5 10 15

Gly Ser Leu Arg Leu Ser Cys Ala Ala Ser Gly Phe Thr Phe Ser Ser
20 25 30

Tyr Ala Met Ser Trp Ala Arg Gln Ala Pro Gly Lys Gly Leu Glu Trp
35 40 45

Val Ser Gly Ile Tyr Arg Asp Gly Ile Asp Thr Tyr Tyr Ala Asp Ser
50 55 60

Val Lys Gly Arg Phe Thr Ile Ser Arg Asp Asn Ala Lys Asn Thr Leu
65 70 75 80

Tyr Leu Gln Met Asn Ser Leu Lys Pro Glu Asp Thr Ala Leu Tyr Tyr
85 90 95

Cys Ala Lys Asp Leu Leu Ala Gly Trp Gly Pro Leu Ile Ser Trp His
100 105 110

Tyr Trp Gly Lys Gly Thr Gln Val Thr Val Ser Ser Ala Ala Xaa Xaa
115 120 125

Gly Gly Gly Gly Ser Gly Gly Gly Gly Ser Lys Trp Phe Arg Val Tyr
130 135 140

Arg Gly Ile Tyr Arg
145

<210> SEQ ID NO 27
<211> LENGTH: 154
<212> TYPE: PRT
<213> ORGANISM: Artificial Sequence
<220> FEATURE:
<223> OTHER INFORMATION: sdAb37 linked to the lytic peptide modified cysteine deleted Tachyplesin-I by a GSAA_linker
<220> FEATURE:
<221> NAME/KEY: SITE
<222> LOCATION: 127,128
<223> OTHER INFORMATION: Xaa can be any amino acid

<400> SEQUENCE: 27

Gly Asp Val Gln Leu Gln Glu Ser Gly Gly Gly Leu Ala Gln Pro Gly
1 5 10 15

Gly Ser Leu Arg Leu Ser Cys Ala Ala Ser Gly Phe Thr Phe Ser Ser
20 25 30

Tyr Ala Met Ser Trp Ala Arg Gln Ala Pro Gly Lys Gly Leu Glu Trp
35 40 45

Val Ser Gly Ile Tyr Arg Asp Gly Ile Asp Thr Tyr Tyr Ala Asp Ser
50 55 60

Val Lys Gly Arg Phe Thr Ile Ser Arg Asp Asn Ala Lys Asn Thr Leu
65 70 75 80

Tyr Leu Gln Met Asn Ser Leu Lys Pro Glu Asp Thr Ala Leu Tyr Tyr
85 90 95

Cys Ala Lys Asp Leu Leu Ala Gly Trp Gly Pro Leu Ile Ser Trp His
100 105 110

Tyr Trp Gly Lys Gly Thr Gln Val Thr Val Ser Ser Ala Ala Xaa Xaa
115 120 125

Gly Gly Gly Gly Ser Glu Ala Ala Ala Lys Gly Gly Gly Gly Ser Lys
130 135 140

Trp Phe Arg Val Tyr Arg Gly Ile Tyr Arg
145 150

<210> SEQ ID NO 28
<211> LENGTH: 157
<212> TYPE: PRT
<213> ORGANISM: Artificial Sequence
<220> FEATURE:
<223> OTHER INFORMATION: sdAb37 linked to the lytic peptide Polybia-MP1 by a GSAA_linker
<220> FEATURE:
<221> NAME/KEY: SITE
<222> LOCATION: 127,128
<223> OTHER INFORMATION: Xaa can be any amino acid

<400> SEQUENCE: 28

Gly Asp Val Gln Leu Gln Glu Ser Gly Gly Gly Leu Ala Gln Pro Gly
1 5 10 15

Gly Ser Leu Arg Leu Ser Cys Ala Ala Ser Gly Phe Thr Phe Ser Ser
20 25 30

Tyr Ala Met Ser Trp Ala Arg Gln Ala Pro Gly Lys Gly Leu Glu Trp
35 40 45

Val Ser Gly Ile Tyr Arg Asp Gly Ile Asp Thr Tyr Tyr Ala Asp Ser
50 55 60

Val Lys Gly Arg Phe Thr Ile Ser Arg Asp Asn Ala Lys Asn Thr Leu
65 70 75 80

Tyr Leu Gln Met Asn Ser Leu Lys Pro Glu Asp Thr Ala Leu Tyr Tyr
85 90 95

Cys Ala Lys Asp Leu Leu Ala Gly Trp Gly Pro Leu Ile Ser Trp His
100 105 110

Tyr Trp Gly Lys Gly Thr Gln Val Thr Val Ser Ser Ala Ala Xaa Xaa
115 120 125

Gly Gly Gly Gly Ser Glu Ala Ala Ala Lys Gly Gly Gly Gly Ser Ile
130 135 140

Asp Trp Lys Lys Leu Leu Asp Ala Ala Lys Gln Ile Leu
145 150 155

<210> SEQ ID NO 29
<211> LENGTH: 167
<212> TYPE: PRT
<213> ORGANISM: Artificial Sequence
<220> FEATURE:
<223> OTHER INFORMATION: sdAb46 linked to the lytic peptide BMAP28A by a GS_linker
<220> FEATURE:
<221> NAME/KEY: SITE
<222> LOCATION: 128,129
<223> OTHER INFORMATION: Xaa can be any amino acid

<400> SEQUENCE: 29

```
Gly Asp Val Gln Leu Gln Glu Ser Gly Gly Gly Leu Val His Pro Gly
1               5                   10                  15

Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Gly Gly Gly Gly Ser Gly Gly Gly Gly Ser Gly Gly Leu Arg Ser
    130                 135                 140

Leu Gly Arg Lys Ile Leu Arg Ala Trp Lys Lys Tyr Gly Pro Ile Ile
145                 150                 155                 160

Val Pro Ile Ile Arg Ile Gly
                165
```

<210> SEQ ID NO 30
<211> LENGTH: 172
<212> TYPE: PRT
<213> ORGANISM: Artificial Sequence
<220> FEATURE:
<223> OTHER INFORMATION: sdAb46 linked to the lytic peptide BMAP28A by a GSAA_linker
<220> FEATURE:
<221> NAME/KEY: SITE
<222> LOCATION: 128,129
<223> OTHER INFORMATION: Xaa can be any amino acid

<400> SEQUENCE: 30

```
Gly Asp Val Gln Leu Gln Glu Ser Gly Gly Gly Leu Val His Pro Gly
1               5                   10                  15

Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95
```

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Gly Gly Gly Gly Ser Glu Ala Ala Ala Lys Gly Gly Gly Gly Ser
    130                 135                 140

Gly Gly Leu Arg Ser Leu Gly Arg Lys Ile Leu Arg Ala Trp Lys Lys
145                 150                 155                 160

Tyr Gly Pro Ile Ile Val Pro Ile Ile Arg Ile Gly
            165                 170

<210> SEQ ID NO 31
<211> LENGTH: 150
<212> TYPE: PRT
<213> ORGANISM: Artificial Sequence
<220> FEATURE:
<223> OTHER INFORMATION: sdAb46 linked to the lytic peptide modified
      cysteine deleted Tachyplesin-I by a GS_linker
<220> FEATURE:
<221> NAME/KEY: SITE
<222> LOCATION: 128,129
<223> OTHER INFORMATION: Xaa can be any amino acid

<400> SEQUENCE: 31

Gly Asp Val Gln Leu Gln Glu Ser Gly Gly Gly Leu Val His Pro Gly
1               5                   10                  15

Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Gly Gly Gly Gly Ser Gly Gly Gly Gly Ser Lys Trp Phe Arg Val
    130                 135                 140

Tyr Arg Gly Ile Tyr Arg
145                 150

<210> SEQ ID NO 32
<211> LENGTH: 155
<212> TYPE: PRT
<213> ORGANISM: Artificial Sequence
<220> FEATURE:
<223> OTHER INFORMATION: sdAb46 linked to the lytic peptide modified
      cysteine deleted Tachyplesin-I by a GSAA_linker
<220> FEATURE:
<221> NAME/KEY: SITE
<222> LOCATION: 128,129
<223> OTHER INFORMATION: Xaa can be any amino acid

<400> SEQUENCE: 32

Gly Asp Val Gln Leu Gln Glu Ser Gly Gly Gly Leu Val His Pro Gly
1               5                   10                  15

```
Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Gly Gly Gly Gly Ser Glu Ala Ala Ala Lys Gly Gly Gly Gly Ser
    130                 135                 140

Lys Trp Phe Arg Val Tyr Arg Gly Ile Tyr Arg
145                 150                 155
```

```
<210> SEQ ID NO 33
<211> LENGTH: 158
<212> TYPE: PRT
<213> ORGANISM: Artificial Sequence
<220> FEATURE:
<223> OTHER INFORMATION: sdAb46 linked to the lytic peptide Polybia-MP1
      by a GSAA_linker
<220> FEATURE:
<221> NAME/KEY: SITE
<222> LOCATION: 128,129
<223> OTHER INFORMATION: Xaa can be any amino acid

<400> SEQUENCE: 33

Gly Asp Val Gln Leu Gln Glu Ser Gly Gly Gly Leu Val His Pro Gly
1               5                   10                  15

Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Gly Gly Gly Gly Ser Glu Ala Ala Ala Lys Gly Gly Gly Gly Ser
    130                 135                 140

Ile Asp Trp Lys Lys Leu Leu Asp Ala Ala Lys Gln Ile Leu
145                 150                 155
```

```
<210> SEQ ID NO 34
<211> LENGTH: 164
<212> TYPE: PRT
<213> ORGANISM: Artificial Sequence
<220> FEATURE:
<223> OTHER INFORMATION: sdAb47 linked to the lytic peptide BMAP28A by a
```

```
      GS_linker
<220> FEATURE:
<221> NAME/KEY: SITE
<222> LOCATION: 125,126
<223> OTHER INFORMATION: Xaa can be any amino acid

<400> SEQUENCE: 34

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Gly Gly
        115                 120                 125

Gly Gly Ser Gly Gly Gly Gly Ser Gly Gly Leu Arg Ser Leu Gly Arg
    130                 135                 140

Lys Ile Leu Arg Ala Trp Lys Lys Tyr Gly Pro Ile Ile Val Pro Ile
145                 150                 155                 160

Ile Arg Ile Gly


<210> SEQ ID NO 35
<211> LENGTH: 169
<212> TYPE: PRT
<213> ORGANISM: Artificial Sequence
<220> FEATURE:
<223> OTHER INFORMATION: sdAb47 linked to the lytic peptide BMAP28A by a
      GSAA_linker
<220> FEATURE:
<221> NAME/KEY: SITE
<222> LOCATION: 125,126
<223> OTHER INFORMATION: Xaa can be any amino acid

<400> SEQUENCE: 35

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Gly Gly
        115                 120                 125
```

Gly Gly Ser Glu Ala Ala Ala Lys Gly Gly Gly Gly Ser Gly Gly Leu
    130                 135                 140

Arg Ser Leu Gly Arg Lys Ile Leu Arg Ala Trp Lys Lys Tyr Gly Pro
145                 150                 155                 160

Ile Ile Val Pro Ile Ile Arg Ile Gly
                165

<210> SEQ ID NO 36
<211> LENGTH: 147
<212> TYPE: PRT
<213> ORGANISM: Artificial Sequence
<220> FEATURE:
<223> OTHER INFORMATION: sdAb47 linked to the lytic peptide modified
      cysteine deleted Tachyplesin-I by a GS_linker
<220> FEATURE:
<221> NAME/KEY: SITE
<222> LOCATION: 125,126
<223> OTHER INFORMATION: Xaa can be any amino acid

<400> SEQUENCE: 36

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Gly Gly
        115                 120                 125

Gly Gly Ser Gly Gly Gly Gly Ser Lys Trp Phe Arg Val Tyr Arg Gly
    130                 135                 140

Ile Tyr Arg
145

<210> SEQ ID NO 37
<211> LENGTH: 152
<212> TYPE: PRT
<213> ORGANISM: Artificial Sequence
<220> FEATURE:
<223> OTHER INFORMATION: sdAb47 linked to the lytic peptide modified
      cysteine deleted Tachyplesin-I by a GSAA_linker
<220> FEATURE:
<221> NAME/KEY: SITE
<222> LOCATION: 125,126
<223> OTHER INFORMATION: Xaa can be any amino acid

<400> SEQUENCE: 37

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser

```
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Gly Gly
        115                 120                 125

Gly Gly Ser Glu Ala Ala Ala Lys Gly Gly Gly Gly Ser Lys Trp Phe
    130                 135                 140

Arg Val Tyr Arg Gly Ile Tyr Arg
145                 150


<210> SEQ ID NO 38
<211> LENGTH: 155
<212> TYPE: PRT
<213> ORGANISM: Artificial Sequence
<220> FEATURE:
<223> OTHER INFORMATION: sdAb47 linked to the lytic peptide Polybia-MP1
      by a GSAA_linker
<220> FEATURE:
<221> NAME/KEY: SITE
<222> LOCATION: 125,126
<223> OTHER INFORMATION: Xaa can be any amino acid

<400> SEQUENCE: 38

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Gly Gly
        115                 120                 125

Gly Gly Ser Glu Ala Ala Ala Lys Gly Gly Gly Gly Ser Ile Asp Trp
    130                 135                 140

Lys Lys Leu Leu Asp Ala Ala Lys Gln Ile Leu
145                 150                 155


<210> SEQ ID NO 39
<211> LENGTH: 166
<212> TYPE: PRT
<213> ORGANISM: Artificial Sequence
<220> FEATURE:
<223> OTHER INFORMATION: sdAb56 linked to the lytic peptide BMAP28A by a
      GS_linker
<220> FEATURE:
<221> NAME/KEY: SITE
<222> LOCATION: 127,128
<223> OTHER INFORMATION: Xaa can be any amino acid

<400> SEQUENCE: 39
```

```
Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Gly Gly Gly Gly Ser Gly Gly Gly Gly Ser Gly Gly Leu Arg Ser Leu
    130                 135                 140

Gly Arg Lys Ile Leu Arg Ala Trp Lys Lys Tyr Gly Pro Ile Ile Val
145                 150                 155                 160

Pro Ile Ile Arg Ile Gly
                165


<210> SEQ ID NO 40
<211> LENGTH: 171
<212> TYPE: PRT
<213> ORGANISM: Artificial Sequence
<220> FEATURE:
<223> OTHER INFORMATION: sdAb56 linked to the lytic peptide BMAP28A by a
      GSAA_linker
<220> FEATURE:
<221> NAME/KEY: SITE
<222> LOCATION: 127,128
<223> OTHER INFORMATION: Xaa can be any amino acid

<400> SEQUENCE: 40

Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Gly Gly Gly Gly Ser Glu Ala Ala Ala Lys Gly Gly Gly Gly Ser Gly
    130                 135                 140

Gly Leu Arg Ser Leu Gly Arg Lys Ile Leu Arg Ala Trp Lys Lys Tyr
145                 150                 155                 160
```

Gly Pro Ile Ile Val Pro Ile Ile Arg Ile Gly
165 170

<210> SEQ ID NO 41
<211> LENGTH: 149
<212> TYPE: PRT
<213> ORGANISM: Artificial Sequence
<220> FEATURE:
<223> OTHER INFORMATION: sdAb56 linked to the lytic peptide modified cysteine deleted Tachyplesin-I by a GS_linker
<220> FEATURE:
<221> NAME/KEY: SITE
<222> LOCATION: 127,128
<223> OTHER INFORMATION: Xaa can be any amino acid

<400> SEQUENCE: 41

Gly Asp Val Gln Leu Val Glu Ser Gly Gly Gly Leu Val Gln Pro Gly
1 5 10 15

Gly Ser Leu Arg Leu Ser Cys Ala Ala Ser Gly Phe Thr Phe Ser Ser
20 25 30

Tyr Trp Met His Trp Val Arg Gln Ala Pro Gly Lys Gly Leu Glu Cys
35 40 45

Val Ser Val Ile Asn Thr Gly Asn Gly Ser Pro Tyr Tyr Ala Asp Ser
50 55 60

Val Lys Gly Arg Phe Thr Ile Ser Thr Asp Asn Ala Lys Asn Thr Leu
65 70 75 80

Tyr Leu Gln Met Asn Ser Leu Lys Ser Glu Asp Thr Ala Val Tyr Tyr
85 90 95

Cys Ala Arg Asp Ile Pro Asp Pro Ala Gly Arg Ala Gly Gly Met Asp
100 105 110

Tyr Trp Gly Lys Gly Thr Gln Val Thr Val Ser Ser Ala Ala Xaa Xaa
115 120 125

Gly Gly Gly Gly Ser Gly Gly Gly Gly Ser Lys Trp Phe Arg Val Tyr
130 135 140

Arg Gly Ile Tyr Arg
145

<210> SEQ ID NO 42
<211> LENGTH: 154
<212> TYPE: PRT
<213> ORGANISM: Artificial Sequence
<220> FEATURE:
<223> OTHER INFORMATION: sdAb56 linked to the lytic peptide modified cysteine deleted Tachyplesin-I by a GSAA_linker
<220> FEATURE:
<221> NAME/KEY: SITE
<222> LOCATION: 127,128
<223> OTHER INFORMATION: Xaa can be any amino acid

<400> SEQUENCE: 42

Gly Asp Val Gln Leu Val Glu Ser Gly Gly Gly Leu Val Gln Pro Gly
1 5 10 15

Gly Ser Leu Arg Leu Ser Cys Ala Ala Ser Gly Phe Thr Phe Ser Ser
20 25 30

Tyr Trp Met His Trp Val Arg Gln Ala Pro Gly Lys Gly Leu Glu Cys
35 40 45

Val Ser Val Ile Asn Thr Gly Asn Gly Ser Pro Tyr Tyr Ala Asp Ser
50 55 60

Val Lys Gly Arg Phe Thr Ile Ser Thr Asp Asn Ala Lys Asn Thr Leu
65 70 75 80

Tyr Leu Gln Met Asn Ser Leu Lys Ser Glu Asp Thr Ala Val Tyr Tyr

```
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Gly Gly Gly Gly Ser Glu Ala Ala Ala Lys Gly Gly Gly Gly Ser Lys
    130                 135                 140

Trp Phe Arg Val Tyr Arg Gly Ile Tyr Arg
145                 150


<210> SEQ ID NO 43
<211> LENGTH: 157
<212> TYPE: PRT
<213> ORGANISM: Artificial Sequence
<220> FEATURE:
<223> OTHER INFORMATION: sdAb56 linked to the lytic peptide Polybia-MP1
      by a GSAA_linker
<220> FEATURE:
<221> NAME/KEY: SITE
<222> LOCATION: 127,128
<223> OTHER INFORMATION: Xaa can be any amino acid

<400> SEQUENCE: 43

Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Gly Gly Gly Gly Ser Glu Ala Ala Ala Lys Gly Gly Gly Gly Ser Ile
    130                 135                 140

Asp Trp Lys Lys Leu Leu Asp Ala Ala Lys Gln Ile Leu
145                 150                 155


<210> SEQ ID NO 44
<211> LENGTH: 162
<212> TYPE: PRT
<213> ORGANISM: Artificial Sequence
<220> FEATURE:
<223> OTHER INFORMATION: sdAb59 linked to the lytic peptide BMAP28A by a
      GS_linker
<220> FEATURE:
<221> NAME/KEY: SITE
<222> LOCATION: 123,124
<223> OTHER INFORMATION: Xaa can be any amino acid

<400> SEQUENCE: 44

Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
            20                  25                  30
```

```
Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Gly Gly Gly Gly
        115                 120                 125

Ser Gly Gly Gly Gly Ser Gly Gly Leu Arg Ser Leu Gly Arg Lys Ile
    130                 135                 140

Leu Arg Ala Trp Lys Lys Tyr Gly Pro Ile Ile Val Pro Ile Ile Arg
145                 150                 155                 160

Ile Gly


<210> SEQ ID NO 45
<211> LENGTH: 167
<212> TYPE: PRT
<213> ORGANISM: Artificial Sequence
<220> FEATURE:
<223> OTHER INFORMATION: sdAb59 linked to the lytic peptide BMAP28A by a
      GSAA_linker
<220> FEATURE:
<221> NAME/KEY: SITE
<222> LOCATION: 123,124
<223> OTHER INFORMATION: Xaa can be any amino acid

<400> SEQUENCE: 45

Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
            20                  25                  30

Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Gly Gly Gly Gly
        115                 120                 125

Ser Glu Ala Ala Ala Lys Gly Gly Gly Gly Ser Gly Gly Leu Arg Ser
    130                 135                 140

Leu Gly Arg Lys Ile Leu Arg Ala Trp Lys Lys Tyr Gly Pro Ile Ile
145                 150                 155                 160

Val Pro Ile Ile Arg Ile Gly
                165


<210> SEQ ID NO 46
<211> LENGTH: 145
<212> TYPE: PRT
```

<213> ORGANISM: Artificial Sequence
<220> FEATURE:
<223> OTHER INFORMATION: sdAb59 linked to the lytic peptide modified cysteine deleted Tachyplesin-I by a GS_linker
<220> FEATURE:
<221> NAME/KEY: SITE
<222> LOCATION: 123,124
<223> OTHER INFORMATION: Xaa can be any amino acid

<400> SEQUENCE: 46

Gly Ala Gln Val Gln Leu Val Glu Ser Gly Gly Gly Leu Val Gln Pro
1 5 10 15

Gly Gly Ser Leu Thr Val Ser Cys Ala Ala Ser Gly Phe Thr Phe Ser
20 25 30

Arg Tyr Gly Val Thr Trp His Arg Gln Ala Pro Gly Lys Glu Arg Glu
35 40 45

Leu Val Ala Asp Ile Ile Phe Thr Gly Leu Asn Pro Thr Tyr Ser Asp
50 55 60

Ser Val Lys Gly Arg Phe Thr Ile Ser Arg Asp Asn Asp Lys Asn Val
65 70 75 80

Ala Tyr Leu Gln Met Asn Ser Leu Lys Pro Glu Asp Thr Ala Lys Tyr
85 90 95

Tyr Cys Asn Val Asn Asp Ile Val Val Arg Gly Asn Tyr Trp Gly Gln
100 105 110

Glu Thr Gln Val Thr Val Ser Ser Ala Ala Xaa Xaa Gly Gly Gly Gly
115 120 125

Ser Gly Gly Gly Gly Ser Lys Trp Phe Arg Val Tyr Arg Gly Ile Tyr
130 135 140

Arg
145

<210> SEQ ID NO 47
<211> LENGTH: 150
<212> TYPE: PRT
<213> ORGANISM: Artificial Sequence
<220> FEATURE:
<223> OTHER INFORMATION: sdAb59 linked to the lytic peptide modified cysteine deleted Tachyplesin-I by a GSAA_linker
<220> FEATURE:
<221> NAME/KEY: SITE
<222> LOCATION: 123,124
<223> OTHER INFORMATION: Xaa can be any amino acid

<400> SEQUENCE: 47

Gly Ala Gln Val Gln Leu Val Glu Ser Gly Gly Gly Leu Val Gln Pro
1 5 10 15

Gly Gly Ser Leu Thr Val Ser Cys Ala Ala Ser Gly Phe Thr Phe Ser
20 25 30

Arg Tyr Gly Val Thr Trp His Arg Gln Ala Pro Gly Lys Glu Arg Glu
35 40 45

Leu Val Ala Asp Ile Ile Phe Thr Gly Leu Asn Pro Thr Tyr Ser Asp
50 55 60

Ser Val Lys Gly Arg Phe Thr Ile Ser Arg Asp Asn Asp Lys Asn Val
65 70 75 80

Ala Tyr Leu Gln Met Asn Ser Leu Lys Pro Glu Asp Thr Ala Lys Tyr
85 90 95

Tyr Cys Asn Val Asn Asp Ile Val Val Arg Gly Asn Tyr Trp Gly Gln
100 105 110

Glu Thr Gln Val Thr Val Ser Ser Ala Ala Xaa Xaa Gly Gly Gly Gly
115 120 125

```
Ser Glu Ala Ala Ala Lys Gly Gly Gly Gly Ser Lys Trp Phe Arg Val
    130                 135                 140

Tyr Arg Gly Ile Tyr Arg
145                 150


<210> SEQ ID NO 48
<211> LENGTH: 153
<212> TYPE: PRT
<213> ORGANISM: Artificial Sequence
<220> FEATURE:
<223> OTHER INFORMATION: sdAb59 linked to the lytic peptide Polybia-MP1
<220> FEATURE:
<221> NAME/KEY: SITE
<222> LOCATION: 123,124
<223> OTHER INFORMATION: Xaa can be any amino acid

<400> SEQUENCE: 48

Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
            20                  25                  30

Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Gly Gly Gly Gly
        115                 120                 125

Ser Glu Ala Ala Ala Lys Gly Gly Gly Gly Ser Ile Asp Trp Lys Lys
    130                 135                 140

Leu Leu Asp Ala Ala Lys Gln Ile Leu
145                 150


<210> SEQ ID NO 49
<211> LENGTH: 163
<212> TYPE: PRT
<213> ORGANISM: Artificial Sequence
<220> FEATURE:
<223> OTHER INFORMATION: sdAb62 linked to the lytic peptide BMAP28A by a
      GS_linker
<220> FEATURE:
<221> NAME/KEY: SITE
<222> LOCATION: 124,125
<223> OTHER INFORMATION: Xaa can be any amino acid

<400> SEQUENCE: 49

Gly Ala Asp Val Lys Leu Val Glu Ser Gly Gly Gly Leu Val Gln Pro
1               5                   10                  15

Gly Gly Ser Leu Arg Leu Ser Cys Ala Val Ser Gly Thr Ile Leu Gly
            20                  25                  30

Leu Asn Met Met Gly Trp Tyr Arg Gln Ala Pro Gly Lys Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
```

```
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Trp Gly
            100                 105                 110

Gln Gly Thr Gln Val Thr Val Ser Ser Ala Ala Xaa Xaa Gly Gly Gly
        115                 120                 125

Gly Ser Gly Gly Gly Gly Ser Gly Gly Leu Arg Ser Leu Gly Arg Lys
    130                 135                 140

Ile Leu Arg Ala Trp Lys Lys Tyr Gly Pro Ile Ile Val Pro Ile Ile
145                 150                 155                 160

Arg Ile Gly


<210> SEQ ID NO 50
<211> LENGTH: 168
<212> TYPE: PRT
<213> ORGANISM: Artificial Sequence
<220> FEATURE:
<223> OTHER INFORMATION: sdAb62 linked to the lytic peptide BMAP28A by a
      GSAA_linker
<220> FEATURE:
<221> NAME/KEY: SITE
<222> LOCATION: 124,125
<223> OTHER INFORMATION: Xaa can be any amino acid

<400> SEQUENCE: 50

Gly Ala Asp Val Lys Leu Val Glu Ser Gly Gly Gly Leu Val Gln Pro
1               5                   10                  15

Gly Gly Ser Leu Arg Leu Ser Cys Ala Val Ser Gly Thr Ile Leu Gly
            20                  25                  30

Leu Asn Met Met Gly Trp Tyr Arg Gln Ala Pro Gly Lys Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Trp Gly
            100                 105                 110

Gln Gly Thr Gln Val Thr Val Ser Ser Ala Ala Xaa Xaa Gly Gly Gly
        115                 120                 125

Gly Ser Glu Ala Ala Ala Lys Gly Gly Gly Gly Ser Gly Gly Leu Arg
    130                 135                 140

Ser Leu Gly Arg Lys Ile Leu Arg Ala Trp Lys Lys Tyr Gly Pro Ile
145                 150                 155                 160

Ile Val Pro Ile Ile Arg Ile Gly
                165


<210> SEQ ID NO 51
<211> LENGTH: 146
<212> TYPE: PRT
<213> ORGANISM: Artificial Sequence
<220> FEATURE:
<223> OTHER INFORMATION: sdAb62 linked to the lytic peptide modified
      cysteine deleted Tachyplesin-I by a GS_linker
<220> FEATURE:
<221> NAME/KEY: SITE
<222> LOCATION: 124,125
<223> OTHER INFORMATION: Xaa can be any amino acid
```

<400> SEQUENCE: 51

Gly Ala Asp Val Lys Leu Val Glu Ser Gly Gly Gly Leu Val Gln Pro
1 5 10 15

Gly Gly Ser Leu Arg Leu Ser Cys Ala Val Ser Gly Thr Ile Leu Gly
20 25 30

Leu Asn Met Met Gly Trp Tyr Arg Gln Ala Pro Gly Lys Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val
65 70 75 80

Ser Leu Gln Met Asn Thr Leu Arg Pro Glu Asp Thr Ala Ile Tyr Tyr
85 90 95

Cys Val Ala Arg Trp Thr Phe Gly Ile Gln Arg Gly Asp Tyr Trp Gly
100 105 110

Gln Gly Thr Gln Val Thr Val Ser Ser Ala Ala Xaa Xaa Gly Gly Gly
115 120 125

Gly Ser Gly Gly Gly Gly Ser Lys Trp Phe Arg Val Tyr Arg Gly Ile
130 135 140

Tyr Arg
145

<210> SEQ ID NO 52
<211> LENGTH: 151
<212> TYPE: PRT
<213> ORGANISM: Artificial Sequence
<220> FEATURE:
<223> OTHER INFORMATION: sdAb62 linked to the lytic peptide modified cysteine deleted Tachyplesin-I by a GSAA_linker
<220> FEATURE:
<221> NAME/KEY: SITE
<222> LOCATION: 124,125
<223> OTHER INFORMATION: Xaa can be any amino acid

<400> SEQUENCE: 52

Gly Ala Asp Val Lys Leu Val Glu Ser Gly Gly Gly Leu Val Gln Pro
1 5 10 15

Gly Gly Ser Leu Arg Leu Ser Cys Ala Val Ser Gly Thr Ile Leu Gly
20 25 30

Leu Asn Met Met Gly Trp Tyr Arg Gln Ala Pro Gly Lys Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val
65 70 75 80

Ser Leu Gln Met Asn Thr Leu Arg Pro Glu Asp Thr Ala Ile Tyr Tyr
85 90 95

Cys Val Ala Arg Trp Thr Phe Gly Ile Gln Arg Gly Asp Tyr Trp Gly
100 105 110

Gln Gly Thr Gln Val Thr Val Ser Ser Ala Ala Xaa Xaa Gly Gly Gly
115 120 125

Gly Ser Glu Ala Ala Ala Lys Gly Gly Gly Gly Ser Lys Trp Phe Arg
130 135 140

Val Tyr Arg Gly Ile Tyr Arg
145 150

<210> SEQ ID NO 53
<211> LENGTH: 154
<212> TYPE: PRT
<213> ORGANISM: Artificial Sequence
<220> FEATURE:
<223> OTHER INFORMATION: sdAb62 linked to the lytic peptide Polybia-MP1 by a GSAA_linker
<220> FEATURE:
<221> NAME/KEY: SITE
<222> LOCATION: 124,125
<223> OTHER INFORMATION: Xaa can be any amino acid

<400> SEQUENCE: 53

```
Gly Ala Asp Val Lys Leu Val Glu Ser Gly Gly Gly Leu Val Gln Pro
1               5                   10                  15

Gly Gly Ser Leu Arg Leu Ser Cys Ala Val Ser Gly Thr Ile Leu Gly
            20                  25                  30

Leu Asn Met Met Gly Trp Tyr Arg Gln Ala Pro Gly Lys Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Trp Gly
            100                 105                 110

Gln Gly Thr Gln Val Thr Val Ser Ser Ala Ala Xaa Xaa Gly Gly Gly
        115                 120                 125

Gly Ser Glu Ala Ala Ala Lys Gly Gly Gly Gly Ser Ile Asp Trp Lys
    130                 135                 140

Lys Leu Leu Asp Ala Ala Lys Gln Ile Leu
145                 150
```

<210> SEQ ID NO 54
<211> LENGTH: 172
<212> TYPE: PRT
<213> ORGANISM: Artificial Sequence
<220> FEATURE:
<223> OTHER INFORMATION: sdAb63 linked to the lytic peptide BMAP28A by a GS_linker
<220> FEATURE:
<221> NAME/KEY: SITE
<222> LOCATION: 133,134
<223> OTHER INFORMATION: Xaa can be any amino acid

<400> SEQUENCE: 54

```
Gly Ala Asp Val Gln Leu Val Glu Ser Gly Gly Gly Met Val Gln Pro
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95

Tyr Cys Ala Ala His Arg Ala Glu Ile Pro Arg Glu Ile Cys Tyr Gly
            100                 105                 110
```

```
Asp Ser Leu Ser Tyr Asn Tyr Trp Gly Gln Gly Thr Gln Val Thr Val
        115                 120                 125

Ser Ser Ala Ala Xaa Xaa Gly Gly Gly Gly Ser Gly Gly Gly Gly Ser
    130                 135                 140

Gly Gly Leu Arg Ser Leu Gly Arg Lys Ile Leu Arg Ala Trp Lys Lys
145                 150                 155                 160

Tyr Gly Pro Ile Ile Val Pro Ile Ile Arg Ile Gly
                165                 170


<210> SEQ ID NO 55
<211> LENGTH: 177
<212> TYPE: PRT
<213> ORGANISM: Artificial Sequence
<220> FEATURE:
<223> OTHER INFORMATION: sdAb63 linked to the lytic peptide BMAP28A by a
      GSAA_linker
<220> FEATURE:
<221> NAME/KEY: SITE
<222> LOCATION: 133,134
<223> OTHER INFORMATION: Xaa can be any amino acid

<400> SEQUENCE: 55

Gly Ala Asp Val Gln Leu Val Glu Ser Gly Gly Gly Met Val Gln Pro
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95

Tyr Cys Ala Ala His Arg Ala Glu Ile Pro Arg Glu Ile Cys Tyr Gly
            100                 105                 110

Asp Ser Leu Ser Tyr Asn Tyr Trp Gly Gln Gly Thr Gln Val Thr Val
        115                 120                 125

Ser Ser Ala Ala Xaa Xaa Gly Gly Gly Gly Ser Glu Ala Ala Ala Lys
    130                 135                 140

Gly Gly Gly Gly Ser Gly Gly Leu Arg Ser Leu Gly Arg Lys Ile Leu
145                 150                 155                 160

Arg Ala Trp Lys Lys Tyr Gly Pro Ile Ile Val Pro Ile Ile Arg Ile
                165                 170                 175

Gly


<210> SEQ ID NO 56
<211> LENGTH: 155
<212> TYPE: PRT
<213> ORGANISM: Artificial Sequence
<220> FEATURE:
<223> OTHER INFORMATION: sdAb63 linked to the lytic peptide modified
      cysteine deleted Tachyplesin-I by a GS_linker
<220> FEATURE:
<221> NAME/KEY: SITE
<222> LOCATION: 133,134
<223> OTHER INFORMATION: Xaa can be any amino acid

<400> SEQUENCE: 56

Gly Ala Asp Val Gln Leu Val Glu Ser Gly Gly Gly Met Val Gln Pro
```

-continued

```
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95

Tyr Cys Ala Ala His Arg Ala Glu Ile Pro Arg Glu Ile Cys Tyr Gly
            100                 105                 110

Asp Ser Leu Ser Tyr Asn Tyr Trp Gly Gln Gly Thr Gln Val Thr Val
        115                 120                 125

Ser Ser Ala Ala Xaa Xaa Gly Gly Gly Gly Ser Gly Gly Gly Gly Ser
    130                 135                 140

Lys Trp Phe Arg Val Tyr Arg Gly Ile Tyr Arg
145                 150                 155
```

<210> SEQ ID NO 57
<211> LENGTH: 160
<212> TYPE: PRT
<213> ORGANISM: Artificial Sequence
<220> FEATURE:
<223> OTHER INFORMATION: sdAb63 linked to the lytic peptide modified cysteine deleted Tachyplesin-I by a GSAA_linker
<220> FEATURE:
<221> NAME/KEY: SITE
<222> LOCATION: 133,134
<223> OTHER INFORMATION: Xaa can be any amino acid

<400> SEQUENCE: 57

```
Gly Ala Asp Val Gln Leu Val Glu Ser Gly Gly Gly Met Val Gln Pro
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95

Tyr Cys Ala Ala His Arg Ala Glu Ile Pro Arg Glu Ile Cys Tyr Gly
            100                 105                 110

Asp Ser Leu Ser Tyr Asn Tyr Trp Gly Gln Gly Thr Gln Val Thr Val
        115                 120                 125

Ser Ser Ala Ala Xaa Xaa Gly Gly Gly Gly Ser Glu Ala Ala Ala Lys
    130                 135                 140

Gly Gly Gly Gly Ser Lys Trp Phe Arg Val Tyr Arg Gly Ile Tyr Arg
145                 150                 155                 160
```

<210> SEQ ID NO 58
<211> LENGTH: 163
<212> TYPE: PRT
<213> ORGANISM: Artificial Sequence
<220> FEATURE:
<223> OTHER INFORMATION: sdAb63 linked to the lytic peptide Polybia-MP1 by a GSAA_linker
<220> FEATURE:
<221> NAME/KEY: SITE
<222> LOCATION: 133,134
<223> OTHER INFORMATION: Xaa can be any amino acid

<400> SEQUENCE: 58

```
Gly Ala Asp Val Gln Leu Val Glu Ser Gly Gly Gly Met Val Gln Pro
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95

Tyr Cys Ala Ala His Arg Ala Glu Ile Pro Arg Glu Ile Cys Tyr Gly
            100                 105                 110

Asp Ser Leu Ser Tyr Asn Tyr Trp Gly Gln Gly Thr Gln Val Thr Val
        115                 120                 125

Ser Ser Ala Ala Xaa Xaa Gly Gly Gly Gly Ser Glu Ala Ala Ala Lys
    130                 135                 140

Gly Gly Gly Gly Ser Ile Asp Trp Lys Lys Leu Leu Asp Ala Ala Lys
145                 150                 155                 160

Gln Ile Leu
```

<210> SEQ ID NO 59
<211> LENGTH: 169
<212> TYPE: PRT
<213> ORGANISM: Artificial Sequence
<220> FEATURE:
<223> OTHER INFORMATION: sdAb65 linked to the lytic peptide BMAP28A by a GS_linker
<220> FEATURE:
<221> NAME/KEY: SITE
<222> LOCATION: 130,131
<223> OTHER INFORMATION: Xaa can be any amino acid

<400> SEQUENCE: 59

```
Gly Ala Gln Val Gln Leu Val Glu Ser Gly Gly Gly Leu Val Gln Leu
1               5                   10                  15

Gly Gly Ser Leu Arg Leu Ser Cys Thr Ala Ser Glu Ile Asp Leu Gln
            20                  25                  30

Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
```

115 120 125

Ala Xaa Xaa Gly Gly Gly Gly Ser Gly Gly Gly Gly Ser Gly Gly Leu
130 135 140

Arg Ser Leu Gly Arg Lys Ile Leu Arg Ala Trp Lys Lys Tyr Gly Pro
145 150 155 160

Ile Ile Val Pro Ile Ile Arg Ile Gly
165

<210> SEQ ID NO 60
<211> LENGTH: 174
<212> TYPE: PRT
<213> ORGANISM: Artificial Sequence
<220> FEATURE:
<223> OTHER INFORMATION: sdAb65 linked to the lytic peptide BMAP28A by a GSAA_linker
<220> FEATURE:
<221> NAME/KEY: SITE
<222> LOCATION: 130,131
<223> OTHER INFORMATION: Xaa can be any amino acid

<400> SEQUENCE: 60

Gly Ala Gln Val Gln Leu Val Glu Ser Gly Gly Gly Leu Val Gln Leu
1 5 10 15

Gly Gly Ser Leu Arg Leu Ser Cys Thr Ala Ser Glu Ile Asp Leu Gln
20 25 30

Tyr Tyr Pro Ile Ala Trp Phe Arg Gln Ala Pro Gly Lys Glu Arg Glu
35 40 45

Gly Val Ser Cys Ile Arg Ala Thr Asp Ser Gly Thr Tyr Tyr Ala Asp
50 55 60

Ser Val Lys Gly Arg Phe Thr Ile Ala Arg Asp Asn Ala Lys Asn Thr
65 70 75 80

Val Tyr Leu Gln Met Asn Asn Leu Ala Pro Glu Asp Thr Ala Val Tyr
85 90 95

Tyr Cys Gly Thr Asp Asp Ser Glu Asp Cys Thr Asp Tyr Ala Pro Ala
100 105 110

His Tyr Gly Tyr Trp Gly Arg Gly Thr Gln Val Thr Val Ser Ser Ala
115 120 125

Ala Xaa Xaa Gly Gly Gly Gly Ser Glu Ala Ala Ala Lys Gly Gly Gly
130 135 140

Gly Ser Gly Gly Leu Arg Ser Leu Gly Arg Lys Ile Leu Arg Ala Trp
145 150 155 160

Lys Lys Tyr Gly Pro Ile Ile Val Pro Ile Ile Arg Ile Gly
165 170

<210> SEQ ID NO 61
<211> LENGTH: 152
<212> TYPE: PRT
<213> ORGANISM: Artificial Sequence
<220> FEATURE:
<223> OTHER INFORMATION: sdAb65 linked to the lytic peptide modified cysteine deleted Tachyplesin-I by a GS_linker
<220> FEATURE:
<221> NAME/KEY: SITE
<222> LOCATION: 130,131
<223> OTHER INFORMATION: Xaa can be any amino acid

<400> SEQUENCE: 61

Gly Ala Gln Val Gln Leu Val Glu Ser Gly Gly Gly Leu Val Gln Leu
1 5 10 15

Gly Gly Ser Leu Arg Leu Ser Cys Thr Ala Ser Glu Ile Asp Leu Gln
20 25 30

```
Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
        115                 120                 125

Ala Xaa Xaa Gly Gly Gly Gly Ser Gly Gly Gly Gly Ser Lys Trp Phe
    130                 135                 140

Arg Val Tyr Arg Gly Ile Tyr Arg
145                 150
```

<210> SEQ ID NO 62
<211> LENGTH: 157
<212> TYPE: PRT
<213> ORGANISM: Artificial Sequence
<220> FEATURE:
<223> OTHER INFORMATION: sdAb65 linked to the lytic peptide modified cysteine deleted Tachyplesin-I by a GSAA_linker
<220> FEATURE:
<221> NAME/KEY: SITE
<222> LOCATION: 130,131
<223> OTHER INFORMATION: Xaa can be any amino acid

<400> SEQUENCE: 62

```
Gly Ala Gln Val Gln Leu Val Glu Ser Gly Gly Gly Leu Val Gln Leu
1               5                   10                  15

Gly Gly Ser Leu Arg Leu Ser Cys Thr Ala Ser Glu Ile Asp Leu Gln
            20                  25                  30

Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
        115                 120                 125

Ala Xaa Xaa Gly Gly Gly Gly Ser Glu Ala Ala Ala Lys Gly Gly Gly
    130                 135                 140

Gly Ser Lys Trp Phe Arg Val Tyr Arg Gly Ile Tyr Arg
145                 150                 155
```

<210> SEQ ID NO 63
<211> LENGTH: 160
<212> TYPE: PRT
<213> ORGANISM: Artificial Sequence
<220> FEATURE:
<223> OTHER INFORMATION: sdAb65 linked to the lytic peptide Polybia-MP1 by a GSAA_linker
<220> FEATURE:

<221> NAME/KEY: SITE
<222> LOCATION: 130,131
<223> OTHER INFORMATION: Xaa can be any amino acid

<400> SEQUENCE: 63

```
Gly Ala Gln Val Gln Leu Val Glu Ser Gly Gly Gly Leu Val Gln Leu
1               5                   10                  15

Gly Gly Ser Leu Arg Leu Ser Cys Thr Ala Ser Glu Ile Asp Leu Gln
            20                  25                  30

Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
        115                 120                 125

Ala Xaa Xaa Gly Gly Gly Gly Ser Glu Ala Ala Ala Lys Gly Gly Gly
    130                 135                 140

Gly Ser Ile Asp Trp Lys Lys Leu Leu Asp Ala Ala Lys Gln Ile Leu
145                 150                 155                 160
```

<210> SEQ ID NO 64
<211> LENGTH: 5
<212> TYPE: PRT
<213> ORGANISM: Vicugna pacos
<220> FEATURE:
<223> OTHER INFORMATION: CDR1 of sdAb26

<400> SEQUENCE: 64

```
Ile Tyr Asp Phe Gly
1               5
```

<210> SEQ ID NO 65
<211> LENGTH: 5
<212> TYPE: PRT
<213> ORGANISM: Vicugna pacos
<220> FEATURE:
<223> OTHER INFORMATION: CDR1 of sdAb37

<400> SEQUENCE: 65

```
Ser Tyr Ala Met Ser
1               5
```

<210> SEQ ID NO 66
<211> LENGTH: 5
<212> TYPE: PRT
<213> ORGANISM: Vicugna pacos
<220> FEATURE:
<223> OTHER INFORMATION: CDR1 of sdAb46

<400> SEQUENCE: 66

```
Asp Tyr Ala Leu Thr
1               5
```

<210> SEQ ID NO 67
<211> LENGTH: 5
<212> TYPE: PRT

-continued

<213> ORGANISM: Vicugna pacos
<220> FEATURE:
<223> OTHER INFORMATION: CDR1 of sdAb47

<400> SEQUENCE: 67

Asn His Trp Met Tyr
1 5

<210> SEQ ID NO 68
<211> LENGTH: 5
<212> TYPE: PRT
<213> ORGANISM: Vicugna pacos
<220> FEATURE:
<223> OTHER INFORMATION: CDR1 of sdAb56

<400> SEQUENCE: 68

Ser Tyr Trp Met His
1 5

<210> SEQ ID NO 69
<211> LENGTH: 5
<212> TYPE: PRT
<213> ORGANISM: Vicugna pacos
<220> FEATURE:
<223> OTHER INFORMATION: CDR1 of sdAb59

<400> SEQUENCE: 69

Arg Tyr Gly Val Thr
1 5

<210> SEQ ID NO 70
<211> LENGTH: 5
<212> TYPE: PRT
<213> ORGANISM: Vicugna pacos
<220> FEATURE:
<223> OTHER INFORMATION: CDR1 of sdAb62

<400> SEQUENCE: 70

Leu Asn Met Met Gly
1 5

<210> SEQ ID NO 71
<211> LENGTH: 5
<212> TYPE: PRT
<213> ORGANISM: Vicugna pacos
<220> FEATURE:
<223> OTHER INFORMATION: CDR1 of sdAb63

<400> SEQUENCE: 71

Arg His Asp Met His
1 5

<210> SEQ ID NO 72
<211> LENGTH: 5
<212> TYPE: PRT
<213> ORGANISM: Vicugna pacos
<220> FEATURE:
<223> OTHER INFORMATION: CDR1 of sdAb65

<400> SEQUENCE: 72

Tyr Tyr Pro Ile Ala
1 5

<210> SEQ ID NO 73
<211> LENGTH: 16
<212> TYPE: PRT
<213> ORGANISM: Vicugna pacos
<220> FEATURE:
<223> OTHER INFORMATION: CDR2 of sdAb26

<400> SEQUENCE: 73

Ser Ile Gly Phe Gly Gly Asn Ile Asp Tyr Ala Asn Ser Val Lys Gly
1 5 10 15

<210> SEQ ID NO 74
<211> LENGTH: 17
<212> TYPE: PRT
<213> ORGANISM: Vicugna pacos
<220> FEATURE:
<223> OTHER INFORMATION: CDR2 of sdAb37

<400> SEQUENCE: 74

Gly Ile Tyr Arg Asp Gly Ile Asp Thr Tyr Tyr Ala Asp Ser Val Lys
1 5 10 15

Gly

<210> SEQ ID NO 75
<211> LENGTH: 17
<212> TYPE: PRT
<213> ORGANISM: Vicugna pacos
<220> FEATURE:
<223> OTHER INFORMATION: CDR2 of sdAb46

<400> SEQUENCE: 75

Gly Ile Asn Trp Asn Gly Asp Asp Thr Tyr Tyr Thr Gln Ser Met Lys
1 5 10 15

Gly

<210> SEQ ID NO 76
<211> LENGTH: 17
<212> TYPE: PRT
<213> ORGANISM: Vicugna pacos
<220> FEATURE:
<223> OTHER INFORMATION: CDR2 of sdAb47

<400> SEQUENCE: 76

Thr Ala Asn Thr Gly Gly Arg Asp Thr Tyr Tyr Ala Asp Ser Val Trp
1 5 10 15

Gly

<210> SEQ ID NO 77
<211> LENGTH: 17
<212> TYPE: PRT
<213> ORGANISM: Vicugna pacos
<220> FEATURE:
<223> OTHER INFORMATION: CDR2 of sdAb56

<400> SEQUENCE: 77

Val Ile Asn Thr Gly Asn Gly Ser Pro Tyr Tyr Ala Asp Ser Val Lys
1 5 10 15

Gly

<210> SEQ ID NO 78
<211> LENGTH: 17
<212> TYPE: PRT
<213> ORGANISM: Vicugna pacos
<220> FEATURE:
<223> OTHER INFORMATION: CDR2 of sdAb59

<400> SEQUENCE: 78

Asp Ile Ile Phe Thr Gly Leu Asn Pro Thr Tyr Ser Asp Ser Val Lys 1 5 10 15

Gly

<210> SEQ ID NO 79
<211> LENGTH: 16
<212> TYPE: PRT
<213> ORGANISM: Vicugna pacos
<220> FEATURE:
<223> OTHER INFORMATION: CDR2 of sdAb62

<400> SEQUENCE: 79

Ser Ile Gly Phe Gly Gly Asn Ile Asp Tyr Ala Asn Ser Val Lys Gly
1 5 10 15

<210> SEQ ID NO 80
<211> LENGTH: 17
<212> TYPE: PRT
<213> ORGANISM: Vicugna pacos
<220> FEATURE:
<223> OTHER INFORMATION: CDR2 of sdAb63

<400> SEQUENCE: 80

Leu Ile Thr Thr Gly Gly Glu Gly Thr Trp Tyr Val Asp Ser Val Lys
1 5 10 15

Gly

<210> SEQ ID NO 81
<211> LENGTH: 17
<212> TYPE: PRT
<213> ORGANISM: Vicugna pacos
<220> FEATURE:
<223> OTHER INFORMATION: CDR2 of sdAb65

<400> SEQUENCE: 81

Cys Ile Arg Ala Thr Asp Ser Gly Thr Tyr Tyr Ala Asp Ser Val Lys
1 5 10 15

Gly

<210> SEQ ID NO 82
<211> LENGTH: 15
<212> TYPE: PRT
<213> ORGANISM: Vicugna pacos
<220> FEATURE:
<223> OTHER INFORMATION: CDR3 of sdAb26

<400> SEQUENCE: 82

Arg Trp Thr Phe Gly Ile Gln Arg Gly Asp Tyr Tyr Ile Trp Ser
1 5 10 15

<210> SEQ ID NO 83
<211> LENGTH: 14
<212> TYPE: PRT
<213> ORGANISM: Vicugna pacos
<220> FEATURE:
<223> OTHER INFORMATION: CDR3 of sdAb37

<400> SEQUENCE: 83

Asp Leu Leu Ala Gly Trp Gly Pro Leu Ile Ser Trp His Tyr
1 5 10

<210> SEQ ID NO 84
<211> LENGTH: 15
<212> TYPE: PRT
<213> ORGANISM: Vicugna pacos
<220> FEATURE:

<223> OTHER INFORMATION: CDR3 of sdAb46

<400> SEQUENCE: 84

Asn Val Gly Gly Asn Trp Val Ser Gly Asp Tyr Gly Leu Asp Tyr
1 5 10 15

<210> SEQ ID NO 85
<211> LENGTH: 12
<212> TYPE: PRT
<213> ORGANISM: Vicugna pacos
<220> FEATURE:
<223> OTHER INFORMATION: CDR3 of sdAb47

<400> SEQUENCE: 85

Glu Val Asn Asp Tyr Leu Glu Tyr Ala Leu Gly Tyr
1 5 10

<210> SEQ ID NO 86
<211> LENGTH: 14
<212> TYPE: PRT
<213> ORGANISM: Vicugna pacos
<220> FEATURE:
<223> OTHER INFORMATION: CDR3 of sdAb56

<400> SEQUENCE: 86

Asp Ile Pro Asp Pro Ala Gly Arg Ala Gly Gly Met Asp Tyr
1 5 10

<210> SEQ ID NO 87
<211> LENGTH: 9
<212> TYPE: PRT
<213> ORGANISM: Vicugna pacos
<220> FEATURE:
<223> OTHER INFORMATION: CDR3 of sdAb59

<400> SEQUENCE: 87

Asn Asp Ile Val Val Arg Gly Asn Tyr
1 5

<210> SEQ ID NO 88
<211> LENGTH: 11
<212> TYPE: PRT
<213> ORGANISM: Vicugna pacos
<220> FEATURE:
<223> OTHER INFORMATION: CDR3 of sdAb62

<400> SEQUENCE: 88

Arg Trp Thr Phe Gly Ile Gln Arg Gly Asp Tyr
1 5 10

<210> SEQ ID NO 89
<211> LENGTH: 19
<212> TYPE: PRT
<213> ORGANISM: Vicugna pacos
<220> FEATURE:
<223> OTHER INFORMATION: CDR3 of sdAb63

<400> SEQUENCE: 89

His Arg Ala Glu Ile Pro Arg Glu Ile Cys Tyr Gly Asp Ser Leu Ser
1 5 10 15

Tyr Asn Tyr

<210> SEQ ID NO 90
<211> LENGTH: 16
<212> TYPE: PRT
<213> ORGANISM: Vicugna pacos
<220> FEATURE:
<223> OTHER INFORMATION: CDR3 of sdAb65

<400> SEQUENCE: 90

Asp Asp Ser Glu Asp Cys Thr Asp Tyr Ala Pro Ala His Tyr Gly Tyr
1 5 10 15

<210> SEQ ID NO 91
<211> LENGTH: 33
<212> TYPE: PRT
<213> ORGANISM: Vicugna pacos
<220> FEATURE:
<223> OTHER INFORMATION: FR1 of sdAb26

<400> SEQUENCE: 91

Met Gly Ala His Val Gln Leu Val Glu Ser Gly Gly Gly Leu Val Gln
1 5 10 15

Pro Gly Gly Ser Leu Arg Leu Ser Cys Glu Gly Ser Gly Met Thr Phe
20 25 30

Ser

<210> SEQ ID NO 92
<211> LENGTH: 32
<212> TYPE: PRT
<213> ORGANISM: Vicugna pacos
<220> FEATURE:
<223> OTHER INFORMATION: FR1 of sdAb37

<400> SEQUENCE: 92

Met Gly Asp Val Gln Leu Gln Glu Ser Gly Gly Gly Leu Ala Gln Pro
1 5 10 15

Gly Gly Ser Leu Arg Leu Ser Cys Ala Ala Ser Gly Phe Thr Phe Ser
20 25 30

<210> SEQ ID NO 93
<211> LENGTH: 32
<212> TYPE: PRT
<213> ORGANISM: Vicugna pacos
<220> FEATURE:
<223> OTHER INFORMATION: FR1 of sdAb46

<400> SEQUENCE: 93

Met Gly Asp Val Gln Leu Gln Glu Ser Gly Gly Gly Leu Val His Pro
1 5 10 15

Gly Gly Ser Leu Arg Leu Ser Cys Val Ala Ser Gly Phe Thr Phe Asp
20 25 30

<210> SEQ ID NO 94
<211> LENGTH: 32
<212> TYPE: PRT
<213> ORGANISM: Vicugna pacos
<220> FEATURE:
<223> OTHER INFORMATION: FR1 of sdAb47

<400> SEQUENCE: 94

Met Gly Asp Val Gln Leu Val Glu Ser Gly Gly Gly Leu Val Gln Pro
1 5 10 15

Gly Gly Ser Leu Arg Leu Ser Cys Thr Ala Ser Gly Phe Thr Phe Gly
20 25 30

<210> SEQ ID NO 95
<211> LENGTH: 32
<212> TYPE: PRT
<213> ORGANISM: Vicugna pacos
<220> FEATURE:
<223> OTHER INFORMATION: FR1 of sdAb56

<400> SEQUENCE: 95

Met Gly Asp Val Gln Leu Val Glu Ser Gly Gly Gly Leu Val Gln Pro
1 5 10 15

Gly Gly Ser Leu Arg Leu Ser Cys Ala Ala Ser Gly Phe Thr Phe Ser
20 25 30

<210> SEQ ID NO 96
<211> LENGTH: 33
<212> TYPE: PRT
<213> ORGANISM: Vicugna pacos
<220> FEATURE:
<223> OTHER INFORMATION: FR1 of sdAb59

<400> SEQUENCE: 96

Met Gly Ala Gln Val Gln Leu Val Glu Ser Gly Gly Gly Leu Val Gln
1 5 10 15

Pro Gly Gly Ser Leu Thr Val Ser Cys Ala Ala Ser Gly Phe Thr Phe
20 25 30

Ser

<210> SEQ ID NO 97
<211> LENGTH: 33
<212> TYPE: PRT
<213> ORGANISM: Vicugna pacos
<220> FEATURE:
<223> OTHER INFORMATION: FR1 of sdAb62

<400> SEQUENCE: 97

Met Gly Ala Asp Val Lys Leu Val Glu Ser Gly Gly Gly Leu Val Gln
1 5 10 15

Pro Gly Gly Ser Leu Arg Leu Ser Cys Ala Val Ser Gly Thr Ile Leu
20 25 30

Gly

<210> SEQ ID NO 98
<211> LENGTH: 33
<212> TYPE: PRT
<213> ORGANISM: Vicugna pacos
<220> FEATURE:
<223> OTHER INFORMATION: FR1 of sdAb63

<400> SEQUENCE: 98

Met Gly Ala Asp Val Gln Leu Val Glu Ser Gly Gly Gly Met Val Gln
1 5 10 15

Pro Gly Gly Ser Leu Arg Leu Ser Cys Ala Ala Ser Gly Phe Ile Phe
20 25 30

Ser

<210> SEQ ID NO 99
<211> LENGTH: 33
<212> TYPE: PRT
<213> ORGANISM: Vicugna pacos
<220> FEATURE:
<223> OTHER INFORMATION: FR1 of sdAb65

<400> SEQUENCE: 99

Met Gly Ala Gln Val Gln Leu Val Glu Ser Gly Gly Gly Leu Val Gln
1 5 10 15

Leu Gly Gly Ser Leu Arg Leu Ser Cys Thr Ala Ser Glu Ile Asp Leu 20 25 30

Gln

<210> SEQ ID NO 100
<211> LENGTH: 14
<212> TYPE: PRT
<213> ORGANISM: Vicugna pacos
<220> FEATURE:
<223> OTHER INFORMATION: FR2 of sdAb26

<400> SEQUENCE: 100

Trp Tyr Arg Gln Val Pro Gly Asn Gln Arg Glu Leu Val Ala
1 5 10

<210> SEQ ID NO 101
<211> LENGTH: 14
<212> TYPE: PRT
<213> ORGANISM: Vicugna pacos
<220> FEATURE:
<223> OTHER INFORMATION: FR2 of sdAb37

<400> SEQUENCE: 101

Trp Ala Arg Gln Ala Pro Gly Lys Gly Leu Glu Trp Val Ser
1 5 10

<210> SEQ ID NO 102
<211> LENGTH: 14
<212> TYPE: PRT
<213> ORGANISM: Vicugna pacos
<220> FEATURE:
<223> OTHER INFORMATION: FR2 of sdAb46

<400> SEQUENCE: 102

Trp Val Arg Gln Ala Pro Gly Lys Gly Leu Glu Trp Val Ser
1 5 10

<210> SEQ ID NO 103
<211> LENGTH: 14
<212> TYPE: PRT
<213> ORGANISM: Vicugna pacos
<220> FEATURE:
<223> OTHER INFORMATION: FR2 of sdAb47

<400> SEQUENCE: 103

Trp Val Arg Gln Thr Pro Gly Lys Gly Leu Glu Trp Val Ala
1 5 10

<210> SEQ ID NO 104
<211> LENGTH: 14
<212> TYPE: PRT
<213> ORGANISM: Vicugna pacos
<220> FEATURE:
<223> OTHER INFORMATION: FR2 of sdAb56

<400> SEQUENCE: 104

Trp Val Arg Gln Ala Pro Gly Lys Gly Leu Glu Cys Val Ser
1 5 10

<210> SEQ ID NO 105
<211> LENGTH: 14
<212> TYPE: PRT
<213> ORGANISM: Vicugna pacos
<220> FEATURE:
<223> OTHER INFORMATION: FR2 of sdAb59

<400> SEQUENCE: 105

Trp His Arg Gln Ala Pro Gly Lys Glu Arg Glu Leu Val Ala
1 5 10

<210> SEQ ID NO 106
<211> LENGTH: 14
<212> TYPE: PRT
<213> ORGANISM: Vicugna pacos
<220> FEATURE:
<223> OTHER INFORMATION: FR2 of sdAb62

<400> SEQUENCE: 106

Trp Tyr Arg Gln Ala Pro Gly Lys Gln Arg Glu Leu Val Ala
1 5 10

<210> SEQ ID NO 107
<211> LENGTH: 14
<212> TYPE: PRT
<213> ORGANISM: Vicugna pacos
<220> FEATURE:
<223> OTHER INFORMATION: FR2 of sdAb63

<400> SEQUENCE: 107

Trp Val Arg Gln Gly Pro Gly Lys Gly Pro Glu Trp Val Ser
1 5 10

<210> SEQ ID NO 108
<211> LENGTH: 14
<212> TYPE: PRT
<213> ORGANISM: Vicugna pacos
<220> FEATURE:
<223> OTHER INFORMATION: FR2 of sdAb65

<400> SEQUENCE: 108

Trp Phe Arg Gln Ala Pro Gly Lys Glu Arg Glu Gly Val Ser
1 5 10

<210> SEQ ID NO 109
<211> LENGTH: 32
<212> TYPE: PRT
<213> ORGANISM: Vicugna pacos
<220> FEATURE:
<223> OTHER INFORMATION: FR3 of sdAb26

<400> SEQUENCE: 109

Arg Phe Thr Ile Ser Arg Asp Gly Asp Lys Asn Met Val Ser Leu Gln
1 5 10 15

Met Asn Thr Leu Arg Pro Glu Asp Thr Ala Ile Tyr Tyr Cys Val Ala
20 25 30

<210> SEQ ID NO 110
<211> LENGTH: 32
<212> TYPE: PRT
<213> ORGANISM: Vicugna pacos
<220> FEATURE:
<223> OTHER INFORMATION: FR3 of sdAb37

<400> SEQUENCE: 110

Arg Phe Thr Ile Ser Arg Asp Asn Ala Lys Asn Thr Leu Tyr Leu Gln
1 5 10 15

Met Asn Ser Leu Lys Pro Glu Asp Thr Ala Leu Tyr Tyr Cys Ala Lys
20 25 30

<210> SEQ ID NO 111
<211> LENGTH: 32
<212> TYPE: PRT
<213> ORGANISM: Vicugna pacos
<220> FEATURE:
<223> OTHER INFORMATION: FR3 of sdAb46

<400> SEQUENCE: 111

Arg Phe Thr Ile Ser Arg Asp Asn Ala Lys Asn Thr Leu Tyr Leu Gln
1 5 10 15

Met Asn Ser Leu Lys Ser Glu Asp Thr Ala Val Tyr Phe Cys Thr Lys
20 25 30

<210> SEQ ID NO 112
<211> LENGTH: 32
<212> TYPE: PRT
<213> ORGANISM: Vicugna pacos
<220> FEATURE:
<223> OTHER INFORMATION: FR3 of sdAb47

<400> SEQUENCE: 112

Arg Phe Thr Ile Ser Gly Asp Asn Ala Lys Asn Thr Leu Tyr Leu Gln
1 5 10 15

Met Asn Asn Leu Lys Ser Glu Asp Thr Ala Ile Tyr Tyr Cys Ala Arg
20 25 30

<210> SEQ ID NO 113
<211> LENGTH: 32
<212> TYPE: PRT
<213> ORGANISM: Vicugna pacos
<220> FEATURE:
<223> OTHER INFORMATION: FR3 of sdAb56

<400> SEQUENCE: 113

Arg Phe Thr Ile Ser Thr Asp Asn Ala Lys Asn Thr Leu Tyr Leu Gln
1 5 10 15

Met Asn Ser Leu Lys Ser Glu Asp Thr Ala Val Tyr Tyr Cys Ala Arg
20 25 30

<210> SEQ ID NO 114
<211> LENGTH: 32
<212> TYPE: PRT
<213> ORGANISM: Vicugna pacos
<220> FEATURE:
<223> OTHER INFORMATION: FR3 of sdAb59

<400> SEQUENCE: 114

Arg Phe Thr Ile Ser Arg Asp Asn Asp Lys Asn Val Ala Tyr Leu Gln
1 5 10 15

Met Asn Ser Leu Lys Pro Glu Asp Thr Ala Lys Tyr Tyr Cys Asn Val
20 25 30

<210> SEQ ID NO 115
<211> LENGTH: 32
<212> TYPE: PRT
<213> ORGANISM: Vicugna pacos
<220> FEATURE:
<223> OTHER INFORMATION: FR3 of sdAb62

<400> SEQUENCE: 115

Arg Phe Thr Ile Ser Arg Asp Gly Asp Lys Asn Met Val Ser Leu Gln
1 5 10 15

Met Asn Thr Leu Arg Pro Glu Asp Thr Ala Ile Tyr Tyr Cys Val Ala
20 25 30

<210> SEQ ID NO 116
<211> LENGTH: 32
<212> TYPE: PRT

<213> ORGANISM: Vicugna pacos
<220> FEATURE:
<223> OTHER INFORMATION: FR3 of sdAb63

<400> SEQUENCE: 116

Arg Phe Ser Ile Ser Arg Asp Asn Ala Lys Asn Thr Val Tyr Leu Gln
1 5 10 15

Met Asn Ala Leu Lys Pro Glu Asp Thr Ala Val Tyr Tyr Cys Ala Ala
20 25 30

<210> SEQ ID NO 117
<211> LENGTH: 32
<212> TYPE: PRT
<213> ORGANISM: Vicugna pacos
<220> FEATURE:
<223> OTHER INFORMATION: FR3 of sdAb65

<400> SEQUENCE: 117

Arg Phe Thr Ile Ala Arg Asp Asn Ala Lys Asn Thr Val Tyr Leu Gln
1 5 10 15

Met Asn Asn Leu Ala Pro Glu Asp Thr Ala Val Tyr Tyr Cys Gly Thr
20 25 30

<210> SEQ ID NO 118
<211> LENGTH: 11
<212> TYPE: PRT
<213> ORGANISM: Vicugna pacos
<220> FEATURE:
<223> OTHER INFORMATION: FR4 of sdAb26

<400> SEQUENCE: 118

Trp Lys Gln Gly Thr Gln Val Thr Val Ser Ser
1 5 10

<210> SEQ ID NO 119
<211> LENGTH: 11
<212> TYPE: PRT
<213> ORGANISM: Vicugna pacos
<220> FEATURE:
<223> OTHER INFORMATION: FR4 of sdAb37

<400> SEQUENCE: 119

Trp Gly Lys Gly Thr Gln Val Thr Val Ser Ser
1 5 10

<210> SEQ ID NO 120
<211> LENGTH: 11
<212> TYPE: PRT
<213> ORGANISM: Vicugna pacos
<220> FEATURE:
<223> OTHER INFORMATION: FR4 of sdAb46

<400> SEQUENCE: 120

Trp Gly Gln Gly Thr Gln Val Thr Val Ser Ser
1 5 10

<210> SEQ ID NO 121
<211> LENGTH: 11
<212> TYPE: PRT
<213> ORGANISM: Vicugna pacos
<220> FEATURE:
<223> OTHER INFORMATION: FR4 of sdAb47

<400> SEQUENCE: 121

Trp Gly Gln Gly Thr Gln Val Thr Val Ser Ser
1 5 10

<210> SEQ ID NO 122
<211> LENGTH: 11
<212> TYPE: PRT
<213> ORGANISM: Vicugna pacos
<220> FEATURE:
<223> OTHER INFORMATION: FR4 of sdAb56

<400> SEQUENCE: 122

Trp Gly Lys Gly Thr Gln Val Thr Val Ser Ser
1 5 10

<210> SEQ ID NO 123
<211> LENGTH: 11
<212> TYPE: PRT
<213> ORGANISM: Vicugna pacos
<220> FEATURE:
<223> OTHER INFORMATION: FR4 of sdAb59

<400> SEQUENCE: 123

Trp Gly Gln Glu Thr Gln Val Thr Val Ser Ser
1 5 10

<210> SEQ ID NO 124
<211> LENGTH: 11
<212> TYPE: PRT
<213> ORGANISM: Vicugna pacos
<220> FEATURE:
<223> OTHER INFORMATION: FR4 of sdAb62

<400> SEQUENCE: 124

Trp Gly Gln Gly Thr Gln Val Thr Val Ser Ser
1 5 10

<210> SEQ ID NO 125
<211> LENGTH: 11
<212> TYPE: PRT
<213> ORGANISM: Vicugna pacos
<220> FEATURE:
<223> OTHER INFORMATION: FR4 of sdAb63

<400> SEQUENCE: 125

Trp Gly Gln Gly Thr Gln Val Thr Val Ser Ser
1 5 10

<210> SEQ ID NO 126
<211> LENGTH: 11
<212> TYPE: PRT
<213> ORGANISM: Vicugna pacos
<220> FEATURE:
<223> OTHER INFORMATION: FR4 of sdAb65

<400> SEQUENCE: 126

Trp Gly Arg Gly Thr Gln Val Thr Val Ser Ser
1 5 10

<210> SEQ ID NO 127
<211> LENGTH: 10
<212> TYPE: PRT
<213> ORGANISM: Artificial Sequence
<220> FEATURE:
<223> OTHER INFORMATION: GS_linker used as linker between the sdAb and the lytic peptide
<220> FEATURE:
<221> NAME/KEY: SITE
<222> LOCATION: 3,4
<223> OTHER INFORMATION: Xaa can be any amino acid

<400> SEQUENCE: 127

Gly Gly Gly Gly Ser Gly Gly Gly Gly Ser
1 5 10

<210> SEQ ID NO 128
<211> LENGTH: 15
<212> TYPE: PRT
<213> ORGANISM: Artificial Sequence
<220> FEATURE:
<223> OTHER INFORMATION: GSAA_linker used as linker between the sdAb and the lytic peptide
<220> FEATURE:
<221> NAME/KEY: SITE
<222> LOCATION: 3,4
<223> OTHER INFORMATION: Xaa can be any amino acid

<400> SEQUENCE: 128

Gly Gly Gly Gly Ser Glu Ala Ala Ala Lys Gly Gly Gly Gly Ser
1 5 10 15

<210> SEQ ID NO 129
<211> LENGTH: 28
<212> TYPE: PRT
<213> ORGANISM: Bos taurus
<220> FEATURE:
<223> OTHER INFORMATION: BMAP28A

<400> SEQUENCE: 129

Gly Gly Leu Arg Ser Leu Gly Arg Lys Ile Leu Arg Ala Trp Lys Lys
1 5 10 15

Tyr Gly Pro Ile Ile Val Pro Ile Ile Arg Ile Gly
20 25

<210> SEQ ID NO 130
<211> LENGTH: 11
<212> TYPE: PRT
<213> ORGANISM: Artificial Sequence
<220> FEATURE:
<223> OTHER INFORMATION: Modified Cysteine deleted Tachyplesin-I

<400> SEQUENCE: 130

Lys Trp Phe Arg Val Tyr Arg Gly Ile Tyr Arg
1 5 10

<210> SEQ ID NO 131
<211> LENGTH: 14
<212> TYPE: PRT
<213> ORGANISM: Polybia paulista
<220> FEATURE:
<223> OTHER INFORMATION: Polybia-MP1

<400> SEQUENCE: 131

Ile Asp Trp Lys Lys Leu Leu Asp Ala Ala Lys Gln Ile Leu
1 5 10

<210> SEQ ID NO 132
<211> LENGTH: 23
<212> TYPE: DNA
<213> ORGANISM: Artificial Sequence
<220> FEATURE:
<223> OTHER INFORMATION: Primer CALL001 used to PCR amplify the VHH variable regions

<400> SEQUENCE: 132
gtcctggctg ctcttctaca agg 23

```
<210> SEQ ID NO 133
<211> LENGTH: 23
<212> TYPE: DNA
<213> ORGANISM: Artificial Sequence
<220> FEATURE:
<223> OTHER INFORMATION: Primer CALL002 used to PCR amplify the VHH
      variable regions

<400> SEQUENCE: 133

ggtacgtgct gttgaactgt tcc                                              23


<210> SEQ ID NO 134
<211> LENGTH: 29
<212> TYPE: DNA
<213> ORGANISM: Artificial Sequence
<220> FEATURE:
<223> OTHER INFORMATION: Primer VHH_back used to PCR amplify the VHH
      variable regions

<400> SEQUENCE: 134

gatgtgcagc tgcaggagtc tggrggagg                                        29


<210> SEQ ID NO 135
<211> LENGTH: 33
<212> TYPE: DNA
<213> ORGANISM: Artificial Sequence
<220> FEATURE:
<223> OTHER INFORMATION: Primer VHH_for used to PCR amplify the VHH
      variable regions

<400> SEQUENCE: 135

ggactagtgc ggccgctgga gacggtgacc tgg                                   33


<210> SEQ ID NO 136
<211> LENGTH: 121
<212> TYPE: PRT
<213> ORGANISM: Vicugna pacos
<220> FEATURE:
<223> OTHER INFORMATION: sdAb14 amino acid sequence

<400> SEQUENCE: 136

Met Gly Met Ala Glu Val Glu Val Val Ala Ser Gly Gly Asp Leu Ala
1               5                   10                  15

Gln Pro Gly Gly Ser Leu Arg Leu Ser Cys Ala Ala Ser Gly Phe Val
            20                  25                  30

Phe Ser Ser Tyr Ala Met Ile Trp Ala Arg Gln Ala Pro Gly Lys Gly
        35                  40                  45

Leu Glu Trp Val Ser Gly Ile Asn Ser Asp Ala Ser Gly Thr Trp Tyr
    50                  55                  60

Ala Asp Ser Val Lys Gly Arg Phe Thr Ile Ser Arg Asp Asn Ala Lys
65                  70                  75                  80

Asn Thr Leu Tyr Leu Gln Met Asn Ser Leu Lys Pro Asp Asp Thr Ala
                85                  90                  95

Val Tyr Phe Cys Leu His Ser Gly His Thr His Thr Arg Tyr Trp Gly
            100                 105                 110

Gln Gly Thr Gln Val Thr Val Ser Ser
        115                 120


<210> SEQ ID NO 137
<211> LENGTH: 129
<212> TYPE: PRT
<213> ORGANISM: Vicugna pacos
<220> FEATURE:
<223> OTHER INFORMATION: sdAb60 amino acid sequence
```

<400> SEQUENCE: 137

Met Gly Met Ala Glu Val Glu Val Val Ala Ser Gly Pro Gly Leu Val
1 5 10 15

Lys Pro Ser Gln Thr Leu Ser Leu Thr Cys Thr Val Ser Gly Asp Ser
20 25 30

Ile Thr Thr Thr Phe Ser His Trp Thr Trp Ile Arg Gln Ser Pro Glu
35 40 45

Lys Gly Leu Glu Trp Met Gly Ala Ile Gly Tyr Gly Gly Ser Ile Tyr
50 55 60

Tyr Ser Pro Ser Phe Lys Ser Arg Thr Ser Ile Ser Arg Asp Thr Ser
65 70 75 80

Arg Asn Gln Phe Thr Leu His Leu Ser Ser Val Thr Pro Glu Asp Thr
85 90 95

Ala Val Tyr Tyr Cys Ala Arg Leu Pro His Ser Ser Gly Tyr Ala Lys
100 105 110

Phe Gly His Leu Asp Tyr Trp Gly Gln Gly Thr Gln Val Thr Val Ser
115 120 125

Ser

<210> SEQ ID NO 138
<211> LENGTH: 124
<212> TYPE: PRT
<213> ORGANISM: Vicugna pacos
<220> FEATURE:
<223> OTHER INFORMATION: sdAbS amino acid sequence

<400> SEQUENCE: 138

Met Gly Met Ala Glu Val Glu Val Val Ala Ser Gly Gly Gly Leu Val
1 5 10 15

Gln Pro Gly Gly Ser Leu Arg Leu Ser Cys Ala Ala Ser Gly Phe Thr
20 25 30

Phe Ser Asn Tyr Trp Met Tyr Trp Ala Arg Gln Ala Pro Gly Lys Gly
35 40 45

Leu Glu Trp Val Ser Ala Ile Asp Gln Ser Gly Thr Thr Thr Arg Tyr
50 55 60

Ala Asp Ser Val Lys Gly Gln Phe Thr Ile Ser Arg Asp Asn Ala Lys
65 70 75 80

His Thr Leu Tyr Leu Gln Met Asn Ser Leu Lys Pro Glu Asp Thr Ala
85 90 95

Leu Tyr Tyr Cys Thr Thr Ser Gly Arg Tyr Tyr Ala Met Asp Tyr Trp
100 105 110

Gly Lys Gly Thr Gln Val Thr Val Ser Thr Ser Ser
115 120

<210> SEQ ID NO 139
<211> LENGTH: 363
<212> TYPE: DNA
<213> ORGANISM: Vicugna pacos
<220> FEATURE:
<223> OTHER INFORMATION: sdAb14 nucleic acid sequence

<400> SEQUENCE: 139
atgggaatgg ccgaggtgga ggtggtggcg tctgggggag acttggcgca gcctgggggg 60
tctctgagac tctcctgtgc agcctctgga ttcgtcttca gtagctatgc catgatctgg 120
gcccgccagg ctccaggaaa ggggctcgag tgggtgtccg gtattaatag tgatgctagt 180

-continued

```
ggcacatggt atgctgactc cgtgaagggc cgattcacta tctccagaga caacgccaag    240

aacacgttgt atctgcaaat gaacagcctg aaacctgatg acacggccgt gtatttctgt    300

cttcatagtg gtcatactca cacgcgctac tggggccagg ggacccaggt caccgtctcc    360

tcg                                                                  363


<210> SEQ ID NO 140
<211> LENGTH: 387
<212> TYPE: DNA
<213> ORGANISM: Vicugna pacos
<220> FEATURE:
<223> OTHER INFORMATION: sdAb60 nucleic acid sequence

<400> SEQUENCE: 140

atgggaatgg ccgaggtgga ggtggtggcg tcgggcccag gcctggtgaa accctcgcag     60

acactctccc tcacctgcac tgtctctggt gactccatca caaccacatt ttctcactgg    120

acctggatcc gccagtcccc agagaagggg ctggagtgga tgggagccat aggttatggt    180

ggcagtattt attacagccc atccttcaag agccgcactt ccatctccag ggacacgtcc    240

aggaaccaat ttaccctgca cctgtcatca gtgactcctg aagacacagc cgtctattac    300

tgtgccagac tcccccatag tagtggctat gccaagttcg gccaccttga ctactggggc    360

caggggaccc aggtcactgt ctcctcc                                        387


<210> SEQ ID NO 141
<211> LENGTH: 372
<212> TYPE: DNA
<213> ORGANISM: Vicugna pacos
<220> FEATURE:
<223> OTHER INFORMATION: sdAbS nucleic acid sequence

<400> SEQUENCE: 141

atgggaatgg ccgaggtgga ggtggtggcg tctgggggag gcttggtgca gcctgggggg     60

tctctaagac tctcctgtgc agcctctgga ttcaccttca gtaactactg gatgtattgg    120

gcccgtcagg ctccagggaa ggggctcgag tgggtgtcag ctatagatca gagtggtact    180

accacaagat atgcagactc cgtgaagggc caattcacca tctctagaga caacgccaag    240

cacacgctgt atctgcaaat gaacagcctg aaacctgagg acacggccct gtattactgt    300

acgacctcag gcaggtacta cgccatggac tactggggca aagggaccca ggtcactgtc    360

tccacatcgt cg                                                        372


<210> SEQ ID NO 142
<211> LENGTH: 162
<212> TYPE: PRT
<213> ORGANISM: Artificial Sequence
<220> FEATURE:
<223> OTHER INFORMATION: sdAb 14 linked to the lytic peptide BMAP28A by
      a GS_linker
<220> FEATURE:
<221> NAME/KEY: SITE
<222> LOCATION: 123,124
<223> OTHER INFORMATION: Xaa can be any amino acid

<400> SEQUENCE: 142

Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45
```

```
Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Gly Gly Gly Gly
        115                 120                 125

Ser Gly Gly Gly Gly Ser Gly Gly Leu Arg Ser Leu Gly Arg Lys Ile
    130                 135                 140

Leu Arg Ala Trp Lys Lys Tyr Gly Pro Ile Ile Val Pro Ile Ile Arg
145                 150                 155                 160

Ile Gly


<210> SEQ ID NO 143
<211> LENGTH: 167
<212> TYPE: PRT
<213> ORGANISM: Artificial Sequence
<220> FEATURE:
<223> OTHER INFORMATION: sdAb 14_ linked to the lytic peptide BMAP28A by
      a GSAA_linker
<220> FEATURE:
<221> NAME/KEY: SITE
<222> LOCATION: 123,124
<223> OTHER INFORMATION: Xaa can be any amino acid

<400> SEQUENCE: 143

Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45

Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Gly Gly Gly Gly
        115                 120                 125

Ser Glu Ala Ala Ala Lys Gly Gly Gly Gly Ser Gly Gly Leu Arg Ser
    130                 135                 140

Leu Gly Arg Lys Ile Leu Arg Ala Trp Lys Lys Tyr Gly Pro Ile Ile
145                 150                 155                 160

Val Pro Ile Ile Arg Ile Gly
                165


<210> SEQ ID NO 144
<211> LENGTH: 150
<212> TYPE: PRT
<213> ORGANISM: Artificial Sequence
<220> FEATURE:
<223> OTHER INFORMATION: sdAb 14 linked to the lytic peptide modified
```

-continued cysteine deleted Tachyplesin-I by a GS_linker
<220> FEATURE:
<221> NAME/KEY: SITE
<222> LOCATION: 123,124
<223> OTHER INFORMATION: Xaa can be any amino acid

<400> SEQUENCE: 144

```
Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45

Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Gly Gly Gly Gly
        115                 120                 125

Ser Glu Ala Ala Ala Lys Gly Gly Gly Gly Ser Lys Trp Phe Arg Val
    130                 135                 140

Tyr Arg Gly Ile Tyr Arg
145                 150
```

<210> SEQ ID NO 145
<211> LENGTH: 150
<212> TYPE: PRT
<213> ORGANISM: Artificial Sequence
<220> FEATURE:
<223> OTHER INFORMATION: sdAb 14 linked to the lytic peptide modified cysteine deleted Tachyplesin-I by a GSAA_linker
<220> FEATURE:
<221> NAME/KEY: SITE
<222> LOCATION: 123,124
<223> OTHER INFORMATION: Xaa can be any amino acid

<400> SEQUENCE: 145

```
Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45

Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Gly Gly Gly Gly
        115                 120                 125

Ser Glu Ala Ala Ala Lys Gly Gly Gly Gly Ser Lys Trp Phe Arg Val
    130                 135                 140
```

```
Tyr Arg Gly Ile Tyr Arg
145                 150


<210> SEQ ID NO 146
<211> LENGTH: 153
<212> TYPE: PRT
<213> ORGANISM: Artificial Sequence
<220> FEATURE:
<223> OTHER INFORMATION: sdAb 14_ linked to the lytic peptide
      Polybia-MP1 by a GSAA_linker
<220> FEATURE:
<221> NAME/KEY: SITE
<222> LOCATION: 123,124
<223> OTHER INFORMATION: Xaa can be any amino acid

<400> SEQUENCE: 146

Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45

Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Gly Gly Gly Gly
        115                 120                 125

Ser Glu Ala Ala Ala Lys Gly Gly Gly Gly Ser Ile Asp Trp Lys Lys
    130                 135                 140

Leu Leu Asp Ala Ala Lys Gln Ile Leu
145                 150


<210> SEQ ID NO 147
<211> LENGTH: 170
<212> TYPE: PRT
<213> ORGANISM: Artificial Sequence
<220> FEATURE:
<223> OTHER INFORMATION: sdAb60 linked to the lytic peptide BMAP28A by a
      GS_linker
<220> FEATURE:
<221> NAME/KEY: SITE
<222> LOCATION: 131,132
<223> OTHER INFORMATION: Xaa can be any amino acid

<400> SEQUENCE: 147

Gly Met Ala Glu Val Glu Val Val Ala Ser Gly Pro Gly Leu Val Lys
1               5                   10                  15

Pro Ser Gln Thr Leu Ser Leu Thr Cys Thr Val Ser Gly Asp Ser Ile
            20                  25                  30

Thr Thr Thr Phe Ser His Trp Thr Trp Ile Arg Gln Ser Pro Glu Lys
        35                  40                  45

Gly Leu Glu Trp Met Gly Ala Ile Gly Tyr Gly Gly Ser Ile Tyr Tyr
    50                  55                  60

Ser Pro Ser Phe Lys Ser Arg Thr Ser Ile Ser Arg Asp Thr Ser Arg
65                  70                  75                  80
```

```
Asn Gln Phe Thr Leu His Leu Ser Ser Val Thr Pro Glu Asp Thr Ala
                85                  90                  95

Val Tyr Tyr Cys Ala Arg Leu Pro His Ser Ser Gly Tyr Ala Lys Phe
            100                 105                 110

Gly His Leu Asp Tyr Trp Gly Gln Gly Thr Gln Val Thr Val Ser Ser
        115                 120                 125

Ala Ala Xaa Xaa Gly Gly Gly Gly Ser Gly Gly Gly Gly Ser Gly Gly
    130                 135                 140

Leu Arg Ser Leu Gly Arg Lys Ile Leu Arg Ala Trp Lys Lys Tyr Gly
145                 150                 155                 160

Pro Ile Ile Val Pro Ile Ile Arg Ile Gly
                165                 170
```

<210> SEQ ID NO 148
<211> LENGTH: 175
<212> TYPE: PRT
<213> ORGANISM: Artificial Sequence
<220> FEATURE:
<223> OTHER INFORMATION: sdAb60_ linked to the lytic peptide BMAP28A by a GSAA_linker
<220> FEATURE:
<221> NAME/KEY: SITE
<222> LOCATION: 131,132
<223> OTHER INFORMATION: Xaa can be any amino acid

<400> SEQUENCE: 148

```
Gly Met Ala Glu Val Glu Val Val Ala Ser Gly Pro Gly Leu Val Lys
1               5                   10                  15

Pro Ser Gln Thr Leu Ser Leu Thr Cys Thr Val Ser Gly Asp Ser Ile
            20                  25                  30

Thr Thr Thr Phe Ser His Trp Thr Trp Ile Arg Gln Ser Pro Glu Lys
        35                  40                  45

Gly Leu Glu Trp Met Gly Ala Ile Gly Tyr Gly Gly Ser Ile Tyr Tyr
    50                  55                  60

Ser Pro Ser Phe Lys Ser Arg Thr Ser Ile Ser Arg Asp Thr Ser Arg
65                  70                  75                  80

Asn Gln Phe Thr Leu His Leu Ser Ser Val Thr Pro Glu Asp Thr Ala
                85                  90                  95

Val Tyr Tyr Cys Ala Arg Leu Pro His Ser Ser Gly Tyr Ala Lys Phe
            100                 105                 110

Gly His Leu Asp Tyr Trp Gly Gln Gly Thr Gln Val Thr Val Ser Ser
        115                 120                 125

Ala Ala Xaa Xaa Gly Gly Gly Gly Ser Glu Ala Ala Ala Lys Gly Gly
    130                 135                 140

Gly Gly Ser Gly Gly Leu Arg Ser Leu Gly Arg Lys Ile Leu Arg Ala
145                 150                 155                 160

Trp Lys Lys Tyr Gly Pro Ile Ile Val Pro Ile Ile Arg Ile Gly
                165                 170                 175
```

<210> SEQ ID NO 149
<211> LENGTH: 153
<212> TYPE: PRT
<213> ORGANISM: Artificial Sequence
<220> FEATURE:
<223> OTHER INFORMATION: sdAb60 linked to the lytic peptide modified cysteine deleted Tachyplesin-I by a GS_linker
<220> FEATURE:
<221> NAME/KEY: SITE
<222> LOCATION: 131,132
<223> OTHER INFORMATION: Xaa can be any amino acid

<400> SEQUENCE: 149

Gly Met Ala Glu Val Glu Val Val Ala Ser Gly Pro Gly Leu Val Lys
1 5 10 15

Pro Ser Gln Thr Leu Ser Leu Thr Cys Thr Val Ser Gly Asp Ser Ile
20 25 30

Thr Thr Thr Phe Ser His Trp Thr Trp Ile Arg Gln Ser Pro Glu Lys
35 40 45

Gly Leu Glu Trp Met Gly Ala Ile Gly Tyr Gly Gly Ser Ile Tyr Tyr
50 55 60

Ser Pro Ser Phe Lys Ser Arg Thr Ser Ile Ser Arg Asp Thr Ser Arg
65 70 75 80

Asn Gln Phe Thr Leu His Leu Ser Ser Val Thr Pro Glu Asp Thr Ala
85 90 95

Val Tyr Tyr Cys Ala Arg Leu Pro His Ser Ser Gly Tyr Ala Lys Phe
100 105 110

Gly His Leu Asp Tyr Trp Gly Gln Gly Thr Gln Val Thr Val Ser Ser
115 120 125

Ala Ala Xaa Xaa Gly Gly Gly Gly Ser Gly Gly Gly Gly Ser Lys Trp
130 135 140

Phe Arg Val Tyr Arg Gly Ile Tyr Arg
145 150

<210> SEQ ID NO 150
<211> LENGTH: 158
<212> TYPE: PRT
<213> ORGANISM: Artificial Sequence
<220> FEATURE:
<223> OTHER INFORMATION: sdAb60 linked to the lytic peptide modified cysteine deleted Tachyplesin-I by a GSAA_linker
<220> FEATURE:
<221> NAME/KEY: SITE
<222> LOCATION: 131,132
<223> OTHER INFORMATION: Xaa can be any amino acid

<400> SEQUENCE: 150

Gly Met Ala Glu Val Glu Val Val Ala Ser Gly Pro Gly Leu Val Lys
1 5 10 15

Pro Ser Gln Thr Leu Ser Leu Thr Cys Thr Val Ser Gly Asp Ser Ile
20 25 30

Thr Thr Thr Phe Ser His Trp Thr Trp Ile Arg Gln Ser Pro Glu Lys
35 40 45

Gly Leu Glu Trp Met Gly Ala Ile Gly Tyr Gly Gly Ser Ile Tyr Tyr
50 55 60

Ser Pro Ser Phe Lys Ser Arg Thr Ser Ile Ser Arg Asp Thr Ser Arg
65 70 75 80

Asn Gln Phe Thr Leu His Leu Ser Ser Val Thr Pro Glu Asp Thr Ala
85 90 95

Val Tyr Tyr Cys Ala Arg Leu Pro His Ser Ser Gly Tyr Ala Lys Phe
100 105 110

Gly His Leu Asp Tyr Trp Gly Gln Gly Thr Gln Val Thr Val Ser Ser
115 120 125

Ala Ala Xaa Xaa Gly Gly Gly Gly Ser Glu Ala Ala Ala Lys Gly Gly
130 135 140

Gly Gly Ser Lys Trp Phe Arg Val Tyr Arg Gly Ile Tyr Arg
145 150 155

<210> SEQ ID NO 151

<211> LENGTH: 161
<212> TYPE: PRT
<213> ORGANISM: Artificial Sequence
<220> FEATURE:
<223> OTHER INFORMATION: sdAb60_ linked to the lytic peptide Polybia-MP1 by a GSAA_linker
<220> FEATURE:
<221> NAME/KEY: SITE
<222> LOCATION: 131,132
<223> OTHER INFORMATION: Xaa can be any amino acid

<400> SEQUENCE: 151

```
Gly Met Ala Glu Val Glu Val Val Ala Ser Gly Pro Gly Leu Val Lys
1               5                   10                  15

Pro Ser Gln Thr Leu Ser Leu Thr Cys Thr Val Ser Gly Asp Ser Ile
            20                  25                  30

Thr Thr Thr Phe Ser His Trp Thr Trp Ile Arg Gln Ser Pro Glu Lys
        35                  40                  45

Gly Leu Glu Trp Met Gly Ala Ile Gly Tyr Gly Gly Ser Ile Tyr Tyr
    50                  55                  60

Ser Pro Ser Phe Lys Ser Arg Thr Ser Ile Ser Arg Asp Thr Ser Arg
65                  70                  75                  80

Asn Gln Phe Thr Leu His Leu Ser Ser Val Thr Pro Glu Asp Thr Ala
                85                  90                  95

Val Tyr Tyr Cys Ala Arg Leu Pro His Ser Ser Gly Tyr Ala Lys Phe
            100                 105                 110

Gly His Leu Asp Tyr Trp Gly Gln Gly Thr Gln Val Thr Val Ser Ser
        115                 120                 125

Ala Ala Xaa Xaa Gly Gly Gly Gly Ser Glu Ala Ala Ala Lys Gly Gly
    130                 135                 140

Gly Gly Ser Ile Asp Trp Lys Lys Leu Leu Asp Ala Ala Lys Gln Ile
145                 150                 155                 160

Leu
```

<210> SEQ ID NO 152
<211> LENGTH: 165
<212> TYPE: PRT
<213> ORGANISM: Artificial Sequence
<220> FEATURE:
<223> OTHER INFORMATION: sdAbS_ linked to the lytic peptide BMAP28A by a GS_linker
<220> FEATURE:
<221> NAME/KEY: SITE
<222> LOCATION: 126,127
<223> OTHER INFORMATION: Xaa can be any amino acid

<400> SEQUENCE: 152

```
Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
```

```
            100                 105                 110

Lys Gly Thr Gln Val Thr Val Ser Thr Ser Ser Ala Ala Xaa Xaa Gly
        115                 120                 125

Gly Gly Gly Ser Gly Gly Gly Gly Ser Gly Gly Leu Arg Ser Leu Gly
    130                 135                 140

Arg Lys Ile Leu Arg Ala Trp Lys Lys Tyr Gly Pro Ile Ile Val Pro
145                 150                 155                 160

Ile Ile Arg Ile Gly
                165


<210> SEQ ID NO 153
<211> LENGTH: 170
<212> TYPE: PRT
<213> ORGANISM: Artificial Sequence
<220> FEATURE:
<223> OTHER INFORMATION: sdAbS_ linked to the lytic peptide BMAP28A by a
      GSAA_linker
<220> FEATURE:
<221> NAME/KEY: SITE
<222> LOCATION: 126,127
<223> OTHER INFORMATION: Xaa can be any amino acid

<400> SEQUENCE: 153

Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Gly
        115                 120                 125

Gly Gly Gly Ser Glu Ala Ala Ala Lys Gly Gly Gly Gly Ser Gly Gly
    130                 135                 140

Leu Arg Ser Leu Gly Arg Lys Ile Leu Arg Ala Trp Lys Lys Tyr Gly
145                 150                 155                 160

Pro Ile Ile Val Pro Ile Ile Arg Ile Gly
                165                 170


<210> SEQ ID NO 154
<211> LENGTH: 148
<212> TYPE: PRT
<213> ORGANISM: Artificial Sequence
<220> FEATURE:
<223> OTHER INFORMATION: sdAbS linked to the lytic peptide modified
      cysteine deleted Tachyplesin-I by a GS_linker
<220> FEATURE:
<221> NAME/KEY: SITE
<222> LOCATION: 126,127
<223> OTHER INFORMATION: Xaa can be any amino acid

<400> SEQUENCE: 154

Gly Met Ala Glu Val Glu Val Val Ala Ser Gly Gly Gly Leu Val Gln
1               5                   10                  15
```

```
Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Gly
        115                 120                 125

Gly Gly Gly Ser Gly Gly Gly Gly Ser Lys Trp Phe Arg Val Tyr Arg
    130                 135                 140

Gly Ile Tyr Arg
145
```

<210> SEQ ID NO 155
<211> LENGTH: 153
<212> TYPE: PRT
<213> ORGANISM: Artificial Sequence
<220> FEATURE:
<223> OTHER INFORMATION: sdAbS linked to the lytic peptide modified cysteine deleted Tachyplesin-I by a GSAA_linker
<220> FEATURE:
<221> NAME/KEY: SITE
<222> LOCATION: 126,127
<223> OTHER INFORMATION: Xaa can be any amino acid

<400> SEQUENCE: 155

```
Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Gly
        115                 120                 125

Gly Gly Gly Ser Glu Ala Ala Ala Lys Gly Gly Gly Gly Ser Lys Trp
    130                 135                 140

Phe Arg Val Tyr Arg Gly Ile Tyr Arg
145                 150
```

<210> SEQ ID NO 156
<211> LENGTH: 156
<212> TYPE: PRT
<213> ORGANISM: Artificial Sequence
<220> FEATURE:

<223> OTHER INFORMATION: sdAbS_ linked to the lytic peptide Polybia-MP1
      by a GSAA_linker
<220> FEATURE:
<221> NAME/KEY: SITE
<222> LOCATION: 126,127
<223> OTHER INFORMATION: Xaa can be any amino acid

<400> SEQUENCE: 156

```
Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Gly
        115                 120                 125

Gly Gly Gly Ser Glu Ala Ala Ala Lys Gly Gly Gly Gly Ser Ile Asp
    130                 135                 140

Trp Lys Lys Leu Leu Asp Ala Ala Lys Gln Ile Leu
145                 150                 155
```

<210> SEQ ID NO 157
<211> LENGTH: 5
<212> TYPE: PRT
<213> ORGANISM: Vicugna pacos
<220> FEATURE:
<223> OTHER INFORMATION: CDR1 of sdAb14

<400> SEQUENCE: 157

```
Ser Tyr Ala Met Ile
1               5
```

<210> SEQ ID NO 158
<211> LENGTH: 7
<212> TYPE: PRT
<213> ORGANISM: Vicugna pacos
<220> FEATURE:
<223> OTHER INFORMATION: CDR1 of sdAb60

<400> SEQUENCE: 158

```
Thr Thr Phe Ser His Trp Thr
1               5
```

<210> SEQ ID NO 159
<211> LENGTH: 5
<212> TYPE: PRT
<213> ORGANISM: Vicugna pacos
<220> FEATURE:
<223> OTHER INFORMATION: CDR1 of sdAbS

<400> SEQUENCE: 159

```
Asn Tyr Trp Met Tyr
1               5
```

<210> SEQ ID NO 160
<211> LENGTH: 17
<212> TYPE: PRT
<213> ORGANISM: Vicugna pacos
<220> FEATURE:
<223> OTHER INFORMATION: CDR2 of sdAb14

<400> SEQUENCE: 160

```
Gly Ile Asn Ser Asp Ala Ser Gly Thr Trp Tyr Ala Asp Ser Val Lys
1               5                   10                  15

Gly
```

<210> SEQ ID NO 161
<211> LENGTH: 16
<212> TYPE: PRT
<213> ORGANISM: Vicugna pacos
<220> FEATURE:
<223> OTHER INFORMATION: CDR2 of sdAb60

<400> SEQUENCE: 161

```
Ala Ile Gly Tyr Gly Gly Ser Ile Tyr Tyr Ser Pro Ser Phe Lys Ser
1               5                   10                  15
```

<210> SEQ ID NO 162
<211> LENGTH: 17
<212> TYPE: PRT
<213> ORGANISM: Vicugna pacos
<220> FEATURE:
<223> OTHER INFORMATION: CDR2 of sdAbS

<400> SEQUENCE: 162

```
Ala Ile Asp Gln Ser Gly Thr Thr Thr Arg Tyr Ala Asp Ser Val Lys
1               5                   10                  15

Gly
```

<210> SEQ ID NO 163
<211> LENGTH: 8
<212> TYPE: PRT
<213> ORGANISM: Vicugna pacos
<220> FEATURE:
<223> OTHER INFORMATION: CDR3 of sdAb14

<400> SEQUENCE: 163

```
Ser Gly His Thr His Thr Arg Tyr
1               5
```

<210> SEQ ID NO 164
<211> LENGTH: 13
<212> TYPE: PRT
<213> ORGANISM: Vicugna pacos
<220> FEATURE:
<223> OTHER INFORMATION: CDR3 of sdAb60

<400> SEQUENCE: 164

```
Leu Pro His Ser Ser Gly Tyr Ala Lys Phe Gly His Leu
1               5                   10
```

<210> SEQ ID NO 165
<211> LENGTH: 7
<212> TYPE: PRT
<213> ORGANISM: Vicugna pacos
<220> FEATURE:
<223> OTHER INFORMATION: CDR3 of sdAbS

<400> SEQUENCE: 165

```
Ser Gly Arg Tyr Tyr Ala Met
```

```
1               5


<210> SEQ ID NO 166
<211> LENGTH: 34
<212> TYPE: PRT
<213> ORGANISM: Vicugna pacos
<220> FEATURE:
<223> OTHER INFORMATION: FR1 of sdAb14

<400> SEQUENCE: 166

Met Gly Met Ala Glu Val Glu Val Val Ala Ser Gly Gly Asp Leu Ala
1               5                   10                  15

Gln Pro Gly Gly Ser Leu Arg Leu Ser Cys Ala Ala Ser Gly Phe Val
            20                  25                  30

Phe Ser


<210> SEQ ID NO 167
<211> LENGTH: 35
<212> TYPE: PRT
<213> ORGANISM: Vicugna pacos
<220> FEATURE:
<223> OTHER INFORMATION: FR1 of sdAb60

<400> SEQUENCE: 167

Met Gly Met Ala Glu Glu Val Glu Val Val Ala Ser Gly Pro Gly Leu
1               5                   10                  15

Val Lys Pro Ser Gln Thr Leu Ser Leu Thr Cys Thr Val Ser Gly Asp
            20                  25                  30

Ser Ile Thr
        35


<210> SEQ ID NO 168
<211> LENGTH: 34
<212> TYPE: PRT
<213> ORGANISM: Vicugna pacos
<220> FEATURE:
<223> OTHER INFORMATION: FR1 of sdAbS

<400> SEQUENCE: 168

Met Gly Met Ala Glu Val Glu Val Val Ala Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Ser


<210> SEQ ID NO 169
<211> LENGTH: 14
<212> TYPE: PRT
<213> ORGANISM: Vicugna pacos
<220> FEATURE:
<223> OTHER INFORMATION: FR2 of sdAb14

<400> SEQUENCE: 169

Trp Ala Arg Gln Ala Pro Gly Lys Gly Leu Glu Trp Val Ser
1               5                   10


<210> SEQ ID NO 170
<211> LENGTH: 14
<212> TYPE: PRT
<213> ORGANISM: Vicugna pacos
<220> FEATURE:
<223> OTHER INFORMATION: FR2 of sdAb60

<400> SEQUENCE: 170
```

Trp Ile Arg Gln Ser Pro Glu Lys Gly Leu Glu Trp Met Gly
1 5 10

<210> SEQ ID NO 171
<211> LENGTH: 14
<212> TYPE: PRT
<213> ORGANISM: Vicugna pacos
<220> FEATURE:
<223> OTHER INFORMATION: FR2 of sdAbS

<400> SEQUENCE: 171

Trp Ala Arg Gln Ala Pro Gly Lys Gly Leu Glu Trp Val Ser
1 5 10

<210> SEQ ID NO 172
<211> LENGTH: 32
<212> TYPE: PRT
<213> ORGANISM: Vicugna pacos
<220> FEATURE:
<223> OTHER INFORMATION: FR3 of sdAb14

<400> SEQUENCE: 172

Arg Phe Thr Ile Ser Arg Asp Asn Ala Lys Asn Thr Leu Tyr Leu Gln
1 5 10 15

Met Asn Ser Leu Lys Pro Asp Asp Thr Ala Val Tyr Phe Cys Leu His
20 25 30

<210> SEQ ID NO 173
<211> LENGTH: 32
<212> TYPE: PRT
<213> ORGANISM: Vicugna pacos
<220> FEATURE:
<223> OTHER INFORMATION: FR3 of sdAb60

<400> SEQUENCE: 173

Arg Thr Ser Ile Ser Arg Asp Thr Ser Arg Asn Gln Phe Thr Leu His
1 5 10 15

Leu Ser Ser Val Thr Pro Glu Asp Thr Ala Val Tyr Tyr Cys Ala Arg
20 25 30

<210> SEQ ID NO 174
<211> LENGTH: 32
<212> TYPE: PRT
<213> ORGANISM: Vicugna pacos
<220> FEATURE:
<223> OTHER INFORMATION: FR3 of sdAbS

<400> SEQUENCE: 174

Gln Phe Thr Ile Ser Arg Asp Asn Ala Lys His Thr Leu Tyr Leu Gln
1 5 10 15

Met Asn Ser Leu Lys Pro Glu Asp Thr Ala Leu Tyr Tyr Cys Thr Thr
20 25 30

<210> SEQ ID NO 175
<211> LENGTH: 11
<212> TYPE: PRT
<213> ORGANISM: Vicugna pacos
<220> FEATURE:
<223> OTHER INFORMATION: FR4 of sdAb14

<400> SEQUENCE: 175

Trp Gly Gln Gly Thr Gln Val Thr Val Ser Ser
1 5 10

<210> SEQ ID NO 176
<211> LENGTH: 13
<212> TYPE: PRT
<213> ORGANISM: Vicugna pacos
<220> FEATURE:
<223> OTHER INFORMATION: FR4 of sdAb60

<400> SEQUENCE: 176

Asp Tyr Trp Gly Gln Gly Thr Gln Val Thr Val Ser Ser
1 5 10

<210> SEQ ID NO 177
<211> LENGTH: 15
<212> TYPE: PRT
<213> ORGANISM: Vicugna pacos
<220> FEATURE:
<223> OTHER INFORMATION: FR4 of sdAbS

<400> SEQUENCE: 177

Asp Tyr Trp Gly Lys Gly Thr Gln Val Thr Val Ser Thr Ser Ser
1 5 10 15

<210> SEQ ID NO 178
<211> LENGTH: 17
<212> TYPE: PRT
<213> ORGANISM: Artificial Sequence
<220> FEATURE:
<223> OTHER INFORMATION: SRGS_linker used as linker between the sdAb and the lytic peptide
<220> FEATURE:
<221> NAME/KEY: SITE
<222> LOCATION: 3,4
<223> OTHER INFORMATION: Xaa can be any amino acid

<400> SEQUENCE: 178

Ser Arg Gly Ser Ser Gly Ser Ser Ser Ser Gly Ser Ser Gly Gly Ser
1 5 10 15

Gly

<210> SEQ ID NO 179
<211> LENGTH: 174
<212> TYPE: PRT
<213> ORGANISM: Artificial Sequence
<220> FEATURE:
<223> OTHER INFORMATION: sdAb26 linked to the lytic peptide BMAP28A by a SRGS_linker
<220> FEATURE:
<221> NAME/KEY: SITE
<222> LOCATION: 128,129
<223> OTHER INFORMATION: Xaa can be any amino acid

<400> SEQUENCE: 179

Gly Ala His Val Gln Leu Val Glu Ser Gly Gly Gly Leu Val Gln Pro
1 5 10 15

Gly Gly Ser Leu Arg Leu Ser Cys Glu Gly Ser Gly Met Thr Phe Ser
20 25 30

Ile Tyr Asp Phe Gly Trp Tyr Arg Gln Val Pro Gly Asn Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val
65 70 75 80

Ser Leu Gln Met Asn Thr Leu Arg Pro Glu Asp Thr Ala Ile Tyr Tyr
85 90 95

Cys Val Ala Arg Trp Thr Phe Gly Ile Gln Arg Gly Asp Tyr Tyr Ile

```
            100                 105                 110

Trp Ser Trp Lys Gln Gly Thr Gln Val Thr Val Ser Ser Ala Ala Xaa
        115                 120                 125

Xaa Ser Arg Gly Ser Ser Gly Ser Ser Ser Ser Gly Ser Ser Gly Gly
    130                 135                 140

Ser Gly Gly Gly Leu Arg Ser Leu Gly Arg Lys Ile Leu Arg Ala Trp
145                 150                 155                 160

Lys Lys Tyr Gly Pro Ile Ile Val Pro Ile Ile Arg Ile Gly
                165                 170


<210> SEQ ID NO 180
<211> LENGTH: 157
<212> TYPE: PRT
<213> ORGANISM: Artificial Sequence
<220> FEATURE:
<223> OTHER INFORMATION: sdAb26 linked to the lytic peptide modified
      cysteine deleted Tachyplesin-I by a SRGS linker
<220> FEATURE:
<221> NAME/KEY: SITE
<222> LOCATION: 128,129
<223> OTHER INFORMATION: Xaa can be any amino acid

<400> SEQUENCE: 180

Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
            20                  25                  30

Ile Tyr Asp Phe Gly Trp Tyr Arg Gln Val Pro Gly Asn Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Tyr Ile
            100                 105                 110

Trp Ser Trp Lys Gln Gly Thr Gln Val Thr Val Ser Ser Ala Ala Xaa
        115                 120                 125

Xaa Ser Arg Gly Ser Ser Gly Ser Ser Ser Ser Gly Ser Ser Gly Gly
    130                 135                 140

Ser Gly Lys Trp Phe Arg Val Tyr Arg Gly Ile Tyr Arg
145                 150                 155


<210> SEQ ID NO 181
<211> LENGTH: 153
<212> TYPE: PRT
<213> ORGANISM: Artificial Sequence
<220> FEATURE:
<223> OTHER INFORMATION: sdAb 26 linked to the lytic peptide Polybia-MP1
      by a GS_linker
<220> FEATURE:
<221> NAME/KEY: SITE
<222> LOCATION: 128,129
<223> OTHER INFORMATION: Xaa can be any amino acid

<400> SEQUENCE: 181

Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
            20                  25                  30
```

```
Ile Tyr Asp Phe Gly Trp Tyr Arg Gln Val Pro Gly Asn Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Tyr Ile
            100                 105                 110

Trp Ser Trp Lys Gln Gly Thr Gln Val Thr Val Ser Ser Ala Ala Xaa
        115                 120                 125

Xaa Gly Gly Gly Gly Ser Gly Gly Gly Gly Ser Ile Asp Trp Lys Lys
    130                 135                 140

Leu Leu Asp Ala Ala Lys Gln Ile Leu
145                 150
```

<210> SEQ ID NO 182
<211> LENGTH: 160
<212> TYPE: PRT
<213> ORGANISM: Artificial Sequence
<220> FEATURE:
<223> OTHER INFORMATION: sdAb 26 linked to the lytic peptide Polybia-MP1 by a SRGS linker
<220> FEATURE:
<221> NAME/KEY: SITE
<222> LOCATION: 128,129
<223> OTHER INFORMATION: Xaa can be any amino acid

<400> SEQUENCE: 182

```
Gly Ala His Val Gln Leu Val Glu Ser Gly Gly Gly Leu Val Gln Pro
1               5                   10                  15

Gly Gly Ser Leu Arg Leu Ser Cys Glu Gly Ser Gly Met Thr Phe Ser
            20                  25                  30

Ile Tyr Asp Phe Gly Trp Tyr Arg Gln Val Pro Gly Asn Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Tyr Ile
            100                 105                 110

Trp Ser Trp Lys Gln Gly Thr Gln Val Thr Val Ser Ser Ala Ala Xaa
        115                 120                 125

Xaa Ser Arg Gly Ser Ser Gly Ser Ser Ser Ser Gly Ser Ser Gly Gly
    130                 135                 140

Ser Gly Ile Asp Trp Lys Lys Leu Leu Asp Ala Ala Lys Gln Ile Leu
145                 150                 155                 160
```

<210> SEQ ID NO 183
<211> LENGTH: 173
<212> TYPE: PRT
<213> ORGANISM: Artificial Sequence
<220> FEATURE:
<223> OTHER INFORMATION: sdAb37 linked to the lytic peptide BMAP28A by a SRGS linker
<220> FEATURE:

<221> NAME/KEY: SITE
<222> LOCATION: 127,128
<223> OTHER INFORMATION: Xaa can be any amino acid

<400> SEQUENCE: 183

```
Gly Asp Val Gln Leu Gln Glu Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Gly Lys Gly Leu Glu Trp
        35                  40                  45

Val Ser Gly Ile Tyr Arg Asp Gly Ile Asp Thr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Asp Leu Leu Ala Gly Trp Gly Pro Leu Ile Ser Trp His
            100                 105                 110

Tyr Trp Gly Lys Gly Thr Gln Val Thr Val Ser Ser Ala Ala Xaa Xaa
        115                 120                 125

Ser Arg Gly Ser Ser Gly Ser Ser Ser Ser Gly Ser Ser Gly Gly Ser
    130                 135                 140

Gly Gly Gly Leu Arg Ser Leu Gly Arg Lys Ile Leu Arg Ala Trp Lys
145                 150                 155                 160

Lys Tyr Gly Pro Ile Ile Val Pro Ile Ile Arg Ile Gly
                165                 170
```

<210> SEQ ID NO 184
<211> LENGTH: 156
<212> TYPE: PRT
<213> ORGANISM: Artificial Sequence
<220> FEATURE:
<223> OTHER INFORMATION: sdAb 37 linked to the lytic peptide modified cysteine deleted Tachyplesin-I by a SRGS linker
<220> FEATURE:
<221> NAME/KEY: SITE
<222> LOCATION: 127,128
<223> OTHER INFORMATION: Xaa can be any amino acid

<400> SEQUENCE: 184

```
Gly Asp Val Gln Leu Gln Glu Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Gly Lys Gly Leu Glu Trp
        35                  40                  45

Val Ser Gly Ile Tyr Arg Asp Gly Ile Asp Thr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Asp Leu Leu Ala Gly Trp Gly Pro Leu Ile Ser Trp His
            100                 105                 110

Tyr Trp Gly Lys Gly Thr Gln Val Thr Val Ser Ser Ala Ala Xaa Xaa
        115                 120                 125

Ser Arg Gly Ser Ser Gly Ser Ser Ser Ser Gly Ser Ser Gly Gly Ser
```

```
    130                 135                 140

Gly Lys Trp Phe Arg Val Tyr Arg Gly Ile Tyr Arg
145                 150                 155


<210> SEQ ID NO 185
<211> LENGTH: 152
<212> TYPE: PRT
<213> ORGANISM: Artificial Sequence
<220> FEATURE:
<223> OTHER INFORMATION: sdAb 37 linked to the lytic peptide Polybia-MP1
      by a GS_linker
<220> FEATURE:
<221> NAME/KEY: SITE
<222> LOCATION: 127,128
<223> OTHER INFORMATION: Xaa can be any amino acid

<400> SEQUENCE: 185

Gly Asp Val Gln Leu Gln Glu Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Gly Lys Gly Leu Glu Trp
        35                  40                  45

Val Ser Gly Ile Tyr Arg Asp Gly Ile Asp Thr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Asp Leu Leu Ala Gly Trp Gly Pro Leu Ile Ser Trp His
            100                 105                 110

Tyr Trp Gly Lys Gly Thr Gln Val Thr Val Ser Ser Ala Ala Xaa Xaa
        115                 120                 125

Gly Gly Gly Gly Ser Gly Gly Gly Gly Ser Ile Asp Trp Lys Lys Leu
    130                 135                 140

Leu Asp Ala Ala Lys Gln Ile Leu
145                 150


<210> SEQ ID NO 186
<211> LENGTH: 159
<212> TYPE: PRT
<213> ORGANISM: Artificial Sequence
<220> FEATURE:
<223> OTHER INFORMATION: sdAb37 linked to the lytic peptide Polybia-MP1
      by a SRGS linker
<220> FEATURE:
<221> NAME/KEY: SITE
<222> LOCATION: 127,128
<223> OTHER INFORMATION: Xaa can be any amino acid

<400> SEQUENCE: 186

Gly Asp Val Gln Leu Gln Glu Ser Gly Gly Gly Leu Ala Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Ala Arg Gln Ala Pro Gly Lys Gly Leu Glu Trp
        35                  40                  45

Val Ser Gly Ile Tyr Arg Asp Gly Ile Asp Thr Tyr Tyr Ala Asp Ser
    50                  55                  60

Val Lys Gly Arg Phe Thr Ile Ser Arg Asp Asn Ala Lys Asn Thr Leu
65                  70                  75                  80
```

```
Tyr Leu Gln Met Asn Ser Leu Lys Pro Glu Asp Thr Ala Leu Tyr Tyr
                85                  90                  95

Cys Ala Lys Asp Leu Leu Ala Gly Trp Gly Pro Leu Ile Ser Trp His
            100                 105                 110

Tyr Trp Gly Lys Gly Thr Gln Val Thr Val Ser Ser Ala Ala Xaa Xaa
        115                 120                 125

Ser Arg Gly Ser Ser Gly Ser Ser Ser Ser Gly Ser Ser Gly Gly Ser
    130                 135                 140

Gly Ile Asp Trp Lys Lys Leu Leu Asp Ala Ala Lys Gln Ile Leu
145                 150                 155
```

<210> SEQ ID NO 187
<211> LENGTH: 174
<212> TYPE: PRT
<213> ORGANISM: Artificial Sequence
<220> FEATURE:
<223> OTHER INFORMATION: sdAb46 linked to the lytic peptide BMAP28A by a SRGS linker
<220> FEATURE:
<221> NAME/KEY: SITE
<222> LOCATION: 128,129
<223> OTHER INFORMATION: Xaa can be any amino acid

<400> SEQUENCE: 187

```
Gly Asp Val Gln Leu Gln Glu Ser Gly Gly Gly Leu Val His Pro Gly
1               5                   10                  15

Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Ser Arg Gly Ser Ser Gly Ser Ser Ser Ser Gly Ser Ser Gly Gly
    130                 135                 140

Ser Gly Gly Gly Leu Arg Ser Leu Gly Arg Lys Ile Leu Arg Ala Trp
145                 150                 155                 160

Lys Lys Tyr Gly Pro Ile Ile Val Pro Ile Ile Arg Ile Gly
                165                 170
```

<210> SEQ ID NO 188
<211> LENGTH: 157
<212> TYPE: PRT
<213> ORGANISM: Artificial Sequence
<220> FEATURE:
<223> OTHER INFORMATION: sdAb46 linked to the lytic peptide modified cysteine deleted Tachyplesin-I by a SRGS linker
<220> FEATURE:
<221> NAME/KEY: SITE
<222> LOCATION: 128,129
<223> OTHER INFORMATION: Xaa can be any amino acid

<400> SEQUENCE: 188

Gly Asp Val Gln Leu Gln Glu Ser Gly Gly Gly Leu Val His Pro Gly
1 5 10 15

Gly Ser Leu Arg Leu Ser Cys Val Ala Ser Gly Phe Thr Phe Asp Asp
20 25 30

Tyr Ala Leu Thr Trp Val Arg Gln Ala Pro Gly Lys Gly Leu Glu Trp
35 40 45

Val Ser Gly Ile Asn Trp Asn Gly Asp Asp Thr Tyr Tyr Thr Gln Ser
50 55 60

Met Lys Gly Arg Phe Thr Ile Ser Arg Asp Asn Ala Lys Asn Thr Leu
65 70 75 80

Tyr Leu Gln Met Asn Ser Leu Lys Ser Glu Asp Thr Ala Val Tyr Phe
85 90 95

Cys Thr Lys Asn Val Gly Gly Asn Trp Val Ser Gly Asp Tyr Gly Leu
100 105 110

Asp Tyr Trp Gly Gln Gly Thr Gln Val Thr Val Ser Ser Ala Ala Xaa
115 120 125

Xaa Ser Arg Gly Ser Ser Gly Ser Ser Ser Ser Gly Ser Ser Gly Gly
130 135 140

Ser Gly Lys Trp Phe Arg Val Tyr Arg Gly Ile Tyr Arg
145 150 155

<210> SEQ ID NO 189
<211> LENGTH: 153
<212> TYPE: PRT
<213> ORGANISM: Artificial Sequence
<220> FEATURE:
<223> OTHER INFORMATION: sdAb46 linked to the lytic peptide Polybia-MP1 by a GS_linker
<220> FEATURE:
<221> NAME/KEY: SITE
<222> LOCATION: 128,129
<223> OTHER INFORMATION: Xaa can be any amino acid

<400> SEQUENCE: 189

Gly Asp Val Gln Leu Gln Glu Ser Gly Gly Gly Leu Val His Pro Gly
1 5 10 15

Gly Ser Leu Arg Leu Ser Cys Val Ala Ser Gly Phe Thr Phe Asp Asp
20 25 30

Tyr Ala Leu Thr Trp Val Arg Gln Ala Pro Gly Lys Gly Leu Glu Trp
35 40 45

Val Ser Gly Ile Asn Trp Asn Gly Asp Asp Thr Tyr Tyr Thr Gln Ser
50 55 60

Met Lys Gly Arg Phe Thr Ile Ser Arg Asp Asn Ala Lys Asn Thr Leu
65 70 75 80

Tyr Leu Gln Met Asn Ser Leu Lys Ser Glu Asp Thr Ala Val Tyr Phe
85 90 95

Cys Thr Lys Asn Val Gly Gly Asn Trp Val Ser Gly Asp Tyr Gly Leu
100 105 110

Asp Tyr Trp Gly Gln Gly Thr Gln Val Thr Val Ser Ser Ala Ala Xaa
115 120 125

Xaa Gly Gly Gly Gly Ser Gly Gly Gly Gly Ser Ile Asp Trp Lys Lys
130 135 140

Leu Leu Asp Ala Ala Lys Gln Ile Leu
145 150

<210> SEQ ID NO 190
<211> LENGTH: 160
<212> TYPE: PRT

<213> ORGANISM: Artificial Sequence
<220> FEATURE:
<223> OTHER INFORMATION: sdAb46 linked to the lytic peptide Polybia-MP1 by a SRGS linker
<220> FEATURE:
<221> NAME/KEY: SITE
<222> LOCATION: 128,129
<223> OTHER INFORMATION: Xaa can be any amino acid

<400> SEQUENCE: 190

```
Gly Asp Val Gln Leu Gln Glu Ser Gly Gly Gly Leu Val His Pro Gly
1               5                   10                  15

Gly Ser Leu Arg Leu Ser Cys Val Ala Ser Gly Phe Thr Phe Asp Asp
            20                  25                  30

Tyr Ala Leu Thr Trp Val Arg Gln Ala Pro Gly Lys Gly Leu Glu Trp
        35                  40                  45

Val Ser Gly Ile Asn Trp Asn Gly Asp Asp Thr Tyr Tyr Thr Gln Ser
    50                  55                  60

Met Lys Gly Arg Phe Thr Ile Ser Arg Asp Asn Ala Lys Asn Thr Leu
65                  70                  75                  80

Tyr Leu Gln Met Asn Ser Leu Lys Ser Glu Asp Thr Ala Val Tyr Phe
                85                  90                  95

Cys Thr Lys Asn Val Gly Gly Asn Trp Val Ser Gly Asp Tyr Gly Leu
            100                 105                 110

Asp Tyr Trp Gly Gln Gly Thr Gln Val Thr Val Ser Ser Ala Ala Xaa
        115                 120                 125

Xaa Ser Arg Gly Ser Ser Gly Ser Ser Ser Ser Gly Ser Ser Gly Gly
    130                 135                 140

Ser Gly Ile Asp Trp Lys Lys Leu Leu Asp Ala Ala Lys Gln Ile Leu
145                 150                 155                 160
```

<210> SEQ ID NO 191
<211> LENGTH: 171
<212> TYPE: PRT
<213> ORGANISM: Artificial Sequence
<220> FEATURE:
<223> OTHER INFORMATION: sdAb47 linked to the lytic peptide BMAP28A by a SRGS linker
<220> FEATURE:
<221> NAME/KEY: SITE
<222> LOCATION: 125,126
<223> OTHER INFORMATION: Xaa can be any amino acid

<400> SEQUENCE: 191

```
Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Ser Arg
        115                 120                 125
```

```
Gly Ser Ser Gly Ser Ser Ser Ser Gly Ser Ser Gly Gly Ser Gly Gly
    130                 135                 140

Gly Leu Arg Ser Leu Gly Arg Lys Ile Leu Arg Ala Trp Lys Lys Tyr
145                 150                 155                 160

Gly Pro Ile Ile Val Pro Ile Ile Arg Ile Gly
                165                 170


<210> SEQ ID NO 192
<211> LENGTH: 154
<212> TYPE: PRT
<213> ORGANISM: Artificial Sequence
<220> FEATURE:
<223> OTHER INFORMATION: sdAb47 linked to the lytic peptide modified
      cysteine deleted Tachyplesin-I by a SRGS linker
<220> FEATURE:
<221> NAME/KEY: SITE
<222> LOCATION: 125,126
<223> OTHER INFORMATION: Xaa can be any amino acid

<400> SEQUENCE: 192

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Ser Arg
        115                 120                 125

Gly Ser Ser Gly Ser Ser Ser Ser Gly Ser Ser Gly Gly Ser Gly Lys
    130                 135                 140

Trp Phe Arg Val Tyr Arg Gly Ile Tyr Arg
145                 150


<210> SEQ ID NO 193
<211> LENGTH: 150
<212> TYPE: PRT
<213> ORGANISM: Artificial Sequence
<220> FEATURE:
<223> OTHER INFORMATION: sdAb47 linked to the lytic peptide Polybia-MP1
      by a GS_linker
<220> FEATURE:
<221> NAME/KEY: SITE
<222> LOCATION: 125,126
<223> OTHER INFORMATION: Xaa can be any amino acid

<400> SEQUENCE: 193

Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45
```

```
Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Gly Gly
        115                 120                 125

Gly Gly Ser Gly Gly Gly Gly Ser Ile Asp Trp Lys Lys Leu Leu Asp
    130                 135                 140

Ala Ala Lys Gln Ile Leu
145                 150
```

<210> SEQ ID NO 194
<211> LENGTH: 157
<212> TYPE: PRT
<213> ORGANISM: Artificial Sequence
<220> FEATURE:
<223> OTHER INFORMATION: sdAb47 linked to the lytic peptide Polybia-MP1 by a SRGS linker
<220> FEATURE:
<221> NAME/KEY: SITE
<222> LOCATION: 125,126
<223> OTHER INFORMATION: Xaa can be any amino acid

<400> SEQUENCE: 194

```
Gly Asp Val Gln Leu Val Glu Ser Gly Gly Gly Leu Val Gln Pro Gly
1               5                   10                  15

Gly Ser Leu Arg Leu Ser Cys Thr Ala Ser Gly Phe Thr Phe Gly Asn
            20                  25                  30

His Trp Met Tyr Trp Val Arg Gln Thr Pro Gly Lys Gly Leu Glu Trp
        35                  40                  45

Val Ala Thr Ala Asn Thr Gly Gly Arg Asp Thr Tyr Tyr Ala Asp Ser
    50                  55                  60

Val Trp Gly Arg Phe Thr Ile Ser Gly Asp Asn Ala Lys Asn Thr Leu
65                  70                  75                  80

Tyr Leu Gln Met Asn Asn Leu Lys Ser Glu Asp Thr Ala Ile Tyr Tyr
                85                  90                  95

Cys Ala Arg Glu Val Asn Asp Tyr Leu Glu Tyr Ala Leu Gly Tyr Trp
            100                 105                 110

Gly Gln Gly Thr Gln Val Thr Val Ser Ser Ala Ala Xaa Xaa Ser Arg
        115                 120                 125

Gly Ser Ser Gly Ser Ser Ser Ser Gly Ser Ser Gly Gly Ser Gly Ile
    130                 135                 140

Asp Trp Lys Lys Leu Leu Asp Ala Ala Lys Gln Ile Leu
145                 150                 155
```

<210> SEQ ID NO 195
<211> LENGTH: 173
<212> TYPE: PRT
<213> ORGANISM: Artificial Sequence
<220> FEATURE:
<223> OTHER INFORMATION: sdAb56 linked to the lytic peptide BMAP28A by a SRGS linker
<220> FEATURE:
<221> NAME/KEY: SITE
<222> LOCATION: 127,128
<223> OTHER INFORMATION: Xaa can be any amino acid

<400> SEQUENCE: 195

```
Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Ser Arg Gly Ser Ser Gly Ser Ser Ser Ser Gly Ser Ser Gly Gly Ser
    130                 135                 140

Gly Gly Gly Leu Arg Ser Leu Gly Arg Lys Ile Leu Arg Ala Trp Lys
145                 150                 155                 160

Lys Tyr Gly Pro Ile Ile Val Pro Ile Ile Arg Ile Gly
                165                 170
```

<210> SEQ ID NO 196
<211> LENGTH: 156
<212> TYPE: PRT
<213> ORGANISM: Artificial Sequence
<220> FEATURE:
<223> OTHER INFORMATION: sdAb56 linked to the lytic peptide modified cysteine deleted Tachyplesin-I by a SRGS linker
<220> FEATURE:
<221> NAME/KEY: SITE
<222> LOCATION: 127,128
<223> OTHER INFORMATION: Xaa can be any amino acid

<400> SEQUENCE: 196

```
Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Ser Arg Gly Ser Ser Gly Ser Ser Ser Ser Gly Ser Ser Gly Gly Ser
    130                 135                 140

Gly Lys Trp Phe Arg Val Tyr Arg Gly Ile Tyr Arg
145                 150                 155
```

<210> SEQ ID NO 197
<211> LENGTH: 152
<212> TYPE: PRT
<213> ORGANISM: Artificial Sequence
<220> FEATURE:
<223> OTHER INFORMATION: sdAb56 linked to the lytic peptide Polybia-MP1 by a GS_linker
<220> FEATURE:
<221> NAME/KEY: SITE
<222> LOCATION: 127,128
<223> OTHER INFORMATION: Xaa can be any amino acid

<400> SEQUENCE: 197

```
Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95

Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Gly Gly Gly Gly Ser Gly Gly Gly Gly Ser Ile Asp Trp Lys Lys Leu
    130                 135                 140

Leu Asp Ala Ala Lys Gln Ile Leu
145                 150
```

<210> SEQ ID NO 198
<211> LENGTH: 159
<212> TYPE: PRT
<213> ORGANISM: Artificial Sequence
<220> FEATURE:
<223> OTHER INFORMATION: sdAb56 linked to the lytic peptide Polybia-MP1 by a GS_linker
<220> FEATURE:
<221> NAME/KEY: SITE
<222> LOCATION: 127,128
<223> OTHER INFORMATION: Xaa can be any amino acid

<400> SEQUENCE: 198

```
Gly Asp Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met His Trp Val Arg Gln Ala Pro Gly Lys Gly Leu Glu Cys
        35                  40                  45

Val Ser Val Ile Asn Thr Gly Asn Gly Ser Pro Tyr Tyr Ala Asp Ser
    50                  55                  60

Val Lys Gly Arg Phe Thr Ile Ser Thr Asp Asn Ala Lys Asn Thr Leu
65                  70                  75                  80

Tyr Leu Gln Met Asn Ser Leu Lys Ser Glu Asp Thr Ala Val Tyr Tyr
                85                  90                  95
```

```
Cys Ala Arg Asp Ile Pro Asp Pro Ala Gly Arg Ala Gly Gly Met Asp
            100                 105                 110

Tyr Trp Gly Lys Gly Thr Gln Val Thr Val Ser Ser Ala Ala Xaa Xaa
        115                 120                 125

Ser Arg Gly Ser Ser Gly Ser Ser Ser Ser Gly Ser Ser Gly Gly Ser
    130                 135                 140

Gly Ile Asp Trp Lys Lys Leu Leu Asp Ala Ala Lys Gln Ile Leu
145                 150                 155


<210> SEQ ID NO 199
<211> LENGTH: 169
<212> TYPE: PRT
<213> ORGANISM: Artificial Sequence
<220> FEATURE:
<223> OTHER INFORMATION: sdAb59 linked to the lytic peptide BMAP28A by a
      SRGS linker
<220> FEATURE:
<221> NAME/KEY: SITE
<222> LOCATION: 123,124
<223> OTHER INFORMATION: Xaa can be any amino acid

<400> SEQUENCE: 199

Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
            20                  25                  30

Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Ser Arg Gly Ser
        115                 120                 125

Ser Gly Ser Ser Ser Ser Gly Ser Ser Gly Gly Ser Gly Gly Gly Leu
    130                 135                 140

Arg Ser Leu Gly Arg Lys Ile Leu Arg Ala Trp Lys Lys Tyr Gly Pro
145                 150                 155                 160

Ile Ile Val Pro Ile Ile Arg Ile Gly
                165


<210> SEQ ID NO 200
<211> LENGTH: 152
<212> TYPE: PRT
<213> ORGANISM: Artificial Sequence
<220> FEATURE:
<223> OTHER INFORMATION: sdAb59 linked to the lytic peptide modified
      cysteine deleted Tachyplesin-I by a SRGS linker
<220> FEATURE:
<221> NAME/KEY: SITE
<222> LOCATION: 123,124
<223> OTHER INFORMATION: Xaa can be any amino acid

<400> SEQUENCE: 200

Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
```

```
            20                  25                  30

Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Ser Arg Gly Ser
        115                 120                 125

Ser Gly Ser Ser Ser Ser Gly Ser Ser Gly Gly Ser Gly Lys Trp Phe
    130                 135                 140

Arg Val Tyr Arg Gly Ile Tyr Arg
145                 150


<210> SEQ ID NO 201
<211> LENGTH: 148
<212> TYPE: PRT
<213> ORGANISM: Artificial Sequence
<220> FEATURE:
<223> OTHER INFORMATION: sdAb59 linked to the lytic peptide Polybia-MP1
      by a GS_linker
<220> FEATURE:
<221> NAME/KEY: SITE
<222> LOCATION: 123,124
<223> OTHER INFORMATION: Xaa can be any amino acid

<400> SEQUENCE: 201

Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
            20                  25                  30

Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Gly Gly Gly Gly
        115                 120                 125

Ser Gly Gly Gly Gly Ser Ile Asp Trp Lys Lys Leu Leu Asp Ala Ala
    130                 135                 140

Lys Gln Ile Leu
145


<210> SEQ ID NO 202
<211> LENGTH: 155
<212> TYPE: PRT
<213> ORGANISM: Artificial Sequence
<220> FEATURE:
<223> OTHER INFORMATION: sdAb59 linked to the lytic peptide Polybia-MP1
      by a SRGS linker
```

<220> FEATURE:
<221> NAME/KEY: SITE
<222> LOCATION: 123,124
<223> OTHER INFORMATION: Xaa can be any amino acid

<400> SEQUENCE: 202

```
Gly Ala Gln Val Gln Leu Val Glu Ser Gly Gly Gly Leu Val Gln Pro
1               5                   10                  15

Gly Gly Ser Leu Thr Val Ser Cys Ala Ala Ser Gly Phe Thr Phe Ser
            20                  25                  30

Arg Tyr Gly Val Thr Trp His Arg Gln Ala Pro Gly Lys Glu Arg Glu
        35                  40                  45

Leu Val Ala Asp Ile Ile Phe Thr Gly Leu Asn Pro Thr Tyr Ser Asp
    50                  55                  60

Ser Val Lys Gly Arg Phe Thr Ile Ser Arg Asp Asn Asp Lys Asn Val
65                  70                  75                  80

Ala Tyr Leu Gln Met Asn Ser Leu Lys Pro Glu Asp Thr Ala Lys Tyr
                85                  90                  95

Tyr Cys Asn Val Asn Asp Ile Val Val Arg Gly Asn Tyr Trp Gly Gln
            100                 105                 110

Glu Thr Gln Val Thr Val Ser Ser Ala Ala Xaa Xaa Ser Arg Gly Ser
        115                 120                 125

Ser Gly Ser Ser Ser Ser Gly Ser Ser Gly Gly Ser Gly Ile Asp Trp
    130                 135                 140

Lys Lys Leu Leu Asp Ala Ala Lys Gln Ile Leu
145                 150                 155
```

<210> SEQ ID NO 203
<211> LENGTH: 170
<212> TYPE: PRT
<213> ORGANISM: Artificial Sequence
<220> FEATURE:
<223> OTHER INFORMATION: sdAb62 linked to the lytic peptide BMAP28A by a SRGS linker
<220> FEATURE:
<221> NAME/KEY: SITE
<222> LOCATION: 124,125
<223> OTHER INFORMATION: Xaa can be any amino acid

<400> SEQUENCE: 203

```
Gly Ala Asp Val Lys Leu Val Glu Ser Gly Gly Gly Leu Val Gln Pro
1               5                   10                  15

Gly Gly Ser Leu Arg Leu Ser Cys Ala Val Ser Gly Thr Ile Leu Gly
            20                  25                  30

Leu Asn Met Met Gly Trp Tyr Arg Gln Ala Pro Gly Lys Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Trp Gly
            100                 105                 110

Gln Gly Thr Gln Val Thr Val Ser Ser Ala Ala Xaa Xaa Ser Arg Gly
        115                 120                 125

Ser Ser Gly Ser Ser Ser Ser Gly Ser Ser Gly Gly Ser Gly Gly Gly
    130                 135                 140
```

-continued

Leu Arg Ser Leu Gly Arg Lys Ile Leu Arg Ala Trp Lys Lys Tyr Gly
145 150 155 160

Pro Ile Ile Val Pro Ile Ile Arg Ile Gly
165 170

<210> SEQ ID NO 204
<211> LENGTH: 153
<212> TYPE: PRT
<213> ORGANISM: Artificial Sequence
<220> FEATURE:
<223> OTHER INFORMATION: sdAb62 linked to the lytic peptide modified cysteine deleted Tachyplesin-I by a SRGS linker
<220> FEATURE:
<221> NAME/KEY: SITE
<222> LOCATION: 124,125
<223> OTHER INFORMATION: Xaa can be any amino acid

<400> SEQUENCE: 204

Gly Ala Asp Val Lys Leu Val Glu Ser Gly Gly Gly Leu Val Gln Pro
1 5 10 15

Gly Gly Ser Leu Arg Leu Ser Cys Ala Val Ser Gly Thr Ile Leu Gly
20 25 30

Leu Asn Met Met Gly Trp Tyr Arg Gln Ala Pro Gly Lys Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val
65 70 75 80

Ser Leu Gln Met Asn Thr Leu Arg Pro Glu Asp Thr Ala Ile Tyr Tyr
85 90 95

Cys Val Ala Arg Trp Thr Phe Gly Ile Gln Arg Gly Asp Tyr Trp Gly
100 105 110

Gln Gly Thr Gln Val Thr Val Ser Ser Ala Ala Xaa Xaa Ser Arg Gly
115 120 125

Ser Ser Gly Ser Ser Ser Ser Gly Ser Ser Gly Gly Ser Gly Lys Trp
130 135 140

Phe Arg Val Tyr Arg Gly Ile Tyr Arg
145 150

<210> SEQ ID NO 205
<211> LENGTH: 149
<212> TYPE: PRT
<213> ORGANISM: Artificial Sequence
<220> FEATURE:
<223> OTHER INFORMATION: sdAb62 linked to the lytic peptide Polybia-MP1 by a GS_linker
<220> FEATURE:
<221> NAME/KEY: SITE
<222> LOCATION: 124,125
<223> OTHER INFORMATION: Xaa can be any amino acid

<400> SEQUENCE: 205

Gly Ala Asp Val Lys Leu Val Glu Ser Gly Gly Gly Leu Val Gln Pro
1 5 10 15

Gly Gly Ser Leu Arg Leu Ser Cys Ala Val Ser Gly Thr Ile Leu Gly
20 25 30

Leu Asn Met Met Gly Trp Tyr Arg Gln Ala Pro Gly Lys Gln Arg Glu
35 40 45

Leu Val Ala Ser Ile Gly Phe Gly Gly Asn Ile Asp Tyr Ala Asn Ser
50 55 60

Val Lys Gly Arg Phe Thr Ile Ser Arg Asp Gly Asp Lys Asn Met Val

```
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Trp Gly
            100                 105                 110

Gln Gly Thr Gln Val Thr Val Ser Ser Ala Ala Xaa Xaa Gly Gly Gly
        115                 120                 125

Gly Ser Gly Gly Gly Gly Ser Ile Asp Trp Lys Lys Leu Leu Asp Ala
    130                 135                 140

Ala Lys Gln Ile Leu
145


<210> SEQ ID NO 206
<211> LENGTH: 156
<212> TYPE: PRT
<213> ORGANISM: Artificial Sequence
<220> FEATURE:
<223> OTHER INFORMATION: sdAb62 linked to the lytic peptide Polybia-MP1
      by a SRGS linker
<220> FEATURE:
<221> NAME/KEY: SITE
<222> LOCATION: 124,125
<223> OTHER INFORMATION: Xaa can be any amino acid

<400> SEQUENCE: 206

Gly Ala Asp Val Lys Leu Val Glu Ser Gly Gly Gly Leu Val Gln Pro
1               5                   10                  15

Gly Gly Ser Leu Arg Leu Ser Cys Ala Val Ser Gly Thr Ile Leu Gly
            20                  25                  30

Leu Asn Met Met Gly Trp Tyr Arg Gln Ala Pro Gly Lys Gln Arg Glu
        35                  40                  45

Leu Val Ala Ser Ile Gly Phe Gly Gly Asn Ile Asp Tyr Ala Asn Ser
    50                  55                  60

Val Lys Gly Arg Phe Thr Ile Ser Arg Asp Gly Asp Lys Asn Met Val
65                  70                  75                  80

Ser Leu Gln Met Asn Thr Leu Arg Pro Glu Asp Thr Ala Ile Tyr Tyr
                85                  90                  95

Cys Val Ala Arg Trp Thr Phe Gly Ile Gln Arg Gly Asp Tyr Trp Gly
            100                 105                 110

Gln Gly Thr Gln Val Thr Val Ser Ser Ala Ala Xaa Xaa Ser Arg Gly
        115                 120                 125

Ser Ser Gly Ser Ser Ser Ser Gly Ser Ser Gly Gly Ser Gly Ile Asp
    130                 135                 140

Trp Lys Lys Leu Leu Asp Ala Ala Lys Gln Ile Leu
145                 150                 155


<210> SEQ ID NO 207
<211> LENGTH: 179
<212> TYPE: PRT
<213> ORGANISM: Artificial Sequence
<220> FEATURE:
<223> OTHER INFORMATION: sdAb63 linked to the lytic peptide BMAP28A by a
      SRGS linker
<220> FEATURE:
<221> NAME/KEY: SITE
<222> LOCATION: 133,134
<223> OTHER INFORMATION: Xaa can be any amino acid

<400> SEQUENCE: 207

Gly Ala Asp Val Gln Leu Val Glu Ser Gly Gly Gly Met Val Gln Pro
1               5                   10                  15
```

Gly Gly Ser Leu Arg Leu Ser Cys Ala Ala Ser Gly Phe Ile Phe Ser
20 25 30

Arg His Asp Met His Trp Val Arg Gln Gly Pro Gly Lys Gly Pro Glu
35 40 45

Trp Val Ser Leu Ile Thr Thr Gly Gly Glu Gly Thr Trp Tyr Val Asp
50 55 60

Ser Val Lys Gly Arg Phe Ser Ile Ser Arg Asp Asn Ala Lys Asn Thr
65 70 75 80

Val Tyr Leu Gln Met Asn Ala Leu Lys Pro Glu Asp Thr Ala Val Tyr
85 90 95

Tyr Cys Ala Ala His Arg Ala Glu Ile Pro Arg Glu Ile Cys Tyr Gly
100 105 110

Asp Ser Leu Ser Tyr Asn Tyr Trp Gly Gln Gly Thr Gln Val Thr Val
115 120 125

Ser Ser Ala Ala Xaa Xaa Ser Arg Gly Ser Ser Gly Ser Ser Ser Ser
130 135 140

Gly Ser Ser Gly Gly Ser Gly Gly Gly Leu Arg Ser Leu Gly Arg Lys
145 150 155 160

Ile Leu Arg Ala Trp Lys Lys Tyr Gly Pro Ile Ile Val Pro Ile Ile
165 170 175

Arg Ile Gly

<210> SEQ ID NO 208
<211> LENGTH: 162
<212> TYPE: PRT
<213> ORGANISM: Artificial Sequence
<220> FEATURE:
<223> OTHER INFORMATION: sdAb63 linked to the lytic peptide modified cysteine deleted Tachyplesin-I by a SRGS linker
<220> FEATURE:
<221> NAME/KEY: SITE
<222> LOCATION: 133,134
<223> OTHER INFORMATION: Xaa can be any amino acid

<400> SEQUENCE: 208

Gly Ala Asp Val Gln Leu Val Glu Ser Gly Gly Gly Met Val Gln Pro
1 5 10 15

Gly Gly Ser Leu Arg Leu Ser Cys Ala Ala Ser Gly Phe Ile Phe Ser
20 25 30

Arg His Asp Met His Trp Val Arg Gln Gly Pro Gly Lys Gly Pro Glu
35 40 45

Trp Val Ser Leu Ile Thr Thr Gly Gly Glu Gly Thr Trp Tyr Val Asp
50 55 60

Ser Val Lys Gly Arg Phe Ser Ile Ser Arg Asp Asn Ala Lys Asn Thr
65 70 75 80

Val Tyr Leu Gln Met Asn Ala Leu Lys Pro Glu Asp Thr Ala Val Tyr
85 90 95

Tyr Cys Ala Ala His Arg Ala Glu Ile Pro Arg Glu Ile Cys Tyr Gly
100 105 110

Asp Ser Leu Ser Tyr Asn Tyr Trp Gly Gln Gly Thr Gln Val Thr Val
115 120 125

Ser Ser Ala Ala Xaa Xaa Ser Arg Gly Ser Ser Gly Ser Ser Ser Ser
130 135 140

Gly Ser Ser Gly Gly Ser Gly Lys Trp Phe Arg Val Tyr Arg Gly Ile
145 150 155 160

Tyr Arg

<210> SEQ ID NO 209
<211> LENGTH: 158
<212> TYPE: PRT
<213> ORGANISM: Artificial Sequence
<220> FEATURE:
<223> OTHER INFORMATION: sdAb63 linked to the lytic peptide Polybia-MP1 by a GS_linker
<220> FEATURE:
<221> NAME/KEY: SITE
<222> LOCATION: 133,134
<223> OTHER INFORMATION: Xaa can be any amino acid

<400> SEQUENCE: 209

```
Gly Ala Asp Val Gln Leu Val Glu Ser Gly Gly Gly Met Val Gln Pro
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95

Tyr Cys Ala Ala His Arg Ala Glu Ile Pro Arg Glu Ile Cys Tyr Gly
            100                 105                 110

Asp Ser Leu Ser Tyr Asn Tyr Trp Gly Gln Gly Thr Gln Val Thr Val
        115                 120                 125

Ser Ser Ala Ala Xaa Xaa Gly Gly Gly Gly Ser Gly Gly Gly Gly Ser
    130                 135                 140

Ile Asp Trp Lys Lys Leu Leu Asp Ala Ala Lys Gln Ile Leu
145                 150                 155
```

<210> SEQ ID NO 210
<211> LENGTH: 165
<212> TYPE: PRT
<213> ORGANISM: Artificial Sequence
<220> FEATURE:
<223> OTHER INFORMATION: sdAb63 linked to the lytic peptide Polybia-MP1 by a SRGS linker
<220> FEATURE:
<221> NAME/KEY: SITE
<222> LOCATION: 133,134
<223> OTHER INFORMATION: Xaa can be any amino acid

<400> SEQUENCE: 210

```
Gly Ala Asp Val Gln Leu Val Glu Ser Gly Gly Gly Met Val Gln Pro
1               5                   10                  15

Gly Gly Ser Leu Arg Leu Ser Cys Ala Ala Ser Gly Phe Ile Phe Ser
            20                  25                  30

Arg His Asp Met His Trp Val Arg Gln Gly Pro Gly Lys Gly Pro Glu
        35                  40                  45

Trp Val Ser Leu Ile Thr Thr Gly Gly Glu Gly Thr Trp Tyr Val Asp
    50                  55                  60

Ser Val Lys Gly Arg Phe Ser Ile Ser Arg Asp Asn Ala Lys Asn Thr
65                  70                  75                  80

Val Tyr Leu Gln Met Asn Ala Leu Lys Pro Glu Asp Thr Ala Val Tyr
                85                  90                  95
```

```
Tyr Cys Ala Ala His Arg Ala Glu Ile Pro Arg Glu Ile Cys Tyr Gly
            100                 105                 110

Asp Ser Leu Ser Tyr Asn Tyr Trp Gly Gln Gly Thr Gln Val Thr Val
        115                 120                 125

Ser Ser Ala Ala Xaa Xaa Ser Arg Gly Ser Ser Gly Ser Ser Ser Ser
    130                 135                 140

Gly Ser Ser Gly Gly Ser Gly Ile Asp Trp Lys Lys Leu Leu Asp Ala
145                 150                 155                 160

Ala Lys Gln Ile Leu
                165


<210> SEQ ID NO 211
<211> LENGTH: 176
<212> TYPE: PRT
<213> ORGANISM: Artificial Sequence
<220> FEATURE:
<223> OTHER INFORMATION: sdAb65 linked to the lytic peptide BMAP28A by a
      SRGS linker
<220> FEATURE:
<221> NAME/KEY: SITE
<222> LOCATION: 130,131
<223> OTHER INFORMATION: Xaa can be any amino acid

<400> SEQUENCE: 211

Gly Ala Gln Val Gln Leu Val Glu Ser Gly Gly Gly Leu Val Gln Leu
1               5                   10                  15

Gly Gly Ser Leu Arg Leu Ser Cys Thr Ala Ser Glu Ile Asp Leu Gln
            20                  25                  30

Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
        115                 120                 125

Ala Xaa Xaa Ser Arg Gly Ser Ser Gly Ser Ser Ser Ser Gly Ser Ser
    130                 135                 140

Gly Gly Ser Gly Gly Gly Leu Arg Ser Leu Gly Arg Lys Ile Leu Arg
145                 150                 155                 160

Ala Trp Lys Lys Tyr Gly Pro Ile Ile Val Pro Ile Ile Arg Ile Gly
                165                 170                 175


<210> SEQ ID NO 212
<211> LENGTH: 159
<212> TYPE: PRT
<213> ORGANISM: Artificial Sequence
<220> FEATURE:
<223> OTHER INFORMATION: sdAb65 linked to the lytic peptide modified
      cysteine deleted Tachyplesin-I by a SRGS linker
<220> FEATURE:
<221> NAME/KEY: SITE
<222> LOCATION: 130,131
<223> OTHER INFORMATION: Xaa can be any amino acid

<400> SEQUENCE: 212

Gly Ala Gln Val Gln Leu Val Glu Ser Gly Gly Gly Leu Val Gln Leu
```

```
1               5                   10                  15

Gly Gly Ser Leu Arg Leu Ser Cys Thr Ala Ser Glu Ile Asp Leu Gln
            20                  25                  30

Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
        115                 120                 125

Ala Xaa Xaa Ser Arg Gly Ser Ser Gly Ser Ser Ser Ser Gly Ser Ser
    130                 135                 140

Gly Gly Ser Gly Lys Trp Phe Arg Val Tyr Arg Gly Ile Tyr Arg
145                 150                 155


<210> SEQ ID NO 213
<211> LENGTH: 155
<212> TYPE: PRT
<213> ORGANISM: Artificial Sequence
<220> FEATURE:
<223> OTHER INFORMATION: sdAb65 linked to the lytic peptide Polybia-MP1
      by a GS_linker
<220> FEATURE:
<221> NAME/KEY: SITE
<222> LOCATION: 130,131
<223> OTHER INFORMATION: Xaa can be any amino acid

<400> SEQUENCE: 213

Gly Ala Gln Val Gln Leu Val Glu Ser Gly Gly Gly Leu Val Gln Leu
1               5                   10                  15

Gly Gly Ser Leu Arg Leu Ser Cys Thr Ala Ser Glu Ile Asp Leu Gln
            20                  25                  30

Tyr Tyr Pro Ile Ala Trp Phe Arg Gln Ala Pro Gly Lys Glu Arg Glu
        35                  40                  45

Gly Val Ser Cys Ile Arg Ala Thr Asp Ser Gly Thr Tyr Tyr Ala Asp
    50                  55                  60

Ser Val Lys Gly Arg Phe Thr Ile Ala Arg Asp Asn Ala Lys Asn Thr
65                  70                  75                  80

Val Tyr Leu Gln Met Asn Asn Leu Ala Pro Glu Asp Thr Ala Val Tyr
                85                  90                  95

Tyr Cys Gly Thr Asp Asp Ser Glu Asp Cys Thr Asp Tyr Ala Pro Ala
            100                 105                 110

His Tyr Gly Tyr Trp Gly Arg Gly Thr Gln Val Thr Val Ser Ser Ala
        115                 120                 125

Ala Xaa Xaa Gly Gly Gly Gly Ser Gly Gly Gly Gly Ser Ile Asp Trp
    130                 135                 140

Lys Lys Leu Leu Asp Ala Ala Lys Gln Ile Leu
145                 150                 155


<210> SEQ ID NO 214
<211> LENGTH: 162
<212> TYPE: PRT
<213> ORGANISM: Artificial Sequence
```

<220> FEATURE:
<223> OTHER INFORMATION: sdAb65 linked to the lytic peptide Polybia-MP1
by a SRGS linker
<220> FEATURE:
<221> NAME/KEY: SITE
<222> LOCATION: 130,131
<223> OTHER INFORMATION: Xaa can be any amino acid

<400> SEQUENCE: 214

Gly Ala Gln Val Gln Leu Val Glu Ser Gly Gly Gly Leu Val Gln Leu
1 5 10 15

Gly Gly Ser Leu Arg Leu Ser Cys Thr Ala Ser Glu Ile Asp Leu Gln
20 25 30

Tyr Tyr Pro Ile Ala Trp Phe Arg Gln Ala Pro Gly Lys Glu Arg Glu
35 40 45

Gly Val Ser Cys Ile Arg Ala Thr Asp Ser Gly Thr Tyr Tyr Ala Asp
50 55 60

Ser Val Lys Gly Arg Phe Thr Ile Ala Arg Asp Asn Ala Lys Asn Thr
65 70 75 80

Val Tyr Leu Gln Met Asn Asn Leu Ala Pro Glu Asp Thr Ala Val Tyr
85 90 95

Tyr Cys Gly Thr Asp Asp Ser Glu Asp Cys Thr Asp Tyr Ala Pro Ala
100 105 110

His Tyr Gly Tyr Trp Gly Arg Gly Thr Gln Val Thr Val Ser Ser Ala
115 120 125

Ala Xaa Xaa Ser Arg Gly Ser Ser Gly Ser Ser Ser Ser Gly Ser Ser
130 135 140

Gly Gly Ser Gly Ile Asp Trp Lys Lys Leu Leu Asp Ala Ala Lys Gln
145 150 155 160

Ile Leu

<210> SEQ ID NO 215
<211> LENGTH: 169
<212> TYPE: PRT
<213> ORGANISM: Artificial Sequence
<220> FEATURE:
<223> OTHER INFORMATION: sdAb14 linked to the lytic peptide BMAP28A by a
SRGS linker
<220> FEATURE:
<221> NAME/KEY: SITE
<222> LOCATION: 123,124
<223> OTHER INFORMATION: Xaa can be any amino acid

<400> SEQUENCE: 215

Gly Met Ala Glu Val Glu Val Val Ala Ser Gly Gly Asp Leu Ala Gln
1 5 10 15

Pro Gly Gly Ser Leu Arg Leu Ser Cys Ala Ala Ser Gly Phe Val Phe
20 25 30

Ser Ser Tyr Ala Met Ile Trp Ala Arg Gln Ala Pro Gly Lys Gly Leu
35 40 45

Glu Trp Val Ser Gly Ile Asn Ser Asp Ala Ser Gly Thr Trp Tyr Ala
50 55 60

Asp Ser Val Lys Gly Arg Phe Thr Ile Ser Arg Asp Asn Ala Lys Asn
65 70 75 80

Thr Leu Tyr Leu Gln Met Asn Ser Leu Lys Pro Asp Asp Thr Ala Val
85 90 95

Tyr Phe Cys Leu His Ser Gly His Thr His Thr Arg Tyr Trp Gly Gln
100 105 110

Gly Thr Gln Val Thr Val Ser Ser Ala Ala Xaa Xaa Ser Arg Gly Ser

```
        115                 120                 125

Ser Gly Ser Ser Ser Ser Gly Ser Ser Gly Gly Ser Gly Gly Gly Leu
    130                 135                 140

Arg Ser Leu Gly Arg Lys Ile Leu Arg Ala Trp Lys Lys Tyr Gly Pro
145                 150                 155                 160

Ile Ile Val Pro Ile Ile Arg Ile Gly
                165


<210> SEQ ID NO 216
<211> LENGTH: 152
<212> TYPE: PRT
<213> ORGANISM: Artificial Sequence
<220> FEATURE:
<223> OTHER INFORMATION: sdAb14 linked to the lytic peptide modified
      cysteine deleted Tachyplesin-I by a SRGS linker
<220> FEATURE:
<221> NAME/KEY: SITE
<222> LOCATION: 123,124
<223> OTHER INFORMATION: Xaa can be any amino acid

<400> SEQUENCE: 216

Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45

Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Ser Arg Gly Ser
        115                 120                 125

Ser Gly Ser Ser Ser Ser Gly Ser Ser Gly Gly Ser Gly Lys Trp Phe
    130                 135                 140

Arg Val Tyr Arg Gly Ile Tyr Arg
145                 150


<210> SEQ ID NO 217
<211> LENGTH: 148
<212> TYPE: PRT
<213> ORGANISM: Artificial Sequence
<220> FEATURE:
<223> OTHER INFORMATION: sdAb14 linked to the lytic peptide Polybia-MP1
      by a GS_linker
<220> FEATURE:
<221> NAME/KEY: SITE
<222> LOCATION: 123,124
<223> OTHER INFORMATION: Xaa can be any amino acid

<400> SEQUENCE: 217

Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45
```

```
Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Gly Gly Gly Gly
        115                 120                 125

Ser Gly Gly Gly Gly Ser Ile Asp Trp Lys Lys Leu Leu Asp Ala Ala
    130                 135                 140

Lys Gln Ile Leu
145
```

<210> SEQ ID NO 218
<211> LENGTH: 155
<212> TYPE: PRT
<213> ORGANISM: Artificial Sequence
<220> FEATURE:
<223> OTHER INFORMATION: sdAb14 linked to the lytic peptide Polybia-MP1 by a SRGS linker
<220> FEATURE:
<221> NAME/KEY: SITE
<222> LOCATION: 123,124
<223> OTHER INFORMATION: Xaa can be any amino acid

<400> SEQUENCE: 218

```
Gly Met Ala Glu Val Glu Val Val Ala Ser Gly Gly Asp Leu Ala Gln
1               5                   10                  15

Pro Gly Gly Ser Leu Arg Leu Ser Cys Ala Ala Ser Gly Phe Val Phe
            20                  25                  30

Ser Ser Tyr Ala Met Ile Trp Ala Arg Gln Ala Pro Gly Lys Gly Leu
        35                  40                  45

Glu Trp Val Ser Gly Ile Asn Ser Asp Ala Ser Gly Thr Trp Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Asp Asp Thr Ala Val
                85                  90                  95

Tyr Phe Cys Leu His Ser Gly His Thr His Thr Arg Tyr Trp Gly Gln
            100                 105                 110

Gly Thr Gln Val Thr Val Ser Ser Ala Ala Xaa Xaa Ser Arg Gly Ser
        115                 120                 125

Ser Gly Ser Ser Ser Ser Gly Ser Ser Gly Gly Ser Gly Ile Asp Trp
    130                 135                 140

Lys Lys Leu Leu Asp Ala Ala Lys Gln Ile Leu
145                 150                 155
```

<210> SEQ ID NO 219
<211> LENGTH: 177
<212> TYPE: PRT
<213> ORGANISM: Artificial Sequence
<220> FEATURE:
<223> OTHER INFORMATION: sdAb60 linked to the lytic peptide BMAP28A by a SRGS linker
<220> FEATURE:
<221> NAME/KEY: SITE
<222> LOCATION: 131,132
<223> OTHER INFORMATION: Xaa can be any amino acid

<400> SEQUENCE: 219

Gly Met Ala Glu Val Glu Val Val Ala Ser Gly Pro Gly Leu Val Lys
1 5 10 15

Pro Ser Gln Thr Leu Ser Leu Thr Cys Thr Val Ser Gly Asp Ser Ile
20 25 30

Thr Thr Thr Phe Ser His Trp Thr Trp Ile Arg Gln Ser Pro Glu Lys
35 40 45

Gly Leu Glu Trp Met Gly Ala Ile Gly Tyr Gly Gly Ser Ile Tyr Tyr
50 55 60

Ser Pro Ser Phe Lys Ser Arg Thr Ser Ile Ser Arg Asp Thr Ser Arg
65 70 75 80

Asn Gln Phe Thr Leu His Leu Ser Ser Val Thr Pro Glu Asp Thr Ala
85 90 95

Val Tyr Tyr Cys Ala Arg Leu Pro His Ser Ser Gly Tyr Ala Lys Phe
100 105 110

Gly His Leu Asp Tyr Trp Gly Gln Gly Thr Gln Val Thr Val Ser Ser
115 120 125

Ala Ala Xaa Xaa Ser Arg Gly Ser Ser Gly Ser Ser Ser Ser Gly Ser
130 135 140

Ser Gly Gly Ser Gly Gly Gly Leu Arg Ser Leu Gly Arg Lys Ile Leu
145 150 155 160

Arg Ala Trp Lys Lys Tyr Gly Pro Ile Ile Val Pro Ile Ile Arg Ile
165 170 175

Gly

<210> SEQ ID NO 220
<211> LENGTH: 160
<212> TYPE: PRT
<213> ORGANISM: Artificial Sequence
<220> FEATURE:
<223> OTHER INFORMATION: sdAb60 linked to the lytic peptide modified cysteine deleted Tachyplesin-I by a SRGS linker
<220> FEATURE:
<221> NAME/KEY: SITE
<222> LOCATION: 131,132
<223> OTHER INFORMATION: Xaa can be any amino acid

<400> SEQUENCE: 220

Gly Met Ala Glu Val Glu Val Val Ala Ser Gly Pro Gly Leu Val Lys
1 5 10 15

Pro Ser Gln Thr Leu Ser Leu Thr Cys Thr Val Ser Gly Asp Ser Ile
20 25 30

Thr Thr Thr Phe Ser His Trp Thr Trp Ile Arg Gln Ser Pro Glu Lys
35 40 45

Gly Leu Glu Trp Met Gly Ala Ile Gly Tyr Gly Gly Ser Ile Tyr Tyr
50 55 60

Ser Pro Ser Phe Lys Ser Arg Thr Ser Ile Ser Arg Asp Thr Ser Arg
65 70 75 80

Asn Gln Phe Thr Leu His Leu Ser Ser Val Thr Pro Glu Asp Thr Ala
85 90 95

Val Tyr Tyr Cys Ala Arg Leu Pro His Ser Ser Gly Tyr Ala Lys Phe
100 105 110

Gly His Leu Asp Tyr Trp Gly Gln Gly Thr Gln Val Thr Val Ser Ser
115 120 125

Ala Ala Xaa Xaa Ser Arg Gly Ser Ser Gly Ser Ser Ser Ser Gly Ser
130 135 140

Ser Gly Gly Ser Gly Lys Trp Phe Arg Val Tyr Arg Gly Ile Tyr Arg
145 150 155 160

<210> SEQ ID NO 221
<211> LENGTH: 156
<212> TYPE: PRT
<213> ORGANISM: Artificial Sequence
<220> FEATURE:
<223> OTHER INFORMATION: sdAb60 linked to the lytic peptide Polybia-MP1 by a GS_linker
<220> FEATURE:
<221> NAME/KEY: SITE
<222> LOCATION: 131,132
<223> OTHER INFORMATION: Xaa can be any amino acid

<400> SEQUENCE: 221

Gly Met Ala Glu Val Glu Val Val Ala Ser Gly Pro Gly Leu Val Lys
1 5 10 15

Pro Ser Gln Thr Leu Ser Leu Thr Cys Thr Val Ser Gly Asp Ser Ile
20 25 30

Thr Thr Thr Phe Ser His Trp Thr Trp Ile Arg Gln Ser Pro Glu Lys
35 40 45

Gly Leu Glu Trp Met Gly Ala Ile Gly Tyr Gly Gly Ser Ile Tyr Tyr
50 55 60

Ser Pro Ser Phe Lys Ser Arg Thr Ser Ile Ser Arg Asp Thr Ser Arg
65 70 75 80

Asn Gln Phe Thr Leu His Leu Ser Ser Val Thr Pro Glu Asp Thr Ala
85 90 95

Val Tyr Tyr Cys Ala Arg Leu Pro His Ser Ser Gly Tyr Ala Lys Phe
100 105 110

Gly His Leu Asp Tyr Trp Gly Gln Gly Thr Gln Val Thr Val Ser Ser
115 120 125

Ala Ala Xaa Xaa Gly Gly Gly Gly Ser Gly Gly Gly Gly Ser Ile Asp
130 135 140

Trp Lys Lys Leu Leu Asp Ala Ala Lys Gln Ile Leu
145 150 155

<210> SEQ ID NO 222
<211> LENGTH: 163
<212> TYPE: PRT
<213> ORGANISM: Artificial Sequence
<220> FEATURE:
<223> OTHER INFORMATION: sdAb60 linked to the lytic peptide Polybia-MP1 by a SRGS linker
<220> FEATURE:
<221> NAME/KEY: SITE
<222> LOCATION: 131,132
<223> OTHER INFORMATION: Xaa can be any amino acid

<400> SEQUENCE: 222

Gly Met Ala Glu Val Glu Val Val Ala Ser Gly Pro Gly Leu Val Lys
1 5 10 15

Pro Ser Gln Thr Leu Ser Leu Thr Cys Thr Val Ser Gly Asp Ser Ile
20 25 30

Thr Thr Thr Phe Ser His Trp Thr Trp Ile Arg Gln Ser Pro Glu Lys
35 40 45

Gly Leu Glu Trp Met Gly Ala Ile Gly Tyr Gly Gly Ser Ile Tyr Tyr
50 55 60

Ser Pro Ser Phe Lys Ser Arg Thr Ser Ile Ser Arg Asp Thr Ser Arg
65 70 75 80

```
Asn Gln Phe Thr Leu His Leu Ser Ser Val Thr Pro Glu Asp Thr Ala
                85                  90                  95

Val Tyr Tyr Cys Ala Arg Leu Pro His Ser Ser Gly Tyr Ala Lys Phe
            100                 105                 110

Gly His Leu Asp Tyr Trp Gly Gln Gly Thr Gln Val Thr Val Ser Ser
        115                 120                 125

Ala Ala Xaa Xaa Ser Arg Gly Ser Ser Gly Ser Ser Ser Ser Gly Ser
    130                 135                 140

Ser Gly Gly Ser Gly Ile Asp Trp Lys Lys Leu Leu Asp Ala Ala Lys
145                 150                 155                 160

Gln Ile Leu


<210> SEQ ID NO 223
<211> LENGTH: 172
<212> TYPE: PRT
<213> ORGANISM: Artificial Sequence
<220> FEATURE:
<223> OTHER INFORMATION: sdAbS linked to the lytic peptide BMAP28A by a
      SRGS linker
<220> FEATURE:
<221> NAME/KEY: SITE
<222> LOCATION: 126,127
<223> OTHER INFORMATION: Xaa can be any amino acid

<400> SEQUENCE: 223

Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Ser
        115                 120                 125

Arg Gly Ser Ser Gly Ser Ser Ser Ser Gly Ser Ser Gly Gly Ser Gly
    130                 135                 140

Gly Gly Leu Arg Ser Leu Gly Arg Lys Ile Leu Arg Ala Trp Lys Lys
145                 150                 155                 160

Tyr Gly Pro Ile Ile Val Pro Ile Ile Arg Ile Gly
                165                 170


<210> SEQ ID NO 224
<211> LENGTH: 155
<212> TYPE: PRT
<213> ORGANISM: Artificial Sequence
<220> FEATURE:
<223> OTHER INFORMATION: sdAbS linked to the lytic peptide modified
      cysteine deleted Tachyplesin-I by a SRGS linker
<220> FEATURE:
<221> NAME/KEY: SITE
<222> LOCATION: 126,127
<223> OTHER INFORMATION: Xaa can be any amino acid

<400> SEQUENCE: 224
```

```
Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Ser
        115                 120                 125

Arg Gly Ser Ser Gly Ser Ser Ser Ser Gly Ser Ser Gly Gly Ser Gly
    130                 135                 140

Lys Trp Phe Arg Val Tyr Arg Gly Ile Tyr Arg
145                 150                 155


<210> SEQ ID NO 225
<211> LENGTH: 151
<212> TYPE: PRT
<213> ORGANISM: Artificial Sequence
<220> FEATURE:
<223> OTHER INFORMATION: sdAbS linked to the lytic peptide Polybia-MP1
      by a GS_linker
<220> FEATURE:
<221> NAME/KEY: SITE
<222> LOCATION: 126,127
<223> OTHER INFORMATION: Xaa can be any amino acid

<400> SEQUENCE: 225

Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Gly
        115                 120                 125

Gly Gly Gly Ser Gly Gly Gly Gly Ser Ile Asp Trp Lys Lys Leu Leu
    130                 135                 140

Asp Ala Ala Lys Gln Ile Leu
145                 150


<210> SEQ ID NO 226
<211> LENGTH: 158
```

```
<212> TYPE: PRT
<213> ORGANISM: Artificial Sequence
<220> FEATURE:
<223> OTHER INFORMATION: sdAbS linked to the lytic peptide Polybia-MP1
      by a SRGS linker
<220> FEATURE:
<221> NAME/KEY: SITE
<222> LOCATION: 126,127
<223> OTHER INFORMATION: Xaa can be any amino acid

<400> SEQUENCE: 226

Gly Met Ala Glu Val Glu Val Val Ala Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Trp Met Tyr Trp Ala Arg Gln Ala Pro Gly Lys Gly Leu
        35                  40                  45

Glu Trp Val Ser Ala Ile Asp Gln Ser Gly Thr Thr Thr Arg Tyr Ala
    50                  55                  60

Asp Ser Val Lys Gly Gln Phe Thr Ile Ser Arg Asp Asn Ala Lys His
65                  70                  75                  80

Thr Leu Tyr Leu Gln Met Asn Ser Leu Lys Pro Glu Asp Thr Ala Leu
                85                  90                  95

Tyr Tyr Cys Thr Thr Ser Gly Arg Tyr Tyr Ala Met Asp Tyr Trp Gly
            100                 105                 110

Lys Gly Thr Gln Val Thr Val Ser Thr Ser Ser Ala Ala Xaa Xaa Ser
        115                 120                 125

Arg Gly Ser Ser Gly Ser Ser Ser Ser Gly Ser Ser Gly Gly Ser Gly
    130                 135                 140

Ile Asp Trp Lys Lys Leu Leu Asp Ala Ala Lys Gln Ile Leu
145                 150                 155


<210> SEQ ID NO 227
<211> LENGTH: 4
<212> TYPE: PRT
<213> ORGANISM: Artificial Sequence
<220> FEATURE:
<223> OTHER INFORMATION: Short connecting sequence
<220> FEATURE:
<221> NAME/KEY: SITE
<222> LOCATION: 3,4
<223> OTHER INFORMATION: Xaa can be any amino acid

<400> SEQUENCE: 227

Ala Ala Xaa Xaa
1


<210> SEQ ID NO 228
<211> LENGTH: 15
<212> TYPE: PRT
<213> ORGANISM: Artificial Sequence
<220> FEATURE:
<223> OTHER INFORMATION: GGGGS linker

<400> SEQUENCE: 228

Gly Gly Gly Gly Ser Gly Gly Gly Gly Ser Gly Gly Gly Gly Ser
1               5                   10                  15
```

SINGLE DOMAIN ANTIBODIES SPECIFICALLY BINDING GLOBO-SERIES GLYCANS

The present application is the national phase entry of PCT Application No. PCT/EP2020/077754, filed Oct. 2, 2020, which claims priority to EP Application Serial No. 19201562.6, filed Oct. 4, 2019, which are incorporated by reference in its entirety.

FIELD OF INVENTION

The present invention relates to the field of single-domain antibodies (sdAb) directed towards the glycans of the globo series, and in particular Globo H. More in detail, the present invention relates to sdAbs specifically binding one or more glycans selected from Globo H, Gb3, Gb4, and Gb5. The invention also provides polypeptides comprising multimeric single domain antibodies, as well as T cell chimeric antigen receptors comprising said anti-glycan sdAbs. Thus, the present invention provides polypeptides that can be used for targeting and/or treating several types of cancers associated with cells over-expressing said Globo H and/or Gb3, Gb4, Gb5. The present invention also relates to recombinant nucleic acid sequences encoding said polypeptides, and expression vectors and host cells comprising the same.

BACKGROUND OF THE INVENTION

Globo-series glycans comprise a group of neutral glycosphingolipids in which a ceramide is linked to a glycan with a root structure of GalNAcβ3Galα4Galβ4Glc. Typically, these glycans are retained on the plasma membrane and cluster into lipid rafts. The endogenous function of this glycan family is largely unknown. Their expression does, however, occur during early stages of development and is thought to mediate cell contact and adhesion. Importantly, changes in these glycans are observed throughout differentiation and during tumorigenesis. Two notable hexasaccharide members of this family are stage-specific embryonic antigen-4 (SSEA-4) and Globo H (FIG. 2). These glycans share a common precursor, SSEA-3 (Galβ3GalNAcβ3Galα4Galβ4Glc), but vary in the terminal monosaccharide: β3-linked N-acetylneuraminic acid for SSEA-4 and α2-linked L-fucose for Globo H.

SSEA-4 is expressed on many stem cell types, on induced pluripotent stem cells, on embryonic carcinoma cells, on breast cancer cells, and on malignant glioma cells, which form the most aggressive and common brain tumors in adults. As a result, antibodies against SSEA-4 could support the targeting of SSEA-4 in cancer vaccines.

Globo H is a hexasaccharide with chemical formula Fucα1→2Galβ1→3GalNAcβ1→3Galα1→4Galβ1→4Glcβ1-O-Cer. Globo H expression has been found on several epithelial cancers such as endometrial colon, ovarian, gastric, pancreatic, lung, prostate, and breast cancers; in normal tissues it is moderately present in breast, colon, esophagus, small intestine, prostate, rectum, testis, and uterine cervix, but only on apical epithelial cells at lumen borders. Wang et al. (PNAS, 2008) found by glycan array that both normal donors and breast cancer patients expressed high levels of antibodies to SSEA-3, but breast cancer patients expressed much higher levels of antibodies to Globo H than normal donors. Because the sites where either SSEA-3 or Globo H could be found in normal tissues are in areas that are considered generally inaccessible to immune cells, both SSEA-3 and Globo H make attractive targets for a cancer vaccine.

However, most carbohydrate antigens are often tolerated by the immune system, and consequently, the immunogenicity induced by them is limited. Further, the production of antibody against a specific immunogen typically involves cooperative interactions between two types of lymphocytes, i.e., B-cells and helper T-cells. Globo H alone cannot activate helper T-cells, which also attributes to the poor immunogenicity of Globo H. Accordingly, immunization with Globo H alone often results in low titers of immunoglobulin M (IgM) and failure to class switch to immunoglobulin G (IgG), as well as ineffective antibody affinity maturation. Recently, it has been demonstrated that with addition of suitable adjuvants, antibodies against Globo H can be induced, including class switching from IgM to IgG. Thus, Globo H is a promising therapeutic target for cancer vaccination. This approach has been tested in clinical trials at various stages against different cancers, including breast cancer, ovarian cancer, prostate cancer, and lung cancer.

The lack of generation of single domain antibodies in response to glycans is supported by previous studies showing that anti-polysaccharide responses in humans are clearly dominated by IgM and $IgG_1$ types whereas heavy chain antibodies from camelids belong to the $IgG_2$ and $IgG_3$ classes (Daley et al., Clin Vaccine Immunol. 2010). Moreover, it is known that interactions between polysaccharides and individual binding sites in a protein are typically weak and binding strength and specificity is enhanced through polymeric interactions between polysaccharides and oligomeric polysaccharide-binding proteins. Being strictly monomeric binders by nature, VHH are in this respect not well suited to bind polysaccharides. Therefore, the person skilled in the art would assume that it is extremely difficult to raise immunoglobulins devoid of light chains against a globo-series glycan.

While conventional antibodies against Globo H have been shown to be promising in cancer diagnosis and therapy (WO 2015/143123 A) better anti-Globo H antibodies are still needed. For the intended uses, monoclonal antibodies, and preferably single domain antibodies are needed. Single domain antibodies (sdAbs or VHH) specifically binding a globo-series glycosphingolipid, such as Globo H or a fragment thereof, have not been disclosed in the art so far, although attempts to make such antibodies have been made. The patent application WO 2015/143123 A discloses conventional anti-Globo H antibodies and pharmaceutical compositions comprising these antibodies to prevent or treat Globo H positive cancers. However these antibodies have CDR sequences that can confer chemical instability, which makes them undesirable for further production scale-up and clinical study.

The international patent application WO 2018/054353 A discloses therapeutic human conventional monoclonal antibodies binding Globo H and having CDR sequences engineered for increased stability against undesirable modifications and large aggregate formation that can occur under high expression manufacturing conditions.

In contrast to conventional mammalian IgG antibodies, sdAbs contain only heavy chains and are devoid of light chains. The antigen binding domain of a single domain antibody is called VHH or Nanobody®. VHHs have several general advantages over conventional antibodies. First, they are only 13-15 kDa in size and about 10-fold smaller than conventional IgG antibodies (150 kDa). They can access better epitopes even in crowded cellular environments, and penetrate better into tissues, organs, and animals.

They have much higher chemical (e.g. up to 8 M urea) and thermal stability (up to 83° C.), and longer shelf life time compared to conventional antibodies.

Thus, it is the objective of the present invention to provide single domain antibodies specifically binding Globo H, as well as globo-serie glycan, such as Gb3 (Globotriaose), Gb4 (Globotetraose), and Gb5 (Globopentaose Gb5).

This objective is solved by the teaching of the independent claims. Further advantageous features, aspects and details of the invention are evident from the dependent claims, the description, the figures, and the examples of the present application.

BRIEF DESCRIPTION OF THE INVENTION

The application is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said at least one single domain antibody binds at least one globo-series glycan selected from Globo H, Gb3, Gb4, and Gb5.

In some embodiments, the polypeptide specifically binding a globo-series glycan comprises at least one single domain antibody having at least 90% sequence identity with a sequence selected from the group consisting of SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 136, SEQ ID NO 137, and SEQ ID NO 138, wherein said single domain antibody binds at least one globo-series glycan selected from Globo H, Gb3, Gb4, and Gb5. In certain embodiments, the polypeptide specifically binding a globo-series glycan comprises at least one single domain antibody that binds at least one globo-series glycan selected from Globo H, Gb3, Gb4, and Gb5, and having at least 90% sequence identity with SEQ ID NO 5.

In particular embodiments, the polypeptide specifically binding a globo-series glycan comprises at least one single domain antibody as disclosed herein, and at least one effector molecule linked to said at least one single domain antibody, wherein the effector molecule is selected from the group consisting of anticancer peptides, lytic peptides, L-rhamnose, galactose-α-1,3-galactose, dinitrophenyl, serum stabilizing molecules, fluorescent molecules, phosphorescent molecules, chemiluminescent molecules, bioluminescent molecules, radio-isotopes, chromophores, disuccinimidyl adipate, human Fc antibody fragments. In more particular embodiments, the polypeptide specifically binding a globo-series glycan comprises at least one single domain antibody that binds at least one globo-series glycan selected from Globo H, Gb3, Gb4, and Gb5, and at least one lytic peptide selected from the group comprising modified cysteine deleted tachyplesin-1, BMAP28A, Polybia-MP1. In still more particular embodiments, the polypeptide specifically binding a globo-series glycan comprising at least one single domain antibody, and further comprising at least one lytic peptide linked to the at least one single domain antibody, has at least 85% sequence identity with a sequence selected from SEQ ID NOs: 19-63, 142-156, 179-226.

The present invention is also directed to a polypeptide specifically binding a globo-series glycan comprising at least one single domain antibody as disclosed herein, wherein said single domain antibody binds at least one globo-series glycan selected from Globo H, Gb3, Gb4, and Gb5, and further comprising at least one extracellular hinge region, at least one transmembrane domain, at least one costimulatory domain, and at least one intracellular activation domain, wherein the single domain antibody is linked to the extracellular hinge region. Said extracellular hinge region, transmembrane domain, costimulatory domain, and intracellular activation domain represent the modules or elements of a T-cell chimeric antigen receptor (CAR). The chimeric antigen receptor as disclosed herein can be used to generate CAR T cells specifically recognizing a globo-series glycan selected from Globo H, Gb3, Gb4, and Gb5. Said CAR T cells can thus be used in the therapy of a cancer, wherein the cancer cells of said cancer express on their surface at least one globo-series glycan selected from Globo H, Gb3, Gb4, and Gb5.

The present invention also provides a polypeptide specifically binding a globo-series glycan comprising at least one single domain antibody, wherein said at least one single domain antibody is a humanized single domain antibody, and wherein said at least one single domain antibody binds at least one globo-series glycan selected from Globo H, Gb3, Gb4, and Gb5. Moreover, the present invention provides a polypeptide specifically binding a globo-series glycan comprising at least one single domain antibody, wherein said at least one single domain antibody is a humanized single domain antibody, and further comprising at least one effector molecule linked to the at least one humanized single domain antibody, wherein said at least one humanized single domain antibody binds at least one globo-series glycan selected from Globo H, Gb3, Gb4, and Gb5. According to the invention the at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering.

The present invention also provides recombinant nucleic acid molecules encoding the polypeptides of the invention, and vectors that comprise said recombinant nucleic acid molecules. Host cells comprising the recombinant nucleic acid molecules or vectors of the invention are also provided herein.

Moreover, the invention also relates to pharmaceutical compositions comprising a therapeutically effective amount of the inventive polypeptide specifically binding a globo-series glycan and comprising at least one single domain antibody, together with at least one pharmaceutically acceptable vehicle, excipient and/or diluent.

The invention also provides for the use of a polypeptide of the invention or of the pharmaceutical composition according to the invention in treatment and/or diagnosis of a cancer, wherein the cancer cells of said cancer express on their surface at least one globo-series glycan selected from Globo H, Gb3, Gb4, and Gb5. In other words, the invention provides for the use of a polypeptide of the invention or of a pharmaceutical composition according to the invention in treatment and/or diagnosis of a cancer, wherein the cancer is characterised by cells expressing on their surface at least one globo-series glycan selected from Globo H, Gb3, Gb4, and Gb5.

The invention also provides for the use of a polypeptide of the invention or of the pharmaceutical composition according to the invention in treatment and/or diagnosis of a cancer, wherein the cancer cells of said cancer express on their surface at least one globo-series glycan selected from Globo H, Gb3, Gb4, and Gb5, and wherein said cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

The invention also provides a diagnostic kit comprising a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said at least one single domain antibody binds at least one globo-series glycan selected from Globo H, Gb3, Gb4, and Gb5, for screening for a cancer characterised by cells expressing on their surface at least one globo-series glycan selected from Globo H, Gb3, Gb4, and Gb5.

A further embodiment of the invention provides a polypeptide as described above wherein the number of single domain antibodies that bind at least one globo-series glycan selected from Globo H, Gb3, Gb4, and Gb5 is at least two. The two or more single domain antibodies are different in sequence or are identical in sequence.

A particular embodiment of the invention provides a polypeptide as described above wherein the number of single domain antibodies that bind at least one globo-series glycan selected from Globo H, Gb3, Gb4, and Gb5 is three. A particular embodiment of the invention provides a polypeptide as described above wherein the number of single domain antibodies that bind at least one globo-series glycan selected from Globo H, Gb3, Gb4, and Gb5 is three, and wherein said single domain antibody has at least 90% sequence identity with SEQ ID NO 5.

DETAILED DESCRIPTION OF THE INVENTION

Definitions

Tumor Associated Antigens (TACAs) and Types

Cancer cells can be distinguished from normal cells for displaying aberrant levels and types of carbohydrate structures on their surfaces. These carbohydrate structures are known as tumor-associated carbohydrate antigens (TACAs). TACAs were considered as promising targets for the design of anticancer vaccines. Unfortunately, carbohydrates alone can only evoke poor immunogenicity because they are unable to induce T-cell-dependent immune responses, which is critical for cancer therapy.

Glycosphingolipids (GSLs) represent a group of complex lipids composed of a glycan structure attached to a lipid tail that contains the sphingolipid ceramide. The basic structure for a glycosphingolipid is a monosaccharide, usually glucose or galactose, attached directly to a ceramide molecule and resulting in, respectively, glucosylceramide (glucocerebroside; GlcCer) or galactosylceramide (galactocerebroside; GalCer). GSLs are ubiquitous in cell membranes, where they are known to participate in cellular processes such as signaling, adhesion, and cell differentiation, among other functions. Certain glycosphingolipids highly expressed in tumor cells or tissues have been defined by specific monoclonal antibodies and thereby identified as tumor-associated carbohydrate antigens (TACAs) resulting from aberrant GSL synthesis in tumors. Tumor cells express aberrant glycosylation in GSLs, displaying either incomplete synthesis leading to an accumulation of precursors, or further addition of glycan residues to form new structures.

While globotriosylceramide (Gb3Cer) and globoside (Gb4Cer) constitute the basis of P-blood group system, galactosyl globoside (Gb5Cer) and sialyl galactosyl globoside (sialyl Gb5Cer), also known as stage-specific embryonic antigen-3 (SSEA-3) and SSEA-4, respectively, are widely used as cell-surface markers to define human embryonic stem cells.

Globo-series GSLs have also been observed in tumors: Globo H (fucosyl Gb5Cer) is overexpressed in many epithelial cancers, such as endometrial, colon, ovarian, gastric, pancreatic, lung, prostate, and breast cancers.

"Globo H" as used herein, refers to a hexasaccharide of formula, Fucα1→2Galβ1→3GalNAcβ1→3Galα1→4Galβ1→4Glcβ1→O-cer, having the structure:

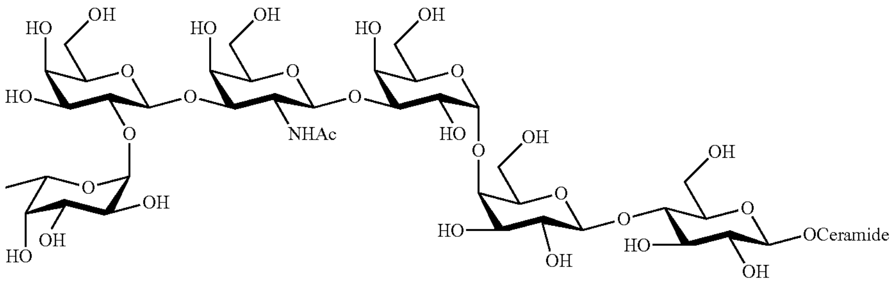

"Globo H-positive cancer" refers to a cancer comprising cancer cells expressing Globo H on their surface.

Studies report also the presence of the truncated forms or fragments of Globo H on the surface of cancer cells. Such truncated forms are Gb3 (Globotriaose), Gb4 (Globotetraose), and Gb5 (Globopentaose) (FIG. 2).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. The terms "antibody" and "immunoglobulin" are used interchangeably in the broadest sense and include monoclonal antibodies (e.g., full length or intact monoclonal antibodies), polyclonal antibodies, human antibodies, multispecific (or heteroconjugate) antibodies (e.g. bispecific antibodies), monovalent antibodies, multivalent antibodies, antigen-binding antibody fragments (e.g. Fab', $F(ab')_2$, Fab, Fv, rIgG, scFv fragments, sdAbs, VHH), antibody fusions, and synthetic antibodies (or antibody mimetics). An antibody can be chimeric, human, humanized and/or affinity matured.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or of a T cell receptor.

As used herein, the term "specific binding" or "specifically binding" or "binds specifically" refers to the interaction between binding pairs (e.g., an antibody and an antigen). In various instances, specifically binding can be embodied by an affinity constant of about $10^{-6}$ moles/liter, about $10^{-7}$ moles/liter, or about $10_{-8}$ moles/liter, or less.

"Binding affinity" generally refers to the strength of the total sum of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen.

The term "vector" as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced. Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors" or "recombinant vectors"). In general, expression vectors of utility in recombinant DNA techniques are often in the form of plasmids. In the present specification, "plasmid" and "vector" may be used interchangeably as the plasmid is the most commonly used form of vector.

"Recombinant polynucleotide" or "recombinant nucleic acid molecule" as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups.

"Oligonucleotide" as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"A globo-series glycan binding single domain antibody (sdAb)" or "sdAb that binds a globo-series glycan selected from Globo H, Gb3, Gb4, and Gb5" refers to a sdAb that binds a globo-series glycan selected from Globo H, Gb3, Gb4, and Gb5 with sufficient affinity such that the sdAb is useful as a diagnostic and/or therapeutic agent by binding the target glycan. A "Globo H binding single domain antibody (sdAb)" or "sdAb that binds Globo H" refers to a sdAb that binds Globo H with sufficient affinity such that the sdAb is useful as a diagnostic and/or therapeutic agent by binding GloboH. A "Gb3 binding single domain antibody (sdAb)" or "sdAb that binds Gb3" refers to a sdAb that binds Gb3 with sufficient affinity such that the sdAb is useful as a diagnostic and/or therapeutic agent by binding Gb3. A "Gb4 binding single domain antibody (sdAb)" or "sdAb that binds Gb4" refers to a sdAb that binds Gb4 with sufficient affinity such that the sdAb is useful as a diagnostic and/or therapeutic agent by binding Gb4. A "Gb5 binding single domain antibody (sdAb)" or "sdAb that binds Gb5" refers to a sdAb that binds Gb5 with sufficient affinity such that the sdAb is useful as a diagnostic and/or therapeutic agent by binding Gb5.

"Full-length antibody", "intact antibody" or "whole antibody" are used herein interchangeably to refer to an antibody having a structure substantially similar to a native antibody structure.

"Antibody fragment" refers to a portion of a full-length antibody which is capable of binding the same antigen as the full-length antibody. Examples of antibody fragments include, but are not limited to, Fv, Fab, Fab', F(ab')2; diabodies; linear antibodies; single-chain antibody molecules (e.g., scFv); single domain antibodies; multispecific antibodies formed from antibody fragments.

The "variable region" or "variable domain" of an antibody refers to the amino-terminal domains of heavy or light chain of the antibody. The variable domains of the heavy chain and light chain (VH and VL, respectively) of a native antibody generally have similar structures. A single VH or VL domain may be sufficient to confer antigen-binding specificity. In particular, "variable region" or "variable domain" of a single domain antibody disclosed herein refers to the amino-terminal domains of the heavy chain.

The term "variable" refers to the fact that certain portions of the variable domains differ extensively in sequence among antibodies and are used in the binding and specificity of each particular antibody for its particular antigen. However, the variability is concentrated in three segments called complementarity-determining regions (CDRs) or hypervariable regions (HVR) both in the light-chain and the heavy-chain variable domains. The more highly conserved portions of variable domains are called framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

"Hypervariable region" or "HVR" as used herein, refers to each of the regions of an antibody variable domain which are hypervariable in sequence and/or form structurally defined loops. Generally, native antibodies comprise four chains with six HVRs; three in the heavy chain variable domains, VH (H1, H2, H3), and three in the light chain variable domains, VL (L1, L2, L3). Single domain antibodies only comprise three HVRs in the heavy chain variable domain. The HVRs generally comprise amino acid residues from the hypervariable loops and/or from the "complementarity determining regions" (CDRs). Unless otherwise indicated, HVR residues and other residues in the variable domain (e.g., FR residues) are numbered herein according to Kabat et al., 1991.

"Complementarity determining region" or "CDR" as used herein, refers to the regions within the hypervariable regions of the variable domain which have the highest sequence variability and/or are involved in antigen recognition. Generally, native antibodies comprise four chains with six CDRs; three in the heavy chain variable domains, VH (H1, H2, H3), and three in the light chain variable domains, VL (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35 of H1, 50-65 of H2, and 95-102 of H3 (Kabat et al., 1991). Single domain antibodies such as those disclosed herein only comprise CDR-H1 or CDR1, CDR-H2 or CDR2, and CDR-H3 or CDR3 as they lack the light chain.

"Native antibody" refers to a naturally occurring immunoglobulin molecule. For example, native IgG antibodies are heterotetrameric glycoproteins of about 150 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies, and is not to be construed as requiring production of the antibody by any particular method.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially a single domain antibody, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., 1991.

"Multivalent antibody" as used herein, is an antibody comprising three or more antigen binding sites. The multivalent antibody is preferably engineered to have the three or more antigen binding sites and is generally not a native sequence IgM or IgA antibody.

"Multispecific antibody" is an antibody having at least two different binding sites, each site with a different binding specificity. A multispecific antibody can be a full length antibody or an antibody fragment, and the different binding sites may bind each to a different antigen or the different binding sites may bind to two different epitopes of the same antigen.

"Fc region" or "Fc antibody fragment" refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences.

"Fab fragment" refers to an antibody fragment that contains a variable and constant domain of the light chain and a variable domain and the first constant domain (CH1) of the heavy chain. Papain digestion of antibodies produces two identical "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. Fab' fragments differ from Fab fragments by the addition of a few residues at the carboxy terminus of the heavy chain CH1 domain including one or more cysteines from the antibody hinge region. F(ab')2 antibody fragments originally were produced as pairs of Fab' fragments which have hinge cysteines between them. Other chemical couplings of antibody fragments also are known in the art.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Single-chain Fv" or "scFv" refers to antibody fragments comprising the VH and VL domains of an antibody, wherein these domains are present in a single polypeptide chain. Generally, an Fv polypeptide further comprises a polypeptide linker between the VH and VL domains which enables the scFv to form the desired antigen binding structure.

"Diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites.

"Naked antibody" refers to an antibody that is not conjugated to a heterologous moiety (e.g., a cytotoxic moiety) or radiolabel.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. Ordinarily, isolated antibody will be prepared by at least one purification step.

The term "substantially similar," "substantially the same", "equivalent", or "substantially equivalent"," as used herein, refer to a sufficiently high degree of similarity between two numeric values (for example, one associated with a test antibody and the other associated with a reference antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the value for the reference/comparator molecule.

"Substantially different" as used herein, refers to a sufficiently high degree of difference between two numeric values (generally one associated with a molecule and the other associated with a reference molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5.

Another embodiment of the present invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with a sequence selected from the group consisting of SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 136, SEQ ID NO 137, and SEQ ID NO 138 (Table 4). A preferred embodiment is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 5 (Table 4). A preferred embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 1. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 3. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 7. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 9. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 11. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 13. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 15. Another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 17. Still another embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 136. A further embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with SEQ ID NO 137. Another further embodiment of the invention is a polypeptide specifically binding a globo-series glycan comprising at least one single domain antibody, wherein said single domain antibody binds at least one globo-series glycan selected from Globo H, Gb3, Gb4, and Gb5, wherein said at least one single domain antibody has at least 90% sequence identity with and SEQ ID NO 138.

Said sequences SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 136, SEQ ID NO 137, and SEQ ID NO 138 (sdAbs or VHHs) are derived from heavy chain antibodies of alpaca (*Vicugna Pacos*), which have been immunized against Globo H glycan.

The invention also relates to recombinant nucleic acid molecules capable of encoding said polypeptides, and to vectors and host cells comprising said recombinant nucleic acid molecules.

Single domain antibodies are antibodies whose complementary determining regions are part of a single domain polypeptide. Single domain antibodies are disclosed in WO1994004678A1 for example. For clarity reasons, the variable domain derived from a heavy chain antibody naturally devoid of light chain is referred to herein as VHH or sdAb (single domain antibody) to distinguish it from the conventional VH of four chain immunoglobulins. Such a VHH molecule can be derived from antibodies raised in Camelidae species, for example in camel, dromedary, llama, alpaca, and guanaco. Other species besides Camelidae may produce heavy chain antibodies naturally devoid of light chain.

According to one aspect of the invention, a single domain antibodies as used herein is a naturally occurring single domain antibody known as heavy chain antibody naturally devoid of light chains and naturally devoid of the constant region 1, or a variant of said variable domain.

sdAbs are about 13-15 kDa, and thus almost ten times smaller than IgG molecules. They are single polypeptides and very stable, both during storage and during utilization, meaning that the integrity of the antigen-binding protein is maintained under storage and/or utilization conditions, which may include elevated temperatures, freeze-thaw cycles, changes in pH or in ionic strength, UV-irradiation, presence of harmful chemicals and the like. Moreover, they are resistant to the action of proteases which is not the case for conventional antibodies. Furthermore, the single domain antibody according to this invention is easy to produce in vitro at high yield, properly folded, and functional. In addition, antibodies generated in alpaca or more generally camelids will recognize epitopes other than those recognised by antibodies generated in vitro through the use of antibody libraries or via immunisation of mammals other than Camelids (WO2005044858A1). As a consequence, sdAbs against GloboH, Gb3, Gb4, or Gb5 may interact more efficiently with the target antigen than conventional antibodies, thereby allowing detection or treatment of cancers characterized by cells expressing GloboH, Gb3, Gb4, or Gb5 at much higher efficiency. Since sdAbs are known to bind into unusual epitopes such as cavities or grooves (WO 2005044858A1), the affinity of such antibodies may be suitable for therapeutic treatment.

Thus, generally, a single domain antibody can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

Thus, a "single domain antibody" according to the present invention comprises an amino acid sequence comprising FR1-FR4 and CDR1-CDR3, or a variant sequence thereof, and their binding specificity to the globo-series sphingolipid is conferred by the amino acid sequence of three complementarity-determining regions CDR1, CDR2, CDR3.

The sequences of the FR1-FR4 and of CDR1-CDR3 of the single domain antibodies disclosed in this invention are SEQ ID NOs: 64-126, 157-177. The annotation of the FR and CDR regions is based on the unique numbering system according to Kabat.

Therefore one embodiment of the present invention is also directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and wherein said single domain antibody comprises complementarity determining regions CDR1, CDR2, and CDR3, wherein:

(a) CDR1 comprises an amino acid sequence selected from SEQ ID NO: 64-72, 157-159, or a variant thereof;

(b) CDR2 comprises an amino acid sequence selected from SEQ ID NO: 73-81, 160-162, or a variant thereof (c) CDR3 comprises an amino acid sequence selected from SEQ ID NO: 82-90, 163-165, or a variant thereof.

Another embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and wherein said single domain antibody comprises complementarity determining regions CDR1, CDR2, and CDR3, wherein:

(a) CDR1 comprises an amino acid sequence having at least 90% sequence identity with a sequence selected from SEQ ID NO: 64-72, 157-159;

(b) CDR2 comprises an amino acid sequence having at least 90% sequence identity with a sequence selected from SEQ ID NO: 73-81, 160-162;

(c) CDR3 comprises an amino acid sequence having at least 90% sequence identity with a sequence selected from SEQ ID NO: 82-90, 163-165.

GloboH is a principal target according to the invention. A single domain antibody directed against a target means a single domain antibody that is capable of binding to said target with an affinity of better than $10^{-6}$ M.

Targets may also be fragments of said principal target. Thus a target is also a fragment of said target, capable of eliciting an immune response. A target is also a fragment of said target, capable of binding to a single domain antibody raised against the full length target. Preferred fragments of the principal target GloboH are Gb3, Gb4, and Gb5.

Binding of the single domain antibody to a glycophingolipid selected from GloboH, Gb3, Gb4, and Gb5 occurs preferably with high affinity: typically, the dissociation constant of the binding between the single domain antibody and the globo-series target glycan is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. In alternative, the dissociation constant of the binding between the single domain antibody and Globo H is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. In alternative, the dissociation constant of the binding between the single domain antibody and Gb3 is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. In alternative, the dissociation constant of the binding between the single domain antibody and Gb4 is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. In alternative, the dissociation constant of the binding between the single domain antibody and Gb5 is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

"Variant Sequences"

According to an aspect of the invention a polypeptide binding to a glycan selected from GloboH, Gb3, Gb4, and Gb5 may be a variant sequence of a full-length polypeptide binding to a glycan selected from GloboH, Gb3, Gb4, and Gb5. According to an aspect of the invention a polypeptide binding to a glycan selected from GloboH, Gb3, Gb4, and Gb5 may comprise a sequence of full-length polypeptide binding to a glycan selected from GloboH, Gb3, Gb4, and Gb5.

According to an aspect of the invention a single domain antibody comprised in the polypeptide binding to a glycan selected from GloboH, Gb3, Gb4, and Gb5 may be a complete single domain antibody (e.g. sdAb or VHH) or a variant sequence thereof.

As used herein, a variant sequence of the present invention may comprise additions, deletions or substitutions of one or more amino acids, which do not substantially alter the functional characteristics of the polypeptides of the invention compared with the unmodified parent polypeptide, also referred to as reference polypeptide.

A variant sequence according to the present invention may be a sequence which exists in other Camelidae species such as, for example, camel, dromedary, llama, alpaca, guanaco etc.

The number of amino acid deletions or substitutions in the variant sequence in comparison with the parent sequence is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids.

Where variant sequence indicates sequence identity, it means a variant sequence which presents a high sequence identity, such as more than 70%, 75%, 80%, 85%, 90%, 95% or 98% sequence identity with the parent sequence and is preferably characterised by similar properties of the parent sequence, namely affinity, said identity calculated as described below.

The percentage of "sequence identity" is determined by comparing two optimally aligned nucleic acid or polypeptide sequences over a "comparison window" on the full length of the reference sequence. A "comparison window" as used herein, refers to the optimal alignment between the reference and variant sequence after that the two sequences are optimally aligned, wherein the variant nucleic acid or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment. Identity percentage is calculated by determining the number of positions at which the identical nucleic acid bases or amino acid residues occurs in both sequences to yield the number of matched positions, dividing the number of matched positions by the total number of positions in the reference sequence (i.e., the full length in amino acid or nucleotide) and multiplying the results by 100 to yield the percentage of sequence identity. Two nucleic acid or polypeptide sequences are said to be "identical" if the sequence of nucleotides or amino acids in the two sequences is the same when optimally aligned as described above.

Alternatively, a variant sequence may also be any amino acid sequence resulting from allowed substitutions at any number of positions of the parent sequence according to the formula below:

Ser substituted by Ser, Thr, Gly, and Asn;

Arg substituted by one of Arg, His, Gin, Lys, and Glu;

Leu substituted by one of Leu, Ile, Phe, Tyr, Met, and Val;

Pro substituted by one of Pro, Gly, Ala, and Thr;
Thr substituted by one of Thr, Pro, Ser, Ala, Gly, His, and Gin;
Ala substituted by one of Ala, Gly, Thr, and Pro;
Val substituted by one of Val, Met, Tyr, Phe, Ile, and Leu;
Gly substituted by one of Gly, Ala, Thr, Pro, and Ser;
Ile substituted by one of Ile, Met, Tyr, Phe, Val, and Leu;
Phe substituted by one of Phe, Trp, Met, Tyr, lie, Val, and Leu;
Tyr substituted by one of Tyr, Trp, Met, Phe, Ile, Val, and Leu;
His substituted by one of His, Glu, Lys, Gin, Thr, and Arg;
Gln substituted by one of Gin, Glu, Lys, Asn, His, Thr, and Arg;
Asn substituted by one of Asn, Glu, Asp, Gin, and Ser;
Lys substituted by one of Lys, Glu, Gln, His, and Arg;
Asp substituted by one of Asp, Glu, and Asn;
Glu substituted by one of Glu, Asp, Lys, Asn, Gln, His, and Arg;
Met substituted by one of Met, Phe, Ile, Val, Leu, and Tyr.

Variants, as used herein, can also be sequences wherein each framework region FR and each complementarity determining region CDR shows at least 80% identity, preferably at least 85% identity, more preferably 90% identity, even more preferably 95% identity with the corresponding region in the reference sequence. In this case sequence identity is determined as described above for the FR1variant versus FR1reference, CDR1variant versus CDR1reference, FR2variant versus FR2reference, CDR2variant versus CDR2reference, FR3variant versus FR3reference, CDR3variant versus CDR3reference and FR4variant versus FR4reference.

In another embodiment, a recombinant nucleic acid sequence encoding any of the above antigen-binding proteins or variant thereof is also part of the present invention.

The invention provides recombinant nucleic acid molecules encoding one or more polypeptides comprising the amino acid sequence selected from the group consisting of: SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 136, SEQ ID NO 137, and SEQ ID NO 138.

Thus, the invention provides recombinant nucleic acid molecules comprising the nucleic acid sequence as set forth in one or more of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141 (Table 4), or a variant thereof. The invention provides a recombinant nucleic acid molecule comprising the nucleic acid sequence as set forth in SEQ ID NO: 2, or a variant thereof. The invention provides a recombinant nucleic acid molecule comprising the nucleic acid sequence as set forth in SEQ ID NO:4, or a variant thereof. The invention provides a recombinant nucleic acid molecule comprising the nucleic acid sequence as set forth as SEQ ID NO: 6, or a variant thereof. The invention provides a recombinant nucleic acid molecule comprising the nucleic acid sequence as set forth in SEQ ID NO: 8, or a variant thereof. The invention provides a recombinant nucleic acid molecule comprising the nucleic acid sequence as set forth in SEQ ID NO: 10, or a variant thereof. The invention provides a recombinant nucleic acid molecule comprising the nucleic acid sequence as set forth in SEQ ID NO: 12, or a variant thereof. The invention provides a recombinant nucleic acid molecule comprising the nucleic acid sequence as set forth in SEQ ID NO: 14, or a variant thereof. The invention provides a recombinant nucleic acid molecule comprising the nucleic acid sequence as set forth in SEQ ID NO: 16, or a variant thereof. The invention provides a recombinant nucleic acid molecule comprising the nucleic acid sequence as set forth in SEQ ID NO: 18, or a variant thereof. The invention provides a recombinant nucleic acid molecule comprising the nucleic acid sequence as set forth in SEQ ID NO: 139, or a variant thereof. The invention provides a recombinant nucleic acid molecule comprising the nucleic acid sequence as set forth in SEQ ID NO: 140, or a variant thereof. The invention provides a recombinant nucleic acid molecule comprising the nucleic acid sequence as set forth in SEQ ID NO: 141, or a variant thereof.

Moreover, the invention provides host cells comprising one or more recombinant nucleic acid molecules as set forth in one or more of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141, or variants thereof. In particular, the invention provides cells comprising one or more recombinant nucleic acid molecules as set forth in SEQ ID NOs: 6, or a variant thereof.

In another aspect, the invention provides recombinant nucleic acid molecules and variants thereof encoding a polypeptide specifically binding to at least one globo-series glycan selected from GloboH, Gb3, Gb4, and Gb5, wherein such variant recombinant nucleic acid molecules share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141 wherein the percentage of sequence identity is determined as described above. These amounts are not meant to be limiting, and increments between the recited percentages are specifically envisioned as part of the disclosure. In particular, the invention provides recombinant nucleic acid molecules and variants thereof encoding a polypeptide specifically binding to at least one globo-series glycan selected from GloboH, Gb3, Gb4, and Gb5, wherein such variant recombinant nucleic acid molecules share at least 80% sequence identity to any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141. More in particular, the invention provides recombinant nucleic acid molecules and variants thereof encoding a polypeptide specifically binding to at least one globo-series glycan selected from GloboH, Gb3, Gb4, and Gb5, wherein such variant recombinant nucleic acid molecules share at least 85% sequence identity to any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141. Still more in particular, the invention provides recombinant nucleic acid molecules and variants thereof encoding a polypeptide specifically binding to at least one globo-series glycan selected from GloboH, Gb3, Gb4, and Gb5, wherein such variant recombinant nucleic acid molecules share at least 90% sequence identity to any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141. Also more in particular, the invention provides recombinant nucleic acid molecules and variants thereof encoding a polypeptide specifically binding to at least one globo-series glycan selected from GloboH, Gb3, Gb4, and Gb5, wherein such variant recombinant nucleic acid molecules share at least 95% sequence identity to any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141. Also still more in particular, the invention provides recombinant nucleic acid molecules and variants thereof encoding a polypeptide specifically binding to at least one globo-series glycan selected from GloboH, Gb3, Gb4, and Gb5, wherein such variant recombinant nucleic acid molecules share at least 98% sequence identity to any of SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 139, SEQ ID NO 140, and SEQ ID NO 141.

Polynucleotides or nucleic acid molecules complementary to any such sequences are also encompassed by the present disclosure. The nucleic acid molecules may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

The nucleic acid molecules may comprise a native sequence (i.e., an endogenous sequence that encodes an antibody or a portion thereof) or may comprise a variant of such a sequence.

Nucleic acid variants contain one or more substitutions, additions, deletions and/or insertions such that the immunoreactivity of the encoded polypeptide specifically binding to at least one globo-series glycan selected from GloboH, Gb3, Gb4, and Gb5 is not substantially different, relative to a native immunoreactive polypeptide of reference. The effect on the immunoreactivity of the encoded polypeptide may generally be assessed as described herein. In some embodiments, nucleic acid variants exhibit at least about 70% identity, in some embodiments, at least about 80% identity, in some embodiments, at least about 85% identity, in some embodiments, at least about 90% identity, and in some embodiments, at least about 95% identity to a nucleic acid sequence that encodes a native single domain antibody of reference or a portion thereof, wherein the percentage of sequence identity is determined as described above. These amounts are not meant to be limiting, and increments between the recited percentages are specifically envisioned as part of the disclosure.

The recombinant nucleic acid molecules of this disclosure can be obtained using chemical synthesis, recombinant methods, or polymerase chain reaction (PCR). Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art.

Suitable cloning vectors and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS $SK^+$) and its derivatives, mp18, mp19, pBR322, pMB9, ColE1, pCR1, RP4, phage DNAs, and shuttle vectors such as pSA3 and pAT28. These and many other cloning vectors are available from commercial vendors such as Merck, BioRad, Strategene, and Invitrogen.

Further, the present invention also envisages expression vectors comprising nucleic acid sequences encoding any of the single domain antibodies here disclosed or variants thereof, as well as host cells comprising such expression vectors. It is implied that an expression vector must be replicable in the host cells either as episomes or as an integral part of the chromosomal DNA. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the recombinant nucleic acid molecules of interest and/or the recombinant nucleic acid molecules themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of the particular procedure will often depend on features of the host cell.

Suitable expression systems include constitutive and inducible expression systems in bacteria or yeasts, virus expression systems, such as baculovirus, semliki forest virus and lentiviruses, or transient transfection in insect or mammalian cells. Particularly preferred are pET expression vectors (Novagen) for the cloning and expression of recombinant proteins in *E. coli*. In the pET system, target genes are cloned in pET plasmids under control of strong bacteriophage T7 transcription and optionally translation signals; expression is induced by providing a source of T7 RNA polymerase in the host cell. T7 RNA polymerase is so selective and active that, when fully induced, almost all of the cell's resources are converted to target gene expression; the desired product can comprise more than 50% of the total cell protein a few hours after induction. The pET-22b(+)

vector carries an N-terminal pelB signal sequence for potential periplasmic localization, plus optional C-terminal His·Tag® sequence.

Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. Particularly preferred are ArcticExpress® *E. Coli* cells. The cloning, expression and/or purification of the antigen-binding proteins can be done according to techniques known by the person skilled in the art, including the Baculovirus-infected Insect Cell system.

Functionalization of the Single Domain Antibodies.

In addition to their optional multivalency and multispecificity, a significant advantage of single domain antibodies (sdAbs) is their ability to be easily cloned and expressed alongside effector molecules on a single DNA plasmid. These extensions enable the use of sdAbs in a wide scope of applications other than antigen binding per se. Thanks to their single domain nature, sdAbs can be readily equipped with various effector functions through molecular or biochemical engineering. Suitable effector molecules have many different functions as for example activation of antibody dependent cell cytotoxicity, lysis of parasitic and cancer cell membranes, in vitro/vivo imaging, and diagnostic. Particularly preferred effector molecules in the present invention are anticancer peptides, lytic peptides, L-rhamnose, galactose-α-1,3-galactose, dinitrophenyl, serum stabilizing molecules, fluorescent molecules, phosphorescent molecules, chemiluminescent molecules, bioluminescent molecules, radio-isotopes, chromophores, disuccinimidyl adipate, human Fc antibody fragments.

Thus, an embodiment of the present invention is directed to a polypeptide specifically binding a globo-series glycan comprising at least one single domain antibody, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is selected from the group consisting of anticancer peptides, lytic peptides, L-rhamnose, galactose-α-1,3-galactose, dinitrophenyl, serum stabilizing molecules, fluorescent molecules, phosphorescent molecules, chemiluminescent molecules, bioluminescent molecules, radio-isotopes, chromophores, disuccinimidyl adipate, human Fc antibody fragments.

In particular, the effector molecule is preferably linked to the C-terminus of the single domain antibody. Moreover, the effector molecule is preferably linked to the C-terminus of the single domain antibody with a linker. Preferred linkers are selected from the group comprising the GS_Linker (SEQ ID NO: 127: GGGGSGGGGS), the GSAA_Linker (SEQ ID NO: 128: GGGGSEAAAKGGGGS), the SRGS_linker (SEQ ID NO: 178: SRGSSGSSSSGSSGGSG), and the GGGGS_linker (SEQ ID NO: 228: GGGGSGGGGSGGGGS. Preferably, a "short connecting sequence" (SEQ ID NO: 227: AAXX, wherein X can be any amino acid) comprising two alanine and a sequence of two amino acids "XX" corresponding to an enzyme restriction site, wherein X can be any amino acid, are linked to the C-terminus of the single domain antibody before the linker sequence.

"Anticancer peptides" are peptides found in plants, animals, and other organisms initially discovered for their antimicrobial activity. These peptides can kill bacteria and cancer cells through membrane interaction. The difference between the bacterial cells or cancer cells and the healthy mammalian cells is found in the charge of the membrane. Both bacteria and cancer cells have an overall negatively charged membrane. Because of the similarity between the membrane of the bacterial and cancer cells, the mechanism by which the membrane disruption takes place and induces cell death is also thought to be similar. Example antimicrobial peptides with anticancer activity are LL-37, Lactoferricin or the C-term of Platelet Factor 4 (PF4). The single domain antibody (sdAb) and the anti cancer peptide are expressed preferably connected with a linker, which are preferably different repeats of (Gly4Ser)n or (Gly2Ser)n units, or of the sequence GGGGSEAAAKGGGGS. Preferred linkers are the GS_Linker (SEQ ID NO: 127: GGGGSGGGGS), the GSAA_Linker (SEQ ID NO: 128: GGGGSEAAAKGGGGS), and the SRGS_linker (SEQ ID NO: 178: SRGSSGSSSSGSSGGSG). More in particular, the linker and the anticancer peptide are linked to the C-terminus of the sdAb. Moreover, a short connecting sequence (SEQ ID NO: 227: AAXX, wherein X can be any amino acid) comprising two alanine and a sequence of two amino acids "XX" corresponding to the enzyme restriction site, wherein X can be any amino acid, are preferably linked to the C-terminus of the single domain antibody before the linker sequence.

"Lytic peptides" according to the present invention comprise modified cysteine deleted Tachyplesin-I ID NO: (KWFRVYRGIYR, SEQ 130), BMAP28A (GGLRSLGRKILRAWKKYGPIIVPIIRIG, SEQ ID NO: 131), Polybia-MP1 (IDWKKLLDAAKQIL, SEQ ID NO: 132).

Tachyplesin-I, an antimicrobial peptide isolated from horseshoe crab, inhibits the growth of many different types of bacteria with its ability to permeabilize the cell membrane. Starting with a previously reported linear tachyplesin analog lacking cysteine (cysteine-deleted tachyplesin, CDT, KWFRVYRGIYRRR-$CONH_2$), the study of Wang et al. (Int J Pept Res Ther. 2014) indicate that elimination of two C-terminal arginine residues from CDT results in a peptide ([des-$Arg^{12,13}$]CDT) with preserved antimicrobial activity but a reduction in hemolysis, a selectivity desirable for a therapeutic agent. As used herein, modified cysteine deleted Tachyplesin-I refers to the sequence KWFRVYRGIYR.

Polybia-MP1 is a lytic peptide from the Brazilian wasp venom with known anti-cancer properties. In vitro studies conducted on Polybia-MP1 provide evidence of killing caused by necrosis as a result of acute cell injury, swelling and bursting via disruption of the membrane or formation of transmembrane pores.

BMAP-28, a bovine antimicrobial peptide of the cathelicidin family, induces membrane permeabilization and death in human tumor cell lines and in activated, but not resting, human lymphocytes.

L-rhamnose, galactose-α-1,3-galactose (αGal) and dinitrophenyl (DNP) can successfully initiate antibody dependent cell cytotoxicity regardless of the fragment crystallizable (Fc) region that is absent in single domain antibodies. Indeed, L-rhamnose, galactose-α-1,3-galactose (αGal) and dinitrophenyl (DNP) are able to recruit naturally produced antibodies to tumor cells. Cells targeted in this way can be recognized by the immune system as foreign and marked for destruction. Recruitment of endogenous antibodies to tumor cells allows for destruction through two antibody-effector mechanisms: complement-dependent cytotoxicity (CDC) and antibody-dependent cell-mediated cytotoxicity (ADCC).

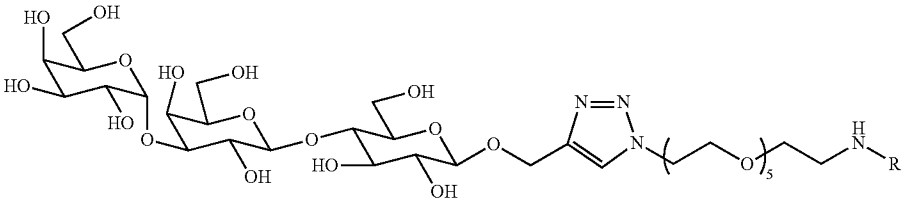

α-Gal

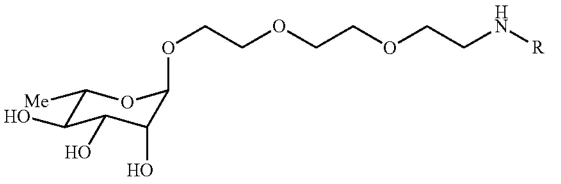

α-Rha

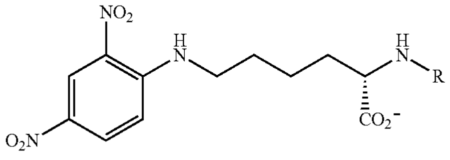

DNP

R =
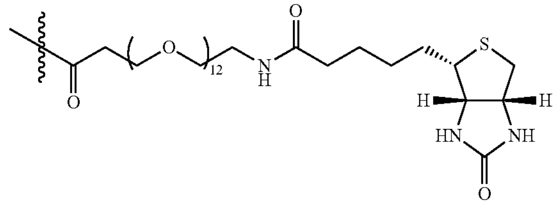

Thus, a preferred embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is a lytic peptide selected from the group comprising cysteine deleted tachyplesin-I, BMAP28A, Polybia-MP1.

A particularly preferred embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is a lytic peptide selected from the group comprising cysteine deleted tachyplesin-I, BMAP28A, Polybia-MP1, wherein the lytic peptide is connected to the C-terminus of the single domain antibody with a linker. Preferred linkers are selected from the group comprising the GS_Linker (SEQ ID NO: 127: GGGGGGGGS), the GSAA_Linker (SEQ ID NO: 128: GGGGSEAAAKGGGGS), and the SRGS_linker (SEQ ID NO: 178: SRGSSGSSSSGSSGGSG). Preferably, a short connecting sequence (SEQ ID NO: 227: AAXX, wherein X can be any amino acid) is linked to the C-terminus of the single domain antibody before the linker sequence A particularly preferred embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is a lytic peptide selected from the group comprising cysteine deleted tachyplesin-1, BMAP28A, Polybia-MP1, and wherein the lytic peptide is connected to the C-terminus of the single domain antibody with a linker. Preferred linkers are selected from the group comprising the GS_Linker (SEQ ID NO: 127: GGGGSGGGGS), the GSAA_Linker (SEQ ID NO: 128: GGGGSEAAAKGGGGS), and the SRGS_linker (SEQ ID NO: 178: SRGSSGSSSSGSSGGSG). Preferably, a short connecting sequence (SEQ ID NO: 227: AAXX, wherein X can be any amino acid) is linked to the C-terminus of the single domain antibody before the linker sequence.

A further preferred embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is a lytic peptide selected from the group comprising cysteine deleted tachyplesin-I, BMAP28A, Polybia-MP1, said polypeptide having at least 85% sequence identity with a sequence selected from SEQ ID NOs: 19-63, 142-156, 179-226.

A further particularly preferred embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is a lytic peptide selected from the group comprising cysteine deleted tachyplesin-I, BMAP28A, Polybia-MP1, wherein the lytic peptide is connected to the C-terminus of the single domain antibody with a linker selected from the group comprising the GS_Linker (SEQ ID NO: 127: GGGGSGGGGS), the GSAA_Linker (SEQ ID NO: 128: GGGGSEAAAKGGGGS), and the SRGS_linker (SEQ ID NO: 178: SRGSSGSSSSGSSGGSG), said polypeptide having at least 85% sequence identity with a sequence selected from SEQ ID NOs: 19-63, 142-156, 179-226. Preferably, a short connecting sequence (SEQ ID NO: 227: AAXX, wherein X can be any amino acid) is linked to the C-terminus of the single domain antibody before the linker sequence.

In other words, preferred embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one effector molecule linked to said single domain antibody, wherein the effector molecule is a lytic peptide selected from the group comprising cysteine deleted tachyplesin-1, BMAP28A, Polybia-MP1, wherein the lytic peptide is connected to the C-terminus of the single domain antibody with a linker selected from the group comprising the GS_Linker (SEQ ID NO: 127: GGGGSGGGGS), the GSAA_Linker (SEQ ID NO: 128: GGGGSEAAAKGGGGS), and the SRGS_linker NO: 178: (SEQ ID SRGSSGSSSSGSSGGSG), wherein a short connecting sequence (SEQ ID NO: 227, wherein X can be any amino acid) is linked to the C-terminus of the single domain antibody before the linker sequence, said polypeptide having at least 85% sequence identity with a sequence selected from SEQ ID NOs: 19-63, 142-156, 179-226.

sdAbs lack the Fc region and therefore cannot induce Fc receptor-dependent effector functions as such. However, a human Fc antibody fragment can be linked or fused to the single domain antibody to restore its capacity to interact with the neonatal Fc receptor or FcRn. An important advantage of a sdAb-Fc fusion construct is the introduction of Fc receptor-dependent effector functions such as antibody-dependent cell-mediated cytotoxicity (ADCC), antibody-dependent cell-mediated phagocytosis (ADCP) and complement-dependent cytotoxicity (CDC). Fc regions (CH2-CH3) of different human and mouse antibody subclasses have been genetically fused to sdAbs. The linkage or fusion of the sdAb to an Fc antibody fragment has also the advantage to greatly increase the serum half-life and enhance target antigen binding through an avidity effect.

Stabilization of the Single Domain Antibodies.

Another strategy to extend the half-life of a sdAb is by coupling the sdAb to long-lived serum proteins or to building blocks that target these long-lived proteins. The long serum half-life of serum albumin, for example, results from its ability to escape from catabolism after cellular uptake. Another approach consists in fusing the sdAb to an albumin binding sdAb.

Thus, the present invention also relates to a polypeptide further comprising one antibody (for example a single domain antibody) directed against one or more serum proteins of a subject, which has significantly prolonged half-life in the circulation of said polypeptide. The serum protein may be any suitable protein found in the serum of subject, or fragment thereof. In one aspect of the invention, the serum protein is serum albumin, serum immunoglobulins, thyroxine-binding protein, transferrin, or fibrinogen. Depending on the intended use such as the required half-life for effective treatment and/or compartmentalisation of the target antigen, the antibody can be directed to one of the above serum proteins.

Single Domain Antibody Based CAR-T Cell Therapy

The term "chimeric antigen receptor", or "CAR" as used herein, refers to an artificially constructed hybrid protein or polypeptide comprising the antigen binding domain of an antibody (e.g., single chain variable fragment (scFv) or a sdAb) linked to a T-cell transmembrane domain, which is in turn linked to a T cell intracellular signaling or activation domain; the linking between the antigen binding domain and the transmembrane domain occurs through a hinge region. Domains or other functional or structural sequence of a CAR, e.g., a transmembrane domain or intracellular activation or signaling domain, is referred to as an element or module of said CAR.

CARs are able to redirect T-cell specificity and reactivity toward a selected target in a non-MHC-restricted manner, exploiting the antigen-binding properties of monoclonal antibodies.

The antigen recognition module, also referred to as ectodomain, of CAR T cells is usually a scFv, linked to a hinge region, a transmembrane region, a costimulatory domain and a cytoplasmic activation domain, such as the CD3-zeta or FcRγ intracellular signaling domain. However, scFvs do not always fold efficiently and can be prone to aggregation. In contrast, the variable regions of heavy-chain-only antibodies (VHHs or sdAbs) are small, stable, single-domain antibody fragments with affinities comparable to traditional scFvs.

A major difficulty in developing CAR T cells for cancer treatment is the lack of targetable antigens (Xie et al., 2018). Most antigens proposed as CAR T cell targets to treat cancers are exclusive to a specific cancer type, and limited information on cancer-specific antigens for the vast majority of cancers renders unsuitable CAR T cell therapy.

Thus, an aspect of particular advantage of the present invention is to provide CARs specifically targeting globo-series glycans, such as Globo H, Gb3, Gb4, or Gb5, that are expressed in a variety of cancers, and that can be used to engineer anti-glycan CAR T cells, which can then be used to treat several different cancers.

Therefore, an embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, and further comprising at least one extracellular hinge region, at least one transmembrane domain, at least one costimulatory domain, and at least one intracellular activation domain, wherein the single domain antibody is linked to the extracellular hinge region. Said polypeptide is a T cell chimeric antigen receptor, wherein the at least one single domain antibody binding at least one globo-series glycan selected from Globo H, Gb3, Gb4, and Gb5, at least one extracellular hinge region, at least one transmembrane domain, at least one costimulatory domain, and at least one intracellular activation domain are comprised in that chimeric antigen receptor in an N-terminal to C-terminal direction.

In other words, an embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, and further comprising in an N-terminal to C-terminal direction at least one CAR extracellular hinge region, at least one CAR transmembrane domain, at least one CAR costimulatory domain, and at least one CAR intracellular activation domain, wherein the single domain antibody is linked to the CAR extracellular hinge region.

More in particular, an embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, and further comprising at least one extracellular CD8-alpha hinge region, at least one CD8-alpha or CD28 transmembrane domain, at least one CD28, 4-IBB, ICOS costimulatory domain, and at least one CD3-zeta intracellular activation domain, wherein the single domain antibody is linked to the extracellular hinge region.

A further embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, further comprising at least one extracellular hinge region, at least one transmembrane domain, at least one costimulatory domain, and at least one intracellular activation domain, wherein the single domain antibody is linked to the extracellular hinge region, and wherein said at least one single domain antibody has at least 90% sequence identity with a sequence selected from the group consisting of SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 136, SEQ ID NO 137, and SEQ ID NO 138.

A further preferred embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, further comprising at least one extracellular hinge region, at least one transmembrane domain, at least one costimulatory domain, and at least one intracellular activation domain, wherein the single domain antibody is linked to the extracellular hinge region, and wherein said at least one single domain antibody is a humanized single domain antibody. It is also disclosed that the single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering.

The present invention is also directed to a recombinant nucleic acid molecule encoding a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, and further comprising at least one extracellular hinge region, at least one transmembrane domain, at least one costimulatory domain, and at least one intracellular activation domain, wherein the single domain antibody is linked to the extracellular hinge region. Moreover, the present invention provides a vector and an host cell comprising a recombinant nucleic acid molecule encoding a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, and further comprising at least one extracellular hinge region, at least one transmembrane domain, at least one costimulatory domain, and at least one intracellular activation domain, wherein the single domain antibody is linked to the extracellular hinge region.

A more preferred embodiment of the invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, further comprising at least one extracellular hinge region, at least one transmembrane domain, at least one costimulatory domain, and at least one intracellular activation domain, wherein the single domain antibody is linked to the extracellular hinge region, for use in treatment of cancer, wherein the cancer cells of said cancer express on their surface at least one globo-series glycan selected from Globo H, Gb3, Gb4, and Gb5.

A more preferred embodiment of the invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, further comprising at least one extracellular hinge region, at least one transmembrane domain, at least one costimulatory domain, and at least one intracellular activation domain, wherein the single domain antibody is linked to the extracellular hinge region, for use in treatment of cancer, wherein the cancer cells of said cancer express on their surface at least one globo-series glycan selected from Globo H, Gb3, Gb4, and Gb5, and wherein the cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

The hinge region of the chimeric antigen receptor is usually derived from the human CD8-alpha chain (exemplary sequence SEQ ID NO: 4 in WO2016019300 A1, or a fragment thereof as described in US20160303166 A1).

The transmembrane domain of the chimeric antigen receptor crosses the plasma membrane and links the extracellular domain and intracellular signal domain. Examples of the transmembrane domain include but are not limited to human CD28 (exemplary sequence: residues 153-179 of SEQ ID NO:4 in US20160303166 A1), CD8-alpha (exemplary sequence SEQ ID NO: 12 in WO2016019300 A1).

The intracellular activation domain transmits the signals necessary for exertion of the effector function of the CAR T cell. More specifically, when the extracellular domain binds with the target Globo H series glycan, an intracellular activation domain transmits the signals necessary for activation of the cells. The intracellular activation domain is usually human CD3-zeta (exemplary sequences SEQ ID NO: 18 or 20 in WO2016019300 A1).

"Costimulatory domain" (CSD) as used herein refers to the portion of the CAR which enhances the proliferation, survival and/or development of memory cells. The CARs of the invention may comprise one or more co-stimulatory domains. Each costimulatory domain can comprise the costimulatory domain of, for example, CD28 (exemplary sequence SEQ ID NO: 44 in WO2016019300 A1), 4-1BB (CD137, exemplary sequence SEQ ID NO: 14 in WO2016019300 A1), and ICOS (exemplary sequence SEQ ID NO:263 in WO2016014553 A1).

Methods for constructing chimeric antigen receptors have been described in the prior art, such as in US20160303166 A1, WO2016014553 A1, Xie et al. PNAS 2018.

Moreover, the present invention also describes a method for generating a genetically engineered chimeric antigen receptor T-cell (CAR T-cell), comprising:

a) generating a chimeric antigen receptor (CAR) construct, having at least one single domain antibody, wherein said single domain antibody binds at least one globo-series glycan selected from Globo H, Gb3, Gb4, and Gb5, at least one extracellular hinge region, at least one transmembrane domain, at least one costimulatory domain, and at least one intracellular activation domain of a chimeric antigen receptor, wherein the single domain antibody is linked to the extracellular hinge region,
b) transfecting T cells removed from blood of a subject,
c) expressing the CAR construct to produce a functional CAR in the T cells to produce a CAR T cell specifically recognizing at least one globo-series glycan selected from Globo H, Gb3, Gb4, and Gb5.

Genetically engineered T cells which may comprise and express the CARs of the invention include, but are not limited to, T-lymphocytes (T-cells), naive T cells (TN), memory T cells (for example, central memory T cells (TCM), effector memory cells (TEM)), natural killer cells, hematopoietic stem cells and/or pluripotent embryonic/induced stem cells capable of giving rise to therapeutically relevant progeny. In an embodiment, the genetically engineered cells are autologous cells. By way of example, individual T-cells of the invention may be $CD4^+/CD8^-$, $CD4^-/CD8^+$, $CD4^-/CD8^-$ or $CD4^+/CD8^+$. The T-cells may be a mixed population of $CD4^+/CD8^-$ and $CD4^-/CD8^+$ cells or a population of a single clone. $CD4^+$ T-cells of the invention may produce IL-2, IFNy, TNFa and other T-cell effector cytokines when co-cultured in vitro with cells expressing the target antigens (i.e. cancer cells expressing a Globo H series glycan). $CD8^+$ T-cells of the invention may lyse antigen-specific target cells when co-cultured in vitro with the target cells (i.e. cancer cells expressing a Globo H series glycan).

Finally, the present invention also describes a method for treating a subject having a cancer, wherein the cancer cells of said cancer express on their surface at least one globo-series glycan selected from Globo H, Gb3, Gb4, and Gb5, comprising administering to the subject having said cancer a chimeric antigen receptor T-cell (CAR T cell) specifically recognizing at least one globo-series glycan selected from Globo H, Gb3, Gb4, and Gb5, wherein said CAR T cell expresses a functional CAR polypeptide comprising a single domain antibody binding at least one globo-series glycan selected from Globo H, Gb3, Gb4, and Gb5 as disclosed herein, at least one extracellular hinge region, at least one transmembrane domain, at least one costimulatory domain, and at least one intracellular activation domain, in an effective amount to treat the subject having said cancer.

Humanisation of the Single Domain Antibodies

A variant sequence of the present invention may include a single domain antibody specifically binding at least one glycan selected from GloboH, GB3, Gb4, and Gb5 which has been humanised. The humanisation of the sdAb is aimed to further reduce the possibility of unwanted immunological reaction in a human individual upon administration. One embodiment of the present invention relates to modified single domain antibodies based upon alpaca antibodies, wherein the amino acid residues of the sdAb not influencing the native affinity of the domain for the target are modified to reduce the sdAb immunogenicity with respect to a human.

More specifically, the invention relates to modified sdAbs, which are modified for administration to humans, and the use of such "humanized" sdAbs in the treatment of diseases in humans. Humanising a single domain antibody according to the present invention comprises a step of replacing one or more of the alpaca amino acids by their human counterpart as found in the human consensus sequence, without that single domain antibody losing its typical character, i.e, the humanisation does not significantly affects the antigen binding capacity of the resulting single domain antibody, and also the polypeptide comprising it. Such methods are known by the skilled person in the art.

Humanization of alpaca single domain antibodies or more generally camelidae single domain antibodies requires the introduction and mutagenesis of a limited amount of amino acids in a single polypeptide chain.

Therefore, one embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and wherein said at least one single domain antibody is a humanized single domain antibody.

In general, the humanized single domain antibody is obtained by replacing any of the following residues either alone or in combination in the alpaca single domain antibody, as described by EP 1687338 B1:

FR1 the hallmark amino acids at position 1, 5, 11, 28 and 30,

FR2: the hallmark amino acids at position 44 and 45,

FR3 the hallmark amino acids at position 74, 75, 76, 83, 84, 93 and 94,

FR4 the hallmark amino acids at position 103, 104, 108 and 111;

wherein the numbering is according to the Kabat numbering.

The humanization of the residues in FR1, FR3, FR4 will have minimal effect on the function and stability of the single domain antibody, whereas the mutations in FR2 at positions 44 and 45 will even stabilize the single domain antibody (Vincke et al., J. Biol. Chem. 2009). However EP 1687338 B1 reports that mutagenesis of Q108L in FR4 can result in lower production level in *Escherichia coli*. Position 108 is solvent exposed in camelid VHH, while in human antibodies this position is buried at the VH-VL interface. The introduction of a non-polar hydrophobic Leu instead of polar uncharged Gln can have a drastic effect on the intrinsic folding/stability of the molecule. Single domain antibody hallmark residues at positions 37 and 47 in FR2 have a major impact on the integrity of the antigen interaction, and thus cannot be humanized (Vincke et al., 2009).

Table 1 reports the hallmark residues in the inventive alpaca sdAbs and the amino acid residues at the corresponding positions of the most closely related human VH domain VH3, as described by U.S. Pat. No. 7,807,162 B2. This table shows that the hallmark amino acids at positions 103 and 111 of the alpaca single domain antibodies disclosed herein are the same as the most common residues of human VH3.

Therefore a further embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering.

As such, humanized polypeptides show a high amino acid sequence homology to human VH framework regions and said polypeptides might be administered to a human directly without expectation of an unwanted immune response therefrom, and without the burden of further humanisation. The invention also relates to recombinant nucleic acids capable of encoding said humanized polypeptides.

A preferred embodiment of the present invention is a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, and further comprising at least one effector molecule linked to said single domain antibody, wherein the effector molecule is selected from the group consisting of anticancer peptides, lytic peptides, L-rhamnose, galactose-α-1,3-galactose, dinitrophenyl, serum stabilizing molecules, fluorescent molecules, phosphorescent molecules, chemiluminescent molecules, bioluminescent molecules, radio-isotopes, chromophores, disuccinimidyl adipate, human Fc antibody fragments. A more preferred embodiment of the present invention is a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, and further comprising at least one effector molecule linked to said single domain antibody, wherein the effector molecule is a lytic peptide selected from the group comprising modified cysteine deleted tachyplesin-I, BMAP28A, Polybia-MP1.

TABLE 1

| Hallmark Residues in the sdAbs disclosed herein (Kabat numbering) | | | | | | | | | | | | | |
|---|---|---|---|---|---|---|---|---|---|---|---|---|---|
| Position | Common residues in Human VH3 | sdAb14 | sdAb26 | sdAb37 | sdAb46 | sdAb47 | sdAb56 | sdAb59 | sdAb60 | sdAb62 | sdAb63 | sdAb65 | sdAbS |
| 1 | E, **Q** | — | H | D | D | D | D | Q | E | D | D | Q | — |
| 5 | **V**, L | V | V | Q | Q | V | V | V | V | V | V | V | V |
| 11 | V, **L** | L | L | L | L | L | L | L | L | L | M | L | L |
| 28 | **T** | V | T | T | T | T | T | T | S | I | I | D | T |
| 30 | **S**, | S | S | S | D | G | S | S | T | G | S | Q | S |
| 37 | I, **V** | A | V | A | V | V | V | H | I | V | V | F | A |
| 44 | G, E | G | Q | G | G | G | G | E | G | Q | G | E | G |
| 45 | L, R | L | R | L | L | L | L | R | L | R | p | R | L |
| 47 | **W**, Y | W | L | W | W | W | C | L | W | L | W | G | W |
| 74 | **S**, A | A | D | A | A | A | A | D | S | D | A | A | A |

TABLE 1-continued

Hallmark Residues in the sdAbs disclosed herein (Kabat numbering)

| Position | Common residues in Human VH3 | sdAb14 | sdAb26 | sdAb37 | sdAb46 | sdAb47 | sdAb56 | sdAb59 | sdAb60 | sdAb62 | sdAb63 | sdAb65 | sdAbS |
|---|---|---|---|---|---|---|---|---|---|---|---|---|---|
| 75 | K | K | K | K | K | K | K | K | R | K | K | K | K |
| 76 | **N**, S | N | N | N | N | N | N | N | N | N | N | N | H |
| 83 | K, **R** | K | R | K | K | K | K | K | T | R | K | A | K |
| 84 | T, D, **A** | P | P | P | S | S | S | P | P | P | P | P | P |
| 93 | **A** | L | V | A | T | A | A | N | A | V | A | G | T |
| 94 | **R** | H | A | K | K | R | R | V | R | A | A | T | T |
| 103 | **W** | W | W | W | W | W | W | W | W | W | W | W | W |
| 104 | **G** | G | K | G | G | G | G | G | G | G | G | G | G |
| 108 | **L**, M, T | Q | Q | Q | Q | Q | Q | Q | Q | Q | Q | Q | Q |
| 111 | **V** | V | V | V | V | V | V | V | V | V | V | V | V |

The amino acids are listed in the one letter code; bold residues: most common residues in human; underlined residues: residues of alpaca sdAbs corresponding to those in human VH3

Pharmaceutical Compositions

"Pharmaceutical composition" refers to a preparation in a form that allows the biological activity of the active ingredient(s) to be effective, and which contain no additional components which are toxic to the subjects to which the formulation is administered.

As used herein, the terms "pharmaceutically acceptable", "physiologically tolerable" and grammatical variations thereof, are used interchangeably and represent that the materials are capable of administration to or upon a mammal without the production of undesirable physiological effects such as nausea, dizziness, gastric upset and the like.

The pharmaceutical composition is designed to facilitate the administering of the inventive polypeptides comprising the single domain antibodies in an effective manner.

"Pharmaceutically acceptable vehicle" refers to an ingredient in a pharmaceutical formulation, other than an active ingredient, which is nontoxic to the subject to whom it is administered. A pharmaceutically acceptable vehicle includes, but is not limited to, a buffer, stabilizer, or preservative.

Examples of suitable vehicles or excipients include, without limitation, lactose, dextrose, sucrose, glucose, powdered sugar, sorbitol, mannitol, xylitol, starches, acacia gum, xanthan gum, guar gum, tara gum, mesquite gum, fenugreek gum, locust bean gum, ghatti gum, tragacanth gum, inositol, molasses, maltodextrin, extract of Irish moss, panwar gum, mucilage of isapol husks, Veegum, larch arabogalactan, calcium silicate, calcium phosphate, dicalcium phosphate, calcium sulfate, kaolin, sodium chloride, polyethylene glycol, alginates, gelatine, microcrystalline cellulose, polyvinylpyrrolidone, cellulose, water, saline, syrup, methylcellulose, ethylcellulose, hydroxypropylnethylcellulose, carboxymethylcellulose, polyacrylic acids such as Carbopols, such as Carbopol941, Carbopol980, Carbopol981, and gum bases such as Pharmagum™ (SPI Pharma Group; New Castle, Del.), and similar. Typically, the compositions of the present invention comprise from about 10% to about 90% by weight of the vehicle, the excipient or combinations thereof.

Preferably, the pharmaceutical composition contains from about 0.001% to about 90%, preferably from about 0.01% to about 75%, more preferably from about 0.1% to 50%, and still more preferably from about 0.1% to 10% by weight of the polypeptide of the present invention, with the remainder consisting of suitable pharmaceutical vehicles, excipients, and/or diluents.

The pharmaceutical composition can be formulated into powders, granules, tablets, capsules, suspensions, emulsions, syrups, oral dosage form, external preparation, suppository or in the form of sterile injectable solutions, such as aerosolized in a usual manner, respectively. When formulated, it can be prepared using a diluent or excipient such as generally used fillers, extenders, binders, wetting agents, disintegrating agents, surface active agents.

In the pharmaceutical composition, the solid preparation for oral administration may be a tablet, pill, powder, granule, or capsule. The solid preparation may further comprise an excipient. Excipients may be, for example, starch, calcium carbonate, sucrose, lactose, or gelatine. In addition, the solid preparation may further comprise a lubricant, such as magnesium stearate, or talc. In the pharmaceutical composition, liquid preparations for oral administration may be best suspensions, solutions, emulsions, or syrups. The liquid formulation may comprise water, or liquid paraffin. The liquid formulation may, for excipients, for example, include wetting agents, sweeteners, aromatics or preservatives. For the purposes of parenteral administration, compositions containing the polypeptides of the invention are preferably dissolved in distilled water and the pH preferably adjusted to about 6 to 8.

Useful preparations of the compositions of the invention for parenteral administration also include sterile aqueous and non-aqueous solvents, suspensions and emulsions.

Examples of useful non-aqueous solvents include propylene glycol, polyethylene glycol, vegetable oil, fish oil, and injectable organic esters.

An embodiment of the present invention is a pharmaceutical composition comprising a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, together with at least one pharmaceutically acceptable vehicle, excipient and/or diluent.

Another embodiment of the present invention is a pharmaceutical composition comprising a globo-series glycan binding polypeptide comprising at least one single domain antibody specifically binding at least one globo-series glycan selected from Globo H, Gb3, Gb4, and Gb5, and further comprising at least one effector molecule linked to said single domain antibody, wherein the effector molecule is selected from the group consisting of anticancer peptides, lytic peptides, L-rhamnose, galactose-α-1,3-galactose, dinitrophenyl, serum stabilizing molecules, fluorescent molecules, phosphorescent molecules, chemiluminescent molecules, bioluminescent molecules, radio-isotopes, chromophores, disuccinimidyl adipate, human Fc antibody fragments, together with at least one pharmaceutically acceptable vehicle, excipient and/or diluent.

Another particular embodiment of the present invention is a pharmaceutical composition comprising a globo-series glycan binding polypeptide comprising at least one single domain antibody specifically binding at least one globo-series glycan selected from Globo H, Gb3, Gb4, and Gb5, and further comprising at least one effector molecule linked to said single domain antibody, wherein the effector molecule is a lytic peptides selected from the group comprising cysteine deleted tachyplesin-I, BMAP28A, Polybia-MP1, together with at least one pharmaceutically acceptable vehicle, excipient and/or diluent.

A more particular embodiment of the present invention is a pharmaceutical composition comprising a globo-series glycan binding polypeptide comprising at least one single domain antibody specifically binding at least one globo-series glycan selected from Globo H, Gb3, Gb4, and Gb5, and further comprising at least one effector molecule linked to said single domain antibody, wherein the effector molecule is a lytic peptides selected from the group comprising cysteine deleted tachyplesin-I, BMAP28A, Polybia-MP1, said polypeptide having at least 85% sequence identity with a sequence selected from SEQ ID NOs: 19-63, 142-156, together with at least one pharmaceutically acceptable vehicle, excipient and/or diluent.

A further embodiment of the present invention is a pharmaceutical composition comprising a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4 in FR4, according to the Kabat numbering, together with at least one pharmaceutically acceptable vehicle, excipient and/or diluent. Slightly reworded one embodiment of the present invention is a pharmaceutical composition comprising one polypeptide comprising at least one humanized single domain antibody specifically binding at least one globo-series glycan selected from Globo H, Gb3, Gb4, and Gb5, together with at least one pharmaceutically acceptable vehicle, excipient and/or diluent.

Uses of the Single Domain Antibodies Against Cancer

Another embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, or the pharmaceutical composition comprising said polypeptide, for use in treatment and/or diagnosis of cancer, wherein the cancer cells of said cancer express on their surface at least one globo-series glycan selected from Globo H, Gb3, Gb4, and Gb5.

Another embodiment of the present invention relates to a polypeptide specifically binding a globo-series glycan comprising at least one single domain antibody, or a variant thereof, wherein said single domain antibody binds at least one globo-series glycan selected from Globo H, Gb3, Gb4, and Gb5, or the pharmaceutical composition comprising said polypeptide, for use in treatment and/or diagnosis of cancer, wherein the cancer cells of said cancer express on their surface at least one globo-series glycan selected from Globo H, Gb3, Gb4, and Gb5, and wherein the cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

Moreover, one aspect of the present invention is directed to a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering, for use in treatment and/or diagnosis of cancer, wherein the cancer cells of said cancer express on their surface at least one globo-series glycan selected from Globo H, Gb3, Gb4, and Gb5. Slightly reworded one embodiment of the present invention relates to a globo-series glycan binding polypeptide comprising at least one humanized single domain antibody specifically binding at least one globo-series glycan selected from Globo H, Gb3, Gb4, and Gb5, for use in treatment and/or diagnosis of cancer, wherein the cancer cells of said cancer express on their surface at least one globo-series glycan selected from Globo H, Gb3, Gb4, and Gb5.

Moreover, one aspect of the present invention is directed to a pharmaceutical composition comprising one globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering, for use in treatment and/or diagnosis of cancer, wherein the cancer cells of said cancer express on their surface at least one globo-series glycan selected from Globo H, Gb3, Gb4, and Gb5.

A preferred embodiment of the present invention is a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, or the pharmaceutical composition comprising said polypeptide, for use in treatment and/or diagnosis of cancer, wherein the cancer cells of said cancer express on their surface at least one globo-series glycan selected from Globo H, Gb3, Gb4, and Gb5, and wherein said cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

A still more preferred embodiment of the present invention is a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, and further comprising at least one effector molecule linked to said single domain antibody, wherein the effector molecule is a lytic peptide selected from the group comprising modified cysteine deleted tachyplesin-I, BMAP28A, Polybia-MP1, or the pharmaceutical composition comprising said polypeptide, for use in treatment of a cancer, wherein the cancer cells of said cancer express on their surface at least one globo-series glycan selected from Globo H, Gb3, Gb4, and Gb5.

A still more preferred embodiment of the present invention is a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, and further comprising at least one effector molecule linked to said single domain antibody, wherein the effector molecule is a lytic peptide selected from the group comprising modified cysteine deleted tachyplesin-I, BMAP28A, Polybia-MP1, or the pharmaceutical composition comprising said polypeptide, for use in treatment of a cancer, wherein the cancer cells of said cancer express on their surface at least one globo-series glycan selected from Globo H, Gb3, Gb4, and Gb5, and wherein said cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

A further embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one CAR extracellular hinge region, at least one CAR transmembrane domain, at least one CAR costimulatory domain, and at least one CAR intracellular activation domain, wherein the single domain antibody is linked to the CAR extracellular hinge region, for use in treatment of cancer, wherein the cancer cells of said cancer express on their surface at least one globo-series glycan selected from Globo H, Gb3, Gb4, and Gb5.

Another further embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one extracellular CD8-alpha hinge region, at least one CD8-alpha or CD28 transmembrane domain, at least one CD28, 4-IBB, ICOS costimulatory domain, and at least one CD3-zeta intracellular activation domain, wherein the single domain antibody is linked to the CAR extracellular hinge region, for use in treatment of cancer, wherein the cancer cells of said cancer express on their surface at least one globo-series glycan selected from Globo H, Gb3, Gb4, and Gb5.

A further embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one CAR extracellular hinge region, at least one CAR transmembrane domain, at least one CAR costimulatory domain, and at least one CAR intracellular activation domain, wherein the single domain antibody is linked to the CAR extracellular hinge region, for use in treatment of cancer, wherein the cancer cells of said cancer express on their surface at least one globo-series glycan selected from Globo H, Gb3, Gb4, and Gb5, and wherein said cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

Another further embodiment of the present invention is directed to a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and further comprising at least one extracellular CD8-alpha hinge region, at least one CD8-alpha or CD28 transmembrane domain, at least one CD28, 4-IBB, ICOS costimulatory domain, and at least one CD3-zeta intracellular activation domain, wherein the single domain antibody is linked to the CAR extracellular hinge region, for use in treatment of cancer, wherein the cancer cells of said cancer express on their surface at least one globo-series glycan selected from Globo H, Gb3, Gb4, and Gb5, and wherein said cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

Also described herein is a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a polypeptide as disclosed herein or a therapeutically effective amount of a pharmaceutical composition comprising said polypeptide.

In particular, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, or a therapeutically effective amount of the pharmaceutical composition comprising said polypeptide.

Also described herein is a method for the treatment of a cancer, wherein the cancer cells of said cancers express on their surface at least one globo-series glycan selected from Globo H, Gb3, Gb4, and Gb5, comprising administering to a patient suffering from said cancer a therapeutically effective amount of a polypeptide as disclosed herein or a therapeutically effective amount of a pharmaceutical composition comprising said polypeptide, wherein said cancer is selected from the group comprising brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

In particular, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering, or a therapeutically effective amount of the pharmaceutical composition comprising said polypeptide.

Moreover, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering, or a therapeutically effective amount of the pharmaceutical composition comprising said polypeptide, wherein said cancer is selected from the group comprising brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

More in particular, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, and further comprising at least one effector molecule linked to said single domain antibody, wherein the effector molecule is a lytic peptide selected from the group comprising modified cysteine deleted tachyplesin-I, BMAP28A, Polybia-MP1, or a therapeutically effective amount of the pharmaceutical composition comprising said polypeptide.

Still more in particular, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, and further comprising at least one effector molecule linked to said single domain antibody, wherein the effector molecule is a lytic peptide selected from the group comprising modified cysteine deleted tachyplesin-I, BMAP28A, Polybia-MP1, or a therapeutically effective amount of the pharmaceutical composition comprising said polypeptide, wherein said cancer is selected from the group comprising brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

Further, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, and further comprising at least one CAR extracellular hinge region, at least one CAR transmembrane domain, at least one CAR costimulatory domain, and at least one CAR intracellular activation domain, wherein the single domain antibody is linked to the CAR extracellular hinge region.

Moreover, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, and further comprising at least one CAR extracellular hinge region, at least one CAR transmembrane domain, at least one CAR costimulatory domain, and at least one CAR intracellular activation domain, wherein the single domain antibody is linked to the CAR extracellular hinge region, and further comprising at least one extracellular CD8-alpha hinge region, at least one CD8-alpha or CD28 transmembrane domain, at least one CD28, 4-IBB, ICOS costimulatory domain, and at least one CD3-zeta intracellular activation domain, wherein the single domain antibody is linked to the CAR extracellular hinge region.

Still more in particular, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, and further comprising at least one CAR extracellular hinge region, at least one CAR transmembrane domain, at least one CAR costimulatory domain, and at least one CAR intracellular activation domain, wherein the single domain antibody is linked to the CAR extracellular hinge region, wherein said cancer is selected from the group comprising brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

Moreover, it is described a method for the treatment of a cancer, wherein the cancer cells of said cancer express on their surface at least one globo-series glycan selected from Globo H, Gb3, Gb4, and Gb5, comprising administering to a patient suffering from said cancer a therapeutically effective amount of a globo-series glycan binding polypeptide comprising at least one single domain antibody specifically binding at least one globo-series glycan selected from Globo H, Gb3, Gb4, and Gb5, and further comprising at least one CAR extracellular hinge region, at least one CAR transmembrane domain, at least one CAR costimulatory domain, and at least one CAR intracellular activation domain, wherein the single domain antibody is linked to the CAR extracellular hinge region, and further comprising at least one extracellular CD8-alpha hinge region, at least one CD8-alpha or CD28 transmembrane domain, at least one CD28, 4-IBB, ICOS costimulatory domain, and at least one CD3-zeta intracellular activation domain, wherein the single domain antibody is linked to the CAR extracellular hinge region, wherein said cancer is selected from the group comprising brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

A further embodiment describes a method of diagnosing a cancer characterized by cancer cells expressing on their surface at least one globo-series glycan selected from Globo H, Gb3, Gb4, and Gb5, comprising the steps of:

a) contacting a sample with a polypeptide specifically binding at least one globo-series glycan selected from Globo H, Gb3, Gb4, and Gb5, as disclosed herein
b) detecting binding of said polypeptide to said sample
c) comparing the binding detected in step b) with a standard, wherein a difference in binding relative to said sample is diagnostic of a cancer characterized by cancer cells expressing on their surface at least one globo-series glycan selected from Globo H, Gb3, Gb4, and Gb5.

"Disorder" is any condition that would benefit from treatment with a substance/molecule or method described herein.

"Cell proliferative disorder" and "proliferative disorder" refer to disorders that are associated with some degree of abnormal cell proliferation, such as cancer.

"Cancer" and "cancerous" refer to, or describe a physiological condition in mammals that is typically characterized by a cell proliferative disorder. Cancer generally can include, but is not limited to, carcinoma, lymphoma (e.g., Hodgkin's and non-Hodgkin's lymphoma), blastoma, sarcoma, and leukemia. More specific examples of cancer can include, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

"Tumour" refers to all neoplastic cell growth and proliferation, whether malignant or benign, and all pre-cancerous and cancerous cells and tissues. The terms "cancer", "cancerous", "cell proliferative disorder", "proliferative disorder", and "tumour" are not mutually exclusive as referred to herein.

"Metastasis" refers to the spread of cancer and/or tumour from its primary site to other places in the body of an individual.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-Globo H antibody to a subject to delay development or slow progression of a cancer, wherein the cancer cells of said cancer express on their surface at least one globo-series glycan selected from Globo H, Gb3, Gb4, and Gb5.

"Pharmaceutical formulation" refers to a preparation in a form that allows the biological activity of the active ingredient(s) to be effective, and which contain no additional components which are toxic to the subjects to which the formulation is administered.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease or disorder in a subject. In the case of a cancer, the therapeutically effective amount of the therapeutic agent is an amount that reduces the number of cancer cells; reduces the primary tumour size; inhibits (i.e. slows to some extent and preferably stop) cancer cell infiltration into peripheral organs; inhibits (i.e. slows to some extent and preferably stop) tumour metastasis; inhibits, to some extent, tumour growth; and/or relieves to some extent one or more of the symptoms associated with the cancer. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

"Individual" or "subject" refers to a mammal, including but not limited to, domesticated animals (e.g., cows, sheep; cats, dogs, and horses), primates (e.g., humans and non-human primates such as monkeys), rabbits, and rodents (e.g., mice and rats).

"Anti-cancer therapeutic" refers to an agent useful for treating cancer. Exemplary anti-cancer therapeutics include, but are not limited to, chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors, a COX-2 inhibitor, interferons, cytokines, antagonists that bind to one or more targets (for example PDGFR-beta, APRIL, BCMA receptor, TRAIL/Apo2), other bioactive and organic chemical agents, and combinations thereof.

Uses of the Single Domain Antibodies for Diagnosis of Cancer

A further embodiment of the present invention is a diagnostic kit for the detection of cells expressing on their surface at least one globo-series glycan selected from Globo H, Gb3, Gb4, and Gb5, comprising a globo-series glycan binding polypeptide comprising at least one single domain antibody specifically binding at least one globo-series glycan selected from Globo H, Gb3, Gb4, and Gb5, wherein said single domain antibody is a variable domain of a heavy chain antibody naturally devoid of a light chain and naturally devoid of the constant region 1, or a variant of said variable domain. Apart from said polypeptide, which is binding to one globo-series glycan selected from Globo H, Gb3, Gb4, and Gb5, the kit may further comprise reagents needed for the labeling and/or detection and/or quantification of the antigen-binding cells.

Slightly reworded, the present invention is also directed to a diagnostic kit comprising a globo-series glycan binding polypeptide comprising at least one single domain antibody specifically binding at least one globo-series glycan selected from Globo H, Gb3, Gb4, and Gb5, or a variant of said variable domain, for screening for a cancer characterized by cells expressing on their surface at least one globo-series glycan selected from Globo H, Gb3, Gb4, and Gb5.

Another aspect of the present invention is a diagnostic kit comprising a globo-series glycan binding polypeptide comprising at least one single domain antibody specifically binding at least one globo-series glycan selected from Globo H, Gb3, Gb4, and Gb5, wherein said single domain antibody is a variable domain of a heavy chain antibody naturally devoid of a light chain and naturally devoid of the constant region 1, or a variant of said variable domain, wherein said at least one single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, for screening for a cancer characterised by cells expressing on their surface at least one globo-series glycan selected from Globo H, Gb3, Gb4, and Gb5.

As mentioned above, the single domain antibodies of the present invention can be used for diagnostic purposes when linked to effector molecules being detectable labels. Suitable detectable labels and techniques for attaching, using and detecting them will be clear to the skilled person and, for example, include, but are not limited to, fluorescent molecules (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent molecules, chemiluminescent molecules or bioluminescent molecules (such as luminal, isoluminol, theromatic acridinium ester, imidazole, acridinium salts, oxalate ester, dioxetane or GFP and its analogs), radio-isotopes, metals, metal chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase).

Therefore, a further embodiment of the present invention is a diagnostic kit comprising a polypeptide specifically binding a globo-series glycan comprising at least one single domain antibody, or a variant of said variable domain, wherein said single domain antibody binds at least one globo-series glycan selected from Globo H, Gb3, Gb4, and Gb5, and further comprising at least one effector molecule linked to said single domain antibody, for screening for a cancer characterized by cells expressing on their surface at least one globo-series glycan selected from Globo H, Gb3, Gb4, and Gb5, wherein the effector molecule is selected from the group comprising fluorescent molecules, phosphorescent molecules, chemiluminescent molecules, bioluminescent molecules, radio-isotopes, and chromophores.

Polypeptides Containing Multimeric Single Domain Antibodies.

An embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, and wherein the number of single domain antibodies that bind at least one globo-series glycan selected from Globo H, Gb3, Gb4, and Gb5 is at least two.

Such polypeptide comprising at least two single domain antibodies has the advantage of higher affinity for the target, as shown for the sdAb46 trimer (FIG. 23).

A particular embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, wherein the number of single domain antibodies that bind at least one globo-series glycan selected from Globo H, Gb3, Gb4, and Gb5 is at least two, and wherein the two or more single domain antibodies are different in sequence.

A more particular embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, wherein the number of single domain antibodies that bind at least one globo-series glycan selected from Globo H, Gb3, Gb4, and Gb5 is at least two, and wherein the two or more single domain antibodies are identical in sequence.

A still more particular embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, and wherein said single domain antibody binds at least one globo-series glycan selected from Globo H, Gb3, Gb4, and Gb5, wherein the number of single domain antibodies that bind at least one globo-series glycan selected from Globo H, Gb3, Gb4, and Gb5 is three, and wherein the two or more single domain antibodies are identical in sequence.

A further more particular embodiment of the present invention is a polypeptide specifically binding a globo-series glycan comprising at least one single domain antibody, wherein said single domain antibody is a variable domain of a heavy chain antibody naturally devoid of a light chain and naturally devoid of the constant region 1, or a variant of said variable domain, wherein said single domain antibody binds at least one globo-series glycan selected from Globo H, Gb3, Gb4, and Gb5, wherein the number of single domain antibodies that bind at least one globo-series glycan selected from Globo H, Gb3, Gb4, and Gb5 is three, and wherein said single domain antibody has at least 90% sequence identity with SEQ ID NO 5.

The single domain antibodies may be joined to form any of the polypeptides specifically binding a globo-series glycan disclosed herein and comprising more than one single domain antibody using methods known in the art or any future method. The single domain antibodies may be joined non-covalently (e.g. using streptavidin/biotin combination, antibody/tag combination) or covalently. They may also be fused by chemical cross-linking by reacting amino acid residues with an organic derivatising agent.

Alternatively, the single domain antibodies may be fused genetically at the DNA level. One way of joining single domain antibodies is via the genetic route by linking single domain antibody coding sequences either directly or via a peptide linker. For example, the C-terminal end of the single domain antibody may be linked to the N-terminal end of the next single domain antibody. This linking mode can be extended in order to link additional single domain antibodies for the construction and production of tri-, tetra-, etc. functional constructs. Moreover the single domain antibodies can be linked to form dimers through glutathione S-transferase (GST) (for example as described in Smith D B, Johnson K S, Gene 1988; Tudyka T, Skerra A, *Protein Sci* 2008), and dodecamers using the scaffold protein dodecin from *Mycobacterium tuberculosis* mtDod (Bordeaux et al., *Sci Rep* 2020; CA3076791A1).

Figure 1:
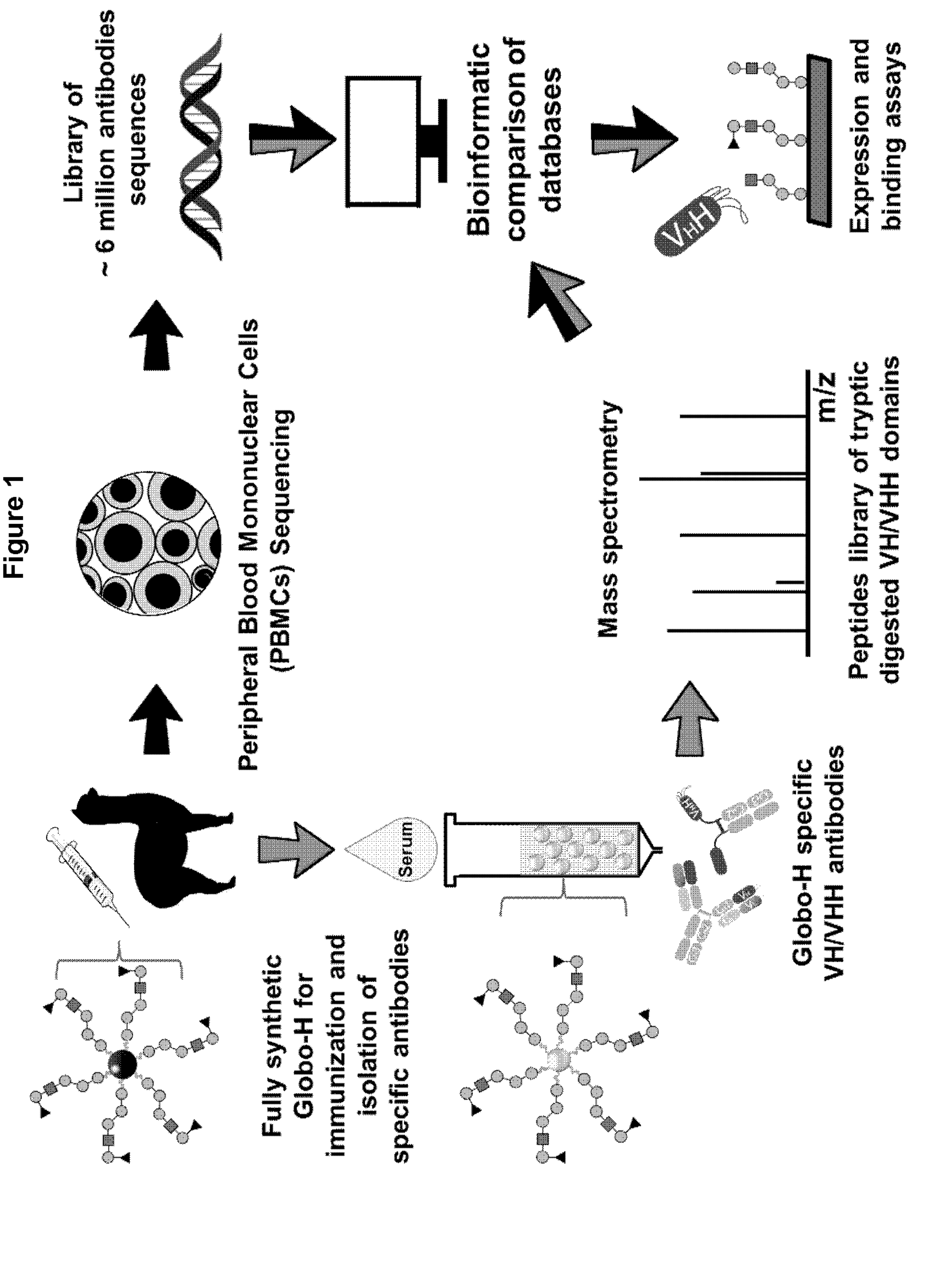
FIG. 1: Scheme of the procedure used for the development of the inventive alpaca sdAbs specifically binding globo-series glycans.
Figure 2:
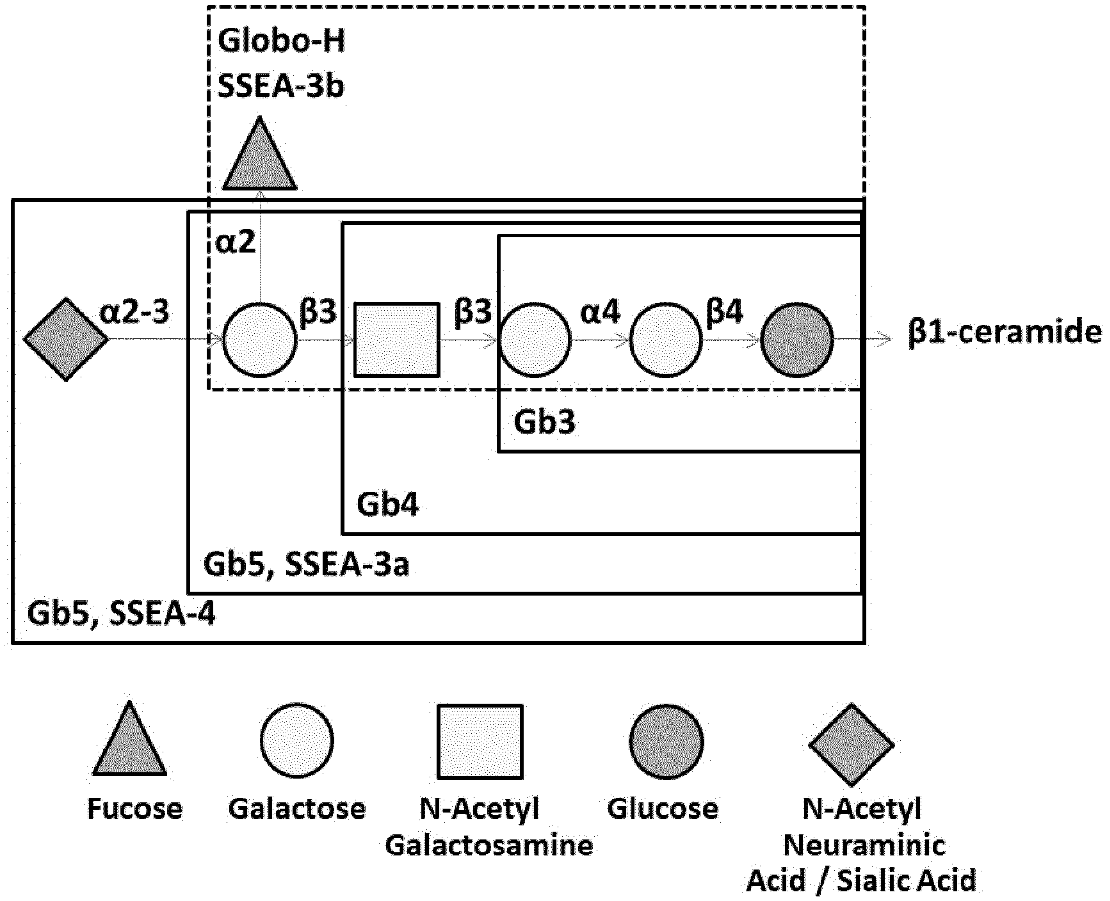
FIG. 2: Structure of globo-series glycans GloboH, Gb3, Gb4, Gb5, SSEA3, and SSEA4.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the scope of the invention as described in the following claims.

EXAMPLES

Methods:

Preparation of CRM197-Thiol GloboH Glycoconjugate for Alpaca Immunization.

1 mg of GloboH functionalized with a thiol linker was reduced with 0.6 equivalent (eq.) of resin-bound Tris(2-carboxyethyl)phosphin (TCEP) in 120 μl of water for 1 h at 1500 rpm. The resin was removed by filtration through a 0.22 μm syringe filter and the filter was washed five times with 50 μl water. The last wash was analyzed by thin-layer chromatography and sugar staining to ensure that no GloboH remained on the filter. The filtrate and all wash fractions were combined and lyophilized. 100 eq. of succinimidyl 3-(bromoacetamido) propionate were dissolved in 30 μl of dimethylformamide (DMF) and added dropwise to a solution of 1 mg CRM197 in 750 μl of coupling buffer (0.1 M $Na_2HPO_4/NaH_2PO_4$ pH 7.4) while stirring. After 1 h, the solution was washed four times with 350 μl of water on an equilibrated 0.5 ml centrifugal filter (Amicon Ultra, MWCO=10k) at 10,000 rpm for 8 min. Before the last wash, a 10 μl aliquot was collected for mass spectrometric analysis. Subsequently, the solution was washed with 350 μl of conjugation buffer (0.1 M $Na_2HPO_4/NaH_2PO_4$ at pH 8.0) and collected in a new tube by centrifugation at 1,000 rpm for 2 min with the filter upside down. The lyophilized, reduced GloboH was restored in conjugation buffer (pH 8) and added to the protein solution. The reaction solution was left slowly stirring for 24 h.

Figure 3:
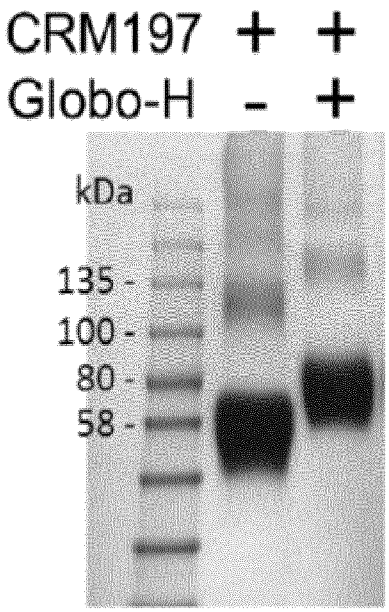
FIG. 3: Electrophoresis blot to assess the load of the CRM197 carrier protein on GloboH.

On the next day, the reaction solution was washed thrice with 350 μl water. Before the last wash, a 10 μl aliquot was collected for mass spectrometric analysis. Subsequently, the solution was washed with 350 μl conjugation buffer (pH 8) and 150 eq. of cysteine were added directly onto the centrifugal filter. After 1 h incubation, the reaction solution was washed thrice with 350 μl water. Before the last wash, a 10 μl aliquot was collected for mass spectrometric analysis. Finally, the solution was washed with 350 μl sterile phosphate buffered saline and collected in a new tube by centrifugation at 1,000 rpm for 2 min with the filter upside down. After mass spectrometric analysis of the samples collected throughout the conjugation, the GloboH loading of CRM197 (shown below) was determined by comparison of the mass peaks before and after conjugation (FIG. 3).

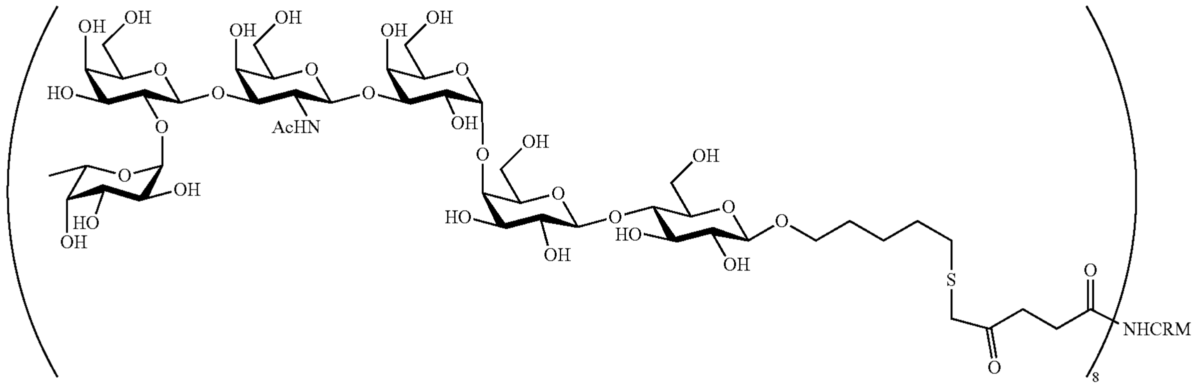

Alpaca Immunization

Adult female alpaca was immunized with CRM197-GloboH glycoconjugates containing 15 μg GloboH/dose in phosphate-buffered saline. The alpaca was injected subcutaneously along the base of the neck using a 22 G needle. A total of 6 weekly immunization rounds included two weeks gap between the thirds and forth injections, so that the vaccination days where: 0/7/14/28/35/42. Whole blood extraction was performed 9 days after the last immunization (day 51).

Isolation of Blood Serum and Peripheral Blood Mononuclear Cells (PBMCs)

Whole blood for serum isolation (150 ml) was collected into 50 ml tubes and incubated at RT for 1 h followed by centrifugation at 2,000g/10 minutes/RT. Serum was aliquoted into sterile 15 ml tube (7.5 ml each), and flash frozen using liquid nitrogen for further storage at −80° C.

For PBMC isolation, 100 ml whole blood was collected into 10 ml EDTA coated tubes (BD Vacutainer™) and inverted 10 times. PBMCs from undiluted whole blood were isolated using UNI-SEPmaxi U16 (NOVAMED) by centrifugation at 1000g/30 min/RT without breaks. PBMC layer was separated into a sterile 50 ml tube and washed with PBS by 3 rounds of centrifugation at 400g/10 min/4c. Final 25 ml were centrifuged and dissolved in 14 ml of RNAlater™. The cells were divided into 1.5 ml RNAse free tubes in 5*107/ml PBMC per vial and stored in a slow freezing container (Mr. Frosty™) at −80° C. for 24 h followed by storage at −80° C.

Glycan Array to Assay the Binding of Serum Antibodies to Synthetic Globo-Series Glycans.

Figure 5:
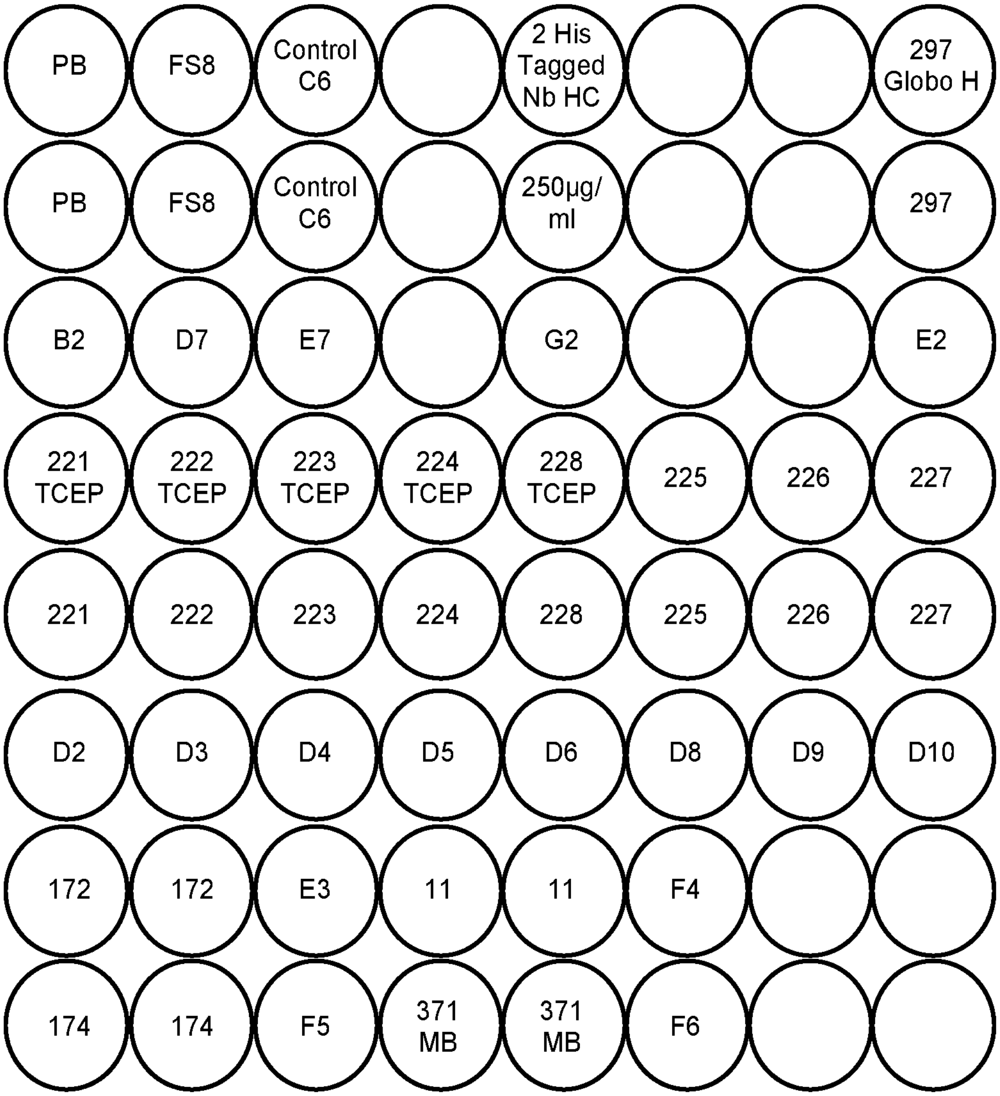
FIG. 5: Printing pattern for glycan arrays. Glycans were printed on epoxy-coated slides in triplicates. Each color shows one specific glycan type. Controls and oligosaccharides are indicated next to the grid and include galactose, 6xHis-tagged sdAb, Globo H and different types of glycosylphosphatidylinositol (GPIs). Legend: Controls; PB, Buffer; FS8, galactose; C6, rhamnose; 2His Tag, sdAb control for 6xHis specific antibody (Atto 6479) 297,Fuc(a1-2)Gal (b1-3)GalNAc(b1-3)Gal(a1-4)Gal(b1-4)Glc(b1-1); aminopentanol-Globo H; 221, Glc(a1-4)GalNac(b1-4)[Man-6-PEtN(a1-2)Man(a1-6)Man(a1-4)GlcN(a1-6)Ino(1-P) phosphothiohexanol-GPI; 222, GalNac(b1-4)[Man-6-PEtN (a1-2)Man(a1-6)]Man(a1-4)GlcN(a1-6)Ino(1-P) phosphothiohexanol-GPI 29 (*T. gondii*); 223, GalNac(b1-4) [Man-6-PEtN(a1-2)Man(a1-6)]Man-2-PEtN(a1-4)GlcN(a1-6)Ino(1-P)phosphothiohexanol-GPI 32 (mammalian); 224, GalNac(b1-4)[Man(a1-2)Man(a1-6)]Man(a1-4)GlcN(a1-6) Ino(1-P)phosphothiohexanol-GPI 37 (unnatural); 228, GlcN (a1-6)Ino(1-P)phosphothiohexanol-GPI Pseudodisaccharide; 225, Glc(a1-4)GalNAc(b1-4)Man(a1-1) aminopentanol-GPI substructure; 226, Glc(a1-4)GalNAc (b1-4)[Man(a1-2)Man(a1-1)aminopentanol-GPI substructure; 227, Glc(a1-4)GalNAc(b1-4) [Man-6-PEtN (a1-2)Man(a1-6)]Man(a1-1)aminopentanol-GPI substructure; 172, Gal(b1-3)GalNAc(b1-3)Gal(a1-4)Gal(b1-4)Glc (b1-1)aminopentanol-GB5(Aminolinker); 174, Gal(a1-4) Gal(b1-4)Glc(b1-1)aminopentanol-GB3 (Aminolinker); 371, GlcNAc(b1-3)Gal(a1-4)Gal(b1-4)Glc(b1-1)aminopentanol; 11, Gal(b1-4)Glc(b1-1)aminohexanol-Lactose (Aminolinker); positions D2-D10, E3, F4-F6 indicate the position of the stock compound on the 96 plate, which are used by the printing robot to individuate the position of each sample.

Glycan microarrays were printed in the lab onto epoxy-coated glass slides using 0.2 mM of synthetic glycans and 250 μg/mL His-tagged sdAb as a control. Each slide contained repeated glycan grids with each containing 16 spots of different glycans. The printing pattern is shown in FIG. 5. The slides were blocked in HEPES buffer (10 mM HEPES (pH 7.4), 1 mM $CaCl_2$), 1 mM $MgCl_2$) supplemented with 1% BSA for 1 hour at 37° C. At the same time 50 μL of 4, 10 and 20 μg/mL of sdAb solutions in the same buffer were incubated with a 1:5000 dilution of 6xHis-specific antibody (Atto647) at 30° C. in the dark. Blocked slides were washed once with HEPES buffer without BSA and once with $ddH_2O$. To get rid of any liquid, the slides were centrifuged at 300 g for 3 min. The slides were assembled onto micro-plate holders to allow separate staining of single grids with different sdAbs. The sdAb/antibody mixture was pipetted into the wells and sdAb-glycan binding was allowed for 1 hour at 30° C. in a humidified chamber in the dark. The wells were washed three times with HEPES buffer supplemented with 0.05% Tween, once with $ddH_2O$, and after drying by centrifugation directly scanned using a Glycan Array Scanner Axon GenePix® 4300A. Binding was analyzed using GenePix Pro7.

VHH cDNA Library Construction and High Throughput Sequencing

RNA was isolated from alpaca PBMC using RNeasy MiniKit (Qiagen). cDNA was created using oligo-dT primers and the SuperScriptll reverse transcriptase kit (Invitrogen). The VHH variable regions were specifically amplified from the cDNA in a two steps nested PCR. In the first step primers CALL001: GTCCTGGCTGCTCTTCTACAAGG (leader sequence specific, SEQ ID NO 132) and CALL002: GGTACGTGCTGTTGAACTGTTCC (CH2 specific, SEQ ID NO 133) where used. After gel purification and size selection of the 600 bp region followed by MinElute cleanup (Qiagen), the second PCR was performed to extract the VHH region using the primers VHH_back: GATGTGCAGCTGCAGGAGTCTGGRGGAGG (SEQ ID NO 134) and VHH_For: GGACTAGTGCGGCCGCTGGAGACGGTGACCTGG (SEQ ID NO 135) followed by gel extraction of the 400 bp band.

Illumina sequencing libraries were created following the TruSeq protocol without shearing, i.e. starting with the end repair step. Each library was sequenced with 2×250 bp chemistry on an Illumina MiSeq instrument yielding 6.9/6.6 million read pairs per sample. BBmerge (https://github.com/BioInfoTools/BBMap/blob/master/sh/bbmerge.sh) was used to overlap forward and reverse reads to reconstruct the original PCR fragments.

Affinity Purification of GloboH Specific Canonical and Heavy Chain Only Antibodies to Isolate the GloboH Binding VHH Fragments from Alpaca Serum Preparation of Synthetic GloboH-Coupled Beads.

1 mg of GloboH functionalized with a thiol linker was reduced with 0.6 eq. of resin-bound TCEP in 120 μl water for 1 h at 1500 rpm at RT. The resin was removed by filtration through a 0.22 μm syringe filter and the filter was washed five times with 50 μl water. The last wash was analyzed by thin-layer chromatography and sugar staining to ensure that no GloboH remained on the filter. The filtrate and all wash fractions were combined and lyophilized. Reduced GloboH was conjugated to 1 ml agarose beads SulfoLink® Coupling Resin (Thermo Fisher Scientific) according to manufacturer instructions.

Separation of IgGs and Heavy Chain Antibodies Using Protein A/G Beads.

For the separation of conventional IgGs and of heavy chain only antibodies, the samples of alpaca serum were thawed and a 7.5 ml aliquot was diluted with 67.5 ml 20 mM Sodium Phosphate at pH=7 and filtered using 0.22 mm filter. 3 ml of Protein A/G Magnetic Beads (Pierce) were pre-washed with 20 mM Sodium phosphate at pH=7. Thereafter, these samples were incubated for 1 h at RT with spinning. After collecting the flow through, the beads were washed with 100 ml of 20 mM Sodium Phosphate at pH=7. Bound antibodies were eluted using 39 ml of 100 mM Citric acid at pH=2.75 into 50 ml tubes pre-filled with 11 ml of 1.5M Tris pH=8.8 for neutralization of eluted antibodies. Elution samples were united, concentrated using Amicon 10 kDa at RT and dialyzed over night with 5 L of 20 mM Sodium Phosphate at pH=7.4.

Isolation of GloboH Specific Antibodies Using Synthetic Glycan-Coupled Beads.

GloboH-coupled beads/empty beads control columns were washed three times with water followed by 20 mM Sodium phosphate pH=7. The sample of dialyzed antibodies obtained using the A/G beads was than evenly distributed between empty and GloboH coupled beads columns pre-equilibrated with dialysis buffer and rotated for 1 h at RT. Flow through from each column was then switched between columns for additional 1 h at RT. Elution from both columns was performed using 20 mM Sodium phosphate pH=7 and increased NaCl concentration (100 mM/500 mM/1M/3M), followed by a final washing step of 20 mm $NaH_2PO_4$ adjusted to pH 5.2. 75 ml volume of each washing steps from both columns were concentrated using Amicon 10 kD and dialyzed overnight at 4° C. against papain digestion buffer (20 mM sodium phosphate/10 mM EDTA PH=7.1).

Papain Cleavage of GloboH Specific Antibodies

Figure 9:
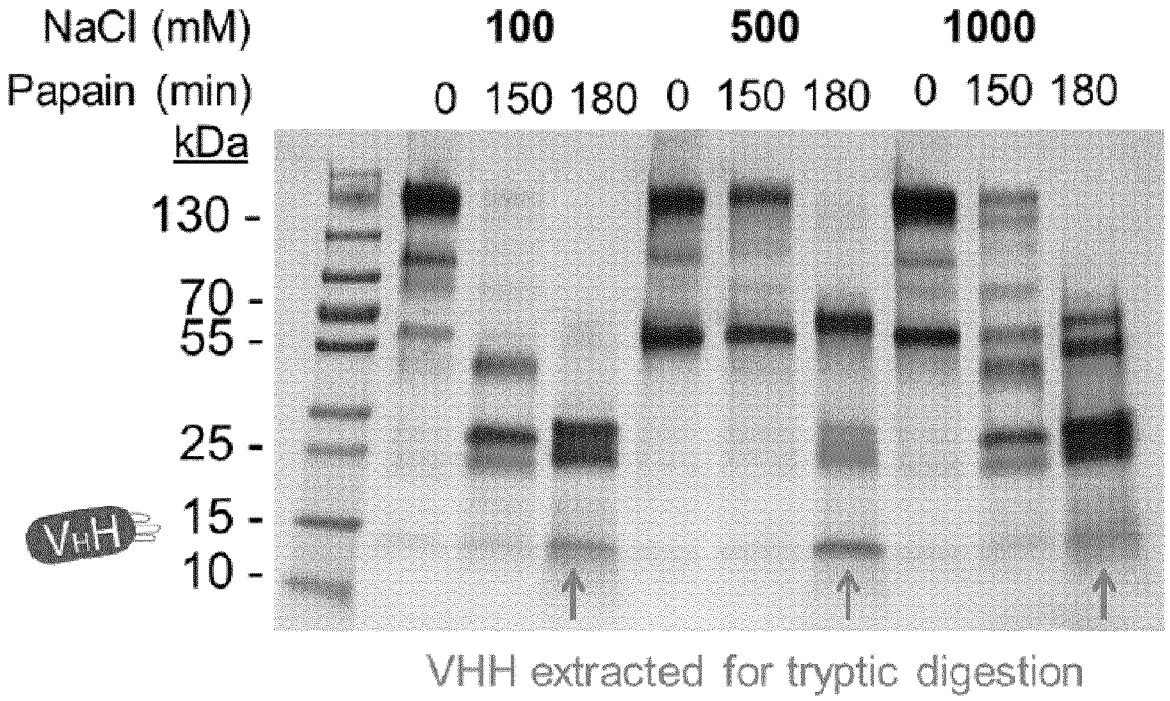
FIG. 9: Gel electrophoresis separation of affinity purified antibodies. Green arrows indicate 13 kDa sdAbs (VHH) that were extracted from gels for further tryptic digestion and mass spectrometry analysis.

Affinity purified antibodies in 20 mm sodium phosphate/10 mm EDTA buffer were incubated with $10^{-20}$ μl of Papain immobilized beads (Thermo Fisher Scientific) 37c/300 rpm for up to 90 min with addition of 5 mM L-Cystein (Sigma-Aldrich). The mixture was then centrifuged and supernatant was loaded on 4-20% acrylamide SDS-PAGE gels for the extraction of the 13 kDa bands corresponding to the VHH domains (FIG. 9).

Mass Spectrometry Analysis of Affinity Purified VHH Fragments.

VHH fragments from SDS-PAGE separation were excised from the gel and digested with trypsin. The resulting tryptic peptides were extracted from the gel and de-salted using C18 StageTips. LC-MS/MS analysis was performed on an Orbitrap Fusion™ Lumos™ Tribrid™ mass spectrometer (Thermo Fisher Scientific) coupled on-line to Ultimate 3000 RSLCano Systems (Dionex, Thermo Fisher Scientific). The eluted peptides are ionized by an EASY-Spray source (Thermo Fisher Scientific). Mobile phase A consists of water, 0.1% v/v formic acid and mobile phase B consists of 80% v/v acetonitrile and 0.1% v/v formic acid. The MS data is acquired in the data-dependent mode with the top-speed option using Lumos instrument with high resolution for both MS1 and MS2 spectra. HCD was applied for fragmentation. Peak lists of MS data were generated using MS convert. Database search against the high throughput cDNA sequencing library was conducted using a combination of in-lab modified Mascot search engine (Matrix Science) and local installation and default parameters of Llama Magic v1.0. (https://github.com/FenyoLab/llama-magic).

Expression of Globo-Series Glycan Binding sdAbs

Transformation of Bacteria:

Plasmid vectors (pET-22(+)b) for transformation contained sdAb sequences fused to a C-terminal Histidin-Tag, an IPTG inducible regulatory system, an ampicillin resistance and a PelB periplasma signal sequence. The vectors were transformed into ArcticExpress® (DE3) *E. coli* competent cells using heat shock transformation according to the manufacturer's protocol. 20 ng of DNA was added to 20-40 μL of bacteria. After heat shock, followed by 1 hour incubation at 37° C. in SOC medium, the transformed cells were spreaded onto LB agar plates containing gentamicin resistance for ArcticExpress® cells and ampicillin resistance for the expression plasmid carrying the desired sdAb sequence. Plates were incubated at 37° C. overnight.

Colony PCR:

Single colonies of the transformed cells were tested for transformation efficiency in Colony PCR. The PCR reaction mix was prepared using 2×PCR Master Mix, 0.1 μM of the according forward and reverse primers and nuclease-free water in 10 μL reactions in PCR tubes on ice. Three clones of each transformation protocol were picked with a 10 μL pipette tip and directly pipetted and resuspended in the reaction mix. The PCR reaction was performed according to manufacturer's recommended thermal cycling conditions, shown in Table 2. 2 μL of 6×DNA Loading Dye was added to the PCR product and analyzed on 1% agarose gels.

TABLE 2

Thermal Cycling Conditions for Colony PCR

| Step | Temperature | Time | Cycles |
|---|---|---|---|
| Initial denaturation | 95 °C | 3 min | 1 |
| Denaturation | 95 °C | 0.5 min | 35 |
| Annealing | Cycles 21-41: 51.4 °C<br>Cycles 56-65: 58 °C | 0.5 min | |
| Extension | 72 °C | 1 min | |
| Final Extension | 72 °C | 10 min | 1 |

Storage of Bacteria:

Colonies of successfully transformed cells were inoculated and grown in 5 mL LB medium supplemented with 50 g/mL ampicillin and 20 μg/ml gentamycin over night at 37° C. in a shaking incubator (250 rpm). The next morning, 750 μL of the overnight culture were mixed with 750 μL 50% glycerol and the stocks were stored in-80° C.

Expression and Purification of GloboH sdAbs from ArcticExpress Cells:

Overnight cultures were started either by inoculating positive clones on LB agar plates after transformation or by inoculation from cryostocks in LB medium supplemented with 50 μg/mL ampicillin and 20 μg/mL gentamicin. The starters were incubated in a 37° C. shaker (250 rpm) over night. The next morning, 150 mL or 1 L main cultures were subcultured with 50 μg/mL ampicillin and the overnight culture in a 1:100 dilution. These cultures were incubated at 30° C. with shaking at 250 rpm until the OD600 reached 0.6. 500 μL of each culture was pipetted in a clean microcentrifuge tube for an expression test as a non-induced sample. The cultures were transferred into a 12° C. shaker at 250 rpm, induced with 0.4 mM IPTG and incubated for 24 hours. After the incubation time another 500 μL sample was taken for each culture as an induced sample. Bacteria were harvested by centrifugation for 20 min at 6000 g at 4° C. and pellets were stored in-20° C. To test expression efficiency, the non-induced and induced samples were diluted with LB medium to an OD600 of 0.1 in 1 mL volumes. These suspensions were centrifuged for 5 min at 14000 g. The pellets were dissolved in 20 μL PBS and 5 μL 5×SDS sample buffer and samples were analyzed by SDS-PAGE.

Lysis of ArcticExpress® Cells and Purification of GloboH sdAbs:

The PelB signal sequence in the sdAb plasmids induced secretion of the expressed sdAbs into the *E. coli* periplasm. To obtain the periplasmic fraction of *E. coli* cells, only the outer membrane needs to be disrupted. Pellets from 150 mL cultures were thawed and resuspended in 300 μL PBS supplemented with protease inhibitor mix. After six freeze and thaw cycles using dry ice and a water bath at 37° C., the samples were centrifuged for 1 hour at 3200 g and 4° C. The lysates were directly used for binding assays on MCF-7 cells. Pellets from 1 L cultures were thawed and resuspended in 20 mL sodium phosphate sample buffer containing protease inhibitors. Freeze and thaw cycles were performed as described before and 20 units of DNAse I were added to the samples before centrifugation at 42000 g for 20 min at 4° C. The lysates were directly used for further purification.

NICKEL-NTA affinity chromatography:

For affinity purification, 1 mL of Nickel-NTA beads were loaded into chromatography columns, washed with two column volumes (CV) of $ddH_2O$ and equilibrated with two CV of sample buffer. The lysates obtained from 1 L of *E. coli* ArcticExpress® cells were added to the beads and incubated for 90 min at RT under rotation. Afterwards, the flowthrough was collected, and the beads were washed with 1 CV of sample buffer, 2 CV of wash buffer 1 and 2 CV of wash buffer 2. The sdAbs were eluted from the Nickel beads with 2 CV of elution buffer. Samples were taken from all purification and washing steps for later SDS-PAGE analysis. The eluates were concentrated in Amicon® Ultra centrifugal filter units with 3 kDa size exclusion limit at 3200 g at 4° C. and concentration was determined during the process by measuring the absorbance at 280 nm with a Nanodrop™. If the concentration did not reach more than 2.5 mg/mL, the eluates were concentrated to a final volume of less than 2 mL and dialyzed in PBS (pH 7.4) at 4° C. overnight using SnakeSkin™ Dialysis Tubing with a 3500 molecular weight cut-off.

SDS-PAGE (FIG. 10A) to Validate the Purification Procedure

To validate the purification process of sdAbs, following samples were taken during the procedure: Pellet (P) and lysate (L) of ArcticExpress® cells after centrifugation of freeze and thaw samples, flowthrough (FT), Wash Fractions 1 and 2 (W1 and W2) and elution after Nickel-NTA (E), and the final sdAb product (sdAb) and/or other protein peaks which showed up in FPLC chromatograms. Samples were prepared with 5×SDS sample buffer and were denaturated for 5 min at 95° C. Discontinuous SDS-PAGE was performed as described by Laemmli and gels were stained with PageBlue™ Protein Stain Solution for 15 min after quick boiling in the microwave. Destaining was performed with $ddH_2O$ and gels were imaged using a Gel Doc EZ Imager.

Size Exclusion Chromatography (FIG. 10B):

Size exclusion was performed using FPLC (Fast Protein Liquid Chromatography) with a HiLoad™ Superdex 16/600 75 pg column connected to an ÄKTA™ Purifier. The dialyzed samples were injected into a 2 mL loading loop and were run in filtered and degassed PBS (pH 7.4) with a flow rate of 0.75 mL/min. Protein peaks were determined with UV280 and 1 mL fractions were collected in 96 deep well plates. SdAbs were expected to elute between 75 to 85 mL, but samples from all protein containing fractions were analyzed in SDS-PAGE. The sdAb containing fractions were combined and concentrated in 3 kDa cut-off Amicons® at 4° C. and 3200 g to a final concentration of ~1 mg/mL and were either used directly for further assays or aliquoted, frozen in liquid nitrogen and stored at −80° C.

Surface Plasmon Resonance (SPR)

SPR measurements were performed using a BIAcore T100 instrument (GE Healthcare). 7.5 μg of synthetic GloboH was immobilized on a commercial C1 sensor chip (GE healthcare) by amine-coupling chemistry. The chip was previously activated with 100 mM Glycine-NaOH (pH=12) supplemented with 0.3% Triton X-100. Immobilization was performed with a contact time of 700 s and a flowrate of 15 L/min in 10 mM sodium acetate buffer (pH 5.5). The chip contains two flow cells, one of them serves as a blank (flow cell 3) and on one of them the glycan was immobilized (flow cell 4). SdAbs were dialyzed in SPR running buffer (HEPES buffer) at 4° C. overnight. Contact, dissociation times, flowrates, and maximum tested concentrations were different for each sdAb and are presented in Table 3. Each sdAb was tested at five different concentrations, where the lower concentrations are serial 1:2 dilutions of the indicated maximum concentration. For regeneration after each association event, the same buffer supplemented with 2 M $MgCl_2$ was used. Sensorgrams were analyzed using the Biacore T200 control and evaluation software (GE Healthcare) and for data analysis the signal difference between both flow cells was evaluated. Equilibrium dissociation constants (KD) were determined by affinity and kinetic analysis. In affinity analysis, binding response based on steady state binding levels was plotted against sdAb concentrations and equilibrium dissociation constants were determined. Kinetic parameters were obtained by fitting sensorgrams to a 1:1 binding model using the BIAevaluation software. Accuracy of the measurements was evaluated by the software and is presented Chi-square values.

TABLE 3

Parameters for SPR measurements using sdAbs37, sdAbs46 and sdAbs62 on a GloboH immobilized C1 chip.

| sdAb | Maximal concentration [μg/mL] | Contact Time [s] | Dissociation Time [s] | Flowrate [μL/min] |
|---|---|---|---|---|
| 37 | 250 | 90 | 450 | 25 |
| 46 | 75 | 60 | 700 | 25 |
| 62 | 220 | 90 | 500 | 50 |

Culture of Mammalian Cells

All cells were cultivated at 37° C. with 5% $CO_2$. MCF-7 cells and HEK293T cells were cultured in DMEM supplemented with 10% fetal bovine serum (FBS), 1% Penicillin/Streptomycin (P/S), 2 mM glutamine and 1% non-essential amino acids. They were passaged every 2-3 days by washing with PBS (w/o $Ca^{2+}$/$Mg^{2+}$) and subsequent trypsinization to detach the adherent cells. Trypsinization was stopped with culture media and the cells were centrifuged for 5 min at 300 g to get rid of trypsin. The pellet was resuspended in fresh media and cells were plated in new culture dishes at 1:3/1:4 ratios for MCF-7 and 1:6/1:8 ratios for HEK293T cells. MDA-MB 231 cells were cultured in RPMI 1640 supplemented with 10% FBS and 1% P/S. Medium was refreshed every 2-3 days and cells were passaged once a week as described above at a ratio of 1:4.

To prepare frozen aliquots, cells from a confluent 75 $cm^2$ culture flask were collected as described before and resuspended in 1 mL culture media supplemented with 5% DMSO and frozen in −80° C. in freezing containers for one day. Frozen cells were transferred into liquid nitrogen. Cells were thawed quickly at 37° C. for 2 min, and immediately resuspended in fresh culture media. They were pelleted to get rid of DMSO, resuspended again in fresh media and seeded in 75 $cm^2$ culture flasks.

Flow Cytometry Analysis of sdAb Binding to Cancer Cells

Establishment of Optimal Settings for FACS Analysis:

to analyze binding of sdAbs to cancer cells in flow cytometry, following parameters needed to be preliminarily determined: concentration of the secondary antibody detecting the sdAbs (anti-6xHis-Tag labeled with Atto647), concentration of the anti-GloboH antibody clone VK9 used as positive control, for each cell line tested, voltages during flow cytometry measurements for forward and sideward scatter, and FITC (fluorescein isothiocyanate) and APC (allophycocyanin) detectors. For each flow cytometry assay, cells were harvested at 70-80% confluency as described above under "Culture of mammalian cells". The cell pellet was resuspended in PBS+1% BSA and 0.5×$10^6$ cells per condition were transferred into 1.5 mL eppendorf tubes. After pelleting these again at 250 g for 5 min, one cell pellet was diluted in PBS as blank cells and one was resuspended in 250 μL FACS buffer (PBS+1% BSA+SYBR™ Safe (emetting in FITC channel). For adjusting the dilution of the anti-His antibody, the dilutions 1:100, 1:500, 1:1000 and 1:5000 in PBS+1% BSA were tested. The pellets were resuspended in 50 μL of the corresponding solution and incubated for 45 min at RT. At the same time, three pellets were incubated in 50 μL of 5, 10 or 20 μg/mL VK9 in PBS+1% BSA. Afterwards the cells were washed twice by centrifugation and resuspension in 500 μL PBS+1% BSA. The VK9 treated samples were stained for another 45 minutes with an anti-mouse secondary antibody (Alexa Fluor 635) at RT and washed afterwards as described before. After the last centrifugation step, the stained cell pellets were resuspended in 250 μL FACS buffer. All samples were transferred into FACS tubes and data acquisition was performed at a FACSCanto™ II device (BD).

Screening for Antibodies Binding to Globo-Series Glycans Using MCF-7 Cells

The *E. coli* lysates obtained from 150 mL cultures as described above were directly tested on MCF-7 cells. To this aim, cells were harvested as described above and 0.5×$10^6$ cells per sample were transferred into 1.5 mL tubes. After centrifugation for 5 min at 300 g the cell pellet was resuspended in 50 μL of the corresponding lysate and was incubated on a shaker for 45 min at RT. Additionally, a negative control with only PBS and a positive control with 5 μg/mL VK9 was included in all runs. Afterwards the cells were washed twice and after the last washing step, all pellets except the VK9 control were resuspended in the anti-His antibody solution determined in the previous step (1:1000 in PBS+1% BSA) and incubated for another 45 min on a shaker at RT. VK9 stained cells were resuspended in 50 μl of a 1:400 dilution of the corresponding fluorescent anti-mouse antibody (AlexaFluor 635). After another two washes, cells were fixed in 100 μL 4% paraformaldehyde (PFA) in PBS and after centrifugation the pellet was resuspended in 250 μL FACS buffer. Data was recorded using the settings as determined in the previous step and analysed using FlowJo® software. The recorded events were gated to select only the single, intact cells for analysis. The gates were applied to all samples and by overlapping the APC histograms of sdAb stained cells with that of the negative control cells, binding could be observed by shifts of the peaks. To quantify the shift and to rank for the strongest potential binders, an additional gate was created on the single cell selection which defines a positive gate for binders. The frequency of $APC^+$ cells on parent gate (single cells) was determined for all sdAbs using the FlowJo® software.

Flow Cytometry Binding Assay of Purified sdAbs on Different Cell Lines

After testing the binding of the *E. coli* lysates as described above, sdAbs were purified from the identified positive binders and further tested for binding on MCF-7 cells. The procedure was the same as described in the screening, with the difference that the cell pellet was resuspended in 50 μL of 0.4 mg/mL purified sdAb solution in PBS instead of *E. coli* lysates. By using the same concentration, binding intensity of the different sdAbs was compared. Additionally, the same binding assay was performed on MDA-MB 231 cells, which express all Globo family glycans and HEK293T cells, which do not express GloboH.

Confocal Laser Scanning Microscopy (LSM)

To validate binding of sdAbs to MCF-7 cells using confocal microscopy, 20,000 cells were seeded on 12 mm cover slips in 24-well cell culture plates two days before the assay to be 50-60% confluent for staining. The medium was aspired and cells were rinsed twice with PBS, before fixing them for 10 min at RT in 4% PFA. To get rid of PFA, the wells were washed 3×5 min in PBS and were then blocked for 1 hour in PBS+1% BSA. A drop of 50 μL of 1 μg/μL purified sdAb was placed on a piece of parafilm and the coverslip with the adherent cells was placed on top. One coverslip stayed in the wells as a negative control, and 5 μg/mL VK9 in PBS was used as a positive control. The coverslips were incubated for 1 hour with the sdAbs at RT in a humidified chamber. Afterwards, they were placed back into the wells and washed 3×5 min in PBS. 200 μL of Atto 647 anti-6xHis antibody (1:5000 in PBS+1% BSA) was added to the cells and incubated for 1 hour at RT, slightly shaking. The VK9 positive control was stained with a 1:400 dilution of mouse-IgG specific (AlexaFluor635) secondary antibody in PBS+1% BSA. After three more washes with PBS, 10 μL of mounting medium were pipetted on a microscopy slide and the coverslips with the stained cells was placed on top. The slides were dried overnight and microscopy was performed the following day using an Axio Imager.M2 confocal LSM 800 (Zeiss). Parameters for the assay were set up based on negative control and VK9 staining as a positive control.

TABLE 4

Description of the sequence listing

| SEQ ID NO | Denomination | Sequence Type |
|---|---|---|
| 1 | sdAb26 | Amino acid |
| 2 | sdAb26 | Nucleic acid |
| 3 | sdAb37 | Amino acid |
| 4 | sdAb37 | Nucleic acid |
| 5 | sdAb46 | Amino acid |
| 6 | sdAb46 | Nucleic acid |
| 7 | sdAb47 | Amino acid |
| 8 | sdAb47 | Nucleic acid |
| 9 | sdAb56 | Amino acid |
| 10 | sdAb56 | Nucleic acid |
| 11 | sdAb59 | Amino acid |
| 12 | sdAb59 | Nucleic acid |
| 13 | sdAb62 | Amino acid |
| 14 | sdAb62 | Nucleic acid |
| 15 | sdAb63 | Amino acid |
| 16 | sdAb63 | Nucleic acid |
| 17 | sdAb65 | Amino acid |
| 18 | sdAb65 | Nucleic acid |
| 19 | sdAb26 linked to the lytic peptide BMAP28A by a GS_linker | Amino acid |
| 20 | sdAb26 linked to the lytic peptide BMAP28A by a GSAA_linker | Amino acid |
| 21 | sdAb26 linked to the lytic peptide modified cysteine deleted Tachyplesin-I by a GS_linker | Amino acid |
| 22 | sdAb26 linked to the lytic peptide modified cysteine deleted Tachyplesin-I by a GSAA_linker | Amino acid |
| 23 | sdAb26 linked to the lytic peptide Polybia-MP1 by a GSAA_linker | Amino acid |
| 24 | sdAb37 linked to the lytic peptide BMAP28A by a GS_linker | Amino acid |
| 25 | sdAb37 linked to the lytic peptide BMAP28A by a GSAA_linker | Amino acid |
| 26 | sdAb37 linked to the lytic peptide modified cysteine deleted Tachyplesin-I by a GS_linker | Amino acid |

TABLE 4-continued

Description of the sequence listing

| SEQ ID NO | Denomination | Sequence Type |
|---|---|---|
| 27 | sdAb37 linked to the lytic peptide modified cysteine deleted Tachyplesin-I by a GSAA_linker | Amino acid |
| 28 | sdAb37 linked to the lytic peptide Polybia-MP1 by a GSAA_linker | Amino acid |
| 29 | sdAb46 linked to the lytic peptide BMAP28A by a GS_linker | Amino acid |
| 30 | sdAb46 linked to the lytic peptide BMAP28A by a GSAA_linker | Amino acid |
| 31 | sdAb46 linked to the lytic peptide modified cysteine deleted Tachyplesin-I by a GS_linker | Amino acid |
| 32 | sdAb46 linked to the lytic peptide modified cysteine deleted Tachyplesin-I by a GSAA_linker | Amino acid |
| 33 | sdAb46 linked to the lytic peptide Polybia-MP1 by a GSAA_linker | Amino acid |
| 34 | sdAb47 linked to the lytic peptide BMAP28A by a GS_linker | Amino acid |
| 35 | sdAb47 linked to the lytic peptide BMAP28A by a GSAA_linker | Amino acid |
| 36 | sdAb47 linked to the lytic peptide modified cysteine deleted Tachyplesin-I by a GS_linker | Amino acid |
| 37 | sdAb47 linked to the lytic peptide modified cysteine deleted Tachyplesin-I by a GSAA_linker | Amino acid |
| 38 | sdAb47 linked to the lytic peptide Polybia-MP1 by a GSAA_linker | Amino acid |
| 39 | sdAb56 linked to the lytic peptide BMAP28A by a GS_linker | Amino acid |
| 40 | sdAb56 linked to the lytic peptide BMAP28A by a GSAA_linker | Amino acid |
| 41 | sdAb56 linked to the lytic peptide modified cysteine deleted Tachyplesin-I by a GS_linker | Amino acid |
| 42 | sdAb56 linked to the lytic peptide modified cysteine deleted Tachyplesin-I by a GSAA_linker | Amino acid |
| 43 | sdAb56 linked to the lytic peptide Polybia-MP1 by a GSAA_linker | Amino acid |
| 44 | sdAb59 linked to the lytic peptide BMAP28A by a GS_linker | Amino acid |
| 45 | sdAb59 linked to the lytic peptide BMAP28A by a GSAA_linker | Amino acid |
| 46 | sdAb59 linked to the lytic peptide modified cysteine deleted Tachyplesin-I by a GS_linker | Amino acid |
| 47 | sdAb59 linked to the lytic peptide modified cysteine deleted Tachyplesin-I by a GSAA_linker | Amino acid |
| 48 | sdAb59 linked to the lytic peptide Polybia-MP1 by a GSAA_linker | Amino acid |
| 49 | sdAb62 linked to the lytic peptide BMAP28A by a GS_linker | Amino acid |
| 50 | sdAb62 linked to the lytic peptide BMAP28A by a GSAA_linker | Amino acid |
| 51 | sdAb62 linked to the lytic peptide modified cysteine deleted Tachyplesin-I by a GS_linker | Amino acid |
| 52 | sdAb62 linked to the lytic peptide modified cysteine deleted Tachyplesin-I by a GSAA_linker | Amino acid |
| 53 | sdAb62 linked to the lytic peptide Polybia-MP1 by a GSAA_linker | Amino acid |
| 54 | sdAb63 linked to the lytic peptide BMAP28A by a GS_linker | Amino acid |
| 55 | sdAb63 linked to the lytic peptide BMAP28A by a GSAA_linker | Amino acid |
| 56 | sdAb63 linked to the lytic peptide modified cysteine deleted Tachyplesin-I by a GS_linker | Amino acid |
| 57 | sdAb63 linked to the lytic peptide modified cysteine deleted Tachyplesin-I by a GSAA_linker | Amino acid |
| 58 | sdAb63 linked to the lytic peptide Polybia-MP1 by a GSAA_linker | Amino acid |
| 59 | sdAb65 linked to the lytic peptide BMAP28A by a GS_linker | Amino acid |
| 60 | sdAb65 linked to the lytic peptide BMAP28A by a GSAA_linker | Amino acid |
| 61 | sdAb65 linked to the lytic peptide modified cysteine deleted Tachyplesin-I by a GS_linker | Amino acid |
| 62 | sdAb65 linked to the lytic peptide modified cysteine deleted Tachyplesin-I by a GSAA_linker | Amino acid |
| 63 | sdAb65 linked to the lytic peptide Polybia-MP1 by a GSAA_linker | Amino acid |

TABLE 4-continued

Description of the sequence listing

| SEQ ID NO | Denomination | Sequence Type |
|---|---|---|
| 64 | CDR1 of sdAb26 | Amino acid |
| 65 | CDR1 of sdAb37 | Amino acid |
| 66 | CDR1 of sdAb46 | Amino acid |
| 67 | CDR1 of sdAb47 | Amino acid |
| 68 | CDR1 of sdAb56 | Amino acid |
| 69 | CDR1 of sdAb59 | Amino acid |
| 70 | CDR1 of sdAb62 | Amino acid |
| 71 | CDR1 of sdAb63 | Amino acid |
| 72 | CDR1 of sdAb65 | Amino acid |
| 73 | CDR2 of sdAb26 | Amino acid |
| 74 | CDR2 of sdAb37 | Amino acid |
| 75 | CDR2 of sdAb46 | Amino acid |
| 76 | CDR2 of sdAb47 | Amino acid |
| 77 | CDR2 of sdAb56 | Amino acid |
| 78 | CDR2 of sdAb59 | Amino acid |
| 79 | CDR2 of sdAb62 | Amino acid |
| 80 | CDR2 of sdAb63 | Amino acid |
| 81 | CDR2 of sdAb65 | Amino acid |
| 82 | CDR3 of sdAb26 | Amino acid |
| 83 | CDR3 of sdAb37 | Amino acid |
| 84 | CDR3 of sdAb46 | Amino acid |
| 85 | CDR3 of sdAb47 | Amino acid |
| 86 | CDR3 of sdAb56 | Amino acid |
| 87 | CDR3 of sdAb59 | Amino acid |
| 88 | CDR3 of sdAb62 | Amino acid |
| 89 | CDR3 of sdAb63 | Amino acid |
| 90 | CDR3 of sdAb65 | Amino acid |
| 91 | FR1 of sdAb26 | Amino acid |
| 92 | FR1 of sdAb37 | Amino acid |
| 93 | FR1 of sdAb46 | Amino acid |
| 94 | FR1 of sdAb47 | Amino acid |
| 95 | FR1 of sdAb56 | Amino acid |
| 96 | FR1 of sdAb59 | Amino acid |
| 97 | FR1 of sdAb62 | Amino acid |
| 98 | FR1 of sdAb63 | Amino acid |
| 99 | FR1 of sdAb65 | Amino acid |
| 100 | FR2 of sdAb26 | Amino acid |
| 101 | FR2 of sdAb37 | Amino acid |
| 102 | FR2 of sdAb46 | Amino acid |
| 103 | FR2 of sdAb47 | Amino acid |
| 104 | FR2 of sdAb56 | Amino acid |
| 105 | FR2 of sdAb59 | Amino acid |
| 106 | FR2 of sdAb62 | Amino acid |
| 107 | FR2 of sdAb63 | Amino acid |
| 108 | FR2 of sdAb65 | Amino acid |
| 109 | FR3 of sdAb26 | Amino acid |
| 110 | FR3 of sdAb37 | Amino acid |
| 111 | FR3 of sdAb46 | Amino acid |
| 112 | FR3 of sdAb47 | Amino acid |
| 113 | FR3 of sdAb56 | Amino acid |
| 114 | FR3 of sdAb59 | Amino acid |
| 115 | FR3 of sdAb62 | Amino acid |
| 116 | FR3 of sdAb63 | Amino acid |
| 117 | FR3 of sdAb65 | Amino acid |
| 118 | FR4 of sdAb26 | Amino acid |
| 119 | FR4 of sdAb37 | Amino acid |
| 120 | FR4 of sdAb46 | Amino acid |
| 121 | FR4 of sdAb47 | Amino acid |
| 122 | FR4 of sdAb56 | Amino acid |
| 123 | FR4 of sdAb59 | Amino acid |
| 124 | FR4 of sdAb62 | Amino acid |
| 125 | FR4 of sdAb63 | Amino acid |
| 126 | FR4 of sdAb65 | Amino acid |
| 127 | GS_linker used as linker between the sdAb and the lytic peptide | Amino acid |
| 128 | GSAA_linker used as linker between the sdAb and the lytic peptide | Amino acid |
| 129 | BMAP28A | Amino acid |
| 130 | Modified Cysteine deleted Tachyplesin-I | Amino acid |
| 131 | Polybia-MP1 | Amino acid |
| 132 | Primer CALL001 used to PCR amplify the VHH variable regions | Nucleic acid |
| 133 | Primer CALL002 used to PCR amplify the VHH variable regions | Nucleic acid |

TABLE 4-continued

Description of the sequence listing

| SEQ ID NO | Denomination | Sequence Type |
|---|---|---|
| 134 | Primer VHH_back used to PCR amplify the VHH variable regions | Nucleic acid |
| 135 | Primer VHH_for used to PCR amplify the VHH variable regions | Nucleic acid |
| 136 | sdAb14 amino acid sequence | Amino acid |
| 137 | sdAb60 amino acid sequence | Amino acid |
| 138 | sdAbS amino acid sequence | Amino acid |
| 139 | sdAb14 nucleic acid sequence | Nucleic acid |
| 140 | sdAb60 nucleic acid sequence | Nucleic acid |
| 141 | sdAbS nucleic acid sequence | Nucleic acid |
| 142 | sdAb 14 linked to the lytic peptide BMAP28A by a GS_linker | Amino acid |
| 143 | sdAb 14_linked to the lytic peptide BMAP28A by a GSAA_linker | Amino acid |
| 144 | sdAb 14 linked to the lytic peptide modified cysteinedeleted Tachyplesin-I by a GS_linker | Amino acid |
| 145 | sdAb 14 linked to the lytic peptide modified cysteine deleted Tachyplesin-I by a GSAA_linker | Amino acid |
| 146 | sdAb 14_linked to the lytic peptide Polybia-MP1 by a GSAA_linker | Amino acid |
| 147 | sdAb60 linked to the lytic peptide BMAP28A by a GS_linker | Amino acid |
| 148 | sdAb60_linked to the lytic peptide BMAP28A by a GSAA_linker | Amino acid |
| 149 | sdAb60 linked to the lytic peptide modified cysteine deleted Tachyplesin-I by a GS_linker | Amino acid |
| 150 | sdAb60 linked to the lytic peptide modified cysteine deleted Tachyplesin-I by a GSAA_linker | Amino acid |
| 151 | sdAb60_linked to the lytic peptide Polybia-MP1 by a GSAA_linker | Amino acid |
| 152 | sdAbS_linked to the lytic peptide BMAP28A by a GS_linker | Amino acid |
| 153 | sdAbS_linked to the lytic peptide BMAP28A by a GSAA_linker | Amino acid |
| 154 | sdAbS linked to the lytic peptide modified cysteine deleted Tachyplesin-I by a GS_linker | Amino acid |
| 155 | sdAbS linked to the lytic peptide modified cysteine deleted Tachyplesin-I by a GSAA_linker | Amino acid |
| 156 | sdAbS_linked to the lytic peptide Polybia-MP1 by a GSAA_linker | Amino acid |
| 157 | CDR1 of sdAb14 | Amino acid |
| 158 | CDR1 of sdAb60 | Amino acid |
| 159 | CDR1 of sdAbS | Amino acid |
| 160 | CDR2 of sdAb14 | Amino acid |
| 161 | CDR2 of sdAb60 | Amino acid |
| 162 | CDR2 of sdAbS | Amino acid |
| 163 | CDR3 of sdAb14 | Amino acid |
| 164 | CDR3 of sdAb60 | Amino acid |
| 165 | CDR3 of sdAbS | Amino acid |
| 166 | FR1 of sdAb14 | Amino acid |
| 167 | FR1 of sdAb60 | Amino acid |
| 168 | FR1 of sdAbS | Amino acid |
| 169 | FR2 of sdAb14 | Amino acid |
| 170 | FR2 of sdAb60 | Amino acid |
| 171 | FR2 of sdAbS | Amino acid |
| 172 | FR3 of sdAb14 | Amino acid |
| 173 | FR3 of sdAb60 | Amino acid |
| 174 | FR3 of sdAbS | Amino acid |
| 175 | FR4 of sdAb14 | Amino acid |
| 176 | FR4 of sdAb60 | Amino acid |
| 177 | FR4 of sdAbS | Amino acid |
| 178 | SRGS linker | Amino acid |
| 179 | sdAb26 linked to the lytic peptide BMAP28A by a SRGS_linker | Amino acid |
| 180 | sdAb26 linked to the lytic peptide modified cysteine deleted Tachyplesin-I by a SRGS_linker | Amino acid |
| 181 | sdAb 26 linked to the lytic peptide Polybia-MP1 by a GS_linker | Amino acid |
| 182 | sdAb 26 linked to the lytic peptide Polybia-MP1 by a SRGS_linker | Amino acid |
| 183 | sdAb37 linked to the lytic peptide BMAP28A by a SRGS_linker | Amino acid |
| 184 | sdAb 37 linked to the lytic peptide modified cysteine deleted Tachyplesin-I by a SRGS_linker | Amino acid |

TABLE 4-continued

| SEQ ID NO | Denomination | Sequence Type |
|---|---|---|
| 185 | sdAb 37 linked to the lytic peptide Polybia-MP1 by a GS_linker | Amino acid |
| 186 | sdAb37 linked to the lytic peptide Polybia-MP1 by a SRGS_linker | Amino acid |
| 187 | sdAb46 linked to the lytic peptide BMAP28A by a SRGS_linker | Amino acid |
| 188 | sdAb46 linked to the lytic peptide modified cysteine deleted Tachyplesin-I by a SRGS_linker | Amino acid |
| 189 | sdAb46 linked to the lytic peptide Polybia-MP1 by a GS_linker | Amino acid |
| 190 | sdAb46 linked to the lytic peptide Polybia-MP1 by a SRGS_linker | Amino acid |
| 191 | sdAb47 linked to the lytic peptide BMAP28A by a SRGS_linker | Amino acid |
| 192 | sdAb47 linked to the lytic peptide modified cysteine deleted Tachyplesin-I by a SRGS_linker | Amino acid |
| 193 | sdAb47 linked to the lytic peptide Polybia-MP1 by a GS_linker | Amino acid |
| 194 | sdAb47 linked to the lytic peptide Polybia-MP1 by a SRGS_linker | Amino acid |
| 195 | sdAb56 linked to the lytic peptide BMAP28A by a SRGS_linker | Amino acid |
| 196 | sdAb56 linked to the lytic peptide modified cysteine deleted Tachyplesin-I by a SRGS linker | Amino acid |
| 197 | sdAb56 linked to the lytic peptide Polybia-MP1 by a GS_linker | Amino acid |
| 198 | sdAb56 linked to the lytic peptide Polybia-MP1 by a GS_linker | Amino acid |
| 199 | sdAb59 linked to the lytic peptide BMAP28A by a SRGS_linker | Amino acid |
| 200 | sdAb59 linked to the lytic peptide modified cysteine deleted Tachyplesin-I by a SRGS_linker | Amino acid |
| 201 | sdAb59 linked to the lytic peptide Polybia-MP1 by a GS_linker | Amino acid |
| 202 | sdAb59 linked to the lytic peptide Polybia-MP1 by a SRGS_linker | Amino acid |
| 203 | sdAb62 linked to the lytic peptide BMAP28A by a SRGS_linker | Amino acid |
| 204 | sdAb62 linked to the lytic peptide modified cysteine deleted Tachyplesin-I by a SRGS_linker | Amino acid |
| 205 | sdAb62 linked to the lytic peptide Polybia-MP1 by a GS_linker | Amino acid |
| 206 | sdAb62 linked to the lytic peptide Polybia-MP1 by a SRGS_linker | Amino acid |
| 207 | sdAb63 linked to the lytic peptide BMAP28A by a SRGS_linker | Amino acid |
| 208 | sdAb63 linked to the lytic peptide modified cysteine deleted Tachyplesin-I by a SRGS_linker | Amino acid |
| 209 | sdAb63 linked to the lytic peptide Polybia-MP1 by a GS_linker | Amino acid |
| 210 | sdAb63 linked to the lytic peptide Polybia-MP1 by a SRGS_linker | Amino acid |
| 211 | sdAb65 linked to the lytic peptide BMAP28A by a SRGS_linker | Amino acid |
| 212 | sdAb65 linked to the lytic peptide modified cysteine deleted Tachyplesin-I by a SRGS_linker | Amino acid |
| 213 | sdAb65 linked to the lytic peptide Polybia-MP1 by a GS_linker | Amino acid |
| 214 | sdAb65 linked to the lytic peptide Polybia-MP1 by a SRGS_linker | Amino acid |
| 215 | sdAb14 linked to the lytic peptide BMAP28A by a SRGS_linker | Amino acid |
| 216 | sdAb14 linked to the lytic peptide modified cysteine deleted Tachyplesin-I by a SRGS_linker | Amino acid |
| 217 | sdAb14 linked to the lytic peptide Polybia-MP1 by a GS_linker | Amino acid |
| 218 | sdAb14 linked to the lytic peptide Polybia-MP1 by a SRGS_linker | Amino acid |
| 219 | sdAb60 linked to the lytic peptide BMAP28A by a SRGS_linker | Amino acid |
| 220 | sdAb60 linked to the lytic peptide modified cysteine deleted Tachyplesin-I by a SRGS_linker | Amino acid |
| 221 | sdAb60 linked to the lytic peptide Polybia-MP1 by a GS_linker | Amino acid |
| 222 | sdAb60 linked to the lytic peptide Polybia-MP1 by a SRGS_linker | Amino acid |
| 223 | sdAbS linked to the lytic peptide BMAP28A by a SRGS_linker | Amino acid |
| 224 | sdAbS linked to the lytic peptide modified cysteine deleted Tachyplesin-I by a SRGS_linker | Amino acid |
| 225 | sdAbS linked to the lytic peptide Polybia-MP1 by a GS_linker | Amino acid |
| 226 | sdAbS linked to the lytic peptide Polybia-MP1 by a SRGS_linker | Amino acid |
| 227 | Short connecting sequence | Amino Acid |
| 228 | GGGGS_linker | Amino acid |

Description of the sequence listing

Purification of Recombinant Globo H Binding Single Domain Antibodies sdAb46, sdAb56, and sdAb59

Previously, Globo H sdAbs were generated by immunizing alpacas with synthetic glycans. The respective gene sequences were identified and obtained as commercially synthesized vectors for protein expression. The strongest Globo H binders were determined in previous screens using MCF7 cancer cells.

Figure 17:
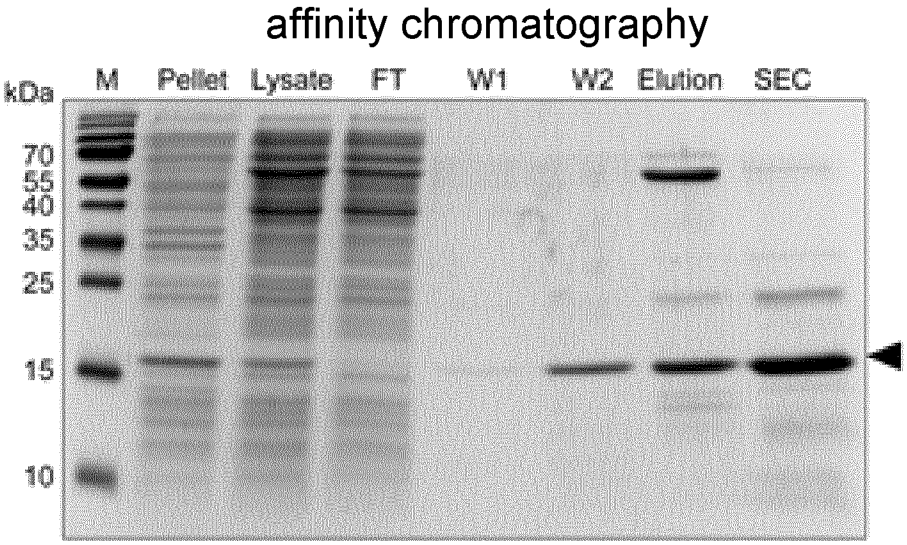
FIG. 17: Purification of Globo H binding sdAbs. SdAbs were expressed in SHuffle Cells®, extracted by French press cell lysis, and purified by $Ni^{2+}$-NTA affinity chromatography and size exclusion chromatography (SEC). a) SDS-PAGE of samples taken during the purification of sdAb46. Gel was stained with PageBlue Protein Staining Solution M, PageRuler Prestained Protein Ladder 10-180 kDa. FT, flow-through. W1, wash 1 fraction. W2, wash 2 fraction. b) SEC chromatogram shows the UV absorbance at 280 nm detecting the elution of proteins. HiLoad 16/600 Superdex 75 (S75) prep grade column was used with FPLC system. Asterisk (*) indicates the fraction used for SDS-PAGE.
Figure 17:
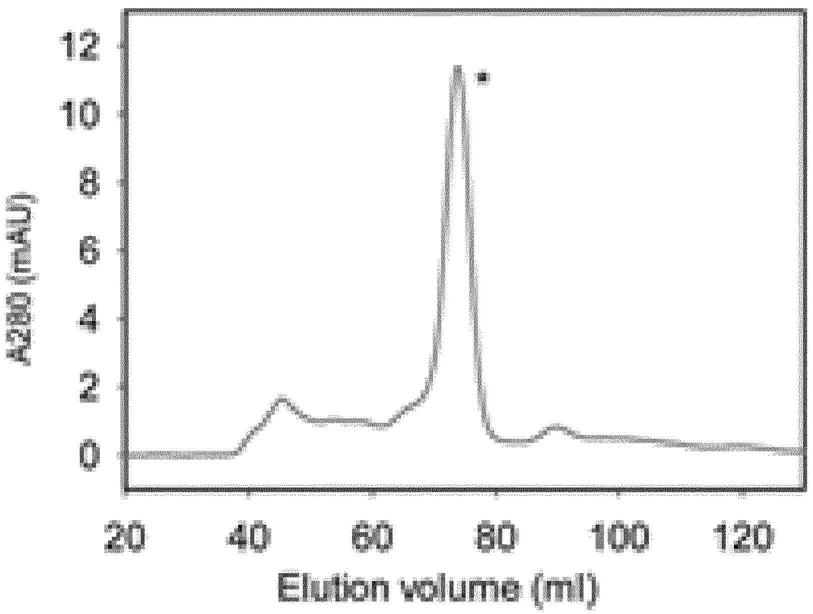

To validate and further characterize the glycan binding, the most promising sdAbs were now analyzed for their binding to synthetic glycans in vitro. Frozen aliquots of purified sdAb37, sdAb62, and sdAb63 were already available; sdAb46, sdAb56, and sdAb59 had to be purified first. Therefore, pET-28b (+)-sdAb plasmids were transformed into SHuffle *E. coli* Competent Cells® that were expanded to 1 L of bacteria cultures. Protein expression was induced with 0.5 mM IPTG. The recombinant sdAbs were His-tagged and were purified by $Ni^{2+}$-NTA affinity chromatography followed by size-exclusion chromatography (SEC) to analyze aggregation or multimerization. Samples of the pellet, lysate, flow-through (FT), wash 1 (W1), wash 2 (W2), the elution from $Ni^{2+}$-NTA affinity chromatography, and the protein-containing fraction of the size-exclusion chromatography (SEC) were taken for SDS-PAGE. FIG. 17*a* shows a representative purification SDS-PAGE image and a chromatogram from SEC. The theoretical molecular weight of sdAb46 is 16.8 kDa, which corresponds to the observed band. While the purified nanobody monomers were partly soluble, large amounts of protein remained in the pellet after lysis. The wash buffer 2 contained 30 mM imidazole, which already led to some nanobody elution and loss of product. However, other protein impurities remained and were still found in the elution. For subsequent size-exclusion chromatography, a HiLoad® 16/600 Superdex® 75 (S75) preparation grade column pre washed with PBS, was used with an FPLC system.

Example 1: Generation and Selection of sdAbs

Immunization of Alpaca

For Alpaca immunization, synthetic Globo H was conjugated to the carrier protein CRM197 (Cross-Reactive-Material-197), which is a mutant version of the diphtheria toxin, where the single amino acid exchange of a glycine in position 52 to a glutamic acid renders the protein non-toxic. Alpaca were immunized with the GloboH-CRM197 conjugate (for details see the Method section) for a total of 6 weekly immunization rounds including a two weeks gap between the thirds and forth injections. Whole blood was collected at the $51^{th}$ day.

Evaluation of the Immune Response in the Immunized Alpaca

Figure 4:
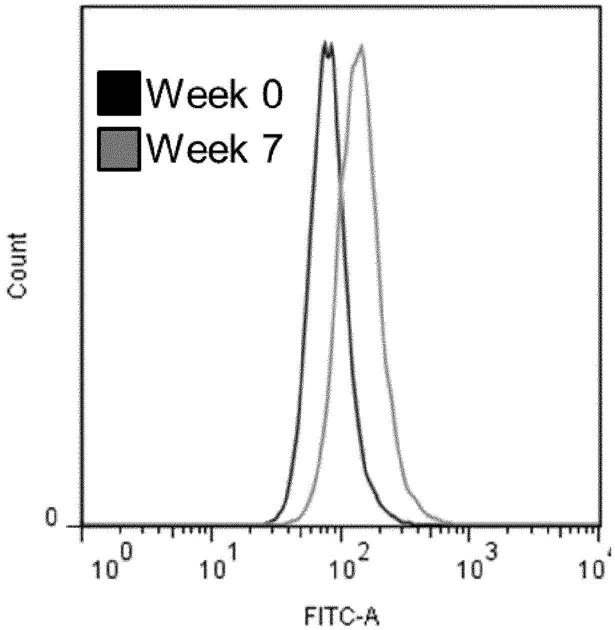
FIG. 4: Binding of serum antibodies to native globo-series glycans. Flow cytometry results of immunized Alpaca serum from weeks 0 (red) and 7 (blue, final week) demonstrate the generation of antibodies capable of binding to breast cancer cells (MCF-7) expressing globo-series glycans.
Figure 6:
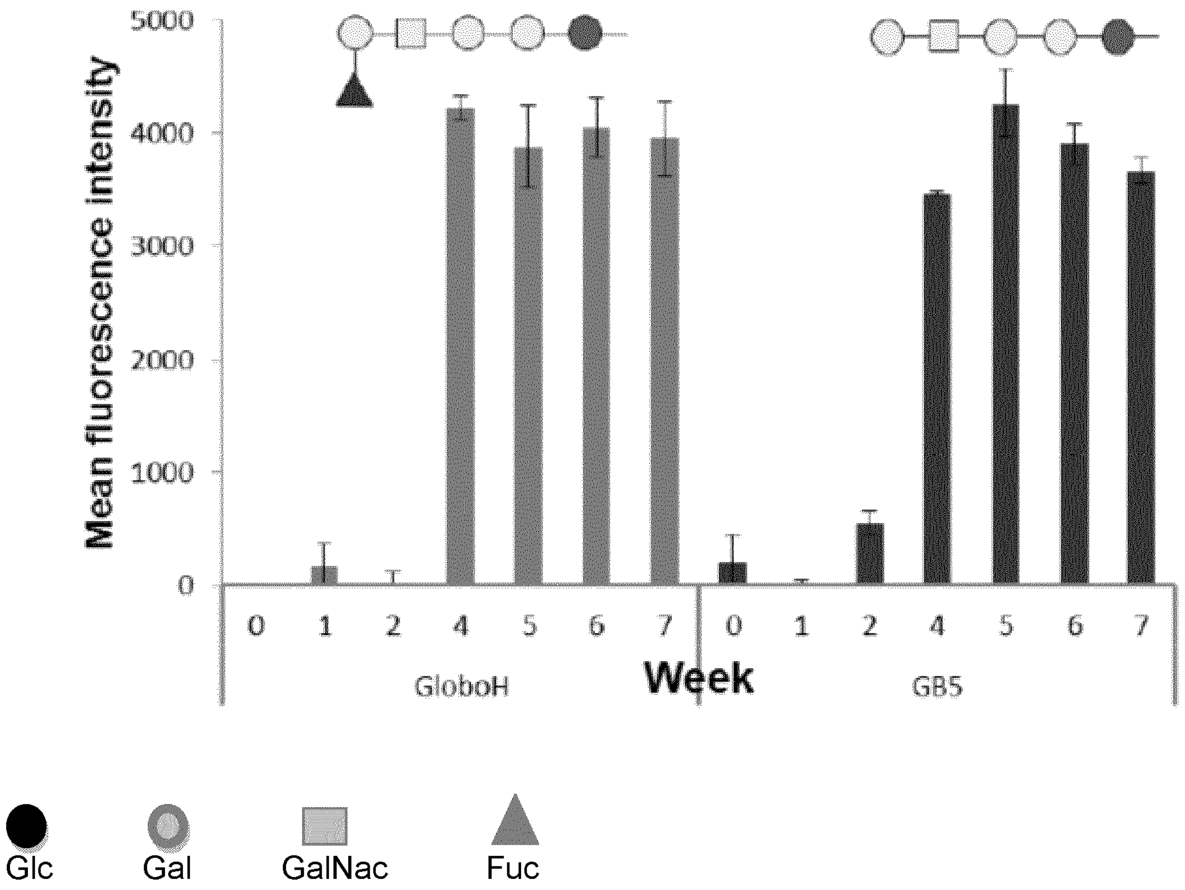
FIG. 6: Quantification of glycan array results showing a gradual increase by weeks in immune response of immunized Alpaca to synthetic Globo H and Gb5.
Figure 7:
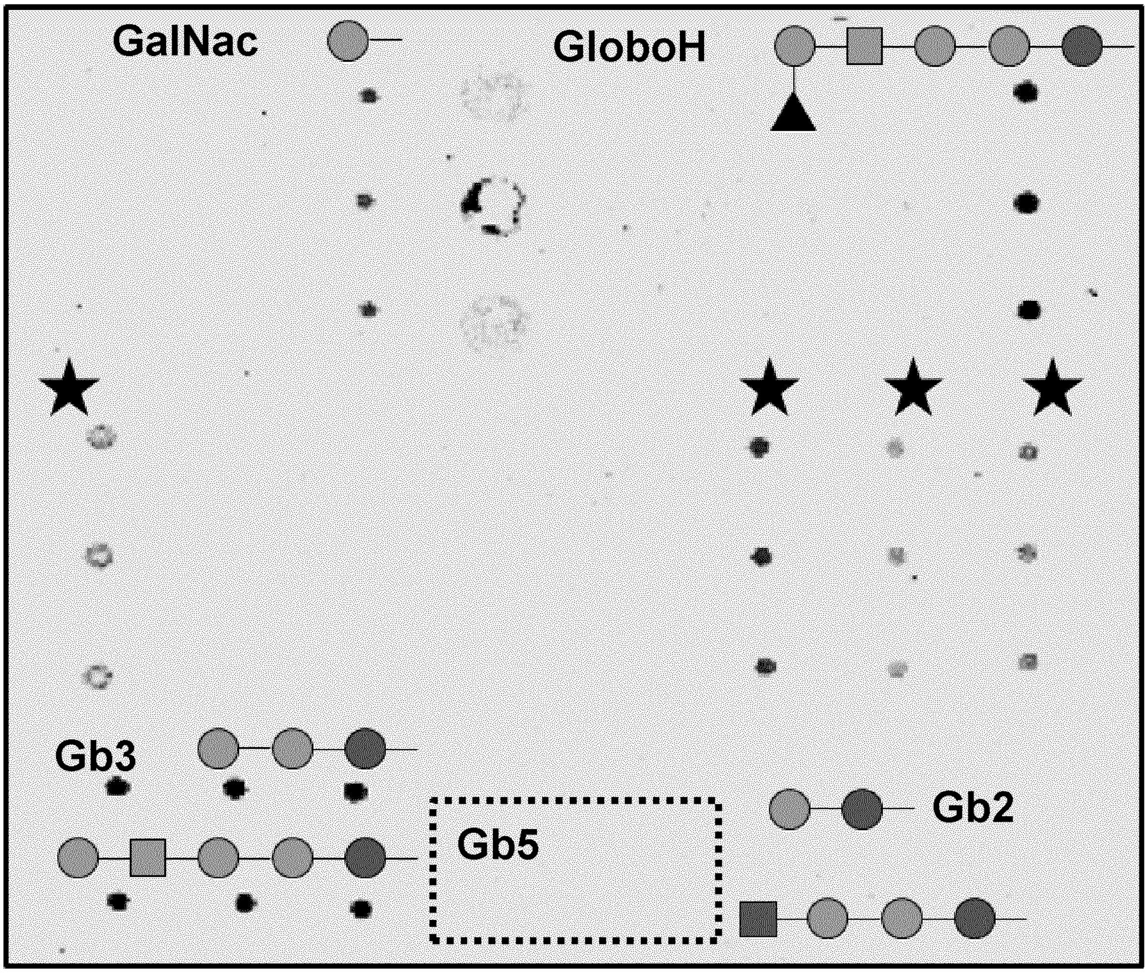
FIG. 7: Glycan array image of week 7 (final week) for serum inspection showing specific binding of serum antibodies to the different globo family synthetic glycans (illustrated structures). Black asterisks represent control glycan structures.

Serum samples collected before (week 0) and at the end (week 7) of the immunization were used to test the binding to native globo family glycans. Serum samples were directly incubated with MCF-7 cells, which are known to express globo family glycans, and incubated for 45 min at RT. Afterwards the cells were washed twice, resuspended in a solution containing FITC-conjugated anti-llama secondary antibodies, and incubated for another 45 min at RT. After other two washes, cells were fixed, resuspended in FACS buffer, and analysed at the flow cytometer. As shown in FIG. 4, serum of alpaca immunized for 7 weeks contained antibodies capable of binding to breast cancer cells (MCF-7). Moreover serum samples were tested using glycan array as described in the detailed Method section. FIG. 6 shows the gradual weekly increase in immune response of immunized Alpaca to synthetic Globo H up to week 7. FIG. 7 depict the glycan array image obtained with the serum samples of the last week 7 showing specific binding of serum antibodies to the different globo family synthetic glycans indicated in the figure.

Library Construction:

Isolation of sdAb Domains from Alpaca Serum.

Figure 8:
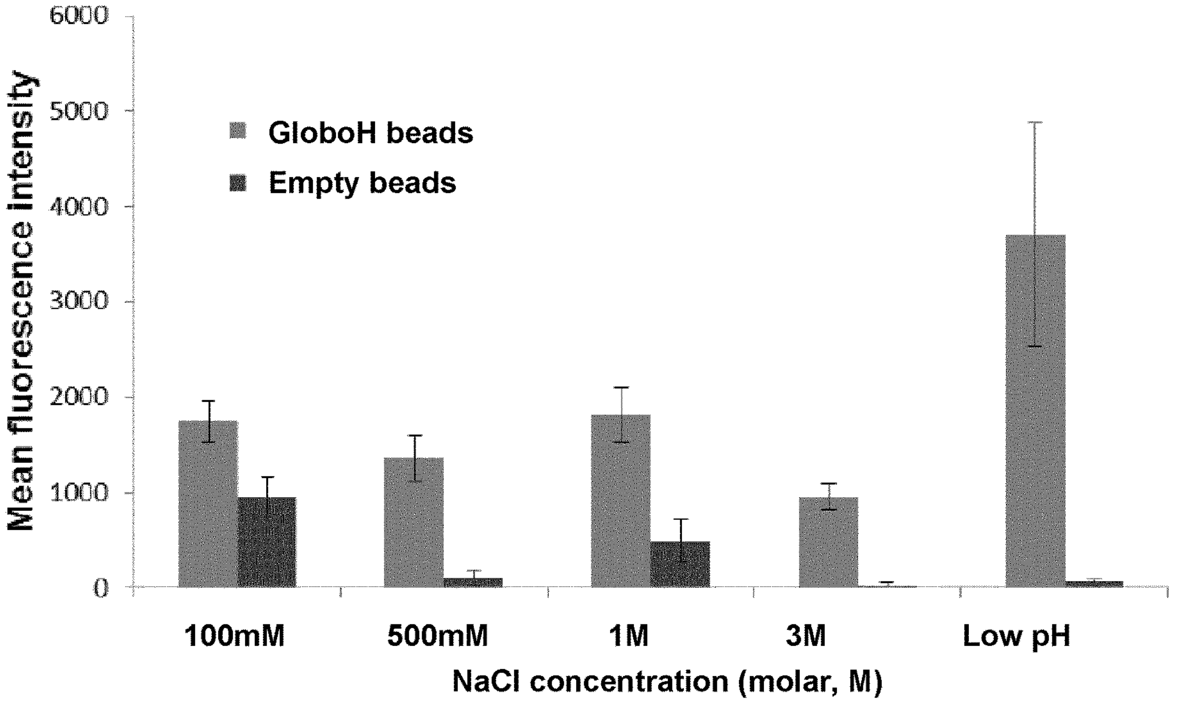
FIG. 8: Analysis of the Globo HGlobo H binding of affinity eluted antibodies by glycan array. Graph bars represent mean fluorescence intensity of eluted antibodies from empty (red) and Globo H coated beads (blue). Results show specificity of affinity purified antibodies which were then taken to gel electrophoresis in order to separate the sdAbs.

Total antibodies were isolated from sera of immunized Alpaca by using Protein A/G Magnetic beads. These samples were then used to isolate GloboH specific sdAbs by affinity purification using Globo H-coated beads, and uncoated control beads. These antibodies were then tested for their binding to Globo H by glycan array. FIG. 8 shows that mean fluorescence intensity obtained with antibody samples eluted from empty (black) and GloboH beads (grey) at different concentrations of sodium chloride. The highest fluorescence intensities were obtained with the samples obtained using sodium chloride at 100 mM, 500 mM and 1M, which were then subjected to gel electrophoresis SDS-PAGE after papain cleavage to obtain the single domain antibodies (sdAb) of 13 kDa. FIG. 9 shows that before digestion, samples obtained with NaCl 100 mM, 500 mM and 1M contained conventional IgGs (150 kDa) and heavy chain only Abs (55 kDa). After papain digestion, these samples contained Fc and Fab fragment (both ca 25 kDa), undigested antibody fragments (ca 50 kDa) and single domain antibodies of 13 kDa. The sdAbs were thus extracted from these bands and subjected to Mass Spectrometry analysis after tryptic digestion.

Retrieval of sdAb Sequences by Bioinformatic Analysis.

The VHH variable regions (sdAb) were specifically amplified by two-step nested PCR using the cDNA of Alpaca PBMCs as described in the Method section, and then subjected to sequencing.

Bioinformatic analysis was performed to retrieve the full length sequences of affinity purified sdAbs, by comparing the two libraries obtained by high-throughput sequencing of the PBMCs (cDNA) and Mass spectrometry (peptides) (procedure depicted in FIG. 1). To this aim were used the “Llama magic software” v1.0. (https://github.com/Fenyo-Lab/llama-magic) and an in-house modified version of Mascot software, which is a search engine for protein identification”. The modified version of the software was able of comparing the very large database of the high throughput sequencing with the very large database of the proteomic analysis, and to run each peptide dissociation spectra from the MS and compare to the open reading frames generated by the high throughput sequencing.

This analysis enabled retrieval of 102 different sdAb sequences, and 36 were chosen for further analysis by recombinant expression in *E. coli* and further binding assays.

Example 2: Expression of Selected sdAbs in *E. coli* and Further Analysis

Figure 10:
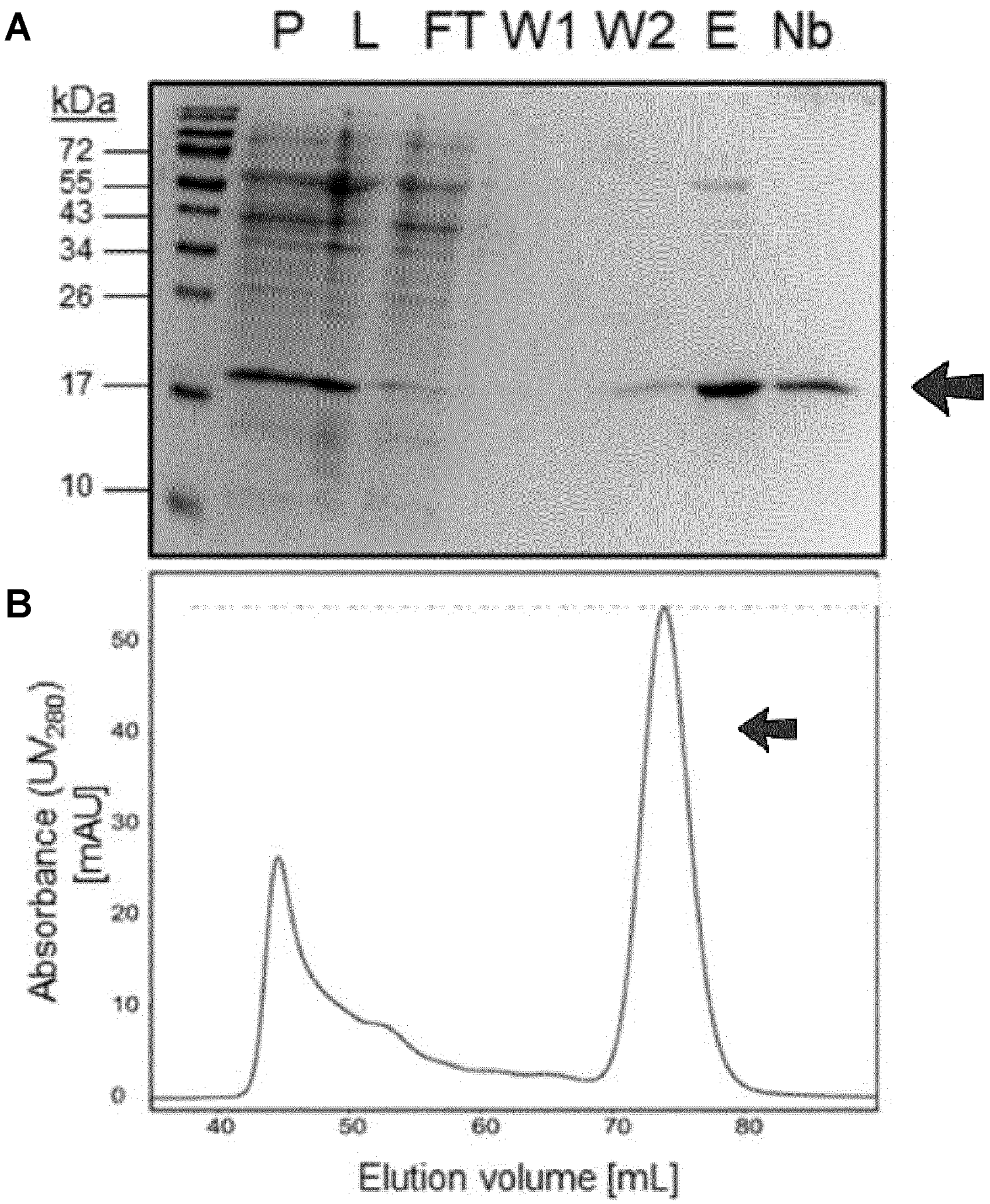
FIG. 10: Recombinant expression in *E. coli* of selected single domain antibody sequences. A) Gel electroporation of samples prelevated after different purification and cleaning steps of the cell extracts from ArcticExpress® *E. Coli* engineered to express sdAb46. Pellet (P) and lysate (L) of ArcticExpress® cells, flowthrough (FT), Wash Fractions 1 and 2 (W1 and W2), eluates after Nickel-NTA (E), and the final sdAb product (sdAb). The arrow indicates final cleaning steps and the presence of a high purity sdAb sample. B) Lower panel shows S200 size exclusion chromatography of sdAb46 which indicates expression in high yield (50 mAU) and elution volume that correlates with a 14 kDa protein (arrow).
Figure 11:
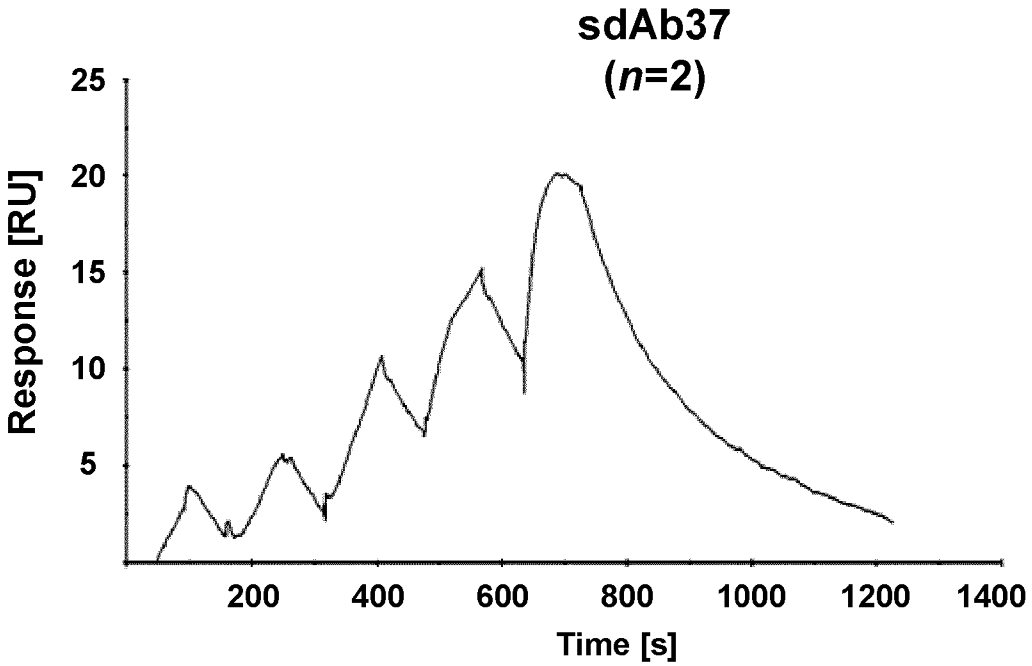
FIGS. 11-13: Binding of purified sdAbs to synthetic Globo H. Synthetic Globo H glycans were immobilized on a C1 surface plasmon resonance chip and different sdAbs were tested for binding. Among the different sdAbs tested, sdAb37 (FIG. 11), sdAb46 (FIG. 12), and sdAb62 (FIG. 13) are shown. SdAb46 showed the highest values with an average of 54 nM affinity.
Figure 12:
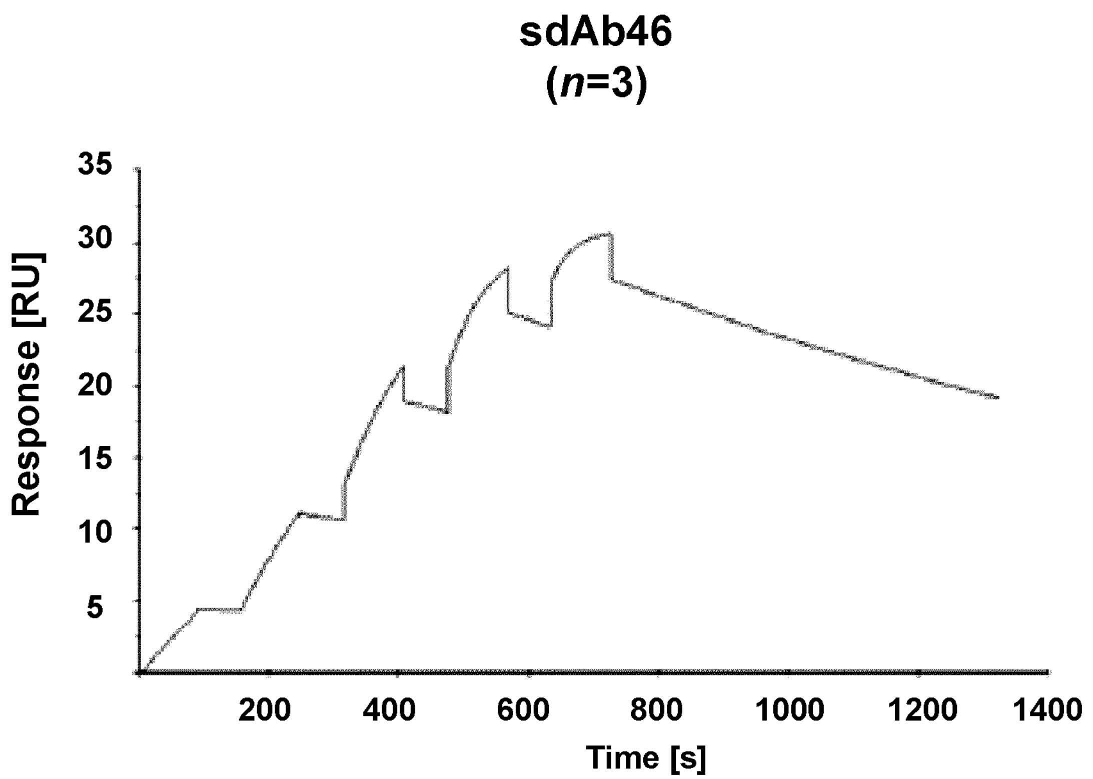
Figure 13:
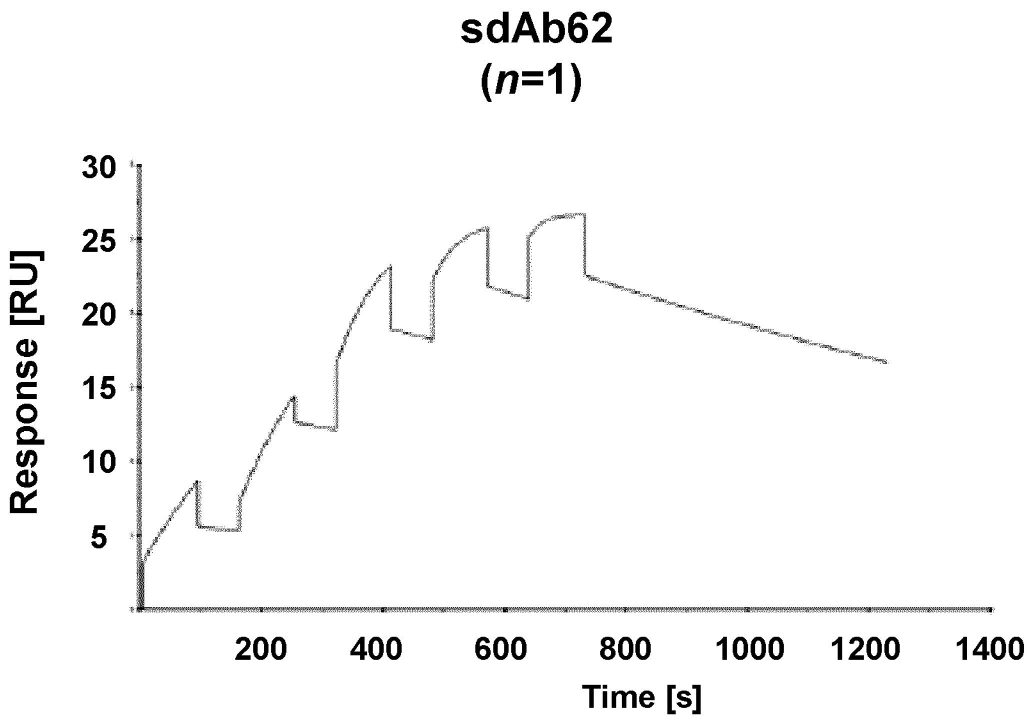
Figure 14:
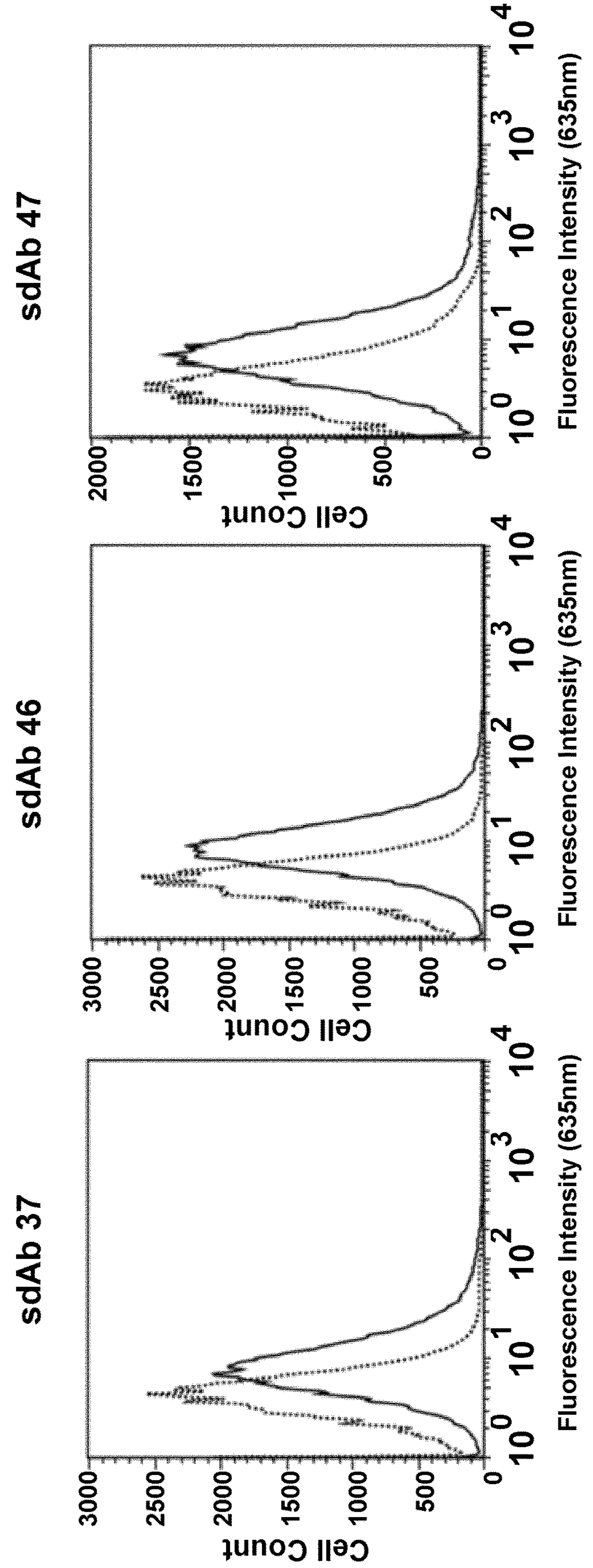
FIG. 14: Binding of purified sdAbs to native globo family glycans expressing cancer cells. Flow cytometry (FACS) assays were performed in order to test binding of different sdAbs to cancer cells (MCF-7) expressing globo family glycans (upper panel). Positive results were further validated using confocal microscopy (lower panel). Commercial available anti Globo H antibody VK9 was used as a positive control, the secondary antibody alone was used to exclude nonspecific binding of secondary antibody (right lowest panel).
Figure 15:
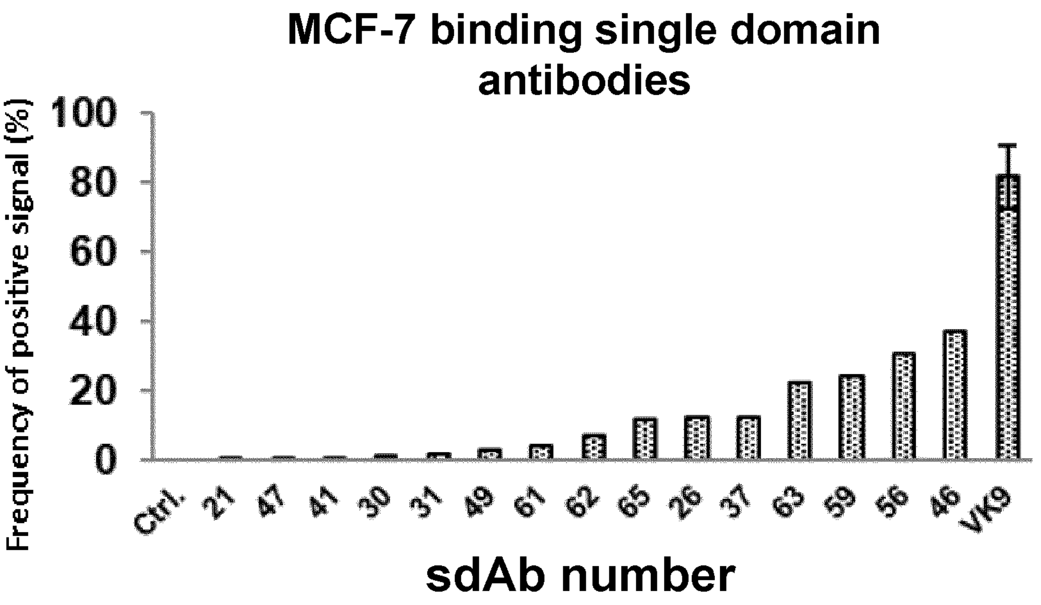
FIG. 15: Graphical representation of FACS results showing binding levels of the expressed and purified sdAbs to MCF-7 cancer cells.

Selected sdAbs sequences were expressed in ArctivExpress® cells (*E. coli*) as described in detail in the Method section. FIG. 10 (panels A and B) demonstrates the validity of the procedure, using sdAb46 as example. The isolated sdAbs were then tested for binding on MCF-7 cells, known to express GloboH Gb4 and Gb5 at low levels, and by surface plasmon resonance (SPR). FIGS. 11-13 show results of the SPR on sdAbs37, sdAbs46, and sdAbs62. SdAb46 showed the highest affinity values, with an average of 54 nM affinity. Moreover the binding of the isolated sdAbs to globo-series glycan expressing cells was tested by flow cytometry (FIG. 14, 15, 16). Also in these experiments sdAb 46 resulted to be the antibody with the highest binding capacity to GloboH.

These results demonstrate that the isolated single domain antibodies could bind with relatively high affinity to both native globo family structures expressed on cancer cells, as well as to synthetic and well characterised globo H structures on the SPR chip.

Figure 16:
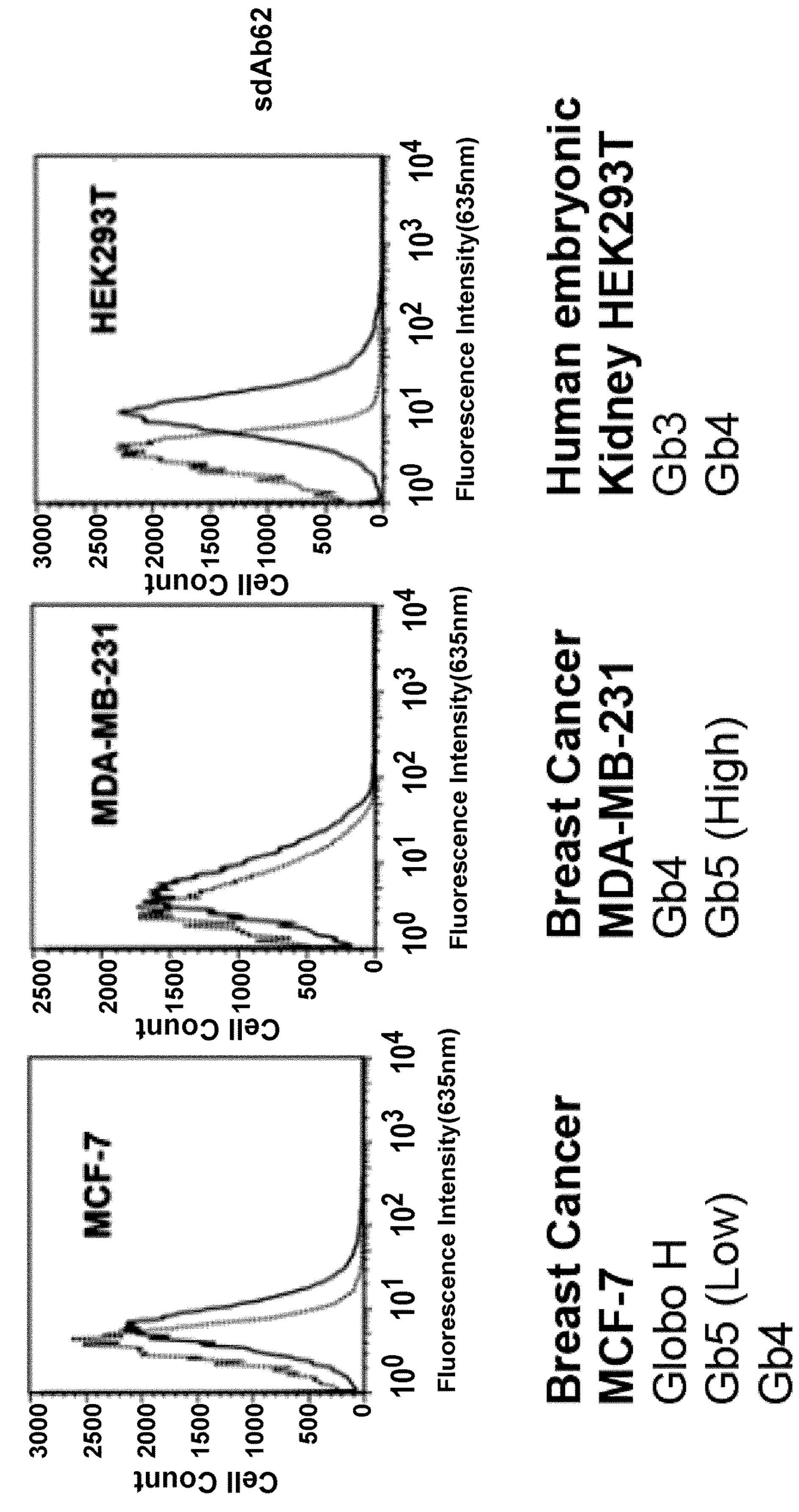
FIG. 16: Binding specificities for different globo-series glycan as tested by FACS binding assay. The specific binding of sdAbs to different cancer cells differs due to differences in expression levels of globo family glycans on the surface of the analysed cancer cells. Specificity of sdAb62 was tested on cancer cell lines that express different globo-series glycans. Results indicate differences in bound population size (black curve) due to distinct Gb3 expression on HEK293 kidney cells.

For example sdAb62 resulted to bind HEK293 cells (FIG. 16) with more affinity than MCF-7 or MDA-MB-231 cells. This finding suggests that sdAb62 bind the glycans Gb3 and Gb4, expressed by HEK293, with more affinity than GloboH, which is expressed by MCF-7 but not by HEK293 cells.

Example 3: NMR Characterizes the Binding Epitope and Bound Conformation of Globo-H to sdAb46

Saturation transfer difference nuclear magnetic resonance (STD NMR) spectroscopy is a powerful technique for the study of glycan-protein interactions at atomic resolution, examining the carbohydrate part in contact with the protein.

Figure 18:
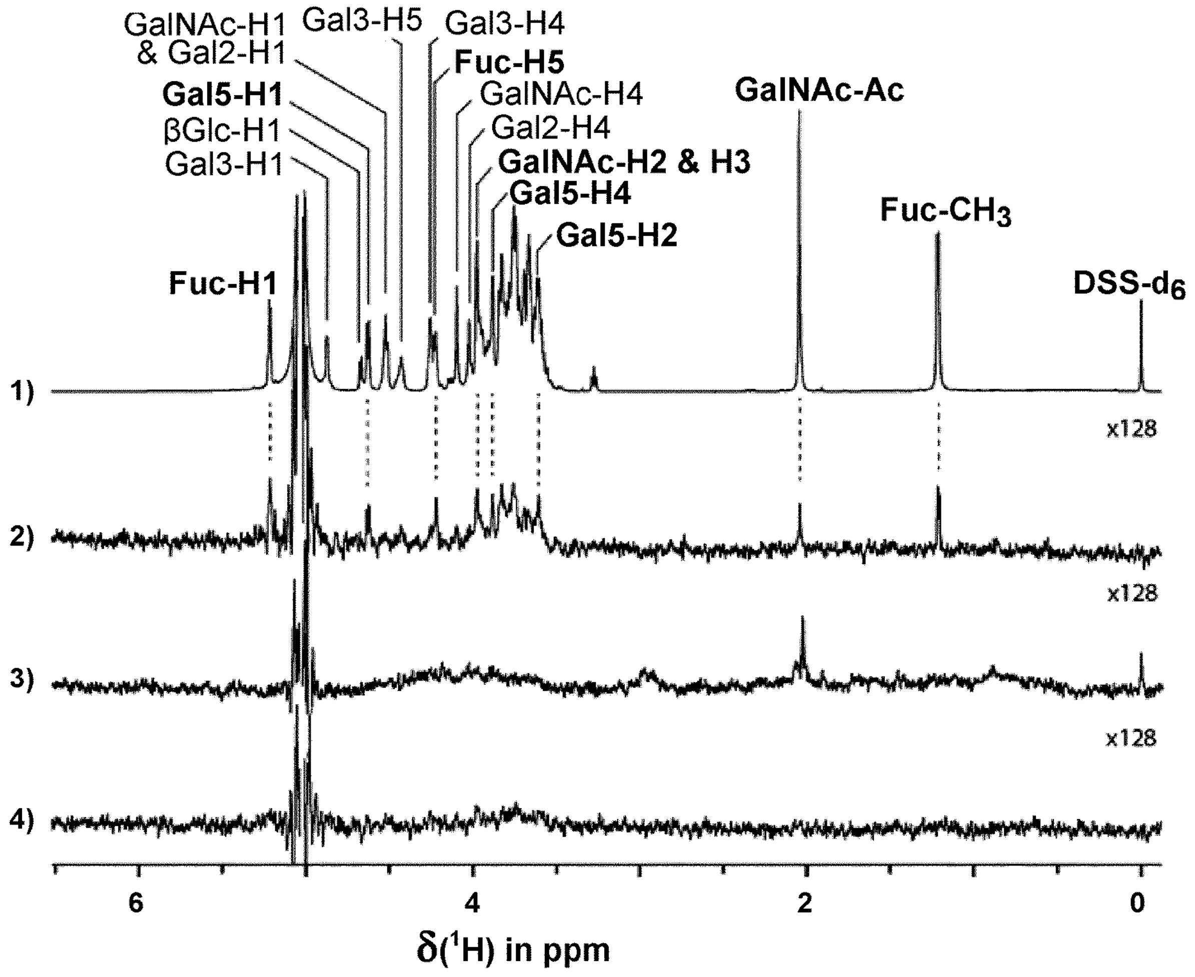
FIG. 18: Binding epitope and bound conformation of Globo-H to sdAb46 as analyzed by Saturation transfer difference nuclear magnetic resonance (STD NMR). a) STD NMR experiments reflecting the interaction of sdAb46 with Globo-H. From top to bottom: (1) Reference spectrum of Globo-H. Isolated signals showing magnetization transfer are highlighted in bold. (2) STD spectrum of 4 mM Globo-H in the presence of 60 μM sdAb46. (3) STD spectrum of 4 mM Gb5 in the presence of 110 μM sdAb46. (4) STD spectrum of 4 mM Globo-H. Residual water signal was not suppressed to allow the observation of Fuc and Gal3 anomeric protons. b) Binding epitope of Globo-H bound to sdAb46 from a single saturation time of 4 s. STD amplification factors for not indicated protons have not been available due to signal overlapping. STD NMR experiments were acquired at 600 MHz and 277 K. XXX=100–67%; XX=67–33%; X=33–0%; c) NOE build-up rates of Globo-H with and without sdAb46 vs mixing time (ms) at 600 MHz and 298 K. Curves represent intra-(Fuc-$CH_3$/Fuc-H5) and inter-pyranose (Fuc-H1/Gal5-H2) moiety connectivities. The sdAb to carbohydrate ratio is 1:16.4. I) Globo-H+sdAb46, Fuc-$CH_3$/Fuc-H5; II): Globo-H+sdAb46, Fuc-H1/Gal5-H2; III) Globo-H free, Fuc-CHs/Fuc-H5, IV) Globo-H free, Fuc-H1/Gal5-H2.

To examine the minimum recognition motif required by sdAb46 for binding, we mapped the binding epitope of sdAb46-bound Globo-H by STD NMR. Large saturation times of 4 s were required for a correct magnetization transfer of saturation from the protein to the ligand. Almost all protons from the Fucα(1-2)Galβ—moieties received saturating magnetization transfers from the protein but due to signal overlap, STD amplification factors were obtained only for a subset of protons (FIG. 18*a*). The corresponding binding epitope suggests that the Fucα(1-2)Galβ-motif makes closer contact with protons located in the protein binding pocket (FIG. 18*b*). Gb5 did not show significative STD signals in the presence of 110 μM sdAb46, suggesting that fucose is required for ligand recognition.

To further support sdAb46 binding to Globo-H, we acquired transferred Nuclear Overhauser effects (trNOEs) from Globo-H in the presence and absence of sdAb46. A significantly faster rate for the NOE build-up was observed for Globo-H in the presence of sdAb46, further confirmed binding of Globo-H to the protein (FIG. 18*c*).

In conclusion, the NMR results demonstrate that the selected single domain antibodies bind specifically to well-defined synthetic structures as well as to cell surfaces containing these epitopes.

Example 4: Molecular Cloning of sdAb46 Trimer

Figure 19:
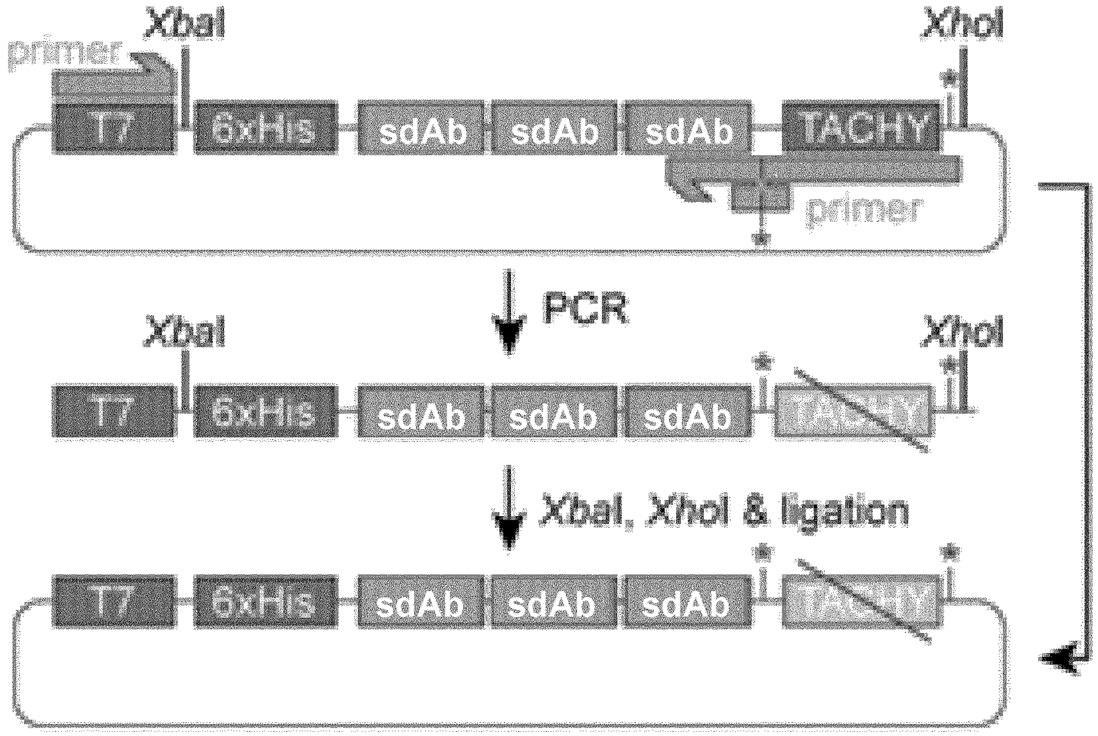
FIG. 19: Generation and purification of a trivalent sdAb46 fusion protein. a), Schematic representation of the molecular cloning strategy. Mutagenesis PCR was performed to insert a stop codon (*) to exclude the lytic peptide TACHY from being expressed. b) Agarose gel electrophoresis of the PCR product (left) and the products of the restriction enzyme digest (right). L, 1 kb DNA ladder. c) Expression test of the sdAb46 trimer construct in SHuffle cells. SDS-PAGE of the bacteria pellet before (pre) and after (post) IPTG induction is shown. d) Solubility test of the sdAb46 trimer construct. SDS-PAGE of pellet and lysate after cell lysis by sonication. e)-f) $Ni^{2+}$-NTA purification of sdAb46 trimer inclusion bodies using FPLC. The chromatogram is shown in e) and the SDS-PAGE gel image of the input, flow-through (FT) and the elution fractions 1-4 is shown in f). M=PageRuler Prestained Protein Ladder 10-180 kDa.
Figure 19:
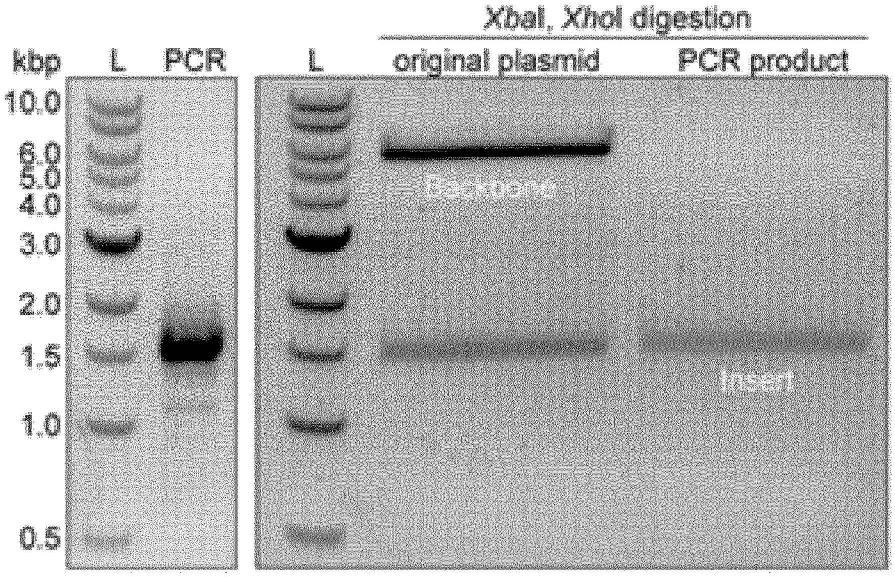

To improve sdAb binding, the next objective was to construct a trivalent version of sdAb46. From a separate project, a commercially obtained expression plasmid was available that encoded for a fusion protein made up of three sdAb46 units joined by GS-linkers, a His-tag at the N-terminus, and a lytic peptide (tachyplesin-I, abbreviated as TACHY) at the C-terminus. A trivalent sdAb46 construct was generated excluding the TACHY peptide by molecular cloning, in which a stop codon was inserted prior to the TACHY-coding sequence (FIG. 19*a*). A mutagenesis primer was designed, and a PCR reaction was performed to generate the DNA sequence including the additional stop codon. The PCR reaction was verified using agarose gel electrophoresis and a product with the size of ~1500 bp (expected size: 1448 bp) was observed. The PCR product and the plasmid were both digested with the same restriction enzymes (XbaI, XhoI) and the products were again run on an agarose gel. For the digest of the 6571 bp plasmid, a 5192 bp and 1385 bp large fragment were expected, but slightly larger bands were observed at around 6000 bp and 1500 bp. Nevertheless, the upper band was assumed to represent the backbone and was extracted and ligated with the digested PCR product that served as the insert. Successful cloning was confirmed by DNA sequencing.

After transformation, the protein was successfully expressed in SHuffle cells, as shown by SDS-PAGE, where a band with the expected size of 46.2 kDa was observed (FIG. 19*b*). The cell pellet was then lysed to assess the solubility of the sdAb46 trimer construct, but unfortunately a band corresponding to the trimer construct was observed only in the pellet sample and not the lysate suggesting the formation of inclusion bodies. This was previously observed for the original sdAb46 trimer-TACHY construct as well. Attempts to optimize the expression conditions (different IPTG concentrations, expression temperature, expression duration) could not improve the solubility for the TACHY construct and, therefore, establishing an inclusion body isolation and refolding protocol for the sdAb46 trimer was considered. The isolation was performed based on the protocol by Li Xu et al. (Biotechnol Appl Bioc, 2017). After the washing steps, a colorless pellet was obtained, which almost completely solubilized in 6 M urea. The solubilized inclusion bodies were further purified by $Ni^{2+}$-NTA purification using an Fast protein liquid chromatography (FPLC) machine equipped with a HisTrap column and eluted with a 5-step imidazole gradient. The second elution step (~39 mM imidazole) was already sufficient to elute the sdAb46 trimer, which was observed in the chromatogram and confirmed by SDS-PAGE. The highest absorbance value at 280 nm, ~170 mAU, was reached with a concentration of ~97 mM imidazole and higher imidazole concentrations resulted in only marginal elution of the remaining bound protein. SDS-PAGE analysis of the flow-through showed that large parts of the target protein remained unbound. Despite this and although not all of the denatured single domain antibody was refolded, 1.1 mg of folded protein was obtained.

Example 5: Cell Binding of the Trivalent Globo H Single Domain Antibody

In vitro binding assays were performed with the Globo H expressing breast cancer cell line MCF7. The neuroblastoma cell line IMR5, which does not express Globo H, was used as a negative control. These types of assays were performed by flow cytometry and fluorescent microscopy.

Figure 20:
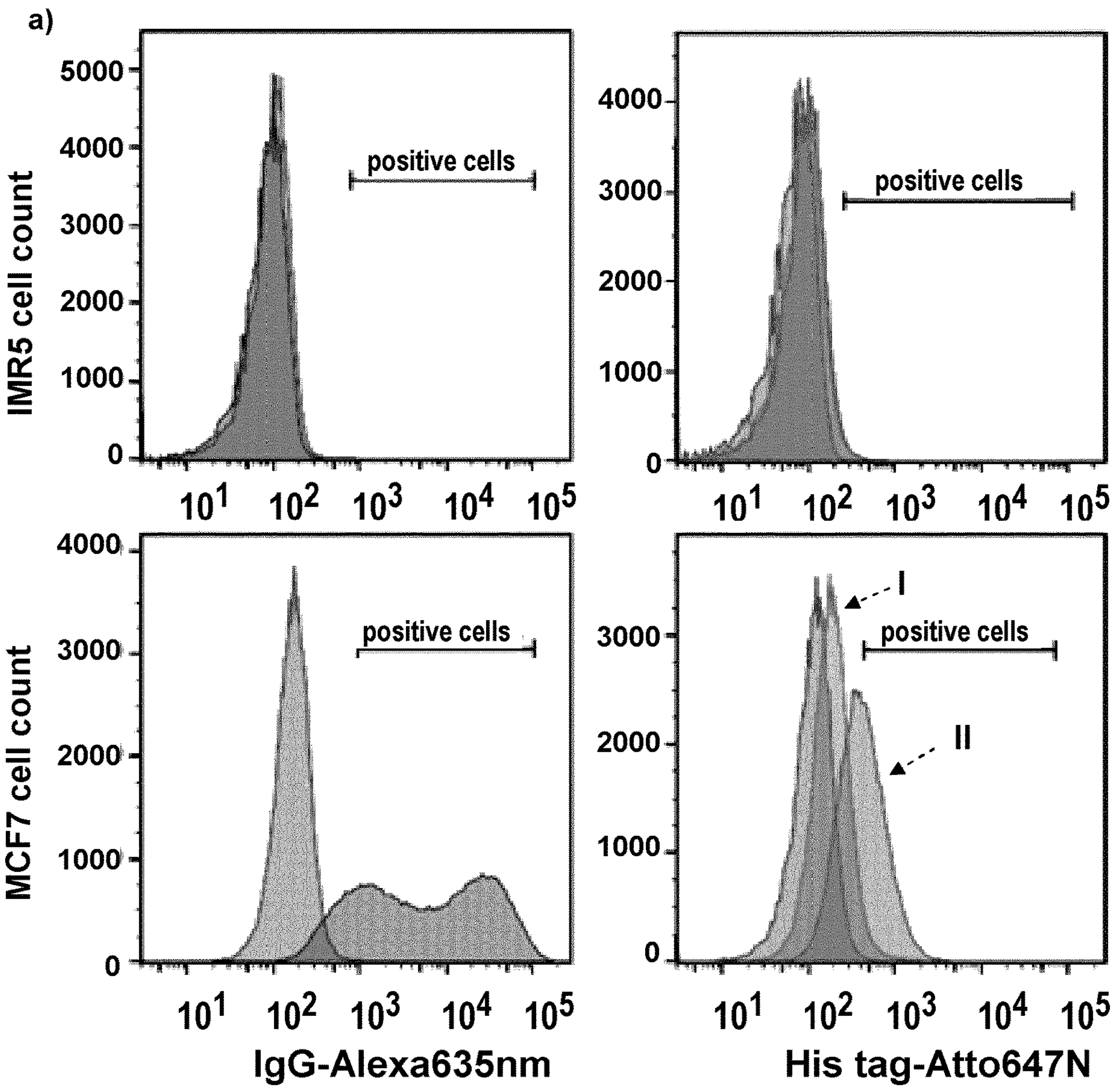
FIG. 20: Binding of sdAb46 monomer and sdAb46 trimer to cancer cells. a)-c) IMR5 neuroblastoma cells (negative control) and MCF7 breast cancer cells were stained with sdAb46 monomer, sdAb46 trimer or Globo H-specific commercial antibody VK9 followed by anti-6xHis-AF647 or anti-IgG-Atto635 secondary antibodies, respectively. a) Flow cytometry histograms show the frequency of fluorescently labeled IMR5 cells (upper panel) and MCF7 cells (lower panel). Secondary antibody only controls are shown in grey on the left. The graphs on left are obtained with the VK9 antibody, the graphs on right with the sdAb46. Data are representative of three independent experiments performed in duplicates or triplicates, each. b) Frequency of positive cells based on the gates indicated in a). c) Confocal laser scanning microscopy of MCF7 (left) and IMR5 (right). RED: detection of signal generated by anti-6xHis-AF647 or anti-IgG-Atto635 secondary antibodies. Cell nuclei were stained with DAPI (BLUE channel). TM light, transmission light. White scale bars, 20 μm.

For flow cytometry, cells were incubated with 0.4 mg/ml of sdAb46 monomer or sdAb46 trimer solution. 5 μg/ml of the anti-Globo H IgG VK9 was used as a positive control. Anti-IgG-Atto635 and anti-6xHis-AF647 were used as secondary antibodies. The fluorescence intensities determined by flow cytometry were plotted compared to the secondary antibody-only negative controls. Binding to cells was quantified using a "positive cell" gate that was created based on the fluorescence intensity of the secondary antibody-only controls (FIG. 20*a*). As expected, VK9 binding was only observed for MCF7 cells (73.47±4.83%) but not for IMR5 cells (0.04±0.13%) confirming Globo H expression on MCF7 cells (FIG. 20*b*). Consistent with previous data, two MCF7 populations were seen in the histogram indicating different Globo H expression levels. A slight shift was observed for IMR5 cells incubated with sdAb46 monomer (1.17±0.71%) and sdAb46 trimer (4.19±3.92%) but MCF7 cells were more frequently bound by the sdAbs (3.65±0.51% for monomer (curve I) and 50.58±20.82% for trimer (curve II)). A two-sample t-test showed that the increased binding to MCF7 is significant for VK9 and both sdAb constructs. As anticipated, the sdAb46 trimer showed an improved MCF7 binding compared to the sdAb46 monomer.

For the assay based on confocal laser scanning microscopy (FIG. 20*c*), cells were seeded on poly-L-lysine coated coverslips and incubated with 0.4 mg/ml of single domain antibody solution or 0.5 μg/ml of VK9. Anti-IgG-Atto635 and anti-6xHis-AF647 were used as secondary antibodies and cell nuclei were stained with DAPI. Secondary antibody controls of MCF7 showed no fluorescence signal for either antibody, but unspecific anti-6xHis-AF647 binding to IMR5 cells was observed. As expected, binding of VK9 to MCF7 and not to IMR5 was observed, and the two MCF7 populations detected in the flow cytometry experiments were also distinguishable in microscopy by different fluorescence intensities. sdAb46 binding was also confirmed, but surprisingly no differences in fluorescence intensities were observed for the monomer and the trimer. Interestingly, the staining pattern of the two sdAb46 forms differed from that of the VK9 antibody, as the two form of sdAb46 were mainly observed intracellularly, whereas VK9 was detected more strongly on the cell membrane and rather as patches. While IMR5 cells were unspecifically stained by anti-6xHis-AF647, increased fluorescence was observed with sdAb46 monomer and trimer, indicating weak Nb binding which is consistent with flow cytometry results.

The invention claimed is:

1. A polypeptide specifically binding a globo-series glycan comprising at least one single domain antibody, wherein said single domain antibody is a variable domain of a heavy chain antibody naturally devoid of a light chain and naturally devoid of the constant region 1, and wherein said single domain antibody binds at least one globo-series glycan selected from Globo H, Gb3, Gb4, and Gb5, wherein said polypeptide binding the least one globo-series glycan comprises complementarity determining regions CDR1, CDR2, and CDR3, wherein:

(a) CDR1 comprises an amino acid sequence selected from SEQ ID NO: 64-72, 157, 158, and 159;

(b) CDR2 comprises an amino acid sequence selected from SEQ ID NO: 73-81, 160, 161, and 162; (c) CDR3 comprises an amino acid sequence selected from SEQ ID NO: 82-90, 163, 164, and 165;

wherein said at least one single domain antibody has a sequence selected from the group consisting of SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 136, SEQ ID NO 137, and SEQ ID NO 138.

2. The polypeptide according to claim 1, further comprising at least one extracellular hinge region, at least one transmembrane domain, at least one costimulatory domain, and at least one intracellular activation domain, wherein the single domain antibody is linked to the extracellular hinge region.

3. The polypeptide according to claim 1, wherein said at least one single domain antibody is a humanized single domain antibody.

4. The polypeptide according to claim 3, wherein said single domain antibody is humanized by replacing one or more amino acid residues located at positions 1, 5, 11, 28 and 30 in FR1, 44 and 45 in FR2, 74, 75, 76, 83, 84, 93 and 94 in FR3; 104 and 108 in FR4, according to the Kabat numbering.

5. A recombinant nucleic acid molecule encoding a polypeptide according to claim 1.

6. A vector comprising the recombinant nucleic acid molecule according to claim 5.

7. A host cell comprising the recombinant nucleic acid molecule according to claim 5.

8. A pharmaceutical composition comprising a polypeptide according to claim 1 together with at least one pharmaceutically acceptable vehicle, excipient and/or diluent.

9. A method for treating a subject having a cancer, wherein the cancer cells of said cancer express on their surface at least one globo-series glycan selected from Globo H, Gb3, Gb4, and Gb5 comprising administering to the subject having said cancer an effective amount of the polypeptide of claim 1, in an effective amount to treat the subject having said cancer.

10. The method according to claim 9, wherein the cancer is selected from brain cancer, liver cancer, bile duct cancer, kidney cancer, breast cancer, prostate cancer, lung cancer, small cell lung cancer, ovarian cancer, cervix cancer, esophagus cancer, stomach cancer, pancreatic cancer and colorectal cancer.

11. A diagnostic kit comprising a polypeptide according to claim 1 and at least one reagent selected from the group consisting of labeling reagent, detection reagent and quantification reagent.

12. The polypeptide according to claim 1 wherein the number of single domain antibodies that bind at least one globo-series glycan selected from Globo H, Gb3, Gb4, and Gb5 is at least two.

13. The polypeptide according to claim 12, wherein the two or more single domain antibodies are different in sequence.

14. The polypeptide according to claim 12, wherein the two or more single domain antibodies are identical in sequence.

15. The polypeptide according to claim 12, wherein the number of single domain antibodies that bind at least one globo-series glycan selected from Globo H, Gb3, Gb4, and Gb5 is three.

16. The polypeptide according to claim 15, wherein said single domain antibody has the sequence of SEQ ID NO 5.

* * * * *